(12) United States Patent
Geiger et al.

(10) Patent No.: US 12,053,490 B2
(45) Date of Patent: Aug. 6, 2024

(54) METHODS AND COMPOSITIONS FOR TREATING CD33+ CANCERS AND IMPROVING IN VIVO PERSISTENCE OF CHIMERIC ANTIGEN RECEPTOR T CELLS

(71) Applicant: ST. JUDE CHILDREN'S RESEARCH HOSPITAL, INC., Memphis, TN (US)

(72) Inventors: Terrence L. Geiger, Memphis, TN (US); Wenting Zheng, Memphis, TN (US); Carol E. O'Hear, Burlingame (CA)

(73) Assignee: ST. JUDE CHILDREN'S RESEARCH HOSPITAL, INC., Memphis, TN (US)

( * ) Notice: Subject to any disclaimer, the term of this patent is extended or adjusted under 35 U.S.C. 154(b) by 781 days.

(21) Appl. No.: 16/759,263

(22) PCT Filed: Oct. 25, 2018

(86) PCT No.: PCT/US2018/057456
§ 371 (c)(1),
(2) Date: Apr. 24, 2020

(87) PCT Pub. No.: WO2019/084234
PCT Pub. Date: May 2, 2019

(65) Prior Publication Data
US 2021/0030793 A1 Feb. 4, 2021

Related U.S. Application Data

(60) Provisional application No. 62/577,494, filed on Oct. 26, 2017.

(51) Int. Cl.
| | |
|---|---|
| *A61K 35/17* | (2015.01) |
| *C07K 14/705* | (2006.01) |
| *C07K 14/725* | (2006.01) |
| *C07K 16/28* | (2006.01) |
| *C12N 15/00* | (2006.01) |
| *C12N 15/62* | (2006.01) |

(52) U.S. Cl.
CPC .......... *A61K 35/17* (2013.01); *C07K 14/7051* (2013.01); *C07K 14/70517* (2013.01); *C07K 14/70578* (2013.01); *C07K 16/2896* (2013.01); *C12N 15/00* (2013.01); *C12N 15/62* (2013.01); *C07K 16/2803* (2013.01); *C07K 2317/622* (2013.01); *C07K 2319/03* (2013.01)

(58) Field of Classification Search
CPC .... A61K 35/17; A61K 31/52; A61K 31/5377; A61K 31/585; A61K 39/001112; A61K 39/001129; A61K 2039/505; A61K 2039/5156; C07K 14/7051; C07K 14/70517; C07K 14/70578; C07K 16/2896; C07K 16/2803; C07K 2317/622; C07K 2319/03; C07K 2319/02; C07K 2317/73; C12N 15/00; C12N 15/62; A61P 35/02
USPC .......................... 435/320.1, 455; 530/387.3
See application file for complete search history.

(56) References Cited

U.S. PATENT DOCUMENTS

| | | | |
|---|---|---|---|
| 8,399,645 B2 | 3/2013 | Campana et al. | |
| 9,777,061 B2 * | 10/2017 | Ebersbach | .............. A61P 43/00 |
| 2016/0053017 A1 | 2/2016 | Orentas et al. | |
| 2017/0145094 A1 | 5/2017 | Galetto | |
| 2017/0218337 A1 | 8/2017 | Friedman | |

FOREIGN PATENT DOCUMENTS

| | | | |
|---|---|---|---|
| CN | 105820255 A | 8/2016 | |
| WO | 2012079000 A1 | 6/2012 | |
| WO | 2015188119 A1 | 12/2015 | |
| WO | 2016201304 A1 | 12/2016 | |
| WO | WO-2017214333 A1 * | 12/2017 | ..... A61K 39/001104 |

OTHER PUBLICATIONS

Rolfs et al., DQ893323.2 (Synthetic construct clone; CD8a molecule (CD8A) gene, encodes complete protein, NCBI Reference Sequence, priority to Mar. 21, 2007). (Year: 2007).*
Alberts, et al. "Molecular Biology of the Cell, Fifth Edition". New York:Garland Science, 2008. pp. 1-3 and 367. (Year: 2008).*
Communication (International Search Report) issued by the International Searching Authority in PCT Application No. PCT/US18/57456 mailed Jan. 30, 2019, 8 pages total.
Communication (Written Opinion) issued by the International Searching Authority in PCT Application No. PCT/US18/57456 mailed Jan. 30, 2019, 5 pages total.
Newman, P.J. et al., "Signal Transduction Pathways Mediated by PECAM-1: New Roles for an Old Molecule in Platelet and Vascular Cell Biology" Arterioscler Thromb Vasc Biol (2003) vol. 23, pp. 953-964.
Kagoya, Y. et al., "BET Bromodomain Inhibition Enhances T Cell Persistence and Function in Adoptive Immunotherapy Models" The Journal of Clinical Investigation (2016) vol. 126, No. 9, pp. 3479-3494.

(Continued)

*Primary Examiner* — Anne Marie S Wehbe
*Assistant Examiner* — Hanan Isam Abuzeineh
(74) *Attorney, Agent, or Firm* — Troutman Pepper Hamilton Sanders LLP

(57) ABSTRACT

The application relates to a chimeric receptor that targets CD33 and allows activation of the co-stimulatory pathway without binding the natural ligand. The application also relates to polynucleotides that encode the chimeric receptor, vectors, and host cells comprising the chimeric receptor. The application also relates to methods for preparing host cells comprising a chimeric antigen receptor in order to improve the in vivo persistence of the chimeric antigen receptor host cells.

23 Claims, 62 Drawing Sheets
Specification includes a Sequence Listing.

(56) References Cited

OTHER PUBLICATIONS

O'Hear, C. et al., "Anti-CD33 Chimeric Antigen Receptor Targeting of Acute Myeloid Leukemia" Haematologica (2017) 16 pages total.
Perkins, M.R. et al., "Manufacturing an Enhanced CAR T Cell Product by Inhibition of the PI3K/Akt Pathway During T Cell Expansion Results in Improved In Vivo Efficacy of Anti-BCMA CAR T Cells" The American Society of Hematology: Blood (2015) vol. 126, Issue 23, 6 pages total.
Kenderian, SS. et al., "CD33-Specific Chimeric Antigen Receptor T Cells Exhibit Potent Preclinical Activity Against Human Acute Myeloid Leukemia" Leukemia (2015) vol. 29, No. 8, pp. 1637-1647.
Co, M.S. et al., "Chimeric and Humanized Antibodies with Specificity for the CD33 Antigen" The Journal of Immunology (1992) vol. 148, No. 4, pp. 1149-1154.
Long, A. H. et al., "4-1BB Costimulation Ameliorates T Cell Exhaustion Induced by Tonic Signaling of Chimeric Antigen Receptors" Nat. Med. (2015) vol. 21, No. 6, pp. 581-590.
Zheng, W., et al., PI3K orchestration of the in vivo persistence of chimeric antigen receptor-modified T cells; Leukemia; May 2018; 32(5): 1157-1167; doi:10.1038/s41375-017-0008-6.

\* cited by examiner

METHODS AND COMPOSITIONS FOR TREATING CD33+ CANCERS AND IMPROVING IN VIVO PERSISTENCE OF CHIMERIC ANTIGEN RECEPTOR T CELLS

CROSS-REFERENCE TO RELATED APPLICATIONS

This application is a U.S. National Phase of International Patent Application No. PCT/US2018/057456, filed on Oct. 25, 2018, which published as WO 2019/084234 A1 on May 2, 2019, and claims priority to U.S. Provisional Application No. 62/577,494, filed on Oct. 26, 2017, all of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Oct. 23, 2018, is named 243734_000102_ST25.txt and is 17,195 bytes in size.

FIELD

The application relates to chimeric antigen receptors (CARs), particularly chimeric T cell antigen receptors and for treating cancers expressing the CD33 receptor, including for example and not limitation, acute myeloid leukemia (AML). The application further relates to methods for improving the in vivo persistence of CAR expressing host cells, including CAR-modified T-cells.

BACKGROUND

Chimeric antigen receptors (CARs) co-express a ligand recognition domain specific for a disease (e.g., tumor) antigen with signaling components that trigger T cell activation and killing of the target cell. First-generation CARs incorporated an anti-tumor specific single chain variable fragment (scFv) linked to the CD3ζ endodomain and showed limited in vivo longevity and anti-tumor efficacy. CARs, incorporating cytoplasmic signaling domains from T cell co-stimulatory molecules such as CD28 and 4-1BB, have improved longevity and tumoricidal activity in preclinical models and clinical trials (3-5).

CAR T cell therapy for B-cell malignancies has improved prognosis for patients with refractory or recurrent disease; therapeutic T cells incorporating anti-CD19 scFv with 4-1BB or CD28 and CD3ζ signaling domains induce high rates of remission (6). In fact, CAR T cells expressing an anti-CD19-41BB-CD3ζ CAR were found to be effective in clinical trials (11-13). In contrast, CAR therapy for myeloid neoplasms is less developed. Recent preclinical data has supported the application of CAR T cells specific for several myeloid antigens, CD123, CD44v6 and CD33 (7-10).

While CAR T cells expressing chimeric receptors generated on the backbone of an anti-CD19-41BB-CD3ζ chimeric antigen receptor were found to potently target both tumor cell lines and primary tumor samples ex vivo, they showed inadequate persistence in preclinical animal models, leading to incomplete tumor clearance and tumor recurrence (10). In vivo persistence of CAR T cells correlates with therapeutic efficacy, yet CAR-specific factors that support persistence are not well resolved. In vivo persistence is associated with the long-term clinical efficacy of CAR T cell mediated therapy, and patients with increased proliferation and persistence of CD19 CAR T cells in the blood are more likely to enter sustained remissions (4, 13-16). Production of CAR T cells that act as a long-lived therapeutic may therefore be essential for complete and long term eradication of malignant cells (1). CAR structure and co-stimulatory domains, and CAR T cell differentiation, exhaustion, and metabolic status during ex vivo expansion may impact anti-tumor efficacy and survival of CAR T cells in vivo (17-21). Both tonic CAR signaling and extrinsic signals, such as through cognate antigen or local cytokines, may also influence CAR T cell persistence. The novel CARs and methods of preparing the CAR-modified cells for administration described herein addresses and elucidate the problems with in vivo persistence and provide for the production of CAR T cells with improved survival and function.

SUMMARY OF THE INVENTION

As specified in the Background section above, there is a great need in the art for treating cancers expressing the CD33 receptor and for improving the in vivo persistence of CAR-modified T cells. The present application addresses these and other needs.

In one aspect, the invention provides a polynucleotide encoding a chimeric receptor comprising (a) an extracellular ligand-binding domain comprising an anti-CD 33 single chain variable fragment (scFv) domain, (b) a hinge, (c) a transmembrane domain, and (d) a cytoplasmic domain comprising a 4-1BB signaling domain and a CD3ζ signaling domain. In some embodiments, the anti-CD33 single chain variable fragment is encoded by the nucleotide sequence of SEQ ID NO: 8 and comprises the amino acid sequence SEQ ID NO: 3. In some embodiments, the 4-1BB signaling domain is encoded by the nucleotide sequence of SEQ ID NO: 9 and comprises amino acids 214-255 of SEQ ID NO: 4. In some embodiments, the CD3ζ signaling domain is encoded by the nucleotide sequence of SEQ ID NO: 10 and comprises the amino acid sequence SEQ ID NO: 5. In some embodiments, the hinge and transmembrane domain comprises the hinge and transmembrane domain of CD8α. In some embodiments, the hinge and transmembrane domain of CD8α is encoded by the nucleotide sequence of SEQ ID NO: 11 and comprises the amino acid sequence SEQ ID NO: 6. In some embodiments, the hinge of CD8α is encoded by nucleic acid sequence of SEQ ID NO: 15 and comprises the amino acid sequence of SEQ ID NO: 13. In some embodiments, the transmembrane domain of CD8α is encoded by nucleotide sequence of SEQ ID NO: 16 and comprises the amino acid sequence SEQ ID NO: 14. In some embodiments, the extracellular ligand-binding domain comprises a signal peptide of CD8α. In some embodiments, the signal peptide of CD8α is encoded by nucleic acid sequence of SEQ ID NO: 12 and comprises the amino acid sequence SEQ ID NO: 7. In some embodiment, the chimeric receptor is encoded by the nucleic acid sequence of SEQ ID NO: 1. In certain embodiments, the chimeric receptor comprises the amino acid sequence SEQ ID NO: 2. In certain embodiments, the polynucleotide is a DNA molecule. In certain embodiments, the polynucleotide is an RNA molecule or derivative thereof.

In one aspect, the invention provides a chimeric receptor encoded by the polynucleotides as described herein.

In one aspect, the invention provides a vector comprising the polynucleotides as described herein. In some embodiments, the polynucleotide of the chimeric receptor is operatively linked to at least one regulatory element for expression of the chimeric receptor.

In one aspect, the invention provides a vector comprising a polynucleotide encoding a chimeric receptor comprising (a) an extracellular ligand-binding domain comprising an anti-CD 33 single chain variable fragment (scFv) domain, (b) a hinge, (c) a transmembrane domain, and (d) a cytoplasmic domain comprising a 4-1BB signaling domain and a CD3ζ signaling domain, wherein the polynucleotide is operatively linked to at least one regulatory element for expression of the chimeric receptor. In some embodiments, the vector is a viral vector. In some embodiments, the viral vector can be an adenoviral vector, an adeno-associated virus vector, an alphaviral vector, a herpes virus vector, a lentiviral vector, a retroviral vector, or vaccinia virus vector. In some embodiments, the viral vector is a retroviral vector.

In one aspect, the invention provides a chimeric receptor comprising (a) an extracellular ligand-binding domain comprising an anti-CD 33 single chain variable fragment (scFv) domain, (b) a hinge, (c) transmembrane domain, and (d) a cytoplasmic domain comprising a 4-1BB signaling domain and a CD3ζ signaling domain. In some embodiments, the anti-CD33 single chain variable fragment comprises the amino acid sequence SEQ ID NO: 3. In some embodiments, the 4-1BB signaling domain comprises amino acids 214-255 of SEQ ID NO: 4. In some embodiments, the CD3ζ signaling domain comprises the amino acid sequence SEQ ID NO: 5. In some embodiments, the hinge and transmembrane domain is the hinge and transmembrane domain of CD8α. In some embodiments, the hinge and transmembrane domain of CD8α comprises the amino acid sequence SEQ ID NO: 6. In some embodiments, the extracellular ligand-binding domain comprises a signal peptide of CD8α. In some embodiments, the signal peptide of CD8α comprises the amino acid sequence SEQ ID NO: 7. In some embodiments, wherein the chimeric receptor comprises the amino acid sequence SEQ ID NO: 2.

In one aspect, the invention provides an isolated host cell comprising the chimeric receptors, the polynucleotides, and/or the vectors as described herein. In some embodiments, the host cell comprises a polynucleotide operatively linked to at least one regulatory element capable of mediating expression of the chimeric receptor in the host cell. In some embodiments, the host cell is a T lymphocyte. In some embodiments, the host cell is a natural killer (NK) cell. In some embodiments, the host cell has been activated and/or expanded ex vivo. In some embodiments, the host cell is an allogeneic cell. In some embodiments, the host cell is an autologous cell. In some embodiments, the host cell is isolated from a subject having a disease, wherein CD33 is expressed. In some embodiments, the disease is a cancer that expresses CD33. In some embodiments, the host cell has been isolated from a subject having a disease such as, but not limited to, acute myeloid leukemia (AML), myelodysplastic syndrome (MDS), chronic myeloid leukemia (CML), or pro-myelocytic leukemia (PML). In some embodiments, the host cell is derived from a blood and/or a tumor sample.

In one aspect, the invention provides a pharmaceutical composition comprising the host cell as described herein and a pharmaceutically acceptable carrier and/or excipient.

In one aspect, the invention provides a method of enhancing a T lymphocyte or a natural killer (NK) cell activity in a subject in need thereof comprising administering to the subject the host cell as described herein.

In one aspect, the invention provides a method of enhancing a T lymphocyte or a natural killer (NK) cell activity in a subject in need thereof comprising administering to the subject an effective amount of a pharmaceutical composition of the invention.

In some aspects, the methods disclosed herein comprise a host cell. In some embodiments, the host cell is an autologous cell. In some embodiments, the methods comprise a subject that has a disease wherein CD33 is expressed. In some embodiments, the disease is a cancer expressing CD33. In some embodiments, the subject has a disease such as, but not limited to, acute myeloid leukemia (AML), myelodysplastic syndrome (MDS), chronic myeloid leukemia (CML), or pro-myelocytic leukemia (PML). In some embodiments, the disease is acute myeloid leukemia (AML).

In one aspect, the invention provides a method of treating a disease in a subject in need thereof comprising administering to the subject the host cell and/or pharmaceutical composition as described herein. In some embodiments, the host cell is an autologous cell. In some embodiments, the subject has a disease, wherein CD33 is expressed. In some embodiments, the disease is a cancer expressing CD33. In some embodiments, the disease can be acute myeloid leukemia (AML), myelodysplastic syndrome (MDS), chronic myeloid leukemia (CML), or pro-myelocytic leukemia (PML). In some embodiments, wherein the disease is acute myeloid leukemia (AML).

In one aspect, the invention provides a method for preparing T lymphocytes or NK cells comprising: a) activating a T lymphocyte/NK cell; b) transducing the T lymphocyte/NK cell with a polynucleotide encoding a chimeric antigen receptor (CAR); c) expanding the transduced T lymphocyte/NK cell; and d) treating with an inhibitor, wherein the inhibitor is a phosphoinositide 3-kinase (PI3K) / Akt pathway inhibitor, an oncogene inhibitor, an oncoprotein inhibitor, or a glycolysis inhibitor. In some embodiments, steps c) and d) are performed simultaneously. In some embodiments, the cells are expanded for at least 2 days prior to treatment with the inhibitor.

In some embodiments, prior to step a) T lymphocytes/NK cells are isolated from a subject sample and optionally purified. In some embodiments, the subject sample is a blood and/or a tumor sample. In some embodiments, the method comprises administering the T lymphocyte/NK cell produced in step d) to a subject. In some embodiments, the T lymphocyte/NK cell is an allogeneic cell to the subject. In some embodiments, the T lymphocyte/NK cell is an autologous cell to the subject. In some embodiments, steps a)-d) are conducted ex vivo. In some embodiments, the isolation/purification step comprises the use of an apheresis ring.

In some embodiments, the isolation/purification comprises isolating the T lymphocyte from the sample using at least one antibody against an antigen such as, but not limited to, CD3, CD14, CD15, CD16, CD19, CD28, CD34, CD36, CD56, CD123, CD235a, or any combinations thereof. In some embodiments, step a) comprises exposing T lymphocyte to a CD3 binding agent or a CD3 binding agent with a CD28 binding agent. In some embodiments, the CD3 binding agent is an anti-CD3 antibody or a CD3-binding fragment thereof. In some embodiments, the anti-CD3 antibody or CD3-binding fragment thereof is present at a concentration of about 0.01 μg/ml about 10 μg/ml. In some embodiments, the CD28 binding agent is an anti-CD28 antibody or a CD28-binding fragment thereof. In some embodiments, the anti-CD28 antibody or CD28-binding fragment thereof is present at a concentration of about 0.01 μg/ml about 10 μg/ml. In some embodiments, the CD3 binding agent and/or the CD28 binding agent are immobilized on a solid surface.

In some embodiments, step c) comprises exposing T lymphocytes to IL-2 at a concentration of 20-200 Units/ml. In some embodiments, step a) is conducted for at least 16-24 hours. In some embodiments, step b) comprises transducing the T lymphocyte with the polynucleotide(s) as disclosed herein. In some embodiments, step b) comprises transducing the
T lymphocyte with a vector as disclosed herein. In some embodiments, the chimeric antigen receptor (CAR) comprises (a) an extracellular ligand-binding domain comprising an anti-CD 33 single chain variable fragment (scFv) domain, (b) a hinge, (c) transmembrane domain, and (d) a cytoplasmic domain comprising a 4-1BB signaling domain and a CD3 signaling domain. In some embodiments, the anti-CD33 single chain variable fragment comprises the amino acid sequence SEQ ID NO: 3. In some embodiments, the 4-1BB signaling domain comprises amino acids 214-255 of SEQ ID NO: 4. In some embodiments, the CD3ζ signaling domain comprises the amino acid sequence SEQ ID NO: 5. In some embodiments, the hinge and transmembrane domain is the hinge and transmembrane domain of CD8α. In some embodiments, the hinge and transmembrane domain of CD8α comprises the amino acid sequence SEQ ID NO: 6. In some embodiments, the extracellular ligand-binding domain comprises a signal peptide of CD8α. In some embodiments, the signal peptide of CD8α comprises the amino acid sequence SEQ ID NO: 7. In some embodiments, the CAR comprises the amino acid sequence SEQ ID NO: 2.

In some embodiments, the CAR comprises an extracellular domain that binds an antigen such as, but not limited to, carbonic anhydrase EX, alpha-fetoprotein, A3, antigen specific for A33 antibody, Ba 733, BrE3-antigen, CA125, CD1, CD1a, CD3, CDS, CD15, CD16, CD19, CD20, CD21, CD22, CD23, CD25, CD30, CD33, CD38, CD45, CD74, CD79a, CD80, CD 138, colon-specific antigen-p (CSAp), CEA (CEACAMS), CEACAM6, CSAp, EGFR, EGP-I, EGP-2, Ep-CAM, FIt-I, Flt-3, folate receptor, HLA-DR, human chorionic gonadotropin (HCG) and its subunits, HER2/neu, hypoxia inducible factor (HIF-I), Ia, IL-2, IL-6, IL-8, insulin growth factor-1 (IGF-I), KC4-antigen, KS-1-antigen, KS1-4, Le-Y, macrophage inhibition factor (MIF), MAGE, MUC1, MUC2, MUC3, MUC4, NCA66, NCA95, NCA90, antigen specific for PAM-4 antibody, placental growth factor, p53, prostatic acid phosphatase, PSA, PSMA, RSS, SIOO, TAC, TAG-72, tenascin, TRAIL receptors, Tn antigen, Thomson-Friedenreich antigens, tumor necrosis antigens, VEGF, ED-B fibronectin, 17-1A-antigen, an angiogenesis marker, an oncogene marker, or an oncogene product. In some embodiments, the CAR-encoding polynucleotide in step b) is comprised within a vector, wherein the polynucleotide is operatively linked to at least one regulatory element for expression of the chimeric receptor. In some embodiments, the vector is a viral vector. In some embodiments, the viral vector can be an adenoviral vector, an adeno-associated virus vector, an alphaviral vector, a herpes virus vector, a lentiviral vector, a retroviral vector, or vaccinia virus vector. In some embodiments, the viral vector is a retroviral vector.

In some embodiments, the PI3K pathway inhibitor used in step c) inhibits PI3K. In some embodiments, the PI3K inhibitor can be, but is not limited to, an anti-PI3K antibody or antigen-binding fragment thereof, aptamer, siRNA, shRNA, miRNA, small molecule inhibitors of PI3K, or a combination thereof. In some embodiments, the PI3K inhibitor can be, but is not limited to, LY294002, XL147, BKM120, GDC-0941, BAY80-6946, PX-866, CH5132799, XL756, BEZ235, and GDC-0980, wortmannin, PI3K II, TGR-1202, AMG-319, GSK2269557, X-339, X-414, RP5090, KAR4141, XL499, OXY11 1A, IPI-145, IPI-443, GSK2636771, BAY 10824391, buparlisib, BYL719, RG7604, MLN1117, WX-037, AEZS-129, PA799, ZSTK474, AS252424, TGX221, TG100115, IC87114, (S)-2-(1-((9H-purin-6-yl)amino)propyl)-5-fluoro-3-phenylquinazolin-4(3H)-one, (S)-2-(1-((9H-purin-6-yl)amino)ethyl)-6-fluoro-3-phenylquinazolin-4(3H)-one, (S)-2-(1-((9H-purin-6-yl)amino)ethyl)-3-(2,6-difluorophenyl)quinazolin-4(3H)-one, and (S)-4-amino-6-41-(5-chloro-4-oxo-3-phenyl-3,4-dihydroquinazolin-2-yl)ethyl)amino) pyrimidine-5-carbonitrile, or pharmaceutically acceptable salts thereof. In some embodiments, the PI3K inhibitor is LY294002. In some embodiments, the PI3K inhibitor is present in a concentration of about 1 µM to about 20 µM.

In some embodiments, the oncoprotein inhibitor used in step c) is a c-Myc inhibitor. In some embodiments, the c-Myc inhibitor can be, but is not limited to, an anti-c-Myc antibody or antigen-binding fragment thereof, aptamer, siRNA, shRNA, microRNA, or a small molecule inhibitor of c-Myc protein or a gene encoding the c-Myc protein, or a combination thereof. In some embodiments, the c-Myc inhibitor is JQ-1 and/or BET bromodomain inhibitors. In some embodiments, the c-Myc inhibitor is present in a concentration of from about 0.5 p.M to about 20 µM.

In some embodiments, the glycolysis inhibitor used in step c) inhibits glycolysis. In some embodiments, the glycolysis inhibitor can be, but is not limited to, Glutl inhibitor (Glutli) phloretin (Phlo), hexokinase inhibitor (HXKi), pyruvate kinase inhibitor (PKi) oxaloacetate, lactate dehydrogenase inhibitor (LDHi) oxamate, TCA cycle inhibitor (TCAi) dichloroacetic acid (DCA), 2DG (2-Deoxy-D-glucose), or a combination thereof. In some embodiments, the glycolysis inhibitor is DCA or 2DG. In some embodiments, the glycolysis inhibitor is present in a concentration of about 100 µm to about 20 mM.

In some embodiments, the T lymphocyte/NK cell is only treated once with the PI3K pathway inhibitor, oncogene inhibitor, and/or glycolysis inhibitor. In some embodiments, the cells are not treated with the PI3K pathway inhibitor, oncogene inhibitor, and/or glycolysis inhibitor before step b). In some embodiments, the T lymphocyte/NK cell is expanded in step c) for a period of about 1 to 2 days. In some embodiments, the resulting T lymphocyte/NK cell exhibits improved in vivo persistence.

In one aspect, the invention provides a T lymphocyte prepared by the methods described herein.

In one aspect, the invention provides a T lymphocyte described herein and a pharmaceutically acceptable carrier or diluent.

In one aspect, the invention provides a method of treating a disease in a subject in need thereof, comprising administering to the subject the T lymphocyte described herein. In one aspect, the invention provides a method of treating a disease in a subject in need thereof, comprising administering to the subject a therapeutically effective amount of the pharmaceutical composition described herein. In some embodiments, the subject has a disease wherein CD33 is expressed. In some embodiments, the disease is cancer expressing CD33. In some embodiments, the disease can be, but is not limited to, acute myeloid leukemia (AML), myelodysplastic syndrome (MDS), chronic myeloid leukemia (CML), or pro-myelocytic leukemia (PML). In some embodiments, the disease is acute myeloid leukemia (AML). In some embodiments, the disease is a cancer such as, but not limited to, renal cell carcinoma, colorectal carcinoma, lymphoma, melanoma, prostate cancer, ovarian cancer, lung cancer, liver cancer, head and neck cancer, bladder cancer, uterine cancer, bone cancer, leukemia, breast cancer, non-melanoma skin cancer, glioma, solid cutaneous tumor, epidermoid carcinoma, metastases of any of thereof, and combinations of any of thereof.

In one aspect, the invention provides an isolated autologous host cell as described herein, wherein the subject is human.

These and other aspects of the present invention will be apparent to those of ordinary skill in the art in the following description, claims and drawings.

BRIEF DESCRIPTION OF THE DRAWINGS

(FIG. 1A) CAR surface staining of CD19 and CD33 CAR-transduced T cells, imaged by confocal microscopy, with CAR shown in red (halo) and DAPI (nucleus) in blue. Red line represents a distance of 5µm. (FIG. 1B) The MOLM-13-CD19 cell line was incubated with CD33 CAR, CD19 CAR or vector-transduced control T cells at the indicated ratios for 24 h (left) or 48 h (right). Residual viable tumor cells were quantified by flow cytometry and normalized to cultures without added T cells. Means of triplicate wells ±SEM are shown. (FIG. 1C) Kaplan-Meier analysis of mice with MOLM-13-CD19 tumors treated with CD33 CAR, CD19 CAR, or vector-control T cells. Significance was determined with the log-rank (Mantel-Cox) test. (FIG. 1D) Xenogen images of mice with MOLM-13-CD19 tumors treated with CD33 CAR, CD19 CAR, or vector-control T cells. Bioluminescent signal intensities are plotted. (FIG. 1E) Total tumor cell number in the spleen, liver, and bone marrow of mice treated with CD33 CAR, CD19 CAR or control T cells at 18 days post transfer. Significance was determined by one-way ANOVA with Tukey's multiple comparison post-test. All data are representative of 2 independent experiments with 5-6 mice per group. * $p<0.05$,  $p<0.01$, * $p<0.001$, **** $p<0.001$.

(FIG. 2A FIG. 2B) CD33 CAR, CD19 CAR, or vector-control T cells were transferred into NSG recipients of MOLM-13-CD19 tumor cells. Organs were harvested at day 5 or 18 post-transfer. Total number of CD3+CD8+ CAR or control T cells were calculated and plotted at 5 (FIG. 2A) and 18 (FIG. 2B) days post transfer. Significance was determined by one-way ANOVA with Tukey's multiple comparison post-test. Data from 2 independent experiments of 4-6 mice per group were pooled. (FIG. 2C-FIG. 2D) CD33 CAR T cells (GFP) and vector-transduced control T cells (RFP) were co-transferred at an input ratio of 0.9:1-1.1:1 into NSG mice in the presence or absence of tumor. Liver and spleen were harvested at day 5 post-transfer. (FIG. 2C) Absolute cell number of CD8+ CAR and control T cells in individual mice in the presence or absence of tumor at day 5. Significance was determined by ratio paired t-test (FIG. 2D) Relative cell numbers were normalized to input ratio of the transferred populations. Ratio of CD4+ control T cells to CD33 CAR T cells in each mouse in the presence and absence of tumor. Statistical significance of each ratio was determined using one sample t-test with theoretical mean of 1 (dashed line). Significance between groups was determined by unpaired t-test. Mean values from each group ±SEM are shown. Data are representative of 3 independent experiments with 4-6 mice per group. * $p<0.05$,  $p<0.01$, * $p<0.001$, **** $p<0.001$ FIG. 3A-3I. Increased CAR T differentiation and activation due to CD3 ITAM signaling. (FIG. 3C) Composition of $T_N$, $T_{CM}$, $T_{EM}$, and $T_{EFF}$ subsets 9 days after activation is shown. (FIG. 3D) Methylation analysis of genomic DNA CpG sites within the IFNγ promotor of CAR- and control-transduced T cells 9 days after activation. Each line represents bisulfite sequencing data from an individual clone (top). Bar graphs show % CpG methylation at each site of the locus in CD33 CAR or control T cells. Percent CpG methylation from all five sites in CD33 CAR or control T cells as averaged and compared by paired ratio t-test (bottom).

(FIG. 4A- FIG. 4C) CD33 CAR and vector-control T cells at a 1:1 ratio were transferred with or without MOLM-13-CD19 cells into NSG mice. (FIG. 4A) Differentiation marker expression levels on CD8+ CAR T cells in the liver and spleen at 5 days post-transfer. (FIG. 4B) Proportions of $T_N$, $T_{CM}$, $T_{EM}$, and $T_{EFF}$ subsets of CD8+ T cells in the liver and spleen at 5 days post-transfer. Significance for FIG. 4A-FIG. 4B was determined by two-way ANOVA with Tukey's multiple comparison post-test. Data are representative of 3 independent experiments. (FIG. 4C) Total cell numbers of $T_N$, $T_{CM}$, $T_{EM}$, and $T_{EFF}$ subsets of CD8+T cells in the liver and spleen at 5 days post-transfer. Significance was determined by paired ratio t-test. (FIG. 4D) CD8+ CCR7+ CD45RA+ $T_N$ and CD8+ CCR7− CD45RA− $T_{EM}$ cells were sorted from CD33 CAR or control T cells and transferred into NSG mice. Cell numbers in the liver and spleen were assessed at 5 days post-transfer. Data was pooled from 2 experiments, with cell numbers normalized to the CD33 CAR $T_{EM}$ group for the respective experiment. Significance was determined by multiple unpaired t-tests. * $p<0.05$,  $p<0.01$, * $p<0.001$, ** $p<0.001$ FIG. 5A-5C. CD33 CAR T cells exhibit a more activated transcriptional profile.

(FIG. 6A) Composition of $T_N$, $T_{CM}$, $T_{EM}$, and $T_{EFF}$ subsets of CD8+ T cells with inhibitor treatment. Significance was determined by two-way ANOVA with Tukey's multiple comparison post-test. (FIG. 6B) Total numbers of $T_N$, $T_{CM}$, $T_{EM}$, and $T_{EFF}$ subsets of CD8+ T cells were determined and normalized to the number of untreated CD33 CAR T cells. Significance was determined by one-way ANOVA with Dunnet's multiple comparison post-test. (FIG. 6C) Relative number of CD8+ T cells after 4 days of inhibitor treatment, normalized to the CAR T cell group. (FIG. 6D) Representative dot plots of CCR7 expression and proliferation as monitored by CellTrace Violet with or without inhibitor treatment. Bar graph indicates percentage of proliferating cells that are CD8+ CCR7+. Significance was determined by one-way ANOVA with Dunnet's multiple comparison post-test. * p<0.05,  p<0.01, * p<0.001, **** p<0.001.

(FIG. 7A) MOLM-13-CD19 cells were incubated with CD33 CAR T cells with or without LY treatment during ex-vivo expansion, or vector-transduced control T cells at the indicated ratios for 24h (left) or 48h (right). Residual viable tumor cells were quantified by flow cytometry and normalized to cultures without added T cells. Means of triplicate wells ±SEM are shown. (FIG. 7B) Quantification of 7AAD+ cells in inhibitor treated CD33 CAR and CD33 CAR T cells 4 days after treatment. (FIG. 7C) CD33 CAR T cells with or without LY treatment during ex-vivo expansion, or vector-transduced control T cells were incubated with MOLM-13-CD19 tumor cells at a 1:1 ratio for 48 hours prior to intracellular cytokine staining. (FIG. 7D) CD33 CAR cells were sorted and treated with 10 µM PI3K inhibitor LY for 6 days. Inhibitor treated CD33 CAR T cells, untreated CD33 CAR T cells, and control T cells were injected into NSG mice. Cell numbers in the liver and spleen were assessed 5 days post-transfer. Data from 3 experiments were independently normalized to the CD33 CAR group and pooled. Significance was determined by one-way ANOVA with Tukey's multiple comparisons post-test. (FIG. 7E) Kaplan-Meier analysis of mice with MOLM-13-CD19 tumors treated with CD33 CAR, CD33 CAR +LY treatment, or vector-control T cells. Significance was determined with the log-rank (Mantel-Cox) test. * p<0.05,  p<0.01, * p<0.001, **** p<0.001.

(FIG. 8A-FIG. 8B) CD33 CAR, CD19 CAR, or control T cells were transferred into NSG mice with 1×10$^6$ MOLM-13-CD19 tumor cells. Liver and spleen were harvested at day 5 or day 18 post-transfer. Total number of CD3+CD4+ CAR or control T cells were calculated and plotted at (FIG. 8A) 5 days and (FIG. 8B) 18 days post transfer. Significance was determined by one-way ANOVA with Tukey's multiple comparison post-test. Data from 2 independent experiments of 4-6 mice per group were pooled. (FIG. 8C-FIG. 8D) CD33 CAR T cells (GFP) and control T cells (RFP) were co-transferred into NSG mice in the presence or absence of tumor. Liver and spleen were harvested at day 5 post-transfer. (FIG. 8C) Absolute cell number of CD4+ CAR and control T cells in the presence or absence of tumor at day 5. Significance was determined by ratio paired t-test. (FIG. 8D) Ratio of CD4+ control T cells to CD33 CAR T cells in each mouse in the presence and absence of tumor. Statistical significance of each ratio was determined using one sample t-test with theoretical mean of 1 (dashed line). Significance between groups was determined by unpaired t-test. Mean values from each group ±SEM are shown. Data are representative of 3 independent experiments with 4-6 mice per group. * p<0.05,  p<0.01, * p<0.001, **** p<0.001.

(FIG. 9A) Differentiation marker expression on CD8+ and CD4+ CD33 CAR or control T cells at 6 or 12 days after initial activation. (FIG. 9B) Summary data of differentiation marker expression on CD8+ and CD4+ CD33 CAR or control T cells at 6 and 12 days after initial activation. Significance was determined using multiple t-tests (FIG. 9C) Representative dot plots showing gating strategy for CD8+ $T_{SCM}$ subset of CAR and control T cells. (FIG. 9D) Representative dot plots and summary data for the composition of CCR7+ CD45RA+ ($T_N$), CCR7+ CD45RA− ($T_{CM}$), CCR7− CD45RA− ($T_{EM}$) and CCR7− CD45RA+ ($T_{EFF}$) CD8+ T cell subsets in CD19 CAR and vector control-transduced T cells at 6 and 12 days post-activation. (FIG. 9E) Percent of Tscm cells among CD8+ CD19 CAR and control T cells 6 and 12 days activation.

(FIG. 10A) Representative histograms showing exhaustion marker expression on CD8+ CD33 CAR T cells at 6 and 12 days after initial activation. (FIG. 10B) Surface expression of CD33 CAR and mutant CAR constructs. (FIG. 10C) Activation and exhaustion marker expression on CD33 CAR and CD33 CAR ITAM mutant CD8+ (top) and CD4+ (bottom) T cells 6 days (left) and 12 days (right) after activation. (FIG. 10D) The MOLM-13-CD19 cell line was incubated with CD33 CAR, CD33 CAR ITAM mutant, or vector-transduced control T cells at the indicated ratios for 24 h (top) or 48 h (bottom). Residual viable tumor cells were quantified by flow cytometry and normalized to cultures without added T cells. Means of triplicate wells ±SEM are shown. * p<0.05,  p<0.01, * p<0.001, **** p<0.001.

(FIG. 11A) Differentiation marker expression levels on CD4+ CAR T cells in the liver and spleen at 5 days post-transfer. (FIG. 11B) Composition of $T_N$, $T_{CM}$, $T_{EM}$ and $T_{EFF}$ subsets of CD4+ T cells in the liver and spleen at 5 days post-transfer. Significance for A-B was determined by two-way ANOVA with Tukey's multiple comparison post-test. Data are representative of 3 independent experiments. (FIG. 11C) Total cell numbers of $T_N$, $T_{CM}$, $T_{EM}$ and $T_{EFF}$ subsets of CD4+ T cells in the liver and spleen at 5 days post-transfer. Significance was determined by paired ratio t-test. * p<0.05,  p<0.01, * p<0.001, **** p<0.001.

(FIG. 12A) -log (p-value) of selected canonical pathways identified by IPA analysis as upregulated in CD8+ CD33 CAR T cells relative to control T cells. (FIG. 12B) Heat maps show genes uniquely dysregulated in CD8+ CD33 CAR T cells, segregated by pathway. (FIG. 12C) Phospho-flow staining of p-AKT, $_p$ERK, and pFOXO-1 in control and CD33 CAR T cells at 12 days after initial stimulation. Significance was determined by unpaired t-test.

(FIG. 13A) Percent of CD8+ CCR7+ CellTrace Violet high cells after 4 days of inhibitor treatment Data are representative of three experiments. Significance was determined by one-way ANOVA with Dunnet's multiple comparison post-test.

(FIG. 14A FIG. 14B) 5 days post-activation, CD33 CAR T cells were treated with LY (LY=LY294002) PI3K inhibitor for 4 days, followed by flow cytometric analysis. (FIG. 14A) Composition of CD8+ $T_N$, $T_{CM}$, $T_{EM}$ and $T_{EFF}$ subsets and (FIG. 14B) Numbers of CD8+inhibitor treated CD33 CAR T cells, untreated CD33 CAR T cells, and control T cells, normalized to the number of untreated CAR T cells. (FIG. 14C) CD33 CAR cells were sorted and treated with 1004 LY inhibitor for 6 days. Inhibitor treated CD33 CAR T cells, untreated CD33 CAR T cells, and control T cells were injected into NSG mice. CD4+ T cell numbers in the liver and spleen were assessed 5 days post-transfer. Data from 3 experiments were independently normalized to the CD33 CAR group and pooled. Significance was determined by one-way ANOVA with Tukey's multiple comparisons post-test.

(FIG. 15A) Reprehensive graph of the mutants. (FIG. 15B) CD8+ T cells at day 10 during in vitro culture. ITAM1+3, ITAM-1+2+3 and ALL mut CD33CAR could rescue the altered T cell differentiation of CD33CAR during in vitro culture. The similar effect of 4-1BB-1 mutated CAR is due to the poor expression of CAR on T cells, not the real rescue effect. (FIG. 15C) CD4+ T cells at day 10 during in vitro culture. (FIG. 15D) Graphs of live tumor cell (% count).

(FIG. 16A) Composition of CCR7− CD45RA+, CCR7− CD45RA−, CCR7+ CD45RA−, CCR7+ CD45RA− subsets of memory effector T cells with PI3Kinhibitors treatment at different concentration. Significance was determined by two-way ANOVA with Tukey's multiple comparison post-test. (FIG. 16B) Total cell numbers of CD8+ T cells at 5 days post inhibitor treatment were calculated. Significance was determined by paired ratio t-test. (FIG. 16C)

(FIG. 17A) Composition of CCR7− CD45RA+, CCR7− CD45RA−, CCR7+ CD45RA−, CCR7+ CD45RA− subsets of memory effector T cells with either one dose of PI3K inhibitor treatment or multiple doses. Significance was determined by two-way ANOVA with Tukey's multiple comparison post-test. (FIG. 17B) Total cell numbers of CD8+ T cells at 5 days post inhibitor treatment were calculated. Significance was determined by paired ratio t-test. (FIG. 17C)

(FIG. 18A) Composition of CCR7− CD45RA+, CCR7− CD45RA−, CCR7+ CD45RA−, CCR7+ CD45RA− subsets of memory effector T cells with c-Myc inhibitors treatment. Significance was determined by two-way ANOVA with Tukey's multiple comparison post-test. (FIG. 18B) Total cell numbers of CD8+ T cells at 5 days post inhibitor treatment were calculated. Significance was determined by paired ratio t-test. (FIG. 18C)

DETAILED DESCRIPTION

Figure 1A:
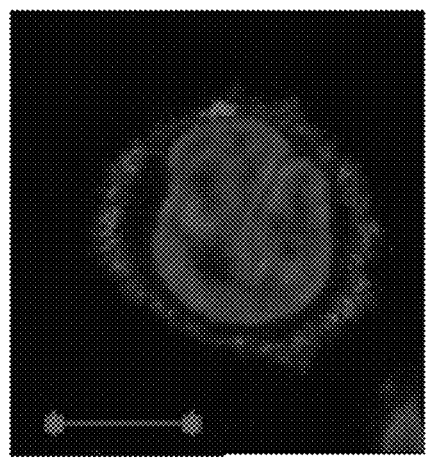
FIG. 1A-1E. CD33 CAR-modified T cells control tumor burden in an AML model.
Figure 1A:
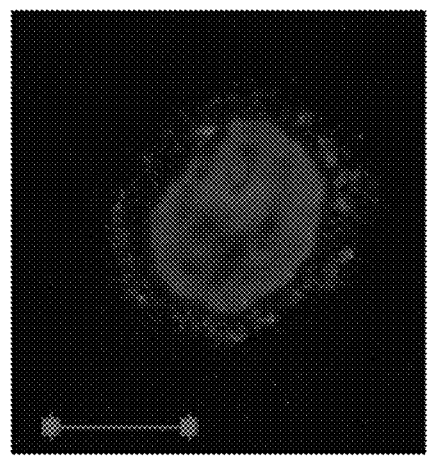

The present invention provides chimeric antigen receptors (CARs), particularly chimeric T cell antigen receptors and for treating diseases expressing the CD33 receptor, including, for example and not limitation, acute myeloid leukemia (AML). The present invention also provides methods and compositions for improving the in vivo persistence of CAR-modified host cells (e.g., T lymphocytes and natural killer cells).

As discussed in more detail herein, the inventors have developed a novel second-generation CD33-specific CAR construct (e.g., SEQ ID NO: 2) that incorporates a 4-1BB-CD3ζ signaling tail (previously proven effective in clinical trials of both chronic and acute lymphocytic leukemia) and a CD33 scFV domain. This CAR construct targets CD33 even at effector to target (E:T) ratios of less than one, which may allow for clinical potency even in the setting of high tumor burden. This CD33+ CAR construct exhibits tonic signaling through the CD3ζ ITAM domains, which leads to upregulated PI3K/AKT pathway that alters host cell differentiation ex vivo and impairs host cell persistence in vivo. For example, the inventors discovered that treatment with a PI3K inhibitor during ex vivo CAR T cell expansion modulated the differentiation program of CAR T cells, preserved a less differentiated phenotype, and improved in vivo persistence compared with current protocol of CAR T cell expansion with IL-2.

The inventors also found that PI3K inhibitor treatment (a nonlimiting exemplary inhibitor is LY294002) improved in vivo persistence without disruption of normal ex vivo proliferation and expansion of CAR T cells, and therefore can be incorporated into CAR T production regimens without impacting yield. This is significant as the inability to produce adequate CAR T numbers for treatment remains a significant limitation for many patients. The inventors also found that c-Myc inhibitor treatment (a nonlimiting exemplary inhibitor is BET bromodomain inhibitors) and glycolysis inhibitor treatment (a nonlimiting exemplary inhibitor is dichloroacetic acid (DCA)) also lead to an improvement in cell differentiation with no reduction in total cell numbers. Interestingly, inhibition of mTOR during ex vivo culturing did not correct the altered CAR T cell differentiation program. As mTOR is downstream of PI3K but upstream of c-Myc, it was surprising and unexpected that PI3K inhibition works to improve in vivo persistence as it is even further upstream in the PI3K/AKT signaling pathway than mTOR. This inhibitor approach can work to improve in vivo persistence in not only the CAR T cells of the present invention, but also other CAR T cells. In certain embodiments, this inhibitor approach is useful for CAR T cells that express a domain(s) such as, but not limited to, the 41BB, CD28, and/or inducible costimulator (ICOS) domains. In certain embodiments, this inhibitor approach is useful for CAR T cells that express a domain(s) such as, but not limited to, the CD3E, FcγR and/or CD3ζ domains.

The inventors developed an anti-CD33-41BB-CD3ζ CAR capable of targeting acute myeloid leukemia (AML) blasts. This was generated on the backbone of an anti-CD19-41BB-CD3ζ CAR found to be highly effective in clinical trials (11-13), through substitution of the CD19 single chain variable fragment (scFv) with one specific for CD33.

In vivo persistence is associated with the long-term clinical efficacy of CAR host cell mediated therapy and is, therefore, a goal of such therapies. CAR structure and co-stimulatory domains, and CAR host cell differentiation, exhaustion, and metabolic status during ex vivo expansion may impact anti-tumor efficacy and survival of CAR host cells in vivo (17-21). Both tonic CAR signaling and extrinsic signals, such as through cognate antigen and/or local cytokines, may also influence CAR host cell persistence. For example, the data presented herein show that tonic CAR signaling occurring during ex vivo expansion of CAR T cells rather than antigen specificity or tumor presence was primarily responsible for inadequate persistence. This was independent of CAR specificity. Tonic CAR signaling through the CD3ζ ITAMs induced a more differentiated and activated phenotype in CD33+ CAR T cells via activation of the PI3K/AKT signaling pathway. Therapeutic T cell terminal differentiation could be ameliorated by treatment with PI3K inhibitors during ex vivo expansion. This preserved CCR7 expression during cell division and maintained the cells in a less differentiated state with heightened in vivo persistence. These results demonstrate how specific CAR signaling domains, through their ligand-independent promotion of terminal differentiation into effector subsets, can limit CAR T cell survival, and support interventions for the production of CAR T cells with improved survival and function.

In summary, the data presented herein show that CAR-expression, in a ligand-independent manner, alters host cell differentiation during ex vivo expansion. For example, CAR-transduced T cells displayed decreased nave and stem memory populations and increased effector subsets relative to vector-transduced control cells, and this was associated with reduced in vivo persistence. Altered persistence was not due to antigen specificity or tumor presence, but was linked to tonic signaling through the CAR, most notably CD3ζ ITAMs, prior to transfer. The inventors identified the PI3K/AKT pathway in CAR T cells as responsible. Treatment with a PI3K inhibitor modulated the differentiation program of CAR T cells, preserved a less differentiated state without affecting T cell expansion and improved in vivo persistence relative to control cells. The inventors also identified that inhibition of the c-Myc regulatory gene also lead to optimal effects on T cell differentiation with no reduction in cell numbers. These results help resolve mechanisms by which tonic signaling modulates CAR T cell fate and identify a novel pharmacologic approach to enhance the durability of CAR T cells for cell-based immunotherapy.

Definitions

The term "chimeric antigen receptor" or "CAR" as used herein is defined as a cell-surface receptor comprising an extracellular ligand binding domain, a transmembrane domain and a cytoplasmic co-stimulatory signaling domain in a combination that is not naturally found together on a single protein. This particularly includes receptors wherein the extracellular domain and the cytoplasmic domain are not naturally found together on a single receptor protein. The chimeric receptors of the present invention are intended primarily for use with T lymphocytes and natural killer (NK) cells.

The term "antigen" refers to any agent (e.g., protein, peptide, polysaccharide, glycoprotein, glycolipid, nucleic acid, portions thereof, or combinations thereof) that, when introduced into a host, animal or human, having an immune system (directly or upon expression as in, e.g., DNA vaccines), is recognized by the immune system of the host and is capable of eliciting an immune response.

The term "4-1BB" refers to a membrane receptor protein also known as CD137, which is a member of the tumor necrosis factor receptor (TNFR) superfamily expressed on the surface of activated T cells as a type of accessory molecule (Kwon et al., Proc. Natl. Acad. Sci. USA 86:1963 (1989); Pollok et al., J. Immunol. 151:771 (1993)). 4-1BB has a molecular weight of 55 kDa and is found as a homodimer. It has been suggested that 4-1BB mediates a signal transduction pathway from outside of the cell to inside (Kim et al., J. Immunol. 151:1255 (1993)). A human 4-1BB gene was isolated from a cDNA library made from activated human peripheral T cell mRNA (Goodwin et al., Eur. J. Immunol. 23:2631 (1993)). The amino acid sequence of human 4-1BB (SEQ ID NO: 4) shows 60% homology to mouse 4-1BB (Kwon et al., Proc. Natl. Acad. Sci. USA 86:1963 (1989); Gen Bank No: NM—011612) which indicates that the sequences are highly conserved. The interaction of 4-1BB and its ligand provides a co-stimulatory signal leading to T cell activation and growth (Goodwin et al., Eur. J. Immunol. 23:2631 (1993); Alderson et al., Eur. J. Immunol. 24:2219 (1994); Hurtado et al., J. Immunol. 155:3360 (1995); Pollock et al., Eur. J. Immunol. 25:488 (1995); DeBenedette et al., J. Exp. Med. 181:985 (1995)). These observations suggest an important role for 4-1BB in the regulation of T cell-mediated immune responses (Ignacio et al., Nature Med. 3:682 (1997)). 4-1BB ligand (CD137L) is claimed and described in U.S. Pat. No. 5,674,704.

The term "host cell" means any cell of any organism that is selected, modified, transformed, grown, used or manipulated in any way, for the production of a substance by the cell, for example the expression by the cell of a gene, a DNA or RNA sequence, a protein or an enzyme. Host cells of the present invention include T lymphocytes and natural killer cells that contain the DNA or RNA sequences encoding the CAR and express the CAR on the cell surface. Host cells may be used for enhancing T lymphocyte activity, natural killer cell activity, treatment of cancer, and treatment of autoimmune disease.

The terms "T cell" and "T lymphocyte" are interchangeable and used synonymously herein. As used herein, T lymphocytes includes thymocytes, naive T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4+ T cell) CD4+ T cell, a cytotoxic T cell (CTL; CD8+ T cell), a tumor infiltrating cytotoxic T cell (TIL; CD 8 T cell), CD4 CD8 T cell, CD4 CD8 T cell, or any other subset of T cells. Other illustrative populations of T cells suitable for use in particular embodiments include naive T cells and memory T cells. Also included are "NKT cells", which refer to a specialized population of T cells that express a semi-invariant αβ T cell receptor, but also express a variety of molecular markers that are typically associated with NK cells, such as NK1. 1. NKT cells include NK1.1+and NK1. 1", as well as CD4+, CD4", CD8+ and CD8" cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T cells (γδ T cells)," which refer to a specialized population that to a small subset of T cells possessing a distinct TCR on their surface, and unlike the majority of T cells in which the TCR is composed of two glycoprotein chains designated α- and β-TCR chains, the TCR in γδ T cells is made up of a γ-chain and a δ-chain. γδ T cells can play a role in immunosurveillance and immunoregulation and were found to be an important source of IL-17 and to induce robust CD8+ cytotoxic T cell response. Also included are "regulatory T cells" or "Tregs" refers to T cells that suppress an abnormal or excessive immune response and play a role in immune tolerance. Tregs cells are typically transcription factor Foxp3-positive CD4-positive T cells and can also include transcription factor Foxp3-negative regulatory T cells that are IL-10-producing CD4-positive T cells.

The terms "natural killer cell" and "NK cell" are used interchangeable and used synonymously herein. As used herein, NK cell refers to a differentiated lymphocyte with a CD 16+CD56+and/or CD57+TCR-phenotype. NKs are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

The terms "activation" or "stimulation" means to induce a change in their biologic state by which the cells (e.g., T cells and NK cells) express activation markers, produce cytokines, proliferate and/or become cytotoxic to target cells. All these changes can be produced by primary stimulatory signals. Co-stimulatory signals can amplify the magnitude of the primary signals and suppress cell death following initial stimulation resulting in a more durable activation state and thus a higher cytotoxic capacity. A "co-stimulatory signal" refers to a signal, which in combination with a primary signal, such as TCR/CD3 ligation, leads to NK cell proliferation and/or upregulation or downregulation of key molecules.

The term "proliferation" refers to an increase in cell division, either symmetric or asymmetric division of cells. The term "expansion" refers to the outcome of cell division and cell death.

The term "differentiation" refers to a method of decreasing the potency or proliferation of a cell or moving the cell to a more developmentally restricted state.

The term "in vivo persistence" refers to continued viability or survival of the engineered host cell once administered to the subject. In certain embodiments, persistence correlates with disease regression or therapeutic efficacy.

An "agent" refers to a compound, small molecule, e.g., small organic molecule, nucleic acid, polypeptide, or a fragment, isoform, variant, analog, or derivative thereof used in the methods of the invention.

The terms "express" and "expression" mean allowing or causing the information in a gene or DNA sequence to become produced, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or transmembrane. The term "intracellular" means something that is inside a cell. The term "extracellular" means something that is outside a cell. The term transmembrane means something that has an extracellular domain outside the cell, a portion embedded in the cell membrane and an intracellular domain inside the cell.

The term "transfection" means the introduction of a "foreign" (i.e., extrinsic or extracellular) nucleic acid into a cell using recombinant DNA technology. The term "transformation" means the introduction of a "foreign" (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences operably linked to polynucleotide encoding the chimeric receptor, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The term "transduction" means the introduction of a foreign nucleic acid into a cell using a viral vector.

The term "engineered" refers to the addition of extra genetic material in the form of DNA or RNA into a cell.

As used herein, the terms "derivative" in the context of proteins or polypeptides refer to: (a) a polypeptide that is at least 40%, 45%, 50%, 55%, 60%, 65%, 70%, 75%, 80%, 85%, 90%, 95%, 98% or 99% identical to the polypeptide it is a derivative of; (b) a polypeptide encoded by a nucleic acid sequence that is at least 40%, 45%, 50%, 55%, 60%, 65%, 70%, 75%, 80%, 85%, 90%, 95%, 98% or 99% identical to a nucleic acid sequence encoding the polypeptide it is a derivative of; (c) a polypeptide that contains 1, 2, 3, 4, 5, 6, 7, 8, 9, 10, 11, 12, 13, 14, 15, 16, 17, 18, 19, 20 or more amino acid mutations (i.e., additions, deletions and/or substitutions) relative to the polypeptide it is a derivative of, (d) a polypeptide encoded by nucleic acids can hybridize under high, moderate or typical stringency hybridization conditions to nucleic acids encoding the polypeptide it is a derivative of; (e) a polypeptide encoded by a nucleic acid sequence that can hybridize under high, moderate or typical stringency hybridization conditions to a nucleic acid sequence encoding a fragment of the polypeptide, it is a derivative of, of at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, or at least 150 contiguous amino acids; or (f) a fragment of the polypeptide it is a derivative of Percent identity can be determined using any method known to one of skill in the art. In a specific embodiment, the percent identity is determined using the "Best Fit" or "Gap" program of the Sequence Analysis Software Package (Version 10; Genetics Computer Group, Inc., University of Wisconsin Biotechnology Center, Madison, Wisconsin). Information regarding hybridization conditions (e.g., high, moderate, and typical stringency conditions) have been described, see, e.g., U.S. Patent Application Publication No. US 2005/0048549 (e.g., paragraphs 72-73).

The terms "vector", "cloning vector" and "expression vector" mean the vehicle by which a DNA or RNA sequence (e.g., a foreign gene) can be introduced into a host cell, so as to transform the host and promote expression (e.g., transcription and translation) of the introduced sequence. Vectors include plasmids, phages, viruses, etc. In certain embodiments, the vector is a viral vector such as, but not limited to, viral vector is an adenoviral, adeno-associated, alphaviral, herpes, lentiviral, retroviral, or vaccinia vector.

A solid support means any surface capable of having an agent attached thereto and includes, without limitation, metals, glass, plastics, polymers, particles, microparticles, co-polymers, colloids, lipids, lipid bilayers, cell surfaces and the like. Essentially any surface that is capable of retaining an agent (including antibodies) bound or attached thereto. A prototypical example of a solid support used herein, is a particle such as a bead or the bottom of a culture dish.

By "enhance" or "promote," or "increase" or "expand" or "improve" refers generally to the ability of a composition contemplated herein to produce, elicit, or cause a greater physiological response (i.e., downstream effects) compared to the response caused by either vehicle or a control molecule/composition. A measurable physiological response may include an increase in T cell expansion, activation, persistence, and/or an increase in cancer cell death killing ability, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. A "decrease" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition, or the response in a particular cell lineage.

The term "cancer" relates generally to a class of diseases or conditions in which abnormal cells divide without control and can invade nearby tissues.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

The term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

The term "protein" is used herein encompasses all kinds of naturally occurring and synthetic proteins, including protein fragments of all lengths, fusion proteins and modified proteins, including without limitation, glycoproteins, as well as all other types of modified proteins (e.g., proteins resulting from phosphorylation, acetylation, myristoylation, palmitoylation, glycosylation, oxidation, formylation, amidation, polyglutamylation, ADP-ribosylation, pegylation, biotinylation, etc.).

The terms "nucleic acid", "nucleotide", and "polynucleotide" encompass both DNA and RNA unless specified otherwise.

The terms "patient", "individual", "subject", and "animal" are used interchangeably herein and refer to mammals, including, without limitation, human and veterinary animals (e.g., cats, dogs, cows, horses, sheep, pigs, etc.) and experimental animal models. In a preferred embodiment, the subject is a human.

Terms "antibody" and "antibodies" refer to monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), intrabodies, minibodies, diabodies and anti-idiotypic (anti-Id) antibodies (including, e.g., anti-Id antibodies to antigen-specific TCR), and epitope-binding fragments of any of the above. The terms "antibody" and "antibodies" also refer to covalent diabodies such as those disclosed in U.S. Pat. Appl. Pub. 2007/0004909 and Ig-DARTS such as those disclosed in U.S. Pat. Appl. Pub. 2009/0060910. Antibodies useful as a TCR-binding molecule include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E.W. Martin.

Singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The practice of the present invention employs, unless otherwise indicated, conventional techniques of statistical analysis, molecular biology (including recombinant techniques), microbiology, cell biology, and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, New York; Ausubel et al. eds. (2005) Current Protocols in Molecular Biology. John Wiley and Sons, Inc.: Hoboken, NJ; Bonifacino et al. eds. (2005) Current Protocols in Cell Biology. John Wiley and Sons, Inc.: Hoboken, NJ; Coligan et al. eds. (2005) Current Protocols in Immunology, John Wiley and Sons, Inc.: Hoboken, NJ; Coico et al. eds. (2005) Current Protocols in Microbiology, John Wiley and Sons, Inc.: Hoboken, NJ; Coligan et al. eds. (2005) Current Protocols in Protein Science, John Wiley and Sons, Inc. : Hoboken, NJ; and Enna et al. eds. (2005) Current Protocols in Pharmacology, John Wiley and Sons, Inc.: Hoboken, NJ. Additional techniques are explained, e.g., in U.S. Pat. No. 7,912,698 and U.S. Patent Appl. Pub. Nos. 2011/0202322 and 2011/0307437.

Chimeric Antigen Receptors of the Invention

In one aspect, the invention provides a chimeric antigen receptor (CAR) for treating CD33 associated diseases.

The CARs of the present invention comprise an extracellular domain, a transmembrane domain and a cytoplasmic domain. The extracellular domain and transmembrane domain can be derived from any desired source for such domains.

The extracellular domain may be obtained from any of the wide variety of extracellular domains or secreted proteins associated with ligand binding and/or signal transduction. See for example, U.S. Pat. Nos. 5,359,046, 5,686,281 and 6,103,521. The extracellular domain may be part of a protein which is monomeric or multimeric (e.g., homodimeric or heterodimeric), or associated with multiple proteins in a non-covalent complex. In certain embodiments, the extracellular domain may consist of an Ig heavy chain. In certain embodiments, the Ig heavy chain can be covalently associated with Ig light chain by virtue of the presence of CH1 and hinge regions. In certain embodiments, the Ig heavy chain may become covalently associated with other Ig heavy/light chain complexes by virtue of the presence of hinge, CH2 and CH3 domains. In the latter case, the heavy/light chain complex that becomes joined to the chimeric construct may constitute an antibody with a specificity distinct from the antibody specificity of the chimeric construct. In certain embodiments, the entire chain may be used. In certain embodiments, a truncated chain may be used, where all or a part of the CH1, CH2, or CH3 domains may be removed or all or part of the hinge region may be removed.

Examples of extracellular domains that binds an antigen include, but are not limited to, carbonic anhydrase EX, alpha-fetoprotein, A3, antigen specific for A33 antibody, Ba 733, BrE3-antigen, CA125, CD1, CD1a, CD3, CDS, CD15, CD16, CD19, CD20, CD21, CD22, CD23, CD25, CD30, CD33, CD38, CD45, CD74, CD79a, CD80, CD 138, colon-specific antigen-p (CSAp), CEA (CEACAMS), CEACAM6, CSAp, EGFR, EGP-I, EGP-2, Ep-CAM, FIt-I, Flt-3, folate receptor, HLA-DR, human chorionic gonadotropin (HCG) and its subunits, HER2/neu, hypoxia inducible factor (HIF-I), Ia, IL-2, IL-6, IL-8, insulin growth factor-1 (IGF-I), KC4-antigen, KS-1-antigen, KS1-4, Le- Y, macrophage inhibition factor (MIF), MAGE, MUC1 , MUC2, MUC3, MUC4, NCA66, NCA95, NCA90, antigen specific for PAM-4 antibody, placental growth factor, p53, prostatic acid phosphatase, PSA, PSMA, RSS, 5100, TAC, TAG-72, tenascin, TRAIL receptors, Tn antigen, Thomson-Friedenreich antigens, tumor necrosis antigens, VEGF, ED-B fibronectin, 17-1A-antigen, an angiogenesis marker, an oncogene marker or an oncogene product.

The transmembrane domain may be derived from the protein contributing the multispecific extracellular inducer clustering domain, the protein contributing the effector function signaling domain, the protein contributing the proliferation signaling portion, or by a totally different protein. In certain embodiments, it will be desirable to utilize the transmembrane domain of the $\zeta$, $\eta$ or Fc$\epsilon$R1$\gamma$ chains which contain a cysteine residue capable of disulfide bonding, so that the resulting chimeric protein will be able to form disulfide linked dimers with itself, or with unmodified versions of the $\zeta$, $\eta$ or Fc$\epsilon$R1$\gamma$ chains or related proteins. In some instances, the transmembrane domain will be selected or modified by amino acid substitution to avoid binding of such domains to the transmembrane domains of the same or different surface membrane proteins to minimize interactions with other members of the receptor complex. In other cases, it will be desirable to employ the transmembrane domain of $\zeta$, $\eta$ or Fc$\epsilon$R1$\gamma$ and -$\beta$, MB1 (Ig$\alpha$.), B29 or CD3-$\gamma$, $\zeta$, or $\eta$, in order to retain physical association with other members of the receptor complex. 100951 The cytoplasmic domain of the chimeric receptors of the invention comprises the 4-1BB signaling domain (214-255 of SEQ ID NO: 4) by itself or combined with any other desired cytoplasmic domain(s) useful in the context of this chimeric receptor type. In certain embodiments, the extracellular domain comprises a single chain variable domain of an anti-CD33 monoclonal antibody (e.g., SEQ ID NO: 3), the transmembrane domain comprises the hinge and transmembrane domain of CD8$\alpha$ (SEQ ID NO: 6), and the cytoplasmic domain comprises the signaling domain of CD3C (SEQ ID NO: 5) and the signaling domain of 4-1BB. The extracellular domain of the preferred embodiment contains the anti-CD33 plus the 21-amino acid signal peptide of CD8$\alpha$ (translated from 63 nucleotides at positions 26-88 of GenBank Accession No. NM—001768; SEQ ID NO: 7). The CD8$\alpha$ hinge (SEQ ID NO: 13) and transmembrane domain (SEQ ID NO: 14) consists of 69 amino acids translated from the 207 nucleotides at positions 815-1021 of GenBank Accession No. NM—001768. The CD3$\zeta$ signaling domain of the preferred embodiment contains 112 amino acids translated from 339 nucleotides at positions 1022-1360 of GenBank Accession No. NM–000734.

The present invention provides a chimeric receptor construct which contains the signaling domain of 4-1BB and fragments thereof. In certain embodiments, an anti-CD33 scFv fragment can be cloned in frame with a human CD8 leader sequence, CD8 transmembrane domain, and 4-1BB-CD3$\zeta$ signaling tail into a vector. In other embodiments, the genetic fragments used in the chimeric receptor can be generated using splicing by overlapping extension by PCR (SOE-PCR), a technique useful for generating hybrid proteins of immunological interest. (Warrens A N, et al. Gene 20; 186: 29-35 (1997)). Other procedures used to generate the polynucleotides and vector constructs of the present invention are well known in the art.

In certain embodiments, the CAR comprises the amino acid sequence of SEQ ID NO: 2. In certain embodiments, the CAR consists of the amino acid sequence of SEQ ID NO: 2. In certain embodiments, the CAR consists essentially of the amino acid sequence of SEQ ID NO: 2.

In certain embodiments, the CAR is a derivative of the CAR encoded by SEQ ID NO: 2. In certain embodiments, the CAR comprises an amino acid sequence that is at least 40%, 45%, 50%, 55%, 60%, 65%, 70%, 75%, 80%, 85%, 90%, 95%, 98% or 99% identical to SEQ ID NO: 2. In certain embodiments, the CAR comprises an amino acid sequence that is at least 40%, 45%, 50%, 55%, 60%, 65%, 70%, 75%, 80%, 85%, 90%, 95%, 98% or 99% identical to SEQ ID NO: 3, amino acids 214-255 of SEQ ID NO: 4, SEQ ID NO: 5, SEQ ID NO: 6, SEQ ID NO: 7, to SEQ ID NO: 13, and/or SEQ ID NO: 14.

The present invention provides vectors comprising a polynucleotide encoding a CAR comprising a nucleotide sequence encoding the proteins disclosed above. In certain embodiments, the polynucleotide encoding the CAR comprises a nucleotide sequence encoding (a) an extracellular ligand-binding domain comprising an anti-CD 33 single chain variable fragment (scFv) domain (e.g., SEQ ID NO: 8), (b) a hinge (e.g., SEQ ID NO: 15), (c) a transmembrane domain (e.g., SEQ ID NO: 16) (e.g., SEQ ID NO: 11 for both hinge and transmembrane domain), and (d) a cytoplasmic domain comprising a 4-1BB signaling domain (e.g., SEQ ID NO: 9) and a CD3ζ signaling domain (e.g., SEQ ID NO: 10). In certain embodiments, the polynucleotide is operatively linked to at least one regulatory element for expression of the chimeric receptor.

In certain embodiments, the polypeptide encodes a CAR, wherein the nucleotide sequence comprises SEQ ID NO: 1. In certain embodiments the polypeptide encodes a CAR, wherein the nucleotide sequence consists of SEQ ID NO: 1. In certain embodiments, the polypeptide encodes a CAR, wherein the nucleotide sequence consists essentially of SEQ ID NO: 1.

In certain embodiments, the polypeptide encodes a CAR, wherein the nucleotide sequence is at least 40%, 45%, 50%, 55%, 60%, 65%, 70%, 75%, 80%, 85%, 90%, 95%, 98% or 99% identical to the nucleotide sequence of SEQ ID NO: 1. In certain embodiments, the polypeptide encodes a CAR, wherein the nucleotide sequence is at least 40%, 45%, 50%, 55%, 60%, 65%, 70%, 75%, 80%, 85%, 90%, 95%, 98% or 99% identical to the nucleotide sequence of SEQ ID NO: 8, SEQ ID NO: 9, SEQ ID NO: 10, SEQ ID NO: 11, SEQ ID NO: 12, SEQ ID NO: 15, and/or SEQ ID NO: 16.

In certain embodiments, the vector is a viral vector. In certain embodiments, the viral vector can be, but is not limited to, adenoviral vector, an adeno-associated virus vector, an alphaviral vector, a herpes virus vector, a lentiviral vector, a retroviral vector, and vaccinia virus vector. In certain embodiments, the viral vector is a retroviral vector.

In certain embodiments, the polynucleotide encoding the CAR is operably linked to at least a regulatory element. The regulatory element can be capable of mediating expression of the CAR in the host cell.

Regulatory elements may include, but are not limited to, promoters, enhancers, and other nucleic acids (e.g., polyadenylation signals) that control or help to control gene transcription. Examples of regulatory elements are described, for example, in Lorence, Recombinant Gene Expression: Reviews and Protocols (Humana Press, New York, NY, 2012) and Goeddel, (1990) Gene Expression Technology: Methods in Enzymology, Vol. 185, Academic Press, San Diego, Calif., each of which are incorporated herein in its entirety for all intended purposes.

Enhancers represent another class of regulatory elements that induce a conformational change in the polynucleotide containing the gene of interest such that the DNA adopts a three-dimensional orientation that is favorable for binding of transcription factors and RNA polymerase at the transcription initiation site. Many enhancer sequences are now known from mammalian genes, and non-limiting examples include enhancers from the genes that encode mammalian globin, elastase, albumin, a-fetoprotein, and insulin.

Methods for Producing CAR-Modified Host Cells

In one aspect, the invention provides methods for enhancing in vivo persistence of CAR-modified host cells in a subject in need thereof. In certain embodiments, the methods disclosed herein reduce host cell differentiation. In certain embodiments, the methods disclosed herein reduce host cell differentiation without altering host cell expansion. In certain embodiments, the methods disclosed herein maintain cell differentiation while increasing in vivo persistence.

In certain embodiments, the host cell is an allogeneic cell. In certain embodiments, the host cell is an autologous cell. In certain embodiments, the host cell is isolated from a subject having a disease, wherein CD33 is expressed. In certain embodiments, the host the cell has been isolated from a subject having a disease such as, but not limited to, acute myeloid leukemia (AML), myelodysplastic syndrome (MDS), chronic myeloid leukemia (CML), or pro-myelocytic leukemia (PML). In certain embodiments, the host cell is derived from a blood and/or a tumor sample.

In certain embodiments, the host cells can be T cells. T cells include, but are not limited to, thymocytes, naive T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4+ T cell) CD4+ T cell, a cytotoxic T cell (CTL; CD8+ T cell), a tumor infiltrating cytotoxic T cell (TIL; CD 8 T cell), CD4 CD8 T cell, CD4 CD8 T cell, or any other subset of T cells. Other illustrative populations of T cells suitable for use in particular embodiments include naive T cells memory T cells, and NKT cells.

In certain embodiments, the host cells can be NK cells. NK cell refers to a differentiated lymphocyte with a CD 16+CD56+and/or CD57+TCR- phenotype.

CAR-modified host cells can be expanded ex vivo for use in adoptive cellular immunotherapy in which infusions of such cells have been shown to have anti-disease reactivity in a disease-bearing host. The compositions and methods of this invention can be used to generate a population of host cells (e.g., T lymphocyte or natural killer cells) that deliver both primary and co-stimulatory signals for use in immunotherapy in the treatment of the disease. In certain embodiments, the disease is a CD33 associated disease. In certain embodiments, the disease is cancer.

In certain embodiments, the methods described herein increase the number host cells comprising one or more markers of naive or developmentally potent host cells. For example, treating a population of host cells with one or more PI3K pathway inhibitor and/or regulatory gene inhibitor (e.g., c-Myc) uncouples host cell proliferation and differentiation signals, and thereby results in an expansion of developmentally potent host cells and provides a more efficacious and persistent host cell than existing host cell therapies.

PI3Ks are a family of conserved intracellular lipid kinases. Upon growth factor receptor-mediated activation of PI3K, Akt is recruited to the membrane through the interaction of its pleckstrin homology domain with PIP3, thus exposing its activation loop.

In certain embodiments, use of the PI3K inhibitors enhances in vivo persistence of CAR-modified host cells by increasing the life span of the modified host cell by about 1 to about 20 days. In certain embodiments, use of PI3K inhibitors enhanced in vivo persistence by about 1 to about 15 days, about 1 to about 10 days, about 2 to about 8 days, or about 3 to about 6 days. In certain embodiments, use of PI3K inhibitors enhanced in vivo persistence by at least about 1 day, at least about 2 days, at least about 3 days, at least about 4 days, at least about 5 days, at least about 6 days, at least about 7 days, at least about 8 days, at least about 9 days, at least about 10 days, at least about 15 days, at least about 20 days. In certain embodiments, use of PI3K inhibitors enhanced in vivo persistence by up to about 1 day, up to about 2 days, up to about 3 days, up to about 4 days, up to about 5 days, up to about 6 days, up to about 7 days, up to about 8 days, up to about 9 days, up to about 10 days, up to about 15 days, or up to about 20 days. In certain embodiments, use of PI3K inhibitors enhanced in vivo persistence by about 3 days.

In certain embodiments, use of the PI3K inhibitors enhances in vivo persistence of CAR-modified host cells by increasing the life span of the modified host cell by about 1 to about 6 months. In certain embodiments, use of PI3K inhibitors enhanced in vivo persistence by about 1 to about 5 months, about 1 to about 4 months, about 1 to about 3 months, about 1 to about 2 months, about 2 to about 4 months, or about 3 to about 5 months. In certain embodiments, use of PI3K inhibitors enhanced in vivo persistence by at least about 1 month, at least about 2 months, at least about 3 months, at least about 4 months, at least about 5 months, or at least about 6 months. In certain embodiments, use of PI3K inhibitors enhanced in vivo persistence by up to about 1 month, up to about 2 months, up to about 3 months, up to about 4 months, up to about 5 months, or up to about 6 months.

In certain embodiments, use of the PI3K inhibitors enhances in vivo persistence of CAR-modified host cells by increasing the life span of the modified host cell by about 0.01 to about 10 fold. In certain embodiments, the life span of the modified host cell is increased by about 0.02 to about 9 fold, about 0.03 to about 8 fold, about 0.04 to about 7 fold, about 0.05 to about 6 fold, about 0.06 to about 5 fold, about 0.07 to about 4 fold, about 0.08 to about 3 fold, about 0.09 to about 2 fold, about 0.1 to about 1 fold, about 0.2 to about 0.9 fold, about 0.3 to about 0.8 fold, about 0.4 to about 0.7 fold, or about 0.5 to about 0.6 fold. In certain embodiments, the life span of the modified host cell is increased by up to about 0.01, about 0.02, about 0.03, about 0.04, about 0.05, about 0.06, about 0.07, about 0.08, about 0.09, about, 0.1, about 0.2, about 0.3, about 0.4, about 0.5, about 0.6, about 0.7, about 0.8, about 0.9, about 1, about 2, about 4, about 6, about 8, or about 10 fold.

Examples of PI3K inhibitors include, but are not limited to, XL147, BKM120, GDC-0941, BAY80-6946, PX-866, CH5132799, XL756, BEZ235, GDC-0980, wortmannin, LY294002, PI3K II, TGR-1202, AMG-319, GSK2269557, X-339, X-414, RP5090, KAR4141, XL499, OXY111A, IPI-145, IPI-443, GSK2636771, BAY 10824391, buparlisib, BYL719, RG7604, MLN1117, WX-037, AEZS-129, PA799, ZSTK474, BYL719, GSK2636771, TGX-221, AS25242, CAL-101, ZSTK474, and IPI-145, AS252424, TGX221, TG100115, IC87114, (S)-2-0-((9H-purin-6-yl)amino)propyl)-5-fluoro-3-phenylquinazolin-4(3H)-one, (S)-2-(1-((9H-purin-6-yl)amino)ethyl)-6-fluoro-3- phenylquinazolin-4 (3H)-one, (S)-2-(l-((9H-purin-6-yl)amino)ethyl)-3-(2,6-difluorophenyl)quinazolin-4(3H)-one, and (S)-4-amino-6-((1-(5-chloro-4-oxo-3-phenyl-3,4-dihydroquinazolin-2-yl) ethyl)amino)pyrimidine-5-carbonitrile; or a pharmaceutically acceptable salt thereof. In certain embodiments, the PI3K inhibitor is a prodrug or solvate of one or more of the PI3K inhibitors listed above. In certain embodiments, the PI3K inhibitor is a PI3Kδ inhibitor such as, but not limited to, (S)-2-1-((9H-purin-6-yl)amino)propyl)-5-fluoro-3-phenylquinazolin-4(3H)-one, (S)-2-(1-((9H-purin-6-yl)amino) ethyl)-6-fluoro-3-phenylquinazolin-4(3H)-one, (S)-2-0-((9H-purin-6-yl)amino)ethyl)-3-(2,6-difluorophenyl) quinazolin-4(3H)-one, and (S)-4-amino-6-((1-(5- chloro-4-oxo-3-phenyl-3,4-dihydroquinazolin-2-yl)ethyl)amino) pyrimidine-5-carbonitrile; or a pharmaceutically acceptable salt thereof. In certain embodiments, the PI3K inhibitor is a prodrug or solvate of S)-2-1-((9H-purin-6-yl)amino)propyl)-5-fluoro-3-phenylquinazolin- 4(3H)-one, (S)-2-(1-((9H-purin-6-yl)amino)ethyl)-6-fluoro-3-phenylquinazolin-4(3H)-one, (S)-2-(1-((9H-purin-6-yl)amino)ethyl)-3-(2,6-difluorophenyOquinazolin-4(3H)-one, or (S)-4-amino-6-((l-(5-chloro-4-oxo-3-phenyl-3,4-dihydroquinazolin-2-yl) ethyl)amino)pyrimidine- 5-carbonitrile, or a combination thereof. In certain embodiments, the PI3K inhibitor is LY294002. In certain embodiments, the PI3K inhibitor is IC87114.

In certain embodiment, a method of producing host cells for administration to a subject comprises contacting the cells with one or more agents that inhibit the PI3K cell signaling pathway. In certain embodiments, the host cells may be treated with the agent during the expansion phases of the manufacturing process. In certain embodiments, the host cells may be treated with the agent only during the expansion phase of the manufacturing process after the host cell has been transduced with the CAR construct. In certain embodiments, the host cells are not treated more than once with the PI3K pathway inhibitor. In certain embodiments, the host cells are not treated with the PI3K pathway inhibitor during the activation phase. In certain embodiments, the host cells are not treated with the PI3K pathway inhibitor prior to the host cells being transduced with the CAR construct.

In certain embodiments, host cells produced by the methods contemplated herein undergo one, two, three, four, or five or more rounds of activation and expansion. In certain embodiments, the PI3K inhibitor is added only in one round. In certain embodiments, the PI3K inhibitor is only added during the last round. In certain embodiments, the PI3K inhibitor is added during every expansion round.

In certain embodiments, the PI3K inhibitor is administered at a concentration of about 0.1 µM to about 1 mM. In certain embodiments, the PI3K inhibitor is administered at a concentration of about 0.1 µM to about 100 µM, about 0.1 µM to about 50 µM, or about 0.1 µM to about 20 µM. In certain embodiments, the PI3K inhibitor is administered at a concentration of about 0.25 µM to about 750 µM, about 0.5 µM to about 500 µM, about 0.75 µM to about 250 µM, about 1 µM to about 100 µM, about 2.5 µM to about 75 µM, about 5 µM to about 50 µM, or about 10 µM to about 25 µM. In certain embodiments, the PI3K inhibitor is administered at a concentration of about 0.1 µM, about 0.2 µM, about 0.4

µM, about 0.6 µM, about 0.8 µM, about 1 µM, about 2 µM, about 4 µM, about 6 µM, about 8 µM, about 10 µM, about 12 µM, about 14 µM, about 16 µM, about 18 µM, about 20 µM, about 25 µM, about 30 µM, about 35 µM, about 40 µM, about 45 µM, about 50 µM, about 55 µM, about 60 µM, about 65 µM, about 70 µM, about 75 µM, about 80 µM, about 85 µM, about 90 µM, about 95 µM, about 100 µM, about 125 µM, about µM, about 150 µM, about 175 µM, about 200 µM, about 225 µM, about 250 µM, about 275 µM, about 300 µM, about 325 µM, about 350 µM, about 375 µM, about 400 µM, about 425 µM, about 450 µM, about 475 µM, about 500 µM, about 525 µM, about 550 µM, about 575 µM, about 600 µM, about 625 µM, about 650 µM, about 675 µM, about 700 µM, about 725 µM, about 750 µM, about 775 µM, about 800 µM, about 825 µM, about 850 µM, about 875 µM, about 900 µM, about 925 µM, about 950 µM, about 975 µM, or about 1 mM. In certain embodiments, the PI3K inhibitor is administered at a concentration of about 0.1 µM to about 20 µM. In certain embodiments, the PI3K inhibitor is administered at a concentration of about 10 µM. In certain embodiments, the PI3K inhibitor is LY294002. In certain embodiments, the PI3K inhibitor is IC87114.

In certain embodiments, the PI3K inhibitor has an IC50 of at least about 1 nM, at least about 2 nM, at least about 5 nM, at least about 10 nM, at least about 50 nM, at least about 10 nM, at least about 200 nM, at least about 500 nM, at least about 1 µM, at least about 10 µM, at least about 50 µM, or at least about 100 µM. IC50 determinations can be accomplished using any conventional techniques known in the art. For example, an IC50 can be determined by measuring the activity of a given enzyme in the presence of a range of concentrations of the inhibitor under study. The experimentally obtained values of enzyme activity then are plotted against the inhibitor concentrations used. In certain embodiments, the concentration of the inhibitor that shows at least 10%, at least 20%, at least 30%, at least 40%, at least 50%, or at least 60% enzyme activity (as compared to the activity in the absence of any inhibitor) is taken as the "IC50" value. Analogously, other inhibitory concentrations can be defined through appropriate determinations of activity.

Regulatory genes encode transcription factors and are involved in controlling the expression of one or more other genes. If mutated or expressed at high levels, the proteins are referred to as oncoproteins. Examples of genes encoding oncoproteins include, but are not limited to, c-myc, N-myc, c-myb, c-fos, c-fos/jun, PCNA, p120; EJ-ras, c-Ha-ras, N-ras, rrg, bcl-2, cdc-2, c-raf-1, c-mos, c-src, c-abl, Bcr-Abl, c-ets, telomerase, cyclins, cyclin dependent kinases; cellular receptors include, for example, EGF receptor, Her-2, c-erbA, VEGF receptor (KDR-1), retinoid receptors, protein kinase regulatory subunit, c-fms, Tie-2, c-raf-1 kinase, PKC-alpha, protein kinase A (R1 alpha); cytokines or growth factors include, for example, CSF-1, IL-6, IL-1a, IL-1b, IL-2, IL-4, IL-6, IL-8, bFGF, VEGF, myeloblastin, or fibronectin. In certain embodiments, the gene encoding an oncoprotein is c-Myc.

In certain embodiments, use of the oncogene or oncoprotein inhibitor enhances in vivo persistence of CAR-modified host cells by increasing the life span of the modified host cell by about 1 to about 20 days. In certain embodiments, use of oncogene or oncoprotein inhibitors enhanced in vivo persistence by about 1 to about 15 days, about 1 to about 10 days, about 2 to about 8 days, or about 3 to about 6 days. In certain embodiments, use of oncogene or oncoprotein inhibitors enhanced in vivo persistence by at least about 1 day, at least about 2 days, at least about 3 days, at least about 4 days, at least about 5 days, at least about 6 days, at least about 7 days, at least about 8 days, at least about 9 days, at least about 10 days, at least about 15 days, at least about 20 days. In certain embodiments, use of oncogene or oncoprotein inhibitors enhanced in vivo persistence by up to about 1 day, up to about 2 days, up to about 3 days, up to about 4 days, up to about 5 days, up to about 6 days, up to about 7 days, up to about 8 days, up to about 9 days, up to about 10 days, up to about 15 days, or up to about 20 days. In certain embodiments, use of oncogene or oncoprotein inhibitors enhanced in vivo persistence by about 3 days.

In certain embodiments, use of the oncogene or oncoprotein inhibitors enhances in vivo persistence of CAR-modified host cells by increasing the life span of the modified host cell by about 1 to about 6 months. In certain embodiments, use of oncogene or oncoprotein inhibitors enhanced in vivo persistence by about 1 to about 5 months, about 1 to about 4 months, about 1 to about 3 months, about 1 to about 2 months, about 2 to about 4 months, or about 3 to about 5 months. In certain embodiments, use of oncogene or oncoprotein inhibitors enhanced in vivo persistence by at least about 1 month, at least about 2 months, at least about 3 months, at least about 4 months, at least about 5 months, or at least about 6 months. In certain embodiments, use of oncogene or oncoprotein inhibitors enhanced in vivo persistence by up to about 1 month, up to about 2 months, up to about 3 months, up to about 4 months, up to about 5 months, or up to about 6 months.

In certain embodiments, use of the oncogene or oncoprotein inhibitor enhances in vivo persistence of CAR-modified host cells by increasing the life span of the modified host cell by about 0.01 to about 10 fold. In certain embodiments, the life span of the modified host cell is increased by about 0.02 to about 9 fold, about 0.03 to about 8 fold, about 0.04 to about 7 fold, about 0.05 to about 6 fold, about 0.06 to about 5 fold, about 0.07 to about 4 fold, about 0.08 to about 3 fold, about 0.09 to about 2 fold, about 0.1 to about 1 fold, about 0.2 to about 0.9 fold, about 0.3 to about 0.8 fold, about 0.4 to about 0.7 fold, or about 0.5 to about 0.6 fold. In certain embodiments, the life span of the modified host cell is increased by up to about 0.01, about 0.02, about 0.03, about 0.04, about 0.05, about 0.06, about 0.07, about 0.08, about 0.09, about, 0.1, about 0.2, about 0.3, about 0.4, about 0.5, about 0.6, about 0.7, about 0.8, about 0.9, about 1, about 2, about 4, about 6, about 8, or about 10 fold.

Examples of oncogene or oncoprotein inhibitors include, but are not limited to, an anti-oncogene antibody or antigen-binding fragment thereof, an anti-oncoprotein antibody or antigen-binding fragment thereof, aptamer, siRNA, shRNA, microRNA, or small molecule inhibitor of the oncoprotein or a gene encoding the oncoprotein, or a combination thereof.

Examples of c-Myc inhibitors include, but are not limited to, an anti-c-Myc antibody or antigen-binding fragment thereof, aptamer, siRNA, shRNA, microRNA, or small molecule inhibitor of c-Myc protein or a gene encoding the c-Myc protein, JQ-1, BET bromodomain inhibitor, or a combination thereof. In certain embodiments, the c-Myc inhibitor is a BET bromodomain. In certain embodiments, the c-Myc inhibitor is JQ-1.

In certain embodiment, a method of producing host cells for administration to a subject comprises contacting the cells with one or more agents that inhibit oncogenes or oncoproteins. In certain embodiments, the host cells may be treated with the agent during the expansion phases of the manufacturing process. In certain embodiments, the host cells may be treated with the agent only during the expansion phase of the manufacturing process after the host cell has been transduced with the CAR construct. In certain embodiments, the host cells are not treated more than once with the oncogene or oncoprotein inhibitor. In certain embodiments, the host cells are not treated with the oncogene or oncoprotein inhibitor during the activation phase. In certain embodiments, the host cells are not treated with the oncogene or oncoprotein inhibitor prior to the host cells being transduced with the CAR construct.

In certain embodiments, host cells produced by the methods contemplated herein undergo one, two, three, four, or five or more rounds of activation and expansion. In certain embodiments, the oncogene or oncoprotein inhibitor is added only in one round. In certain embodiments, the oncogene or oncoprotein inhibitor is only added during the last round. In certain embodiments, the oncogene or oncoprotein inhibitor is added during every expansion round.

In certain embodiments, the oncogene or oncoprotein inhibitor is administered at a concentration of about 0.1 µM to about 2 µM or about 0.5 µM to about 2 µM. In certain embodiments, the oncogene or oncoprotein inhibitor is administered at a concentration of about 0.2 µM to about 1.9 µM, about 0.3 µM to about 1.8 µM, about 0.4 µM to about 1.7 µM, about 0.5 µM to about 1.6 µM, about 0.6 µM to about 1.5 µM, about 0.7 µM to about 1.4 µM, about 0.8 µM to about 1.3 µM, or about 0.9 µM to about 1.2 µM. In certain embodiments, the oncogene or oncoprotein inhibitor is administered at a concentration of about 0.1 µM, about 0.2 µM, about 0.3 µM, about 0.4 µM, about 0.5 µM, about 0.6 µM, about 0.7 µM, about 0.8 µM, about 0.9 µM, about 1 µM, about 1.2 µM, about 1.3 µM, about 1.4 µM, about 1.5 µM, about 1.6 µM, about 1.7 µM, about 1.8 µM, about 1.9 µM, or about 2.0 µM. In certain embodiments, the c-Myc inhibitor is BET bromodomain. In certain embodiments, the c-Myc inhibitor is JQ-1.

In certain embodiments, the oncogene or oncoprotein inhibitor has an IC50 of at least about 1 nM, at least about 2 nM, at least about 5 nM, at least about 10 nM, at least about 50 nM, at least about 10 nM, at least about 200 nM, at least about 500 nM, at least about 1 µM, at least about 10 µM, at least about 50 µM, or at least about 100 µM. IC50 determinations can be accomplished using any conventional techniques known in the art. For example, an IC50 can be determined by measuring the expression of a gene in the presence of a range of concentrations of the inhibitor under study. The experimentally obtained values of activity then are plotted against the inhibitor concentrations used. In certain embodiments, the concentration of the inhibitor that shows at least 10%, at least 20%, at least 30%, at least 40%, at least 50%, or at least 60% enzyme activity (as compared to the activity in the absence of any inhibitor) is taken as the "IC50" value. Analogously, other inhibitory concentrations can be defined through appropriate determinations of activity.

Genes related to glycolysis (e.g., GAPDH, PFKP, TPI1) are upregulated in CD33 CAR T cells. Glycolysis is the metabolic pathway that converts glucose C6H12O6 into pyruvate $CH_3COCOO^- + H^+$, and as such controlling the glycolysis pathway is one way to control the metabolism of the cell.

In certain embodiments, use of the glycolysis inhibitor enhances in vivo persistence of CAR-modified host cells by increasing the life span of the modified host cell by about 1 to about 20 days. In certain embodiments, use of glycolysis inhibitors enhanced in vivo persistence by about 1 to about 15 days, about 1 to about 10 days, about 2 to about 8 days, or about 3 to about 6 days. In certain embodiments, use of glycolysis inhibitors enhanced in vivo persistence by at least about 1 day, at least about 2 days, at least about 3 days, at least about 4 days, at least about 5 days, at least about 6 days, at least about 7 days, at least about 8 days, at least about 9 days, at least about 10 days, at least about 15 days, at least about 20 days. In certain embodiments, use of glycolysis inhibitors enhanced in vivo persistence by up to about 1 day, up to about 2 days, up to about 3 days, up to about 4 days, up to about 5 days, up to about 6 days, up to about 7 days, up to about 8 days, up to about 9 days, up to about 10 days, up to about 15 days, or up to about 20 days. In certain embodiments, use of glycolysis inhibitors enhanced in vivo persistence by about 3 days.

In certain embodiments, use of the glycolysis inhibitors enhances in vivo persistence of CAR-modified host cells by increasing the life span of the modified host cell by about 1 to about 6 months. In certain embodiments, use of glycolysis inhibitors enhanced in vivo persistence by about 1 to about 5 months, about 1 to about 4 months, about 1 to about 3 months, about 1 to about 2 months, about 2 to about 4 months, or about 3 to about 5 months. In certain embodiments, use of glycolysis inhibitors enhanced in vivo persistence by at least about 1 month, at least about 2 months, at least about 3 months, at least about 4 months, at least about 5 months, or at least about 6 months. In certain embodiments, use of glycolysis inhibitors enhanced in vivo persistence by up to about 1 month, up to about 2 months, up to about 3 months, up to about 4 months, up to about 5 months, or up to about 6 months.

In certain embodiments, use of the glycolysis inhibitor enhances in vivo persistence of CAR-modified host cells by increasing the life span of the modified host cell by about 0.01 to about 10 fold. In certain embodiments, the life span of the modified host cell is increased by about 0.02 to about 9 fold, about 0.03 to about 8 fold, about 0.04 to about 7 fold, about 0.05 to about 6 fold, about 0.06 to about 5 fold, about 0.07 to about 4 fold, about 0.08 to about 3 fold, about 0.09 to about 2 fold, about 0.1 to about 1 fold, about 0.2 to about 0.9 fold, about 0.3 to about 0.8 fold, about 0.4 to about 0.7 fold, or about 0.5 to about 0.6 fold. In certain embodiments, the life span of the modified host cell is increased by up to about 0.01, about 0.02, about 0.03, about 0.04, about 0.05, about 0.06, about 0.07, about 0.08, about 0.09, about, 0.1, about 0.2, about 0.3, about 0.4, about 0.5, about 0.6, about 0.7, about 0.8, about 0.9, about 1, about 2, about 4, about 6, about 8, or about 10 fold.

Examples of glycolysis inhibitors include, but are not limited to, Glut1 inhibitor (Glut1i) phloretin (Phlo), hexokinase inhibitor (HXKi), pyruvate kinase inhibitor (PKi) oxaloacetate, lactate dehydrogenase inhibitor (LDHi) oxamate, TCA cycle inhibitor (TCAi) dichloroacetic acid (DCA), or 2DG (2-Deoxy-D-glucose). In certain embodiments, the glycolysis inhibitor is DCA.

In certain embodiment, a method of producing host cells for administration to a subject comprises contacting the cells with one or more agents that inhibit glycolysis. In certain embodiments, the host cells may be treated with the agent during the expansion phases of the manufacturing process. In certain embodiments, the host cells may be treated with the agent only during the expansion phase of the manufacturing process after the host cell has been transduced with the CAR construct. In certain embodiments, the host cells are not treated more than once with the glycolysis inhibitor. In certain embodiments, the host cells are not treated with the glycolysis inhibitor during the activation phase. In certain embodiments, the host cells are not treated with the glycolysis inhibitor prior to the host cells being transduced with the CAR construct.

In certain embodiments, host cells produced by the methods contemplated herein undergo one, two, three, four, or five or more rounds of activation and expansion. In certain embodiments, the glycolysis inhibitor is added only in one round. In certain embodiments, the glycolysis inhibitor is only added during the last round. In certain embodiments, the glycolysis inhibitor is added during every expansion round.

In certain embodiments, the glycolysis inhibitor is administered at a concentration of about 0.1 µM to about 20 mM. In certain embodiments, the oncoprotein inhibitor is administered at a concentration of about 0.25 µM to about 750 µM, about 0.5 µM to about 500 µM, about 0.75 µM to about 250 µM, about 1 µM to about 100 µM, about 2.5 µM to about 75 µM, about 5 µM to about 50 µM, about 10 µM to about 25 µM, about 1 mM to about 20 mM, about 2 mM to about 18 mM, about 3 mM to about 16 mM, about 4 mM to about 14 mM, about 5 mM to about 12 mM, about 6 mM to about 10 mM, or about 7 mM to about 9 mM. In certain embodiments, the glycolysis inhibitor is administered at a concentration of about 0.1 µM, about 0.2 µM, about 0.4 µM, about 0.6 µM, about 0.8 µM, about 1 µM, about 2 µM, about 4 µM, about 6 µM, about 8 µM, about 10 µM, about 12 µM, about 14 µM, about 16 µM, about 18 µM, about 20 µM, about 25 µM, about 30 µM, about 35 µM, about 40 µM, about 45 µM, about 50 µM, about 55 µM, about 60 µM, about 65 µM, about 70 µM, about 75 µM, about 80 µM, about 85 µM, about 90 µM, about 95 µM, about 100 µM, about 125 µM, about µM, about 150 µM, about 175 µM, about 200 µM, about 225 µM, about 250 µM, about 275 µM, about 300 µM, about 325 µM, about 350 µM, about 375 µM, about 400 µM, about 425 µM, about 450 µM, about 475 µM, about 500 µM, about 525 µM, about 550 µM, about 575 µM, about 600 µM, about 625 µM, about 650 µM, about 675 µM, about 700 µM, about 725 µM, about 750 µM, about 775 µM, about 800 µM, about 825 µM, about 850 µM, about 875 µM, about 900 µM, about 925 µM, about 950 µM, about 975 µM, about 1 mM, about 5 mM, about 10 mM, about 15 mM, or about 20 mM. In certain embodiments, the glycolysis inhibitor is administered at a concentration of about 10 mM. In certain embodiments, the glycolysis inhibitor is DCA.

In certain embodiments, the glycolysis inhibitor has an IC50 of at least about 1 nM, at least about 2 nM, at least about 5 nM, at least about 10 nM, at least about 50 nM, at least about 10 nM, at least about 200 nM, at least about 500 nM, at least about 1 µM, at least about 10 µM, at least about 50 µM, or at least about 100 µM. IC50 determinations can be accomplished using any conventional techniques known in the art. For example, an IC50 can be determined by measuring the expression of a gene in the presence of a range of concentrations of the inhibitor under study. The experimentally obtained values of activity then are plotted against the inhibitor concentrations used. In certain embodiments, the concentration of the inhibitor that shows at least 10%, at least 20%, at least 30%, at least 40%, at least 50%, or at least 60% enzyme activity (as compared to the activity in the absence of any inhibitor) is taken as the "IC50" value. Analogously, other inhibitory concentrations can be defined through appropriate determinations of activity.

Isolation/Enrichment

The host cells may be autologous/autogeneic ("self") or non-autologous ("non-self," e.g., allogeneic, syngeneic or xenogeneic). In certain embodiments, the host cells are obtained from a mammalian subject. In other embodiments, the host cells are obtained from a primate subject. In certain embodiments, the host cells are obtained from a human subject.

T lymphocytes can be obtained from sources such as, but not limited to, peripheral blood mononuclear cells, bone marrow, lymph nodes tissue, cord blood, thymus issue, tissue from a site of infection, ascites, pleural effusion, spleen tissue, or tumors. In certain embodiments, T lymphocytes can be obtained from blood collected from a subject using techniques generally known to the skilled person, such as sedimentation, e.g., FICOLL™ separation.

In certain embodiments, cells from the circulating blood of a subject are obtained by apheresis. An apheresis device typically contains lymphocytes, including T cells, monocytes, granulocytes, B cells, other nucleated white blood cells, red blood cells, and platelets. In certain embodiments, the cells collected by apheresis may be washed to remove the plasma fraction and to place the cells in an appropriate buffer or media for subsequent processing. The cells can be washed with PBS or with another suitable solution that lacks calcium, magnesium, and most, if not all other, divalent cations. A washing step may be accomplished by methods known to those in the art, such as, but not limited to, using a semiautomated flowthrough centrifuge (e.g., Cobe 2991 cell processor, or the Baxter CytoMate). After washing, the cells may be resuspended in a variety of biocompatible buffers, cell culture medias, or other saline solution with or without buffer.

In certain embodiments, host cells can be isolated from peripheral blood mononuclear cells (PBMCs) by lysing the red blood cells and depleting the monocytes. As an example, the cells can be sorted by centrifugation through a PERCOLL™ gradient. In certain embodiments, after isolation of PBMC, both cytotoxic and helper T lymphocytes can be sorted into naive, memory, and effector T cell subpopulations either before or after activation, expansion, and/or genetic modification.

In certain embodiments, T lymphocytes can be enriched. For example, a specific subpopulation of T lymphocytes, expressing one or more markers such as, but not limited to, CD3, CD4, CD8, CD14, CD15, CD16, CD19, CD27, CD28, CD34, CD36, CD45RA, CD45RO, CD56, CD62, CD62L, CD122, CD123, CD127, CD235a, CCR7, HLA-DR or a combination thereof using either positive or negative selection techniques. In certain embodiments, the T lymphocytes for use in the compositions of the invention do not express or do not substantially express one or more of the following markers: CD57, CD244, CD160, PD-1, CTLA4, TIM3, and LAG3.

In certain embodiments, NK cells can be enriched. For example, a specific subpopulation of lymphocytes, expressing one or more markers such as, but not limited to, CD2, CD16, CD56, CD57, CD94, CD122 or a combination thereof using either positive or negative selection techniques.

Stimulation/Activation

In order to reach sufficient therapeutic doses of host cell compositions, host cells are often subjected to one or more rounds of stimulation/activation. In certain embodiments, a method of producing host cells for administration to a subject comprises stimulating the host cells to become activated in the presence of one or more stimulatory signals or agents. In certain embodiments, a method of producing host cells for administration to a subject comprises stimulating the host cells to become activated and to proliferate in the presence of one or more stimulatory signals or agents.

Host cells (e.g., T lymphocytes and NK cells) can be activated by inducing a change in their biologic state by which the cells express activation markers, produce cytokines, proliferate and/or become cytotoxic to target cells. All these changes can be produced by primary stimulatory signals. Co-stimulatory signals amplify the magnitude of the primary signals and suppress cell death following initial stimulation resulting in a more durable activation state and thus a higher cytotoxic capacity.

T cells can be activated generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety.

In certain embodiments, the T cell based host cells can be activated by binding to an agent that activates CD3. In certain embodiments, the T cell based host cell can be activated by binding to an agent that activates the CD3 and another agent that activates CD28. In such an instant, the first agent stimulates a TCR/CD3 complex-associated signal in the T cells and the second agent provides a secondary stimulus by binding CD28 as accessory molecule.

In other embodiments, a CD2 binding agent may be used to provide a primary stimulation signal to the T cells or NK cells. For example, and not by limitation, CD2 binding agents include, but are not limited to, CD2 ligands and anti-CD2 antibodies, e.g., the Tl 1.3 antibody in combination with the Tl 1.1 or Tl 1.2 antibody (Meuer, S. C. et al. (1984) Cell 36:897-906) and the 9.6 antibody (which recognizes the same epitope as TI 1.1) in combination with the 9-1 antibody (Yang, S. Y. et al. (1986) J. Immunol. 137:1097-1100). Other antibodies which bind to the same epitopes as any of the above described antibodies can also be used.

In certain embodiments, the host cells are activated by administering phorbol myristate acetate (PMA) and ionomycine. In certain embodiments, the host cells are activated by administering an appropriate antigen that induces activation and then expansion. In certain embodiments, PMA, ionomycine, and/or appropriate antigen are administered with CD3 and/or CD28 to induce activation and/or expansion.

In general, the activating agents used in the present invention include, but are not limited to, an antibody, a fragment thereof and a proteinaceous binding molecule with antibody-like functions. Examples of (recombinant) antibody fragments are Fab fragments, Fv fragments, single-chain Fv fragments (scFv), a divalent antibody fragment such as an (Fab)2'-fragment, diabodies, triabodies (Iliades, P., et al., FEBS Lett (1997) 409, 437-441), decabodies (Stone, E., et al., Journal of Immunological Methods (2007) 318, 88-94) or other domain antibodies (Holt, L. J., et al., Trends Biotechnol. (2003), 21, 11, 484-490). The divalent antibody fragment may be a (Fab)2'-fragment, or a divalent single-chain Fv fragment while the monovalent antibody fragment may be a Fab fragment, a Fv fragment, and a single-chain Fv fragment (scFv).

In certain embodiments, one or more binding sites of the CD3 or CD28 agents may be a bivalent proteinaceous artificial binding molecule such as a dimeric lipocalin mutein (i.e., duocalin). In certain embodiments the receptor binding reagent may have a single second binding site, (i.e., monovalent). Examples of monovalent agents include, but are not limited to, a monovalent antibody fragment, a proteinaceous binding molecule with antibody-like binding properties or an MHC molecule. Examples of monovalent antibody fragments include, but are not limited to a Fab fragment, a Fv fragment, or a single-chain Fv fragment (scFv), including a divalent single-chain Fv fragment.

The agent that specifically binds CD3 includes, but is not limited to, an anti-CD3-antibody, a divalent antibody fragment of an anti-CD3 antibody, a monovalent antibody fragment of an anti-CD3-antibody, or a proteinaceous CD3 binding molecule with antibody-like binding properties. The agent that specifically binds CD28 includes, but is not limited to, an anti-CD28-antibody, a divalent antibody fragment of an anti-CD28 antibody, a monovalent antibody fragment of an anti-CD28-antibody, or a proteinaceous CD28 binding molecule with antibody-like binding properties. A proteinaceous CD3 or CD28 binding molecule with antibody-like binding properties can be an aptamer, a mutein based on a polypeptide of the lipocalin family, a glubody, a protein based on the ankyrin scaffold, a protein based on the crystalline scaffold, an adnectin, or an avimer.

In certain embodiments, the activating agent (e.g., CD3 and/or CD28 binding agents) can be present in a concentration of about 0.1 to about 10 µg/ml. In certain embodiments, the activating agent (e.g., CD3 and/or CD28 binding agents) can be present in a concentration of about 0.2 µg/ml to about 9 µg/ml, about 0.3 µg/ml to about 8 µg/ml, about 0.4 µg/ml to about 7 µg/ml, about 0.5 µg/ml to about 6 µg/ml, about 0.6 µg/ml to about 5 µg/ml, about 0.7 µg/ml to about 4 µg/ml, about 0.8 µg/ml to about 3 µg/ml, or about 0.9 µg/ml to about 2 µg/ml. In certain embodiments, the activating agent (e.g., CD3 and/or CD28 binding agents) is administered at a concentration of about 0.1 µg/ml, about 0.2 µg/ml, about 0.3 µg/ml, about 0.4 µg/ml, about 0.5 µg/ml, about 0.6 µg/ml, about 0.7 µg/ml, about 0.8 µM, about 0.9 µg/ml, about 1 µg/ml, about 2 µg/ml, about 3 µg/ml, about 4 µM, about 5 µg/ml, about 6 µg/ml, about 7 µg/ml, about 8 µg/ml, about 9 µg/ml, or about 10 µg/ml. In certain embodiments, the CD3 and/or CD28 binding agents can be present in a concentration of 1 µg/ml. In certain embodiments, the CD3 and/or CD28 binding agents can be present in the same or different concentration.

In certain embodiments, the activating agent is attached to a solid support such as, but not limited to, a bead, an absorbent polymer present in culture plate or well or other matrices such as, but not limited to, Sepharose or glass; may be expressed (such as in native or recombinant forms) on cell surface of natural or recombinant cell line by means known to those skilled in the art. In certain embodiments, a costimulatory ligand is presented on an antigen presenting cell (e.g., an aAPC, dendritic cell, B cell, and the like) that specifically binds a cognate costimulatory molecule on a host cell, thereby providing a signal which, in addition to the primary signal provided by, for instance, binding of a TCR/CD3 complex, mediates a desired T cell response. Suitable costimulatory ligands include, but are not limited to, CD28, CD7, B7-1 (CD80), B7-2 (CD86), PD-L 1, PD-L2, 4-1BBL, OX4OL, inducible costimulatory ligand (ICOS-L), intercellular adhesion molecule (ICAM), CD30L, CD40, CD70, CD83, HLA-G, MICA, MICB, HVEM, lymphotoxin beta receptor, ILT3, ILT4, an agonist or antibody that binds Toll ligand receptor, and a ligand that specifically binds with B7-H3.

In a particular embodiment, a costimulatory ligand comprises an antibody or antigen binding fragment thereof that specifically binds to a costimulatory molecule present on a T lymphocytes, including but not limited to, CD27, CD28, 4-IBB, OX40, CD30, CD40, PD-1, 1COS, lymphocyte function-associated antigen- 1 (LFA-1), CD7, LIGHT, NKG2C, B7-H3, or a ligand that specifically binds with CD83.

NK cells can be activated generally using methods as described, for example, in U.S. Pat. Nos. 7,803,376, 6,949,520, 6,693,086, 8,834,900, 9,404,083, 9,464,274, 7,435,596, 8,026,097, 8,877,182; U.S. Patent Applications US2004/0058445, US2007/0160578, US2013/0011376, US2015/0118207, US2015/0037887; and PCT Patent Application WO2016/122147, each of which is incorporated herein by reference in its entirety for all intended purposes.

In certain embodiments, the NK based host cells can be activated by, for example and not limitation, inhibition of inhibitory receptors on NK cells (e.g., KIR2DL1, KIR2DL2/3, KIR2DL4, KIR2DL5A, KIR2DL5B, KIR3DL1, KIR3DL2, KIR3DL3, LILRB1, NKG2A, NKG2C, NKG2E or LILRBS receptor), activation of CD3 as described hereinabove, immunostimulatory nucleic acids (e.g., CpG nucleic acids, T-rich nucleic acids, and poly-G nucleic acids).

In other embodiments, interferons or macrophage-derived cytokines can be used to activate NK cells. For example, and not limitation, such interferons such as interferon alpha or interferon gamma, and such cytokines such as IL-15, IL-2, IL-12, or IL-7.

Transduction

The host cells are engineered after stimulation/activation. In certain embodiments, the host cells are genetically engineered to express a CAR. In certain embodiments, the CAR is that described above. In certain embodiments, the CAR is other than that described above. In certain embodiments, the host cells are modified within 12 hours, 16 hours, 24 hours, 36 hours, or 48 hours of stimulation/activation. In certain embodiments, the cells are modified within 16 to 24 hours after stimulation/activation. In certain embodiments, the host cells are modified within 24 hours.

In certain embodiments, the host cells can be transduced by methods ordinarily used by one of skill in the art. In certain embodiments, the host cells can be transduced via retroviral transduction. References describing retroviral transduction of genes are Anderson et al., U.S. Pat. No. 5,399,346; Mann et al., Cell 33:153 (1983); Temin et al., U.S. Pat. No. 4,650,764; Temin et al., U.S. Pat. No. 4,980,289; Markowitz et al., J. Virol. 62:1120 (1988); Temin et al., U.S. Pat. No. 5,124,263; International Patent Publication No. WO 95/07358, published Mar. 16, 1995, by Dougherty et al.; and Kuo et al., Blood 82:845 (1993).

Expansion/Proliferation

After the host cells are activated and transduced, the cells are cultured to proliferate. T cells may be cultured for at least 1, 2, 3, 4, 5, 6, or 7 days, at least 2 weeks, at least 1, 2, 3, 4, 5, or 6 months or more with 1, 2, 3, 4, 5, 6, 7, 8, 9, or 10 or more rounds of expansion. In various embodiments, T cell compositions are manufactured in the presence of one or more inhibitors of the PI3K pathway as described above. The inhibitors may target one or more activities in the pathway or a single activity. Without wishing to be bound to any particular theory, it is contemplated that treatment or contacting T cells with one or more inhibitors of the PI3K pathway during the expansion phases of the manufacturing process preferentially increases young host cells, thereby producing superior therapeutic host cell compositions.

Agents that can be used for the expansion of T cells can include, but are not limited to, interleukins, such as IL-2, IL-7, IL-15, or IL-21 (see for example Cornish et al. 2006, Blood. 108(2):600-8, Bazdar and Sieg, 2007, Journal of Virology, 2007, 81(22):12670-12674, Battalia et al, 2013, Immunology, 139(1):109-120). Other illustrative examples for agents that may be used for the expansion of T cells are agents that bind to CD8, CD45 or CD90, such as αCD8, αCD45 or αCD90 antibodies. Illustrative examples of T cell population including antigen-specific T cells, T helper cells, cytotoxic T cells, natural killer T cell, memory T cell (an illustrative example of memory T cells are CD62L1CD81 specific central memory T cells) or regulatory T cells (an illustrative example of Treg are CD4+CD25+CD45RA+ Treg cells).

Additional agents that can be used to expand T lymphocytes includes methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety for all intended purposes.

In certain embodiments, the agent(s) used for expansion (e.g., IL-2) are administered at about 20 units/ml to about 200 units/ml. In certain embodiments, the agent(s) used for expansion (e.g., IL-2) are administered at about 25 units/ml to about 190 units/ml, about 30 units/ml to about 180 units/ml, about 35 units/ml to about 170 units/ml, about 40 units/ml to about 160 units/ml, about 45 units/ml to about 150 units/ml, about 50 units/ml to about 140 units/ml, about 55 units/ml to about 130 units/ml, about 60 units/ml to about 120 units/ml, about 65 units/ml to about 110 units/ml, about 70 units/ml to about 100 units/ml, about 75 units/ml to about 95 units/ml, or about 80 units/ml to about 90 units/ml. In certain embodiments, the agent(s) used for expansion (e.g., IL-2) are administered at about 20 units/ml, about 25 units/ml, about 30 units/ml, 35 units/ml, 40 units/ml, 45 units/ml, about 50 units/ml, about 55 units/ml, about 60 units/ml, about 65 units/ml, about 70 units/ml, about 75 units/ml, about 80 units/ml, about 85 units/ml, about 90 units/ml, about 95 units/ml, about 100 units/ml, about 105 units/ml, about 110 units/ml, about 115 units/ml, about 120 units/ml, about 125 units/ml, about 130 units/ml, about 135 units/ml, about 140 units/ml, about 145 units/ml, about 150 units/ml, about 155 units/ml, about 160 units/ml, about 165 units/ml, about 170 units/ml, about 175 units/ml, about 180 units/ml, about 185 units/ml, about 190 units/ml, about 195 units/ml, or about 200 units/ml. In certain embodiments, the agent(s) used for expansion (e.g., IL-2) are administered at about 5 mg/ml to about 10 ng/ml. In certain embodiments, the agent(s) used for expansion (e.g., IL-2) are administered at about 5.5 ng/ml to about 9.5 ng/ml, about 6 ng/ml to about 9 ng/ml, about 6.5 ng/ml to about 8.5 ng/ml, or about 7 ng/ml to about 8 ng/ml. In certain embodiments, the agent(s) used for expansion (e.g., IL-2) are administered at about 5 ng/ml, 6 ng/ml, 7 ng/ml, 8 ng/ml, 9, ng/ml, or 10 ng/ml.

In certain embodiments, IL-2 is used for expansion.

After the host cells are activated and transduced, the cells are cultured to proliferate. NK cells may be cultured for at least 1, 2, 3, 4, 5, 6, or 7 days, at least 2 weeks, at least 1, 2, 3, 4, 5, or 6 months or more with 1, 2, 3, 4, 5, 6, 7, 8, 9, or 10 or more rounds of expansion. In certain embodiments, the NK cells may be cultured for about 3 to about 14 days about 5 to about 12 days, or about 7 to about 10 days. In various embodiments, NK cell compositions are manufactured in the presence of one or more inhibitors of the PI3K pathway as described above (e.g., PI3K inhibitors and/or c-Myc inhibitors). The inhibitors may target one or more activities in the pathway or a single activity. Without wishing to be bound to any particular theory, it is contemplated that treatment or contacting NK cells with one or more inhibitors of the PI3K pathway during the expansion phases of the manufacturing process preferentially increases young host cells, thereby producing superior therapeutic host cell compositions.

Agents that can be used for the expansion of natural killer cells can include agents that bind to CD16 or CD56, such as for example aCD16 or aCD56 antibodies. In certain embodiments, the binding agent includes antibodies (see for example Hoshino et al, Blood. 1991 Dec. 15; 78(12):3232-40). Other agents that may be used for expansion of NK cells may be IL-15 (see for example Vitale et al. 2002. The Anatomical Record. 266:87-92).

Conditions appropriate for T cell culture include an appropriate media (e.g., Minimal Essential Media or RPMI Media 1640 or, X-vivo 15, (Lonza RPMI 1640, Clicks, AIM-V, DMEM, MEM, a-MEM, F-12, X-Vivo 1 5, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion.

Examples of other additives for host cell expansion include, but are not limited to, surfactant, piasmanate, pH buffers such as HEPES, or reducing agents such as N-acetyl-cysteine and 2-mercaptoethanol, Antibiotics (e.g., penicillin and streptomycin), are included only in experimental cultures, not in cultures of cells that are to be infused into a subject. The target cells are maintained under conditions necessary to support growth, for example, an appropriate temperature (e.g., 37° C.) and atmosphere {e.g., air plus 5% $CO_2$).

Illustrative Embodiments

In one aspect, the invention provides methods for preparing host cells. The embodiments here are merely illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. For example, while certain embodiments below are focused around T cells, the same disclosure could be applicable to other host cells (e.g., NK cells).

In certain embodiments, the method for preparing host cells (e.g., T cells or NK cells) comprises a) activating the host cells; b) transducing the host cell with a polynucleotide encoding a CAR of the invention; c) expanding the transduced host cell; d) treating the host cells with an inhibitor of the phosphoinositide 3-kinase (PI3K) / Akt pathway, a glycolysis inhibitor, an oncoprotein inhibitor and/or an oncogene inhibitor. In certain embodiments, any of the inhibitors listed above can be used in this method in the concentrations and regimens disclosed above. In certain embodiment, steps c) and d) are performed simultaneously. In certain embodiments, the host cells are expanded for about 1, 2, 3, 4, 5, 6, 7, or 8 days prior to addition of the inhibitor. In certain embodiments, the host cells are expanded for at least 4 days prior to the addition of the inhibitor. In certain embodiments, the host cells are expended for no more than 8 days. In certain embodiments, the host cells are treated with the inhibitor for about 1, 2, 3, 4, 5, 6, 7, 8, 9, 10, 11, 12, 13, or 14 days. In certain embodiments, the cells are expanded for at least 2 days prior to treatment with the inhibitor. In certain embodiments, the cells are expanded for at least 4 days prior to treatment with the inhibitor. In certain embodiments, the cells are expanded for no more than 9 days prior to treatment with the inhibitor.

In certain embodiments, the cells are expanded prior to the addition of the inhibitor and following treatment with the inhibitor are expanded again without the presence of the inhibitor. In certain embodiments, the cells are then treated with the inhibitor again.

In certain embodiments, host cells produced by the methods contemplated herein undergo one, two, three, four, or five or more rounds of activation and expansion. In certain embodiments, the inhibitor is added only in one round. In certain embodiments, the inhibitor is only added during the last round. In certain embodiments, the inhibitor is added during every expansion round.

In certain embodiments, prior to step a), the host cells (e.g., T cells or NK cells) are isolated from the subject sample and optionally purified. In certain embodiments, the sample is a blood or a tumor sample. In certain embodiments, the host cells are allogeneic to the subject. In certain embodiments, the host cells are autologous to the subject. In certain embodiments, the isolation/purification step comprises the use of an apheresis ring. In certain embodiments, the isolation/purification comprises isolating the host cells (e.g., T cells or NK cells) from the sample using at least one antibody against an antigen such as, but not limited to, CD3, CD14, CD15, CD16, CD19, CD28, CD34, CD36, CD56, CD123, CD235a, and any combinations thereof.

In certain embodiments, the method further comprises administering the host cells (e.g., T cells or NK cells) produced in step d) to a subject.

In certain embodiments, steps a)-d) are conducted ex vivo.

In certain embodiments, step a) comprises exposing host cells (e.g., T cells or NK cells) to a CD3 binding agent or a CD3 binding agent with a CD28 binding agent. In certain embodiments, the CD3 binding agent is an anti-CD3 antibody or a CD3-binding fragment thereof. In certain embodiments, the anti-CD3 antibody or CD3-binding fragment thereof is present at a concentration of about 0.01 µg/ml—about 10 µg/ml (as discussed in greater detail above). In certain embodiments, the CD28 binding agent is an anti-CD28 antibody or a CD28-binding fragment thereof. In certain embodiments, the anti-CD28 antibody or CD28-binding fragment thereof is present at a concentration of about 0.01 µg/ml about 10 µg/ml (as discussed in greater detail above). In certain embodiments, the CD3 binding agent and/or the CD28 binding agent are immobilized on a solid surface.

In certain embodiments, step c) comprises exposing host cells (e.g., T cells or NK cells) to IL-2 at a concentration of 50-200 Unit/ml (as discussed in greater detail above).

In certain embodiments, step a) is conducted for at least 16-24 hours.

In certain embodiments, T cells are isolated from a subject sample (e.g., blood or tumor sample). In certain embodiments, the isolation/purification step comprises the use of an apheresis ring. In certain embodiments, wherein the isolation/purification comprises isolating the T cells from the sample using at least one antibody against an antigen such as, but not limited to, CD3, CD14, CD15, CD16, CD19, CD28, CD34, CD36, CD56, CD123, CD235a, and any combinations thereof.

In certain embodiments, the method for preparing T cells comprises a) activating the host cells by exposing the T cells to a CD3 binding agent and a CD28 binding agent for 12-24 hours; b) transducing the host cell with a polynucleotide encoding a CAR of the invention; c) expanding the transduced host cell for 1-2 days; d) treating the host cells with an inhibitor of the phosphoinositide 3-kinase (PI3K)/Akt pathway (e.g., LY-294002), a glycolysis inhibitor (e.g., DCA), an oncoprotein inhibitor and/or an oncogene inhibitor (e.g., JQ-1). Additional examples of inhibitors and regimens are listed above.

Therapeutic Methods of the Invention

In certain embodiments, the compositions comprise one or more polypeptides, polynucleotides, vectors comprising same, and host cell compositions, as disclosed herein. Compositions include, but are not limited to pharmaceutical compositions. In certain embodiments, the compositions of the present invention comprise an amount of modified host cells manufactured by the methods disclosed herein.

In one aspect, the invention provides a method for treating a disease or disorder associated in a subject in need thereof, comprising administering to the subject a therapeutically effective amount of the host cells disclosed herein comprising a CAR as disclosed herein. In certain embodiments, the host cells expressing the CAR are prepared by the methods as disclosed above.

In certain embodiments, the disease or disorder is a CD33 associated disease or disorder can be acute myeloid leukemia (AML), myelodysplastic syndrome (MDS), chronic myeloid leukemia (CML), or pro-myelocytic leukemia (PML).

In certain embodiments, the disease or disorder is cancer. In certain embodiments, the cancer can be, but is not limited to, renal cell carcinoma, colorectal carcinoma, lymphoma, melanoma, prostate cancer, ovarian cancer, lung cancer, liver cancer, head and neck cancer, bladder cancer, uterine cancer, bone cancer, leukemia, breast cancer, non-melanoma skin cancer, glioma, solid cutaneous tumor, epidermoid carcinoma, or metastases of any of thereof In certain embodiments, composition coir prising the host cells manufactured by the methods. described herein may be administered. at a dosage of $10^2$ to 10 cells/kg body weight, $10^5$ to $10^9$ cells/kg body weight, $10^5$ to $10^8$ cells/kg body weight, $10^5$ to $10^7$ cells/kg body weight, $10^7$ to $10^9$ cells/kg body weight, or 10' to 10' cells/kg body weight, including all integer values within those ranges. The number of host cells will depend on the therapeutic use for which the composition is intended for, Host cells modified to express an engineered TCR or CAR may be administered multiple times at dosages listed above. The host cells may be allogeneic, syngeneic, xenogeneic, or autologous to the patient undergoing therapy.

The compositions and methods described in the present invention may be utilized in conjunction with other types of therapy for cancer, such as chemotherapy, surgery, radiation, gene therapy, and so forth.

In certain embodiments of any of the above methods of the invention, the composition is administered in a therapeutically effective amount. The dosages of the composition administered in the methods of the invention will vary widely, depending upon the subject's physical parameters, the frequency of administration, the manner of administration, the clearance rate, and the like. The initial dose may be larger, and might be followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to achieve in vivo persistence of CAR containing host cells.

Compositions comprising modified host cells disclosed herein may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Compositions comprising modified host cells disclosed herein may comprise one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In certain embodiments, the compositions are formulated for parenteral administration, e.g., intravascular (intravenous or intraarterial), intraperitoneal or intramuscular administration. In certain embodiments, the composition is reconstituted from a lyophilized preparation prior to administration.

It is also contemplated that when used to treat various diseases/disorders, the compositions and methods of the present invention can be utilized with other therapeutic methods/agents suitable for the same or similar diseases/disorders. Such other therapeutic methods/agents can be co-administered (simultaneously or sequentially) to generate additive or synergistic effects. Suitable therapeutically effective dosages for each agent may be lowered due to the additive action or synergy.

In one embodiment of any of the above methods of the invention, the method further comprises administering to the subject one or more additional compounds selected from the group consisting of immuno-suppresives, biologicals, probiotics, prebiotics, and cytokines (e.g., IFN or IL-22).

As a non-limiting example, the invention can be combined with other therapies that block inflammation (e.g., via blockage of ILL INFa/(3, IL6, TNF, IL23, etc.).

The methods and compositions of the invention can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 41BB, OX40, etc.). The methods of the invention can be also combined with other treatments that possess the ability to modulate NKT function or stability, including but not limited to CD1d, CD1d-fusion proteins, CD dimers or larger polymers of CD either unloaded or loaded with antigens, CD1d-chimeric antigen receptors (CD1d-CAR), or any other of the five known CD1 isomers existing in humans (CD1a, CD1b, CD1c, CD1e). The methods of the invention can also be combined with other treatments such as midostaurin, enasidenib, or a combination thereof.

Therapeutic methods of the invention can be combined with additional immunotherapies and therapies. For example, when used for treating cancer, the compositions of the invention can be used in combination with conventional cancer therapies, such as, e.g., surgery, radiotherapy, chemotherapy or combinations thereof, depending on type of the tumor, patient condition, other health issues, and a variety of factors. In certain aspects, other therapeutic agents useful for combination cancer therapy with the inhibitors of the invention include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000). In one embodiment, the XX of the invention can be used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases or any combinations thereof (e.g., anti-hVEGF antibody A4.6.1, bevacizumab or ranibizumab).

Non-limiting examples of chemotherapeutic compounds which can be used in combination treatments of the present invention include, for example, aminoglutethimide, amsacrine, anastrozole, asparaginase, azacitidine, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, decitabine, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, or vinorelbine.

These chemotherapeutic compounds may be categorized by their mechanism of action into, for example, following groups: anti-metabolites/anti-cancer agents, such as pyrimidine analogs (e.g., 5-fluorouracil, floxuridine, capecitabine, gemcitabine or cytarabine) or purine analogs, folate antagonists or related inhibitors (mercaptopurine, thioguanine, pentostatin or 2-chlorodeoxyadenosine (cladribine)); anti-proliferative/antimitotic agents including natural products such as vinca alkaloids (vinblastine, vincristine, or vinorelbine), microtubule disruptors such as taxane (paclitaxel, docetaxel), vincristin, vinblastin, nocodazole, epothilones or navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide or etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) or mitomycin; enzymes (L-asparaginase which systemically metabolizes L-asparagine or deprives cells which do not have the capacity to synthesize their own asparagine); antiplatelet agents; antiproliferative/antimitotic alkylating agents such as nitrogen mustards (mechlorethamine, cyclophosphamide or analogs, melphalan, chlorambucil), ethylenimines or methylmelamines (hexamethylmelamine or thiotepa), alkyl sulfonates-busulfan, nitrosoureas (carmustine (BCNU) or analogs, streptozocin), trazenes-dacarbazinine (DTIC); anti-proliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) or aromatase inhibitors (letrozole, anastrozole); anticoagulants (heparin, synthetic heparin salts or other inhibitors of thrombin); fibrinolytic agents (such as tissue plasminogen activator, streptokinase or urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) or growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors or differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin or mitoxantrone, topotecan, irinotecan), corticosteroids (cortisone, dexamethasone, hydrocortisone, methylpednisolone, prednisone, or prenisolone); growth factor signal transduction kinase inhibitors; mitochondrial dysfunction inducers or caspase activators; or chromatin disruptors.

In accordance with the present invention there may be numerous tools and techniques within the skill of the art, such as those commonly used in molecular biology, pharmacology, and microbiology. Such tools and techniques are described in detail in e.g., Sambrook et al. (2001) Molecular Cloning: A Laboratory Manual. 3rd ed. Cold Spring Harbor Laboratory Press: Cold Spring Harbor, New York; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc. : Hoboken, N.J.; and Enna et al. eds. (2005) Current Protocols in Pharmacology, John Wiley and Sons, Inc.: Hoboken, NJ.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

Development of the Novel CD33-specific CAR and its Effects on Cancers Expressing the CD33 Receptor Anti-CD19-41BB-CD3ζ has proven to be potent and effective in both pre-clinical studies and patients with acute lymphocytic leukemia (ALL). T cells expressing this new CAR showed comparable anti-tumor efficacy and in vivo persistence (21). The anti-CD19 scFv was replaced with a distinct CD33-specific scFv (22). The activity of these CD33-specific CAR T cells was compared with T cells expressing the CD19-41BB-CD3ζ CAR, described above, in an AML model. So that both CD19 and CD33 CAR-transduced cells could recognize the AML targets, the CD33+ MOLM-13 AML cell line was transduced with CD19, generating AML cells co-expressing the CD19 and CD33 ligands (MOLM-13-CD19). Vector transduced cells were used as controls unless otherwise specified.

Figure 1B:
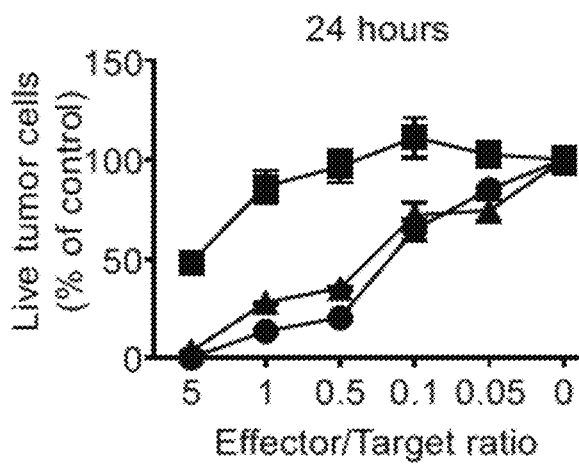
Figure 1B:
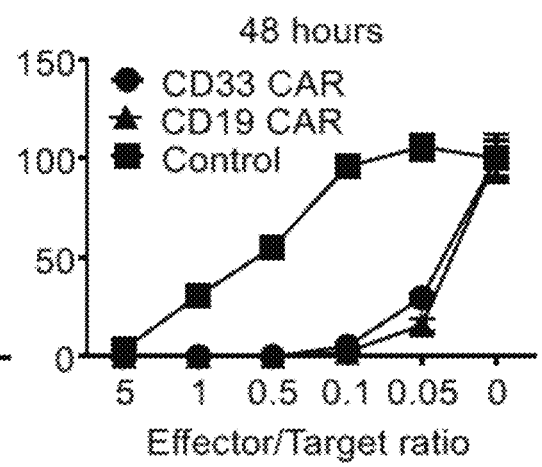

Sorted CD33 CAR, CD19 CAR, and control T cells showed similar transduction efficiencies and expression of an internal ribosome entry site (IRES)-linked GFP. Neither CD19 or CD33 CAR T cells exhibited cell surface clustering of CAR, which has been correlated to enhanced T cell exhaustion and reduced CAR T cell efficacy (FIG. 1A) (21, 50). To determine the impact of CAR specificity on therapeutic T cell function, the cytolytic potential of the CD33 and CD19 CAR-transduced T cells was assessed against the MOLM-13-CD19 tumor cells ex vivo. The CARs equivalently redirected CTLs against the AML cell line, with strong, with near complete killing of tumor cells at effector to target ratios as low 0.05:1 after 48 hours of co-culture (FIG. 1A-1B).

Figure 1C:
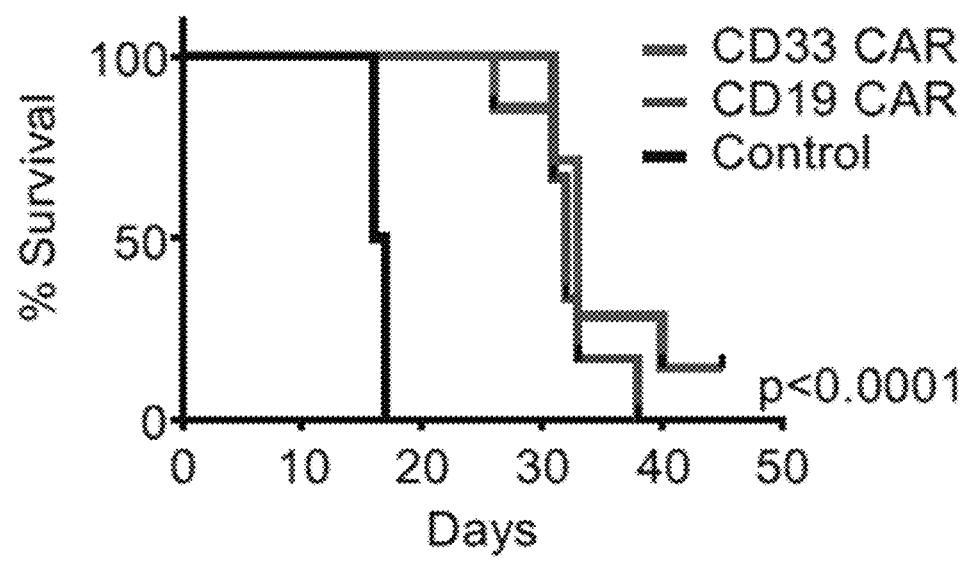
Figure 1D:
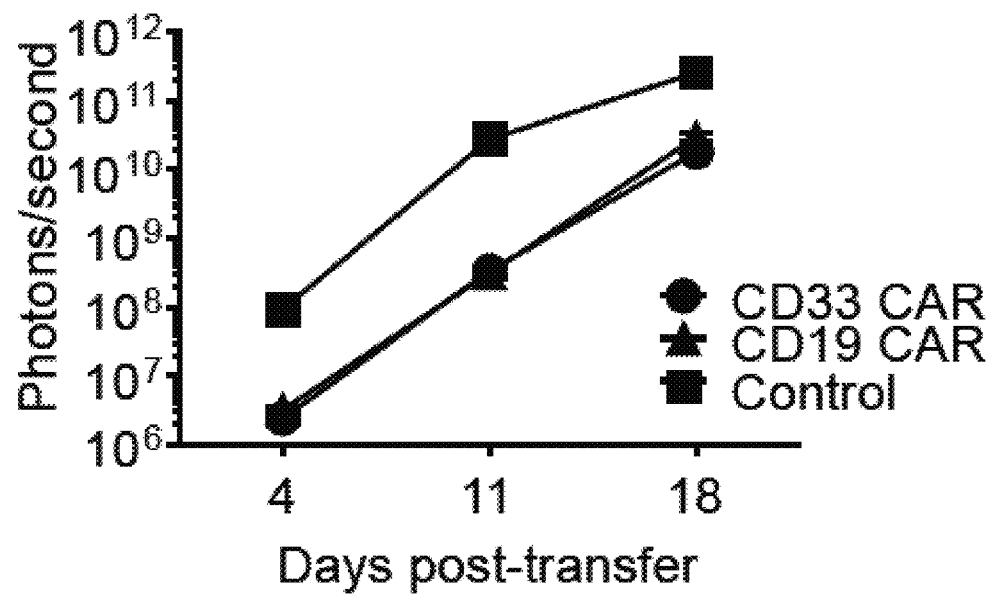
Figure 1D:
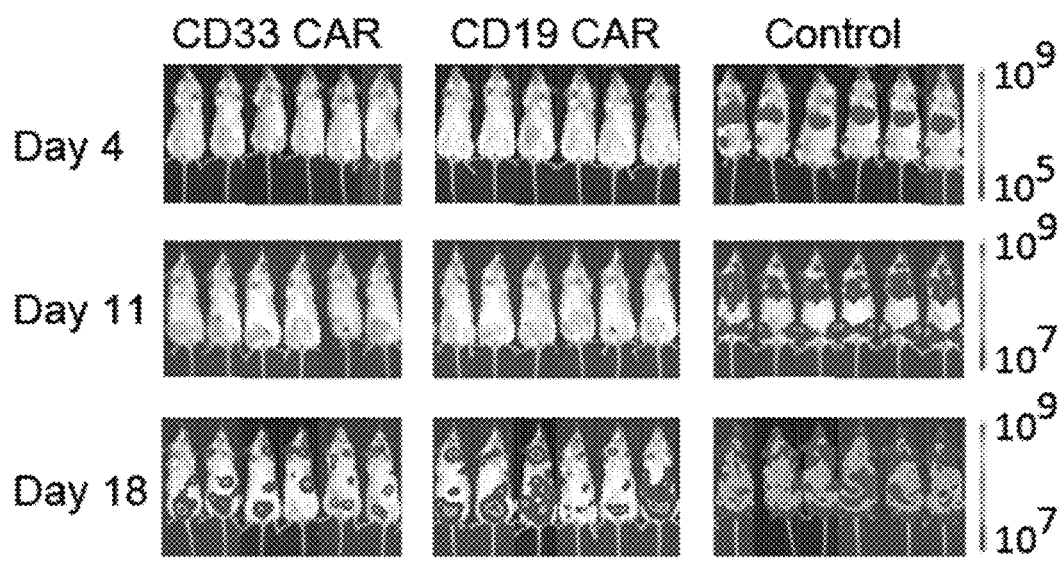
Figure 1E:
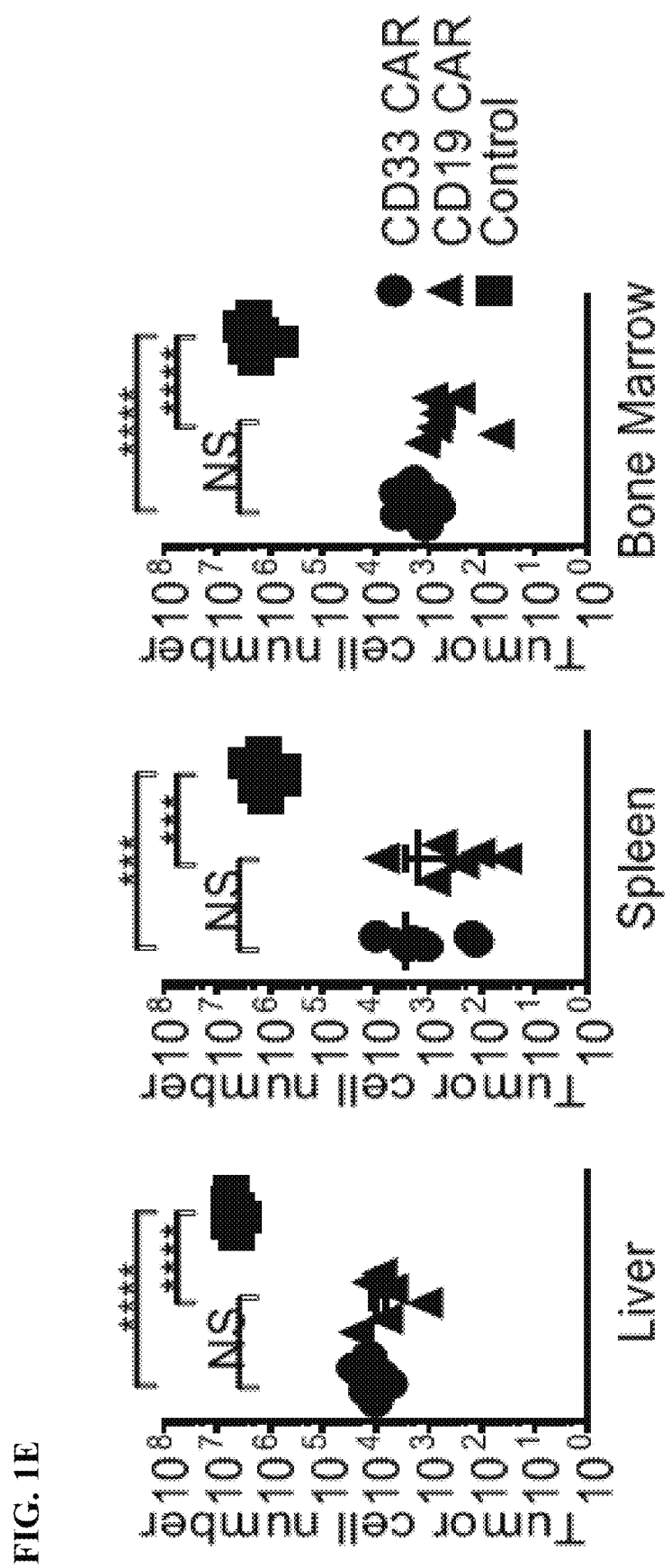

Next the efficacy of CD33- and CD19-specific CARs against AML in vivo was tested using a xenogeneic transplant model. NSG mice received $1\times10^6$ luciferase-expressing MOLM-13-CD19 cells, followed by $6\times10^6$ CAR- or control T cells. Mice were imaged weekly and followed for survival, or harvested at day 18 for analysis of tumor burden in the liver, spleen and bone marrow. The CD33 and CD19 CAR-modified T cells extended median survival from 17 days in the control group to 33 and 32 days respectively, indicating that they equivalently delayed AML progression (FIG. 1B). At 18 days post-transfer, a large tumor burden was detected in the control cohort, and this was significantly reduced with CAR T cell therapy (FIGS. 1C and 1D). Thus, there was no significant difference in the overall anti-tumor efficacy of CD33 CAR T cells and T cells expressing the clinically-established CD19 CAR either ex vivo or in vivo in targeting AML.

Materials and Methods

Mice: NSG mice (NOD.Cg-Prkdc$^{scid}$ Il2rg$^{tm1wjl}$/SzJ) were obtained from The Jackson Laboratory.

Cell line and culture conditions: AML cell line MOLM-13 transduced with firefly luciferase (MOLM-13-luc) was provided by Dr. Sharyn Baker (St. Jude Children's Research Hospital) and was stably transduced to express human CD19 (MOLM-13-CD19). Transfected cells were single cell sorted (FACSAria II, BD Bioscience) to isolate a stably transduced cell line. MOLM-13-CD19 and Phoenix-AMPHO cells (ATCC-CRL-3213) were cultured in RPMI-1640 and DMEM (Life Technologies) supplemented with 10% heat-inactivated FBS (ATLANTA biologicals), 100 U/ml penicillin, 100 µg/ml streptomycin and 292 µg/ml L-glutamine (Life Technologies).

Retroviral CAR constructs and Retrovirus Production: An anti-CD33 scFv fragment (24) and anti-CD19 scFv fragment (53) were cloned in frame with a human CD8 leader sequence, CD8 transmembrane domain, and 4-1BB-CD3 signaling tail in the MSCV-IRES-GFP vector. Empty MSCV-IRES-GFP and MSCV-IRES-RFP vectors were used as negative controls. To generate the mutant CD33 CAR constructs, the following mutations were introduced within the CAR signaling domain: EED237-239 and EEE248-250 of the 4-1BB domain were changed to AAA (numbering based on GenBank: AAA53133), and Y72, Y83, Y111, Y123, Y142 and Y153, the tyrosines comprising the three ITAMs in the CD3ζ domain were mutated to phenylalanines (numbering based on GenBank: NP932170).

Mutations were generated using the QuikChange Site Directed Mutagenesis kit (Agilent Technologies). Three separate constructs were generated that contained the mutations to the 4-1BB domain only (CD33 41BB), the mutations to the CD3ζ ITAMs only (CD33 ITAM), or all mutations to both domains (CD33 41BB ITAM). Phoenix-AMPHO cells were transfected with CAR constructs or empty vector. Cell supernatant containing retrovirus was collected 2 and 3 days post-transfection and either used immediately for T cell transduction or frozen and stored at −80° C.

Transduction of human T cells: Leukocytes obtained from apheresis rings were isolated by density gradient centrifugation. T cells were isolated using the human Pan T Cell Isolation Kit (Miltenyi Biotec) according to manufacturer's protocol. T cells were stimulated with plate-bound anti-human CD3 and CD28 antibodies (eBioscience) in RPMI with 100 U/mL recombinant IL-2 for 24h prior to transduction on RetroNectin-coated plates (TaKaRa Bio Inc.) according to manufacturer's instructions. GFP or RFP positive transduced T cells were sorted and expanded in culture for 5-7 days, supplementing with fresh IL-2 (Peptrotech) every 2 days.

Example 2

In vivo Persistence of CAR-Modified T Cells

Figure 2A:
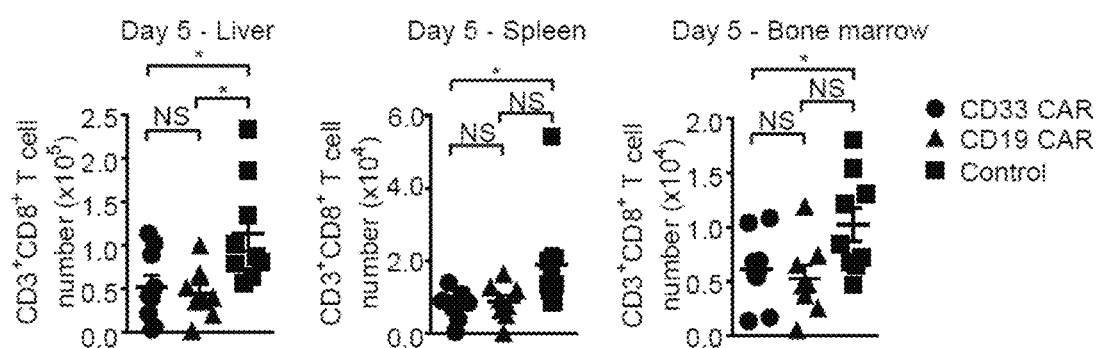
FIG. 2A-2D. Poor persistence of CAR T cells is cell intrinsic and independent of tumor antigen.
Figure 2B:
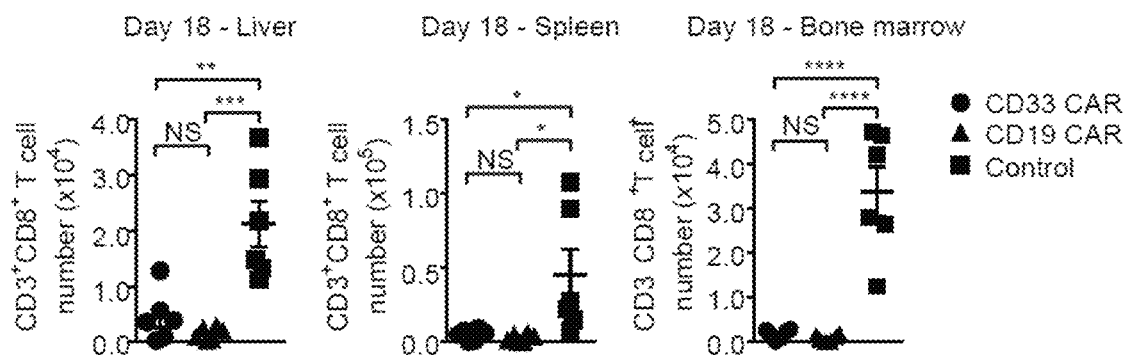
Figure 8A:
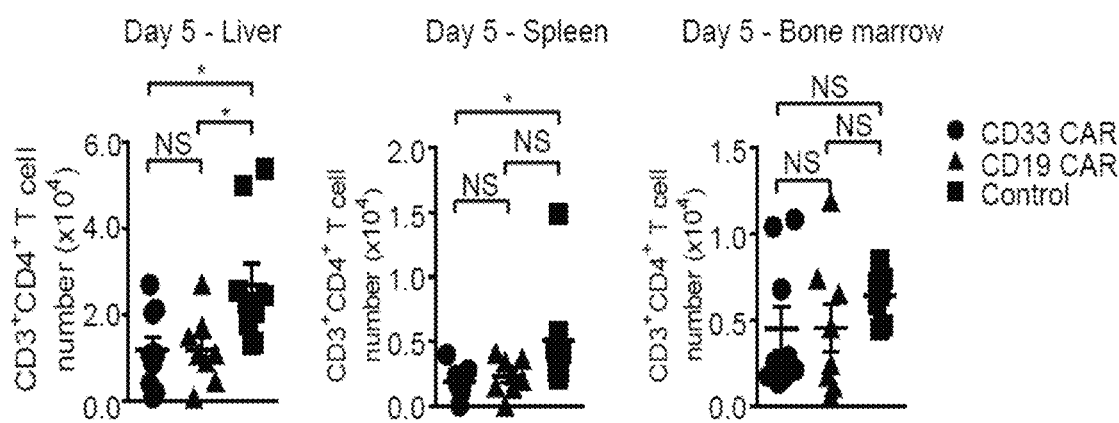
FIG. 8A-8D.
Figure 8B:
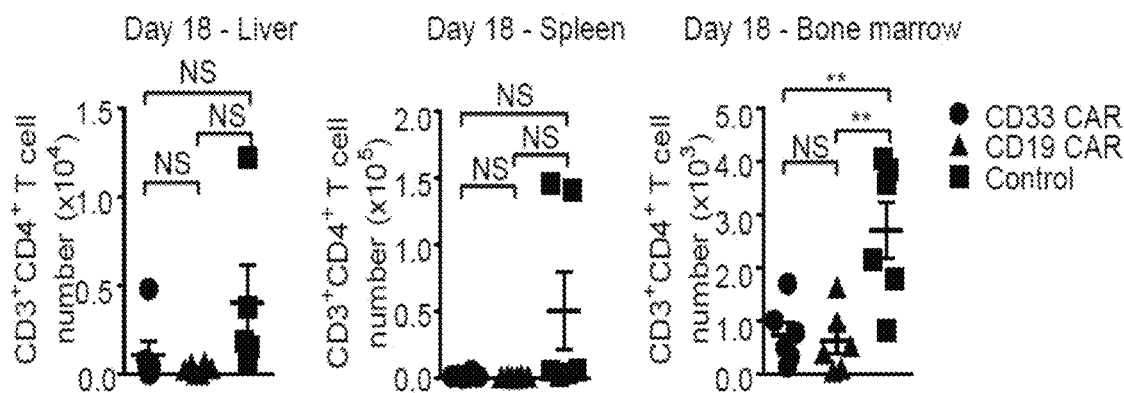

Poor survival of CAR T cells is largely cell intrinsic and independent of tumor antigen To assess CAR T cell survival, absolute numbers of CAR and control T cells were determined at days 5 and 18 in the AML model of Example 1. At day 5, the number of control CD8$^+$ T cells in the liver, spleen and bone marrow was significantly greater than CD33 and CD19 CAR T cells (FIG. 2A). At day 18, while control T cells persisted in all organs, few CD33 and CD19 CAR T cells were seen (FIG. 2B). There was no significant difference between the numbers of CD33 and CD19 CAR T cells in any organ at either time point. Similar trends were observed for CD4+ T cells, although significance was only reached in the liver and spleen at day 5 and bone marrow at day 18 (FIG. 8A and 8B). Therefore, both CD33 and CD19 CAR T cells had comparably reduced persistence relative to control T cells in vivo. Further, the specificity of the CAR scFv for CD19 or CD33 did not significantly impact in vivo persistence in the setting of an anti-AML response.

It was possible that the differential persistence of CAR and control T cells resulted from effects of tumor recognition or presence. Alternatively, T cell intrinsic differences could have been responsible for their distinct survival. To assess CAR and control T cells in identical environments, equal numbers of CD33-specific CAR T cells and control T cells were co-transferred into NSG mice with or without MOLM-13-CD19 tumors. An approximately 1:1 ratio of transferred CAR to control T cells was maintained in the CD4+ and $CD8^+$ populations. Absolute and relative numbers of CD33 CAR and control T cells were measured 5 days later. Relative cell numbers were normalized to the input ratio of CAR to control T cells for analyses.

Figure 2C:
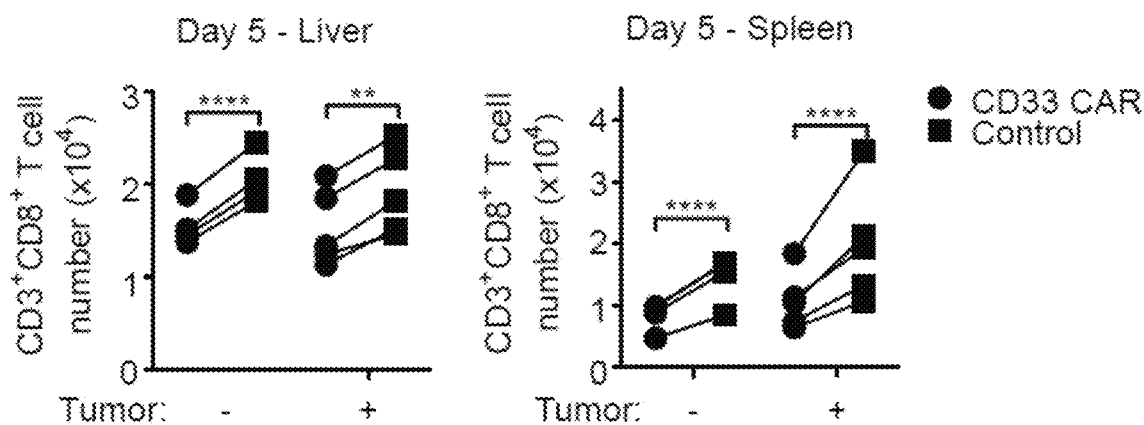
Figure 2D:
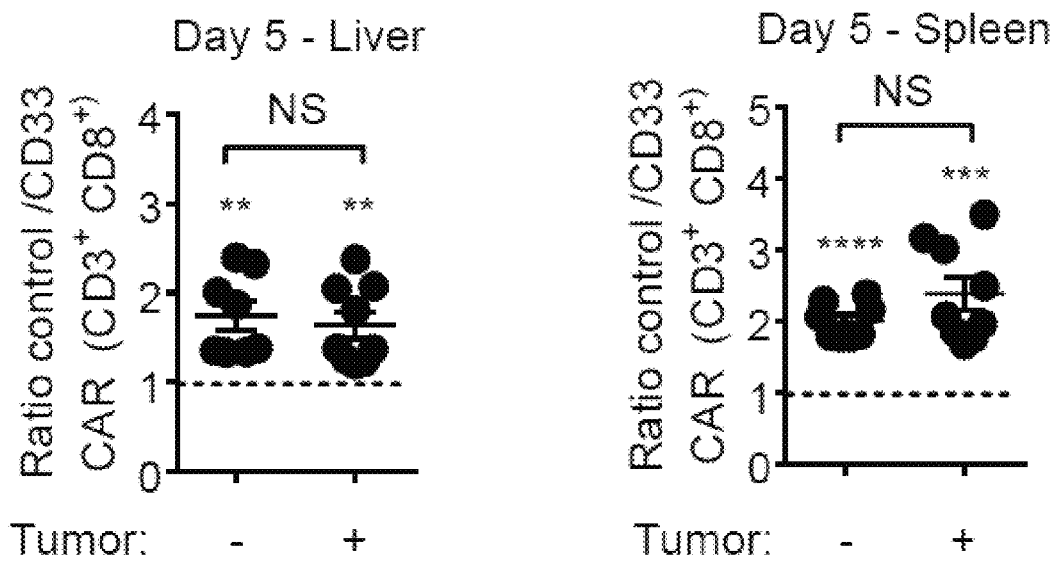

Significantly fewer $CD8^+$ CD33 CAR T cells than $CD8^+$ control T cells were identified in the liver and spleen in these mice. This was true regardless of the presence of tumor (FIG. 2C). Further, the ratio of $CD8^+$ control T cells to CD33 CAR T cells in single mice was not significantly different regardless of the presence of tumor (FIG. 2D). This indicates that tumor did not detectably impact the accelerated attrition of CAR relative to control T cells.

Figure 8C:
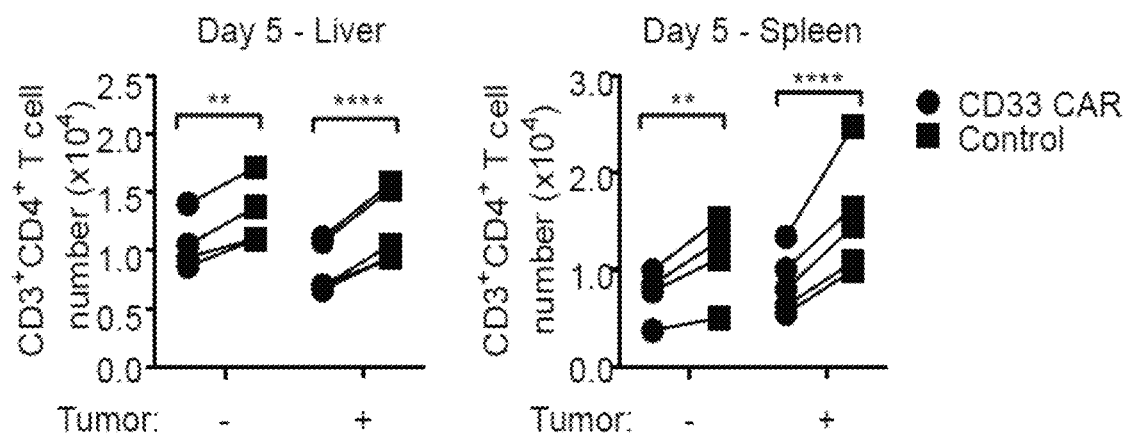
Figure 8D:
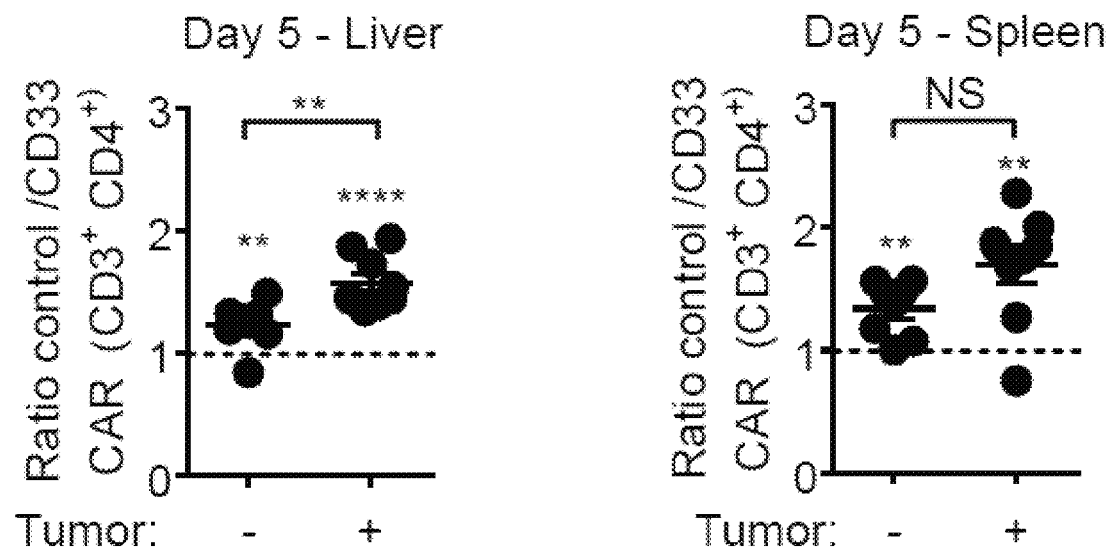

Similarly, fewer CD4+ CD33 CAR T cells than control CD4+ T cells were identified in either the presence or absence of tumor. This led to a ratio of control to CAR CD4+ T cells >1 (FIGS. 8C and 8D). Whereas the ratio of control to CAR $CD8^+$ T cells was similarly elevated regardless of the presence of tumor (FIGS. 2C and 2D), in the case of CD4+ T cells the impact of tumor was less clear. In the liver, the control to CAR T cell ratio was greater in the presence of tumor. A similar trend was seen in the spleen, suggesting a role for tumor in modulating the diminished CD4+ CAR T cell number (FIGS. 8C and 8D). Overall, these data indicate that diminished persistence of CD33 CAR T cells in vivo is largely tumor-independent, though tumor effects may be superimposed on this.

Ex vivo tonic CAR signaling promotes T cell activation and differentiation

The CAR and control T cells were stimulated pre-transfer with mitogen in the absence of cognate CD33 ligand. Hence these populations should be identical unless CAR expression in itself modulated T cell differentiation. To better define this, the inventors measured the percent and total number of $CD45RA^+$ $CCR7^+$ naïve T cell ($T_N$), $CD45RA^-$ $CCR7^+$ central memory T cell ($T_{CM}$), $CD45RA^-$ $CCR7^-$ effector memory T cell ($T_{EM}$), and $CD45RA^+$ $CCR7^-$ effector T cell ($T_{EFF}$) subsets, as well as $CD62L^+CCR7^+$ $CD45RA^+CD45RO^-CD95^+$ stem memory T cells ($T_{SCM}$) in the ex vivo activated populations. CD45RA, CCR7, CD62L and CD45RO expression levels were also determined (23).

Figure 3A:
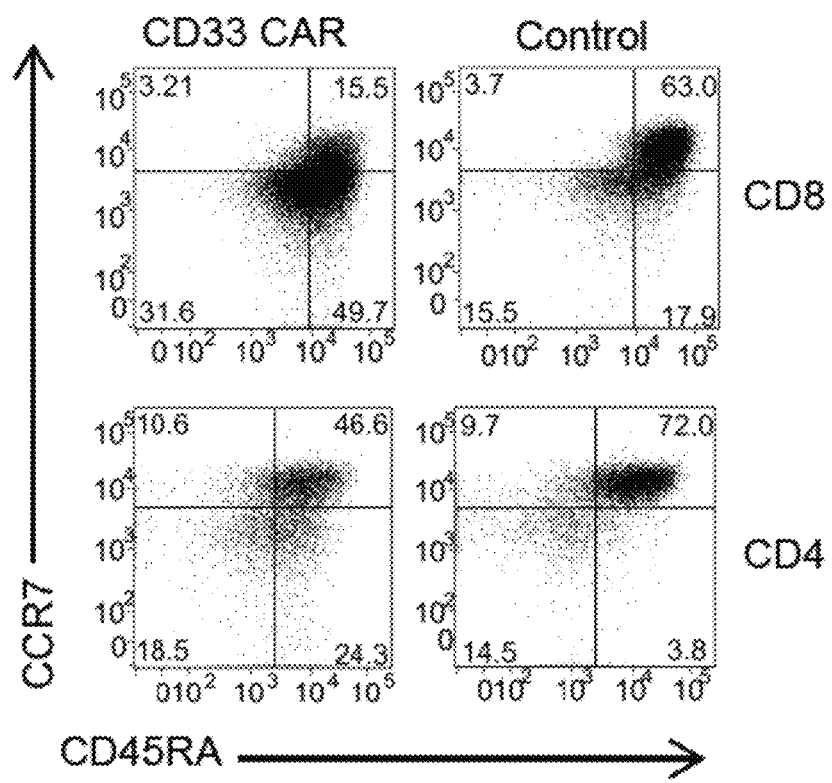
(FIG. 3A) Representative dot plots and summary data for the composition of CCR7+CD45RA+ ($T_N$), CCR7+ CD45RA− ($T_{CM}$), CCR7− CD45RA− ($T_{EM}$) and CCR7−CD45RA+($T_{EFF}$) CD8+ T cell subsets 6 and 12 days post-activation.
Figure 3A:
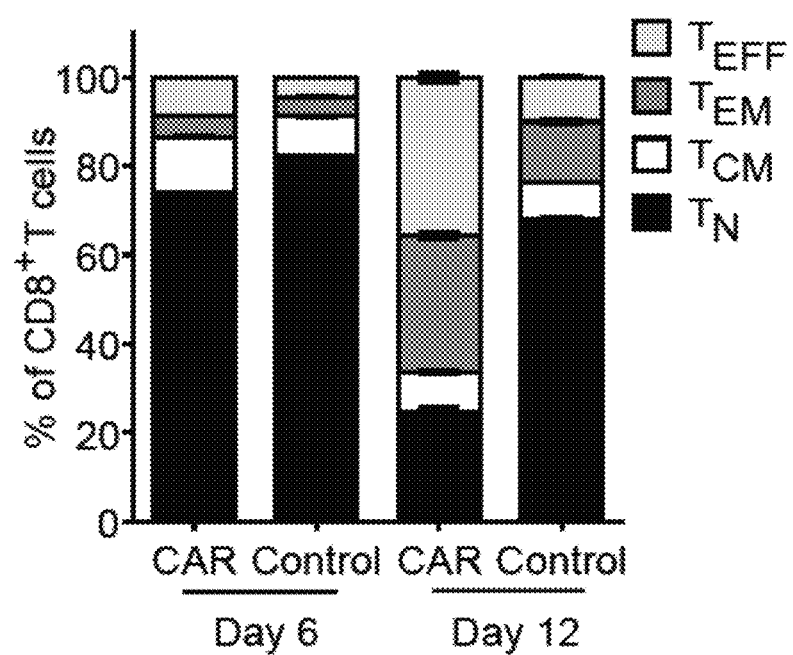
Figure 3B:
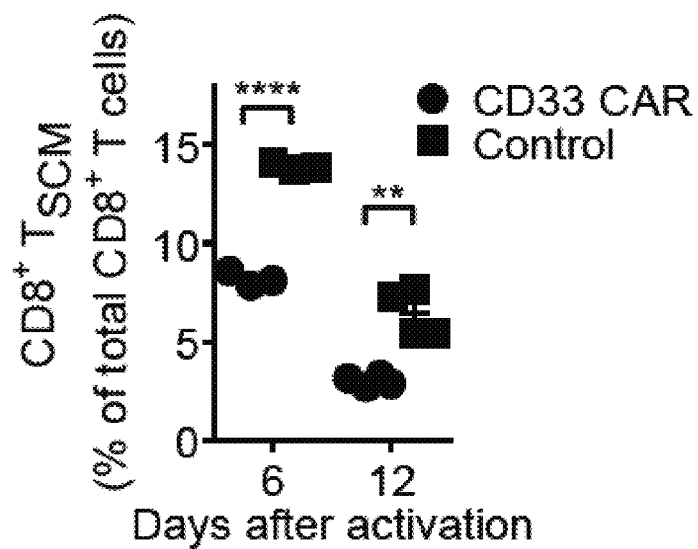
(FIG. 3B) Percent of $T_{SCM}$ cells among CD8+ cells 6 and 12 days activation.
Figure 9A:
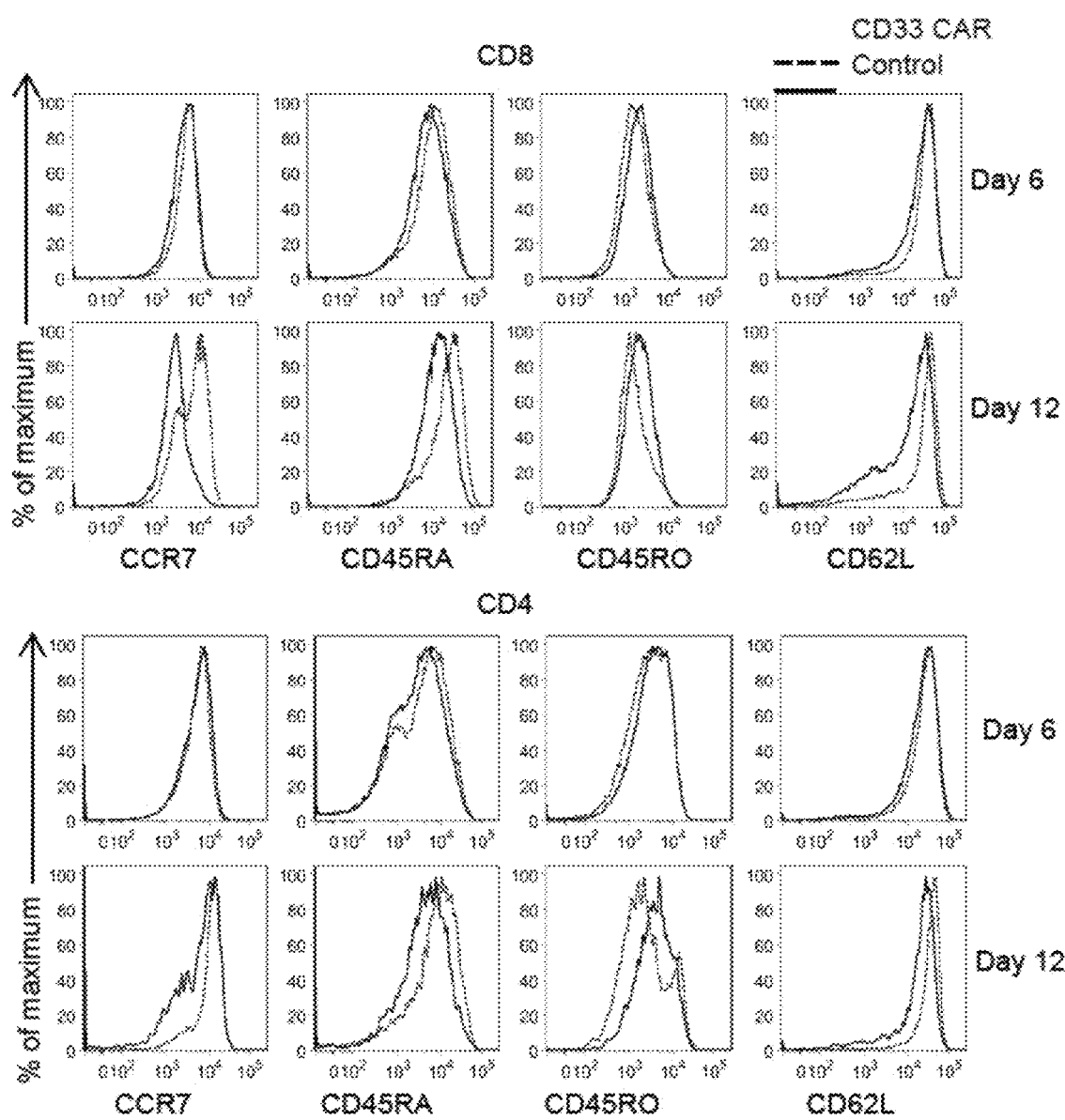
FIG. 9A-9E.
Figure 9B:
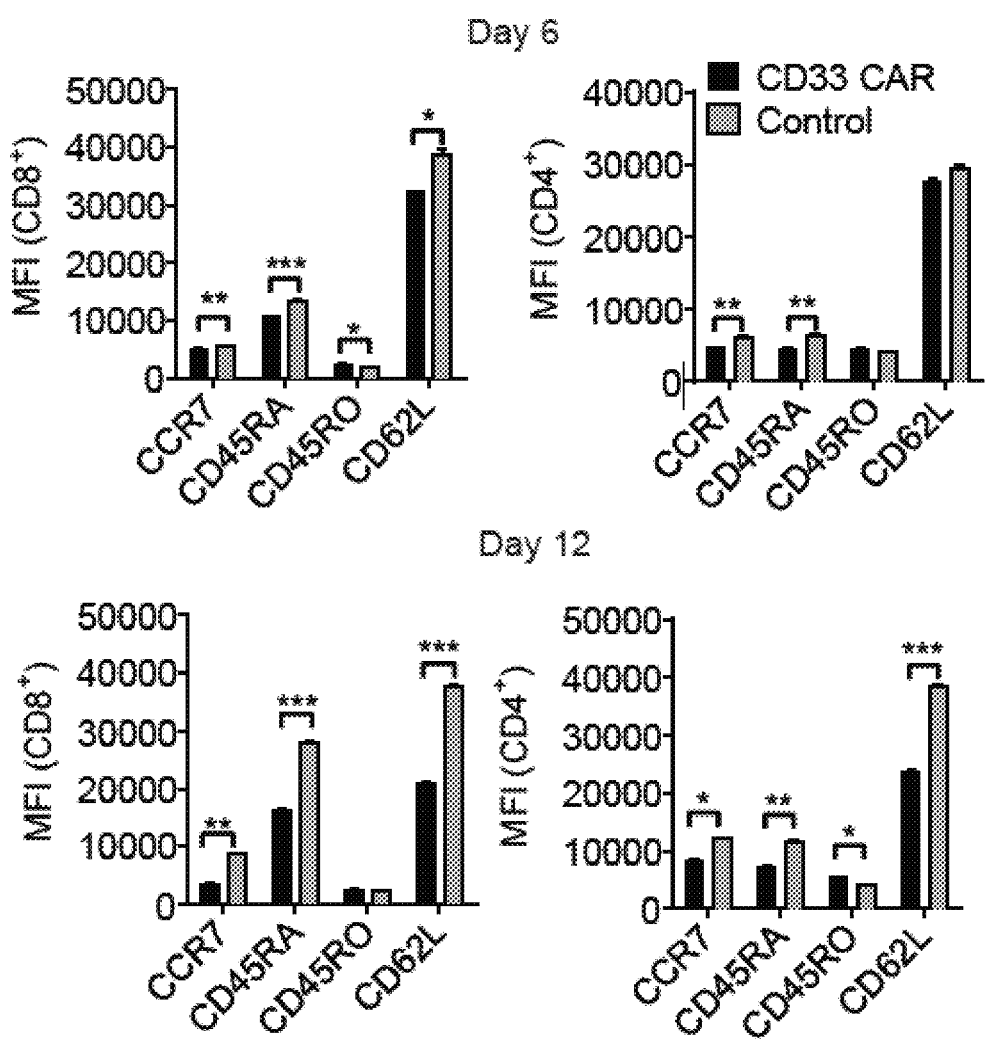
Figure 9C:
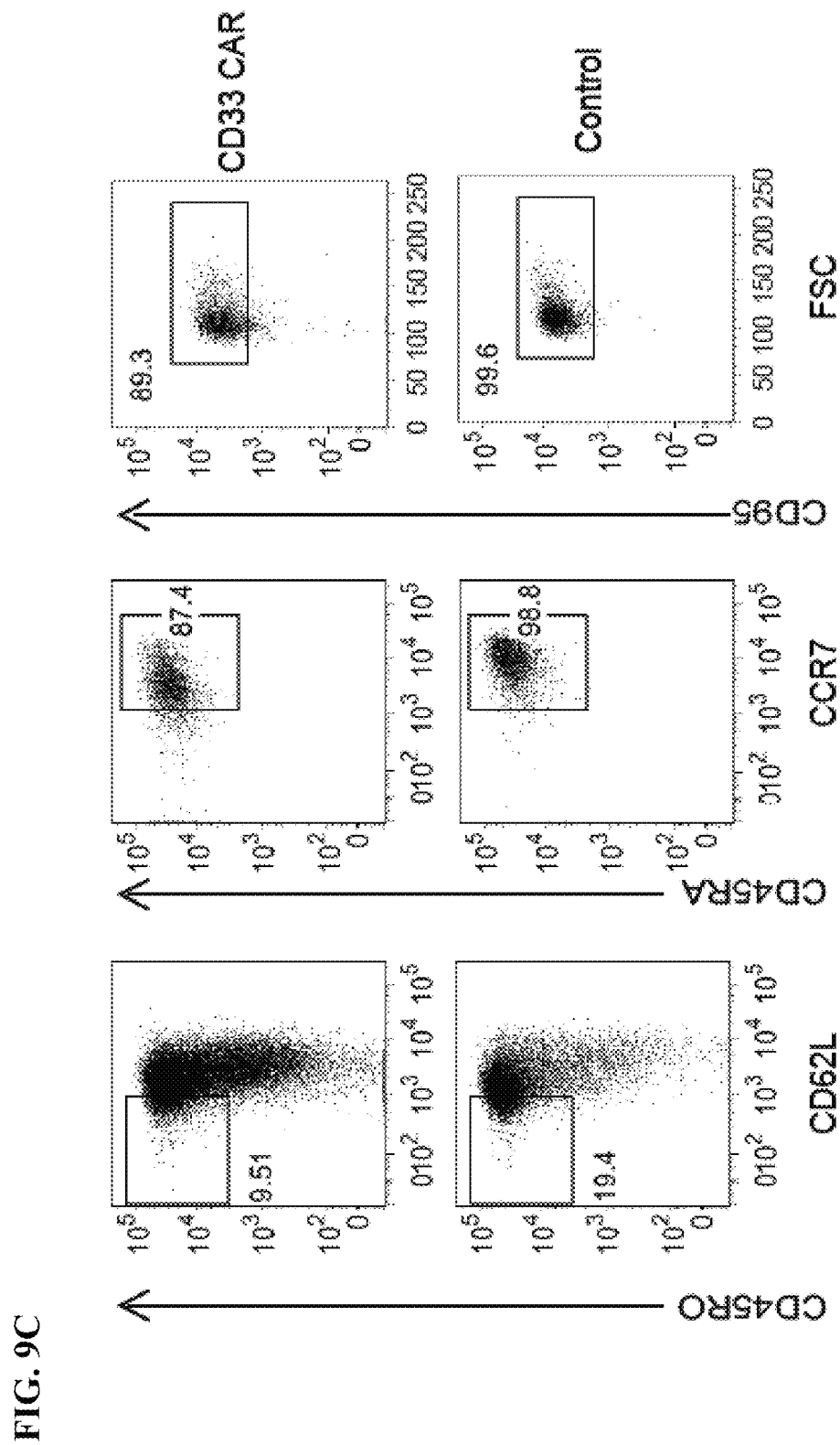
Figure 9D:
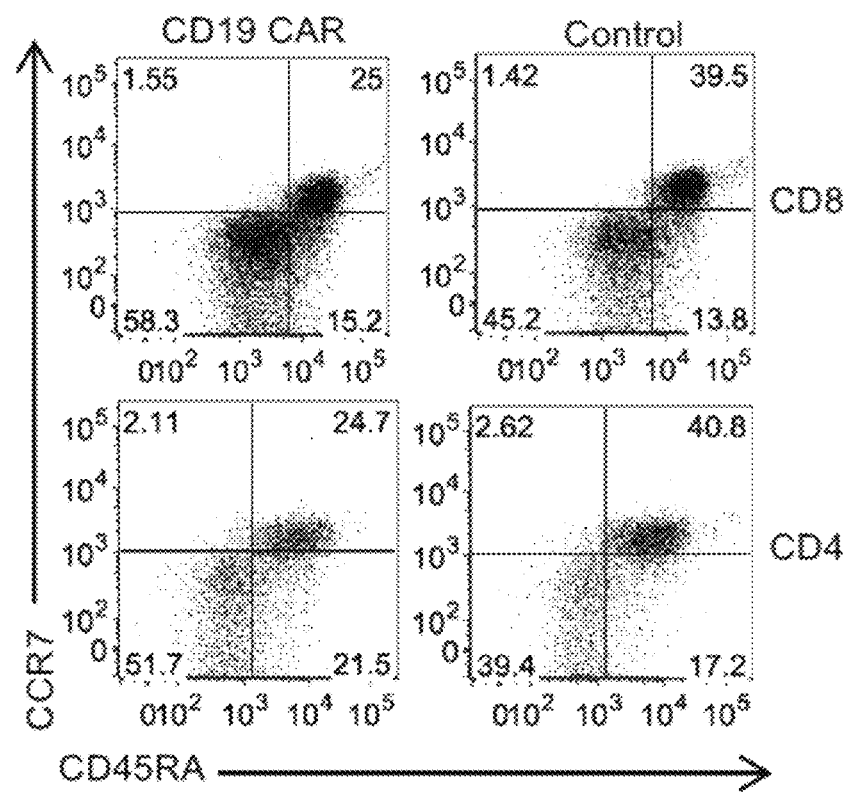
Figure 9D:
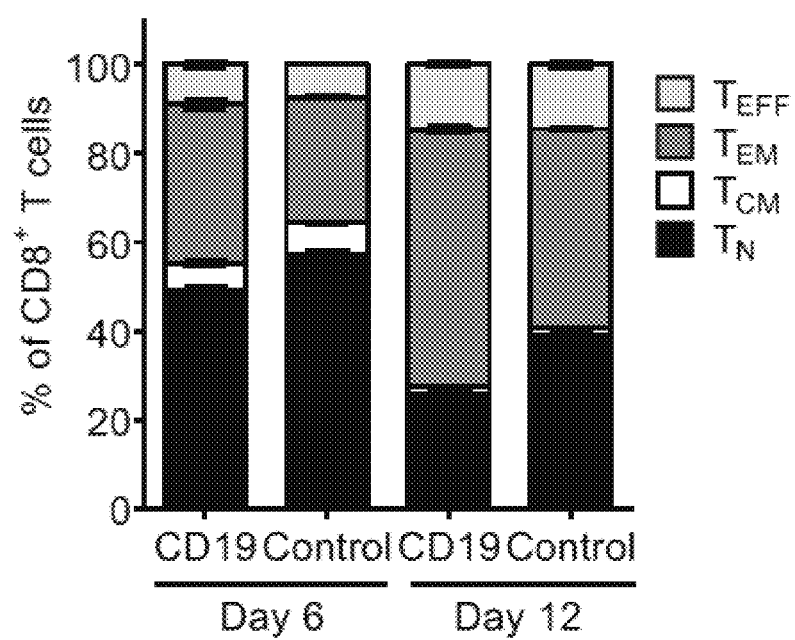
Figure 9E:
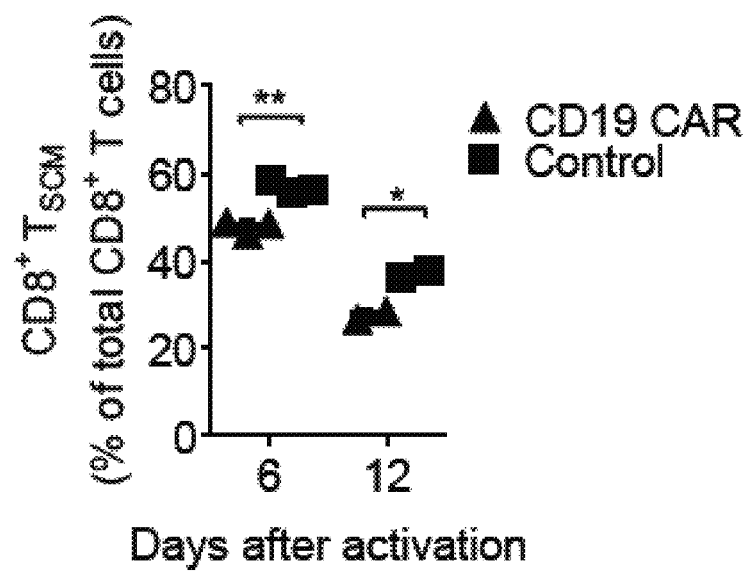

By day 6 post-stimulation (i.e., day 5 after transduction), purified cells transduced with CD33 CAR showed subtle but significant decreases in expression levels of CD45RA, CCR7 and CD62L, and a trend toward a small increase in CD45RO expression, relative to control T cells in both $CD8^+$ and $CD4^+$ subsets (FIGS. 9A and 9B). These differences were accentuated at day 12. On average, over 60% of the control $CD8^+$ T cells bore a CCR7+CD45RA+ $T_N$ phenotype at day 12, compared to 24% of CAR T cells (FIG. 3A). Correspondingly, an increased proportion of CD33 CAR T cells differentiated into $CCR7^-CD45RA^+T_{EFF}$ cells and $CCR7^-CD45RA^-$ $T_{EM}$ cells. Moreover, as early as day 6, $CD8^+$ and $CD4^+$ control T cells contained about two-fold more $T_{SCM}$ cells than CD33 CAR T cells (FIG. 3B, FIG. 9C). Skewing of T cell differentiation toward effector phenotypes, and reduction in $T_N$ and $T_{SCM}$ populations during ex vivo expansion was also observed in CD19 CAR T cells (FIGS. 9D and 9E). This indicates that CD33 and CD19 CAR T cells stimulated in the absence of cognate ligand are less able to form long-lived stem memory cells relative to control T cells, and increasingly differentiate into shorter-lived effector forms. Given the similarly altered in vivo persistence and differentiation phenotype in CD33 and CD19 CAR T cells, the inventors focused further experiments on CD33 CAR.

Figure 3C:
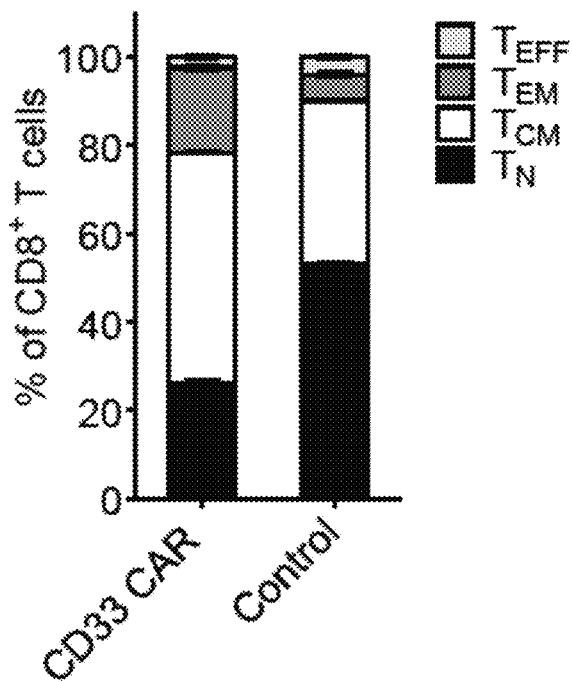
(FIG. 3C-3D) Nave CD8+CD45RA+CD45RO−CCR7+CD95− T cells were sorted from donor samples and transduced with CD33 CAR or control vector.
Figure 3D:
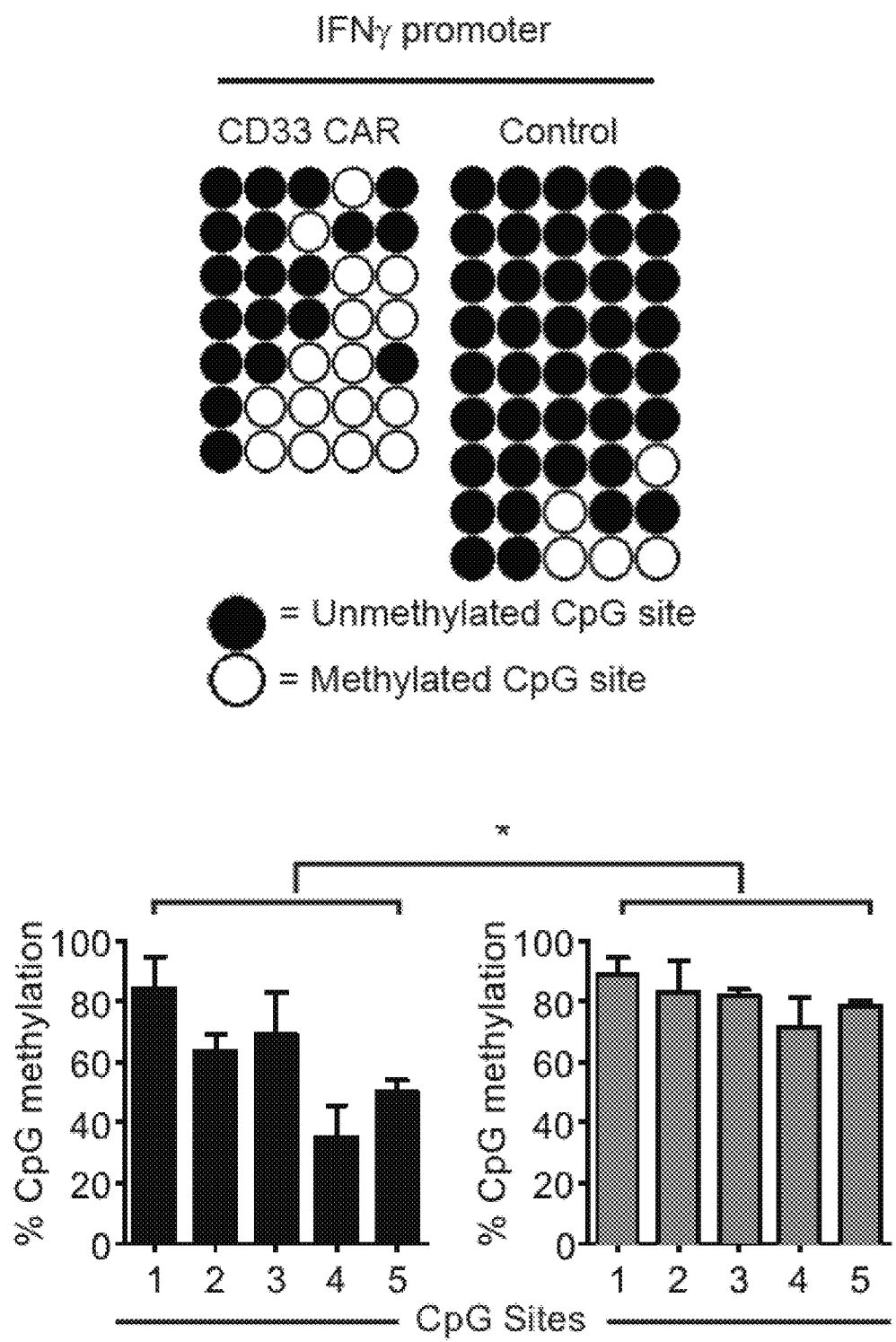

It was possible that use of bulk T cells for CAR and control transductions influenced the observed differences in post-transduction T cell subsets, and thus naive $CD8^+$ $CD45RA^+$ $CD45RO^-$ $CCR7^+$ $CD95^-$ T cells were sorted prior to transduction with CD33 CAR or control vector. Again, a significant reduction in the $T_N$ subset and corresponding increase in the $T_{EM}$ population was observed, indicating that even purified naive T cells transduced with CAR exhibit altered differentiation, relative to control cells (FIG. 3C). To confirm the enhanced effector-like phenotype of CD33 CAR T cells, the IFNγ locus of $CD8^+$ CAR and control T cells was assessed by bisulfate sequencing. The methylation profile of five CpG sites within this locus are highly dependent on differentiation status, being highly methylated in $T_N$ cells, and almost completely demethylated in $T_{SCM}$, $T_{CM}$, and $T_{EM}$ cells (Abdelsamed et. al., J. Exp. Med., in press). Control T cells were more highly methylated at the IFNγ CpG sites, whereas the CD33 CAR T cells were more demethylated indicating that CD33 CAR T cells are less likely to maintain a naive phenotype and more readily differentiate into short-lived effector cells, supporting flow cytometric phenotyping results (FIG. 3D).

Figure 3E:
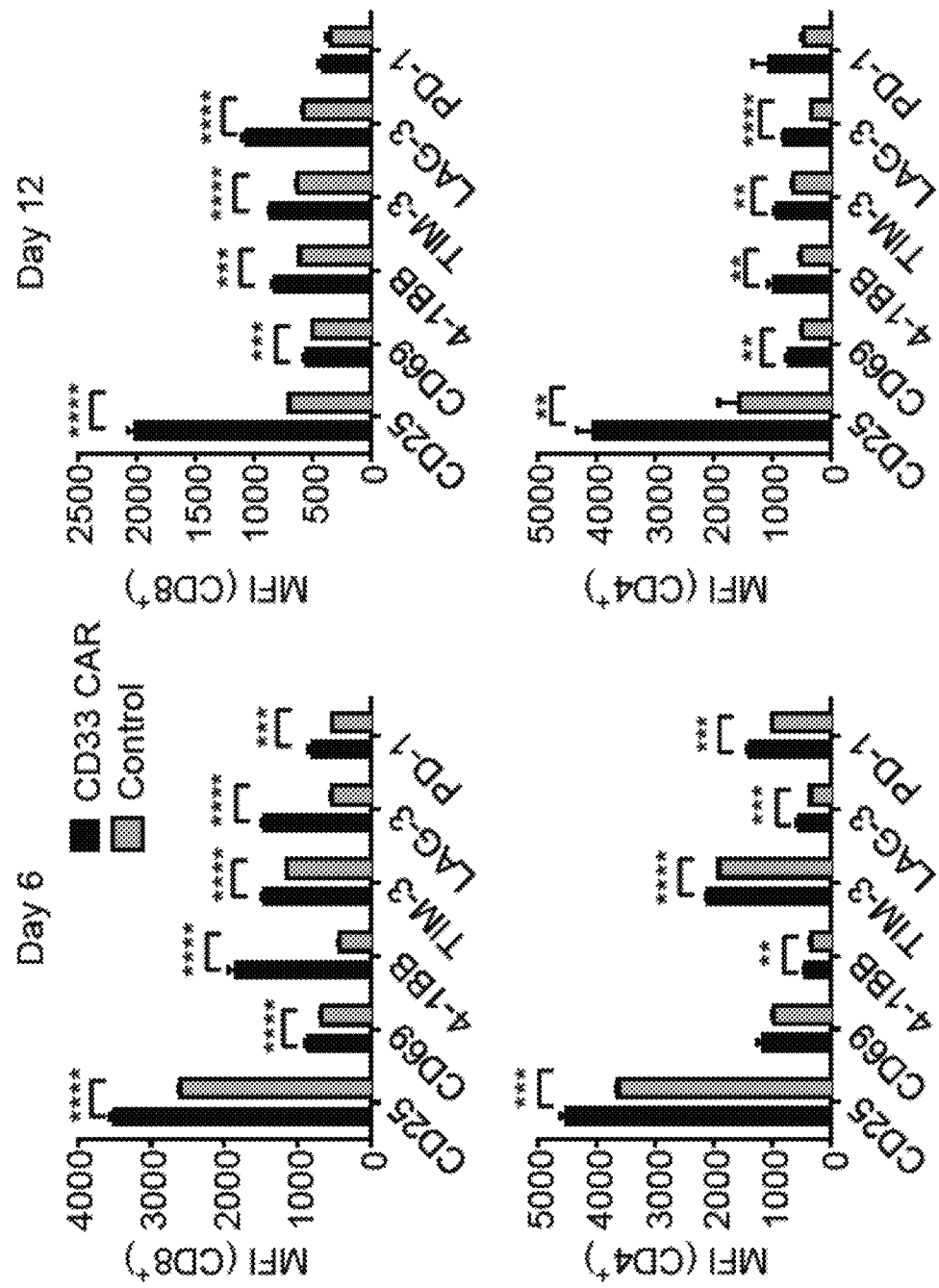
(FIG. 3E) Activation and exhaustion marker expression on CD8+ (top) and CD4+ (bottom) T cells 6 days (left) and 12 days (right) after activation.
Figure 3F:
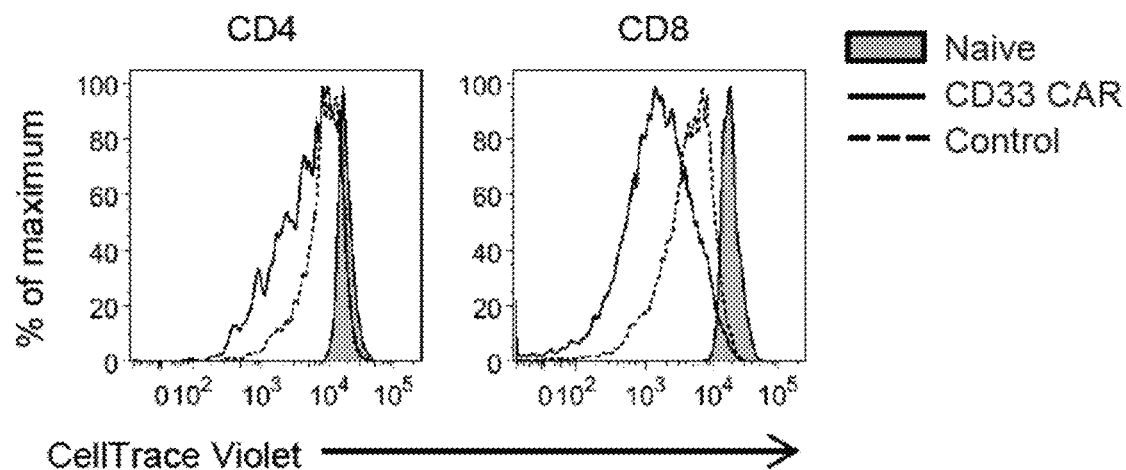
(FIG. 3F) Proliferation of CD33 CAR and control T cells. Cells were labeled with CellTrace Violet 5 days after initial activation and cultured with IL-2 for 4 additional days. Histograms show naive T cells (shaded), CD33 CAR T cells (solid line), and control T cells (dashed line).
Figure 3G:
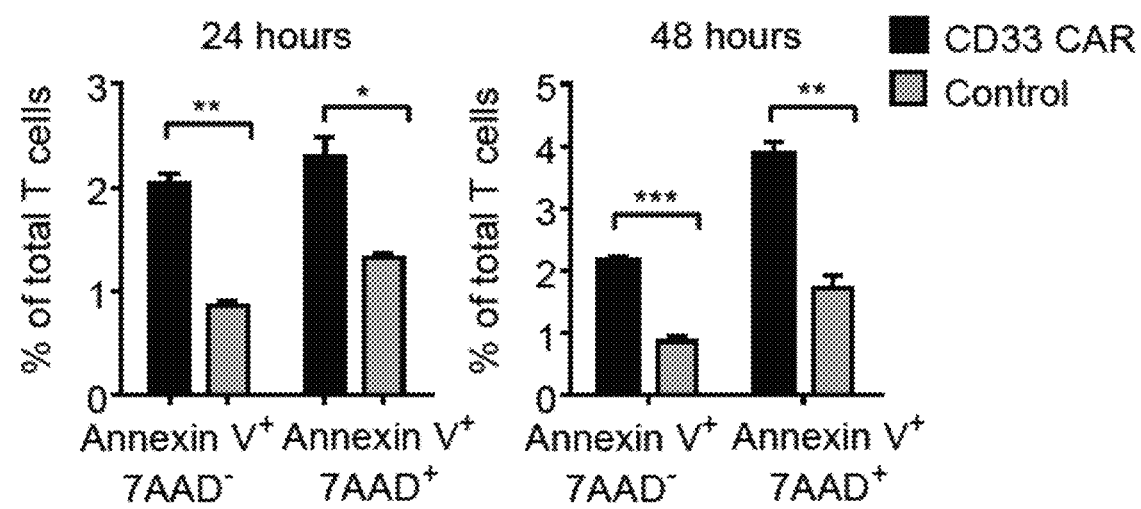
(FIG. 3G) Quantification of early and late apoptosis in CD33 CAR and vector-control T cells isolated at day 12 and recultured for the indicated time.
Figure 3H:
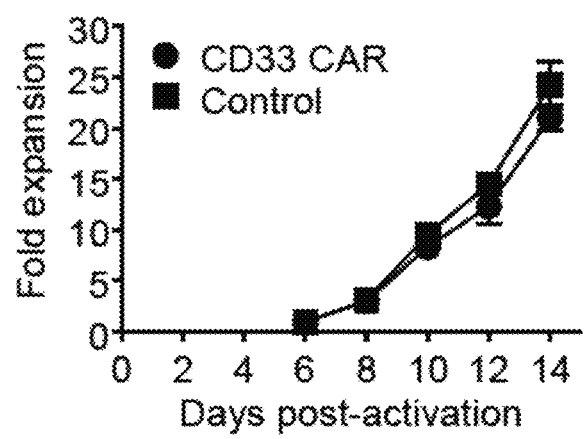
(FIG. 3H) Expansion of CD33 CAR and control T cells during ex vivo culture for 14 days.
Figure 10A:
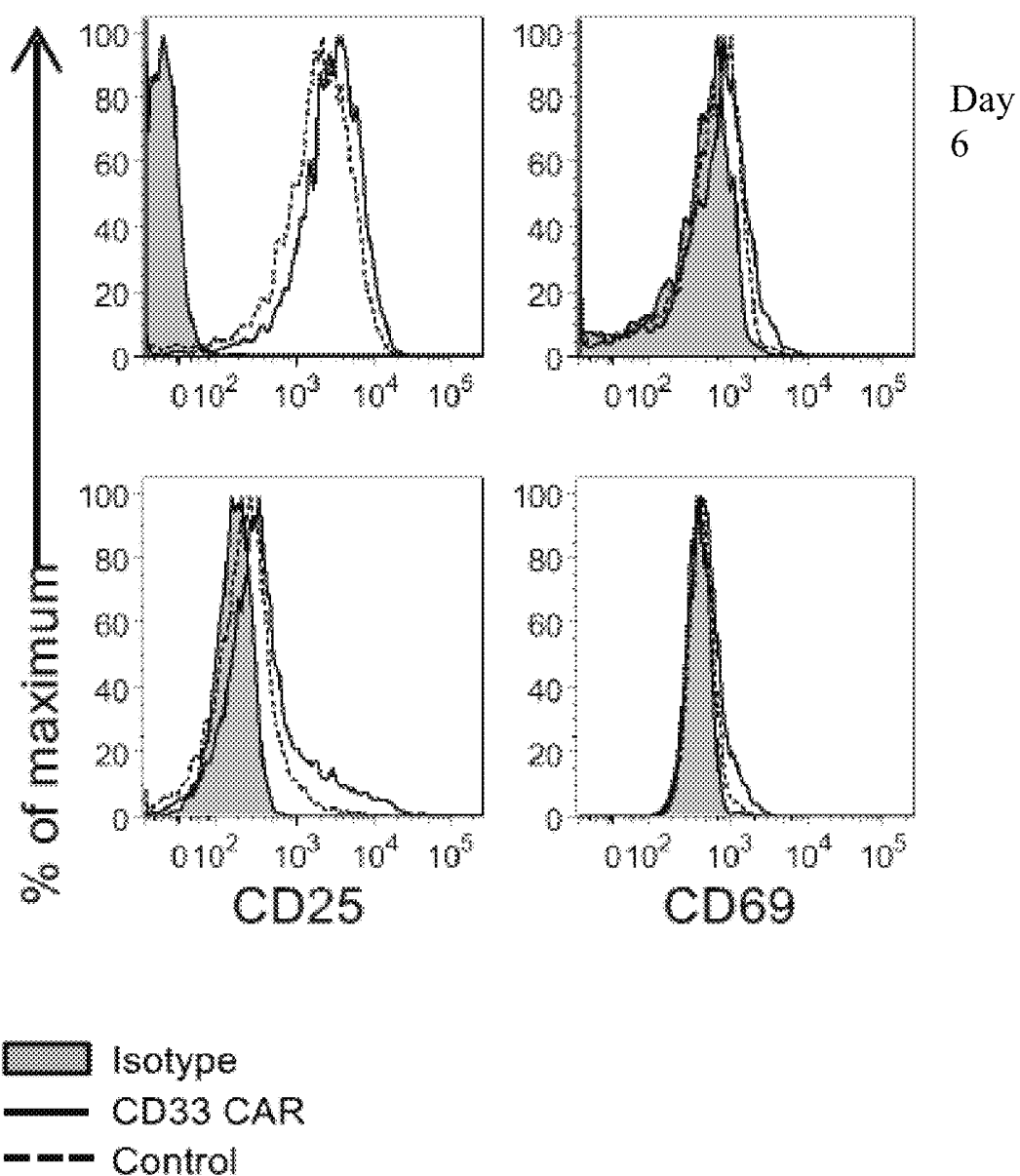
FIG. 10A-10D.
Figure 10A:
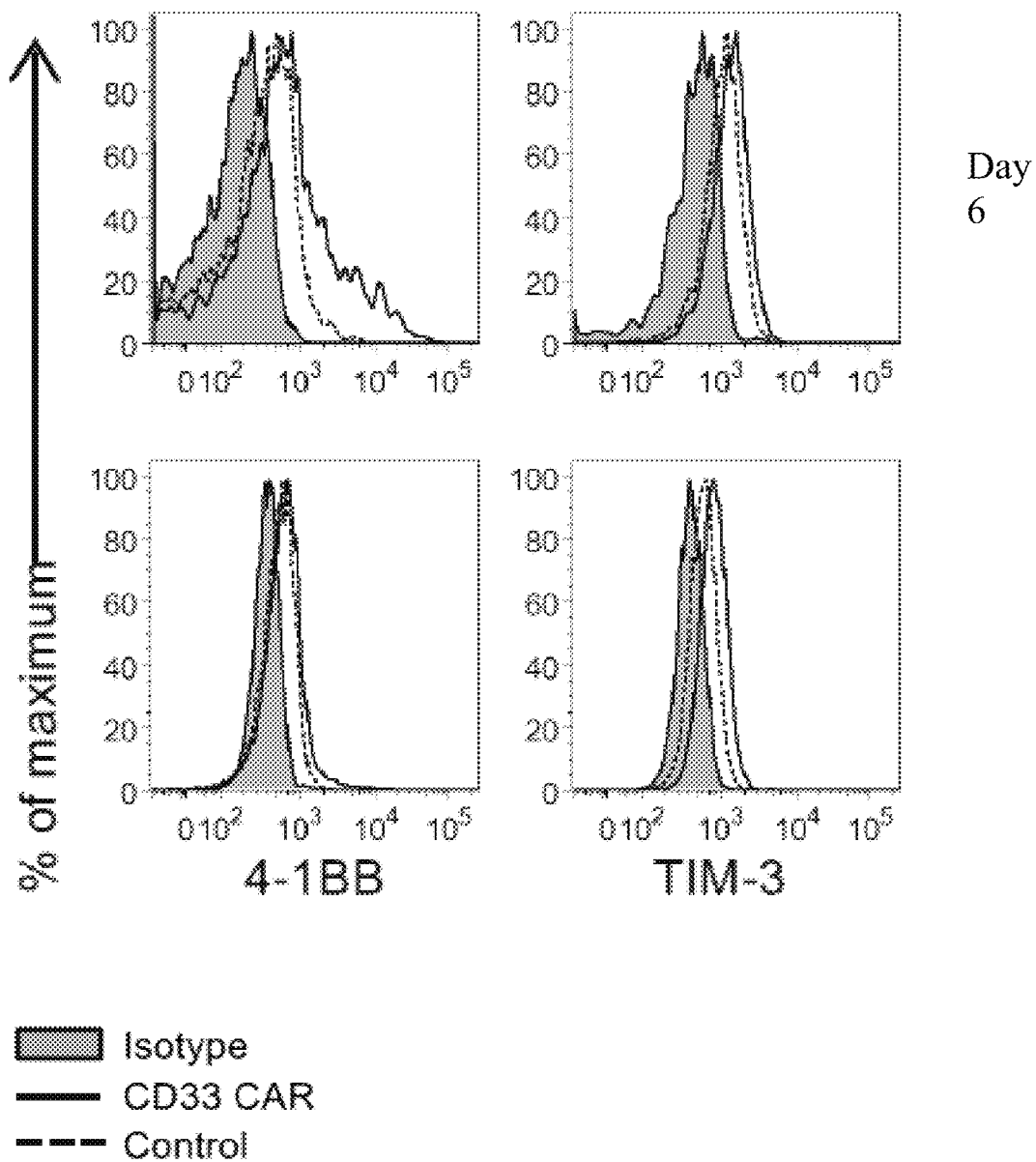
Figure 10A:
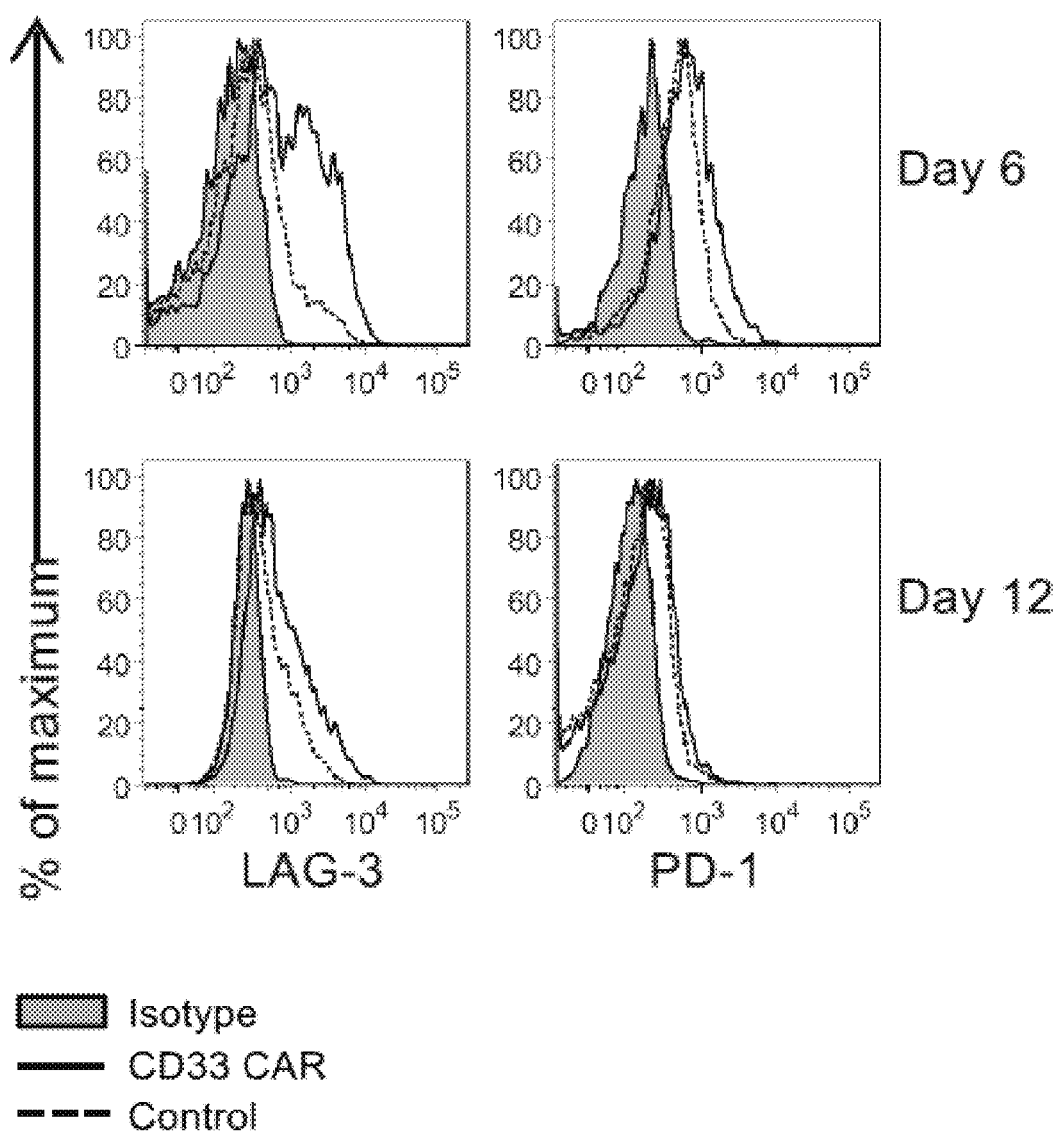

Both $CD8^+$ and CD4+ CD33 CAR T cells demonstrated increased expression of activation markers CD25, CD69, and 4-1BB, as well as exhaustion markers TIM-3, LAG-3, and PD-1, relative to control T cells at 6 and 12 days post-activation (FIG. 3E and FIG. 10A). Consistent with these changes, CD33 CAR T cells proliferated more strongly than control cells in the presence of IL-2 (FIG. 3F). They also showed elevated frequencies of early and late apoptosis (FIG. 3G). The increase in ex vivo proliferation and cell death of CAR relative to control T cells was balanced, and the overall expansion of CD33 CAR T cells was similar to that of control T cells (FIG. 3H). Together, these studies demonstrate that purified, mitogen-stimulated CD33 CAR T cells expanded in the absence of cognate antigen demonstrate increased activation and terminal effector differentiation during ex vivo culture compared with control T cells.

Figure 10B:
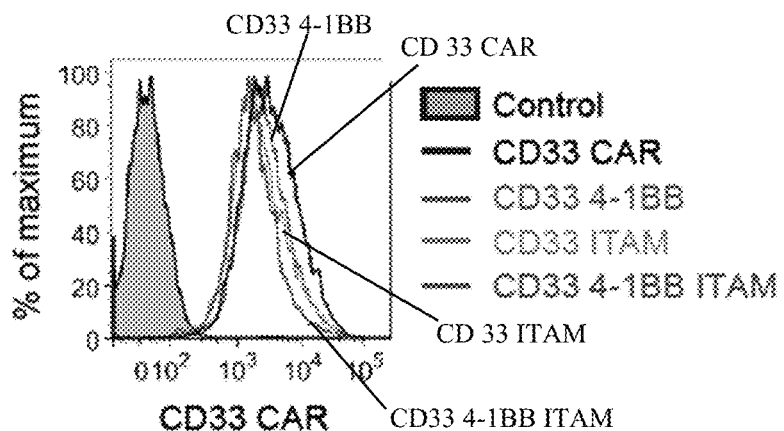

The inventors hypothesized that tonic signaling through the 4-1BB and CD3ζ domains may have influenced CAR T cell differentiation and exhaustion. To test this, the inventors generated CD33 CAR constructs in which the signaling motifs of the 4-1BB costimulatory domain and CD3ζ domain were mutated. Alanine substitutions were made to two acidic amino acid motifs, EED (237-239) and EEE (248-250) of 4-1BB, reported to bind TRAF family members (CD33 41BB) (27, 28). The inventors generated a second construct in which six tyrosine residues of CD3ζ that comprise the 3 ITAMs that bind ZAP70 were substituted with phenylalanine residues (CD33 ITAM) (29). Lastly, both the 4-1BB and CD3ζ domains were mutated (CD33 41BB ITAM). CAR surface expression was similar to that of the original CD33 CAR construct (FIG. 10B).

Figure 3I:
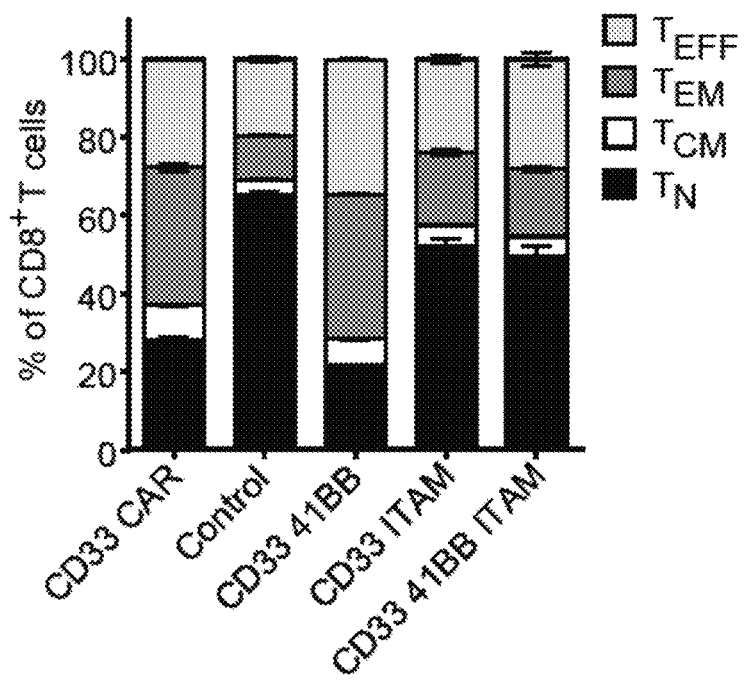
(FIG. 3I) Composition of $T_N$, $T_{CM}$, $T_{EM}$, and $T_{EFF}$ subsets of CD33 41BB, CD33 ITAM, and CD33 41BB ITAM CD8+ CAR T cells relative to CD33 CAR and vector-control T cells 12 days after stimulation. Statistical significance for FIG. 3A, FIG. 3C, and FIG. 3I was determined by two-way ANOVA with Tukey's multiple comparison post-test. Statistical significance for FIG. 3B, FIG. 3E, and FIG. 3G was determined with Holm-Sidak corrected multiple t-tests. All data are representative of 3-5 individual donors and at least 3 individual experiments. * $p<0.05$,  $p<0.01$, * $p<0.001$, **** $p<0.001$.
Figure 10C:
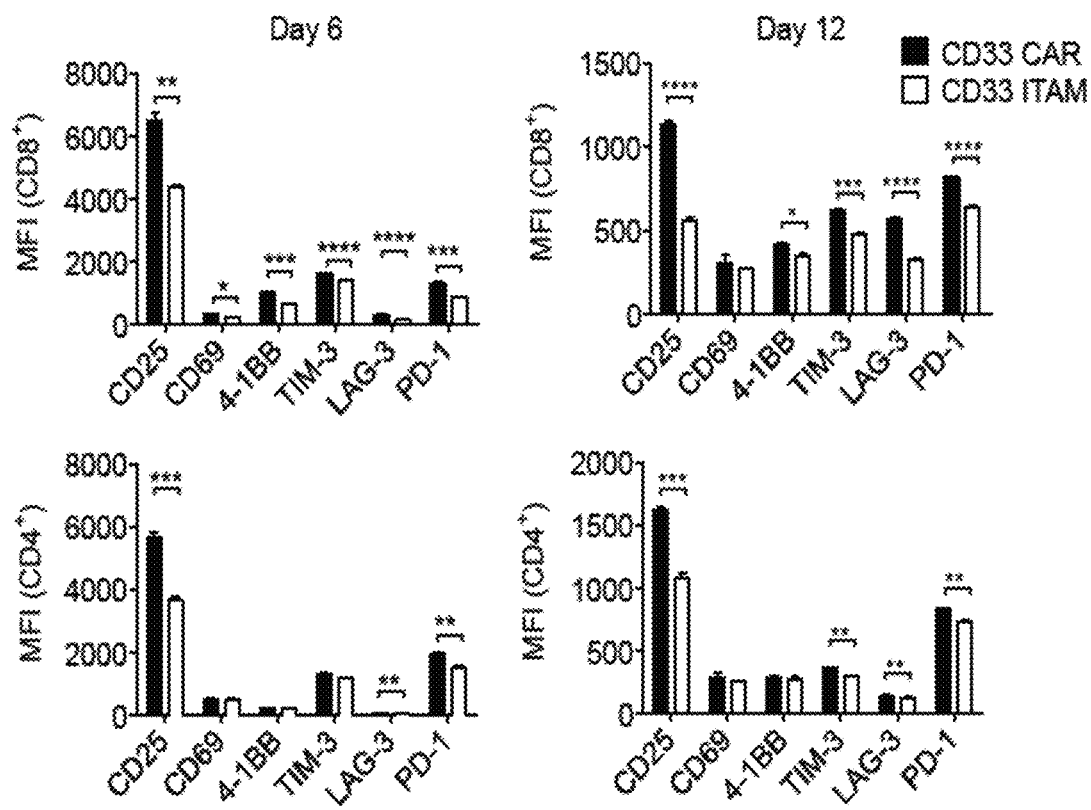
Figure 10D:
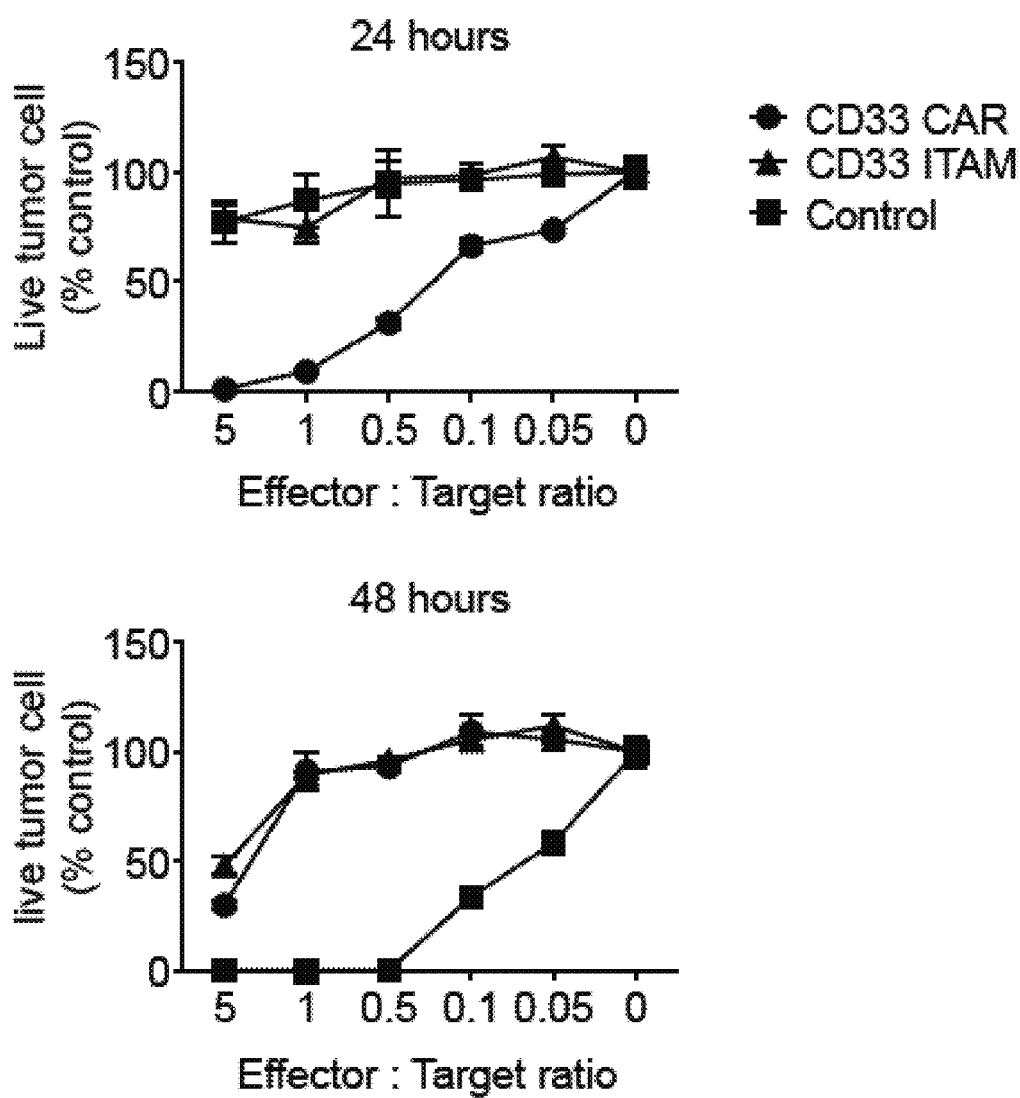

The CD33 ITAM and CD33 41BB ITAM mutants had similar differentiation profiles as control T cells with culture. Each showed a significant increase in the proportion of $T_N$ cells and a decrease in the proportion of TEFF relative to CD33 CAR T cells (FIG. 3I). In contrast, mutation of the 4-1BB signaling domain alone (CD33 41BB) did not impact differentiation status. Expression of activation and exhaustion markers were also reduced in CD33 ITAM mutant T cells, relative to CD33 CAR T cells (FIG. 10C). This indicates that cell intrinsic signaling through the CAR CD3ζ ITAM domains during ex vivo T cell expansion leads to a more activated and effector-differentiated phenotype. Although mutation of critical signaling components of the domain lead to CAR T cells that are phenotypically similar to control T cells, it also resulted in abrogation of CAR T cell activity (FIG. 10D).

Figure 4A:
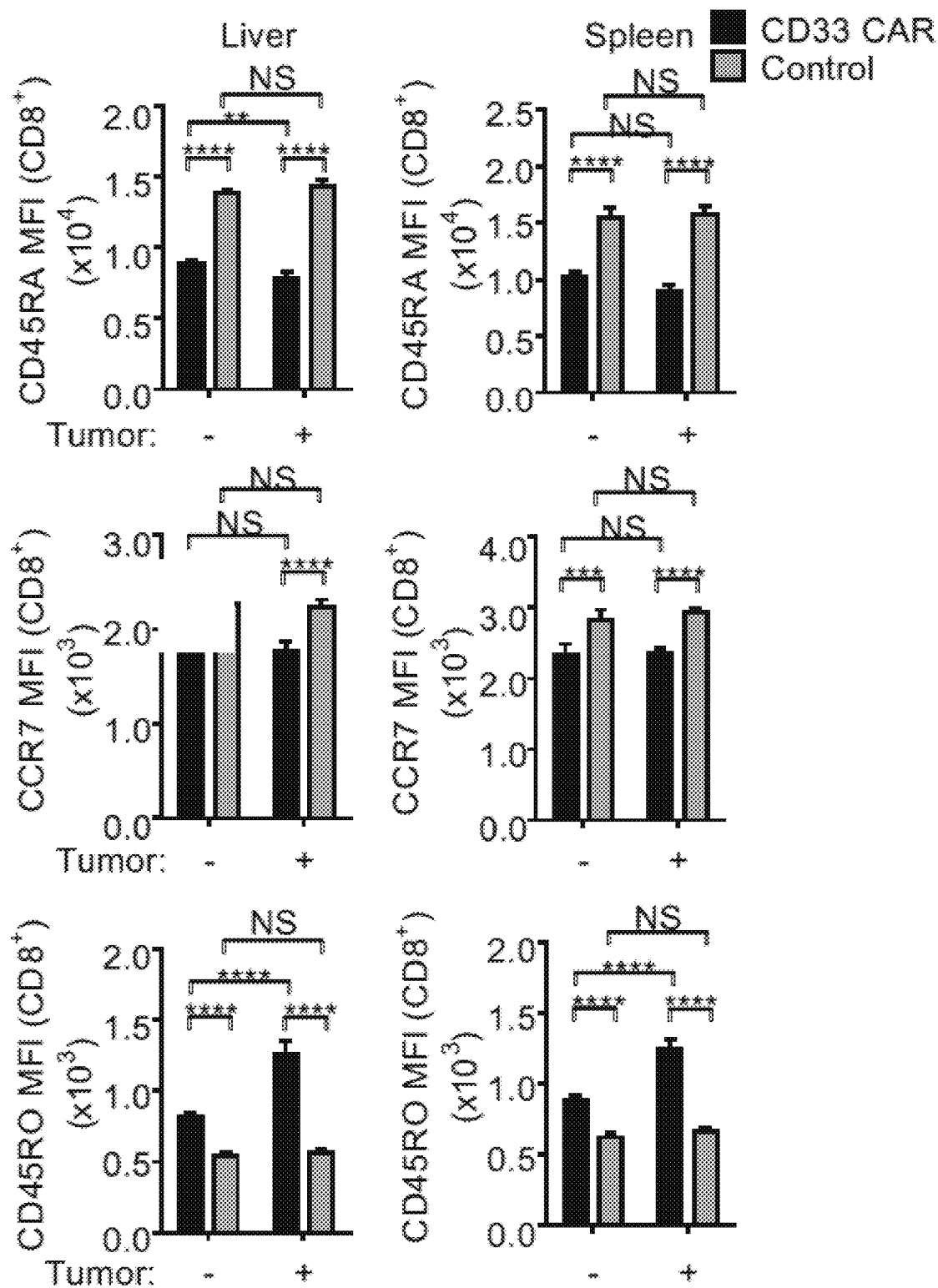
FIG. 4A-4D. Differentiation status of CAR T cells influences cell persistence in vivo.
Figure 4B:
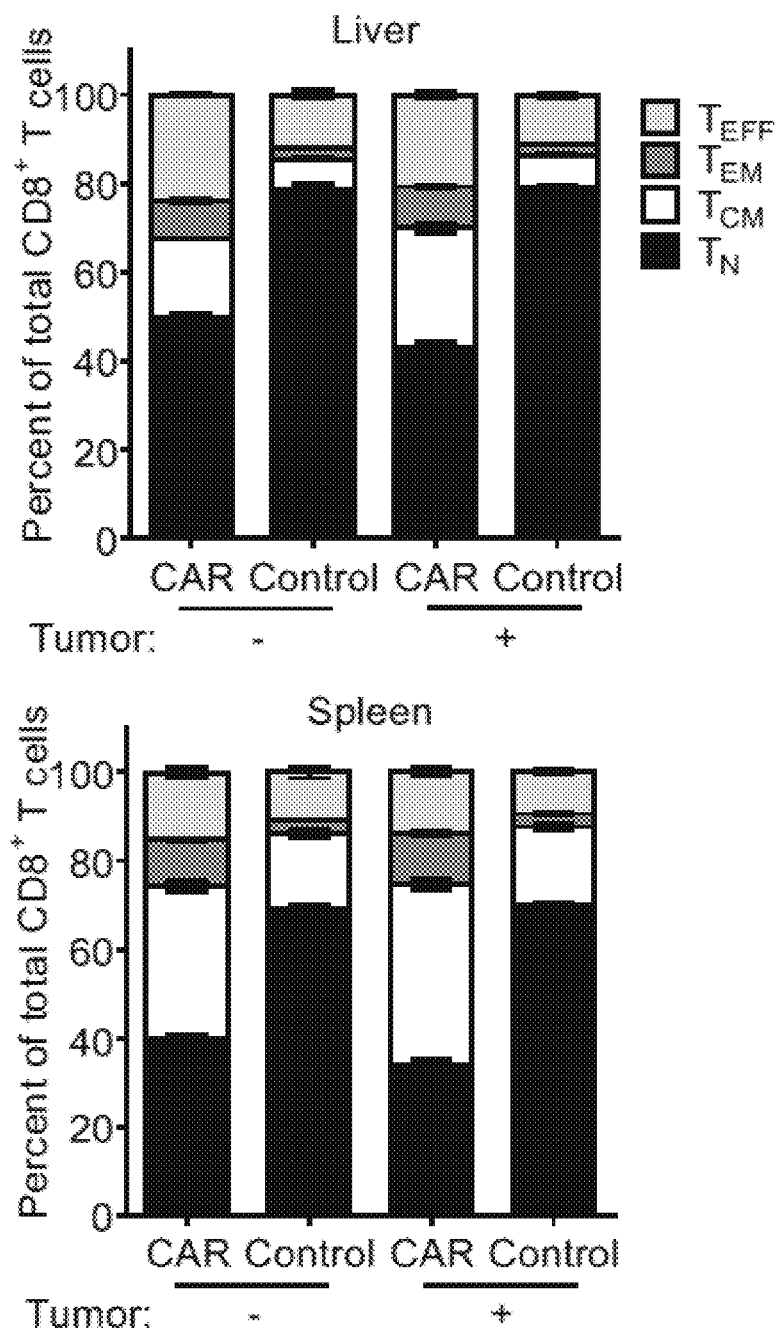
Figure 4C:
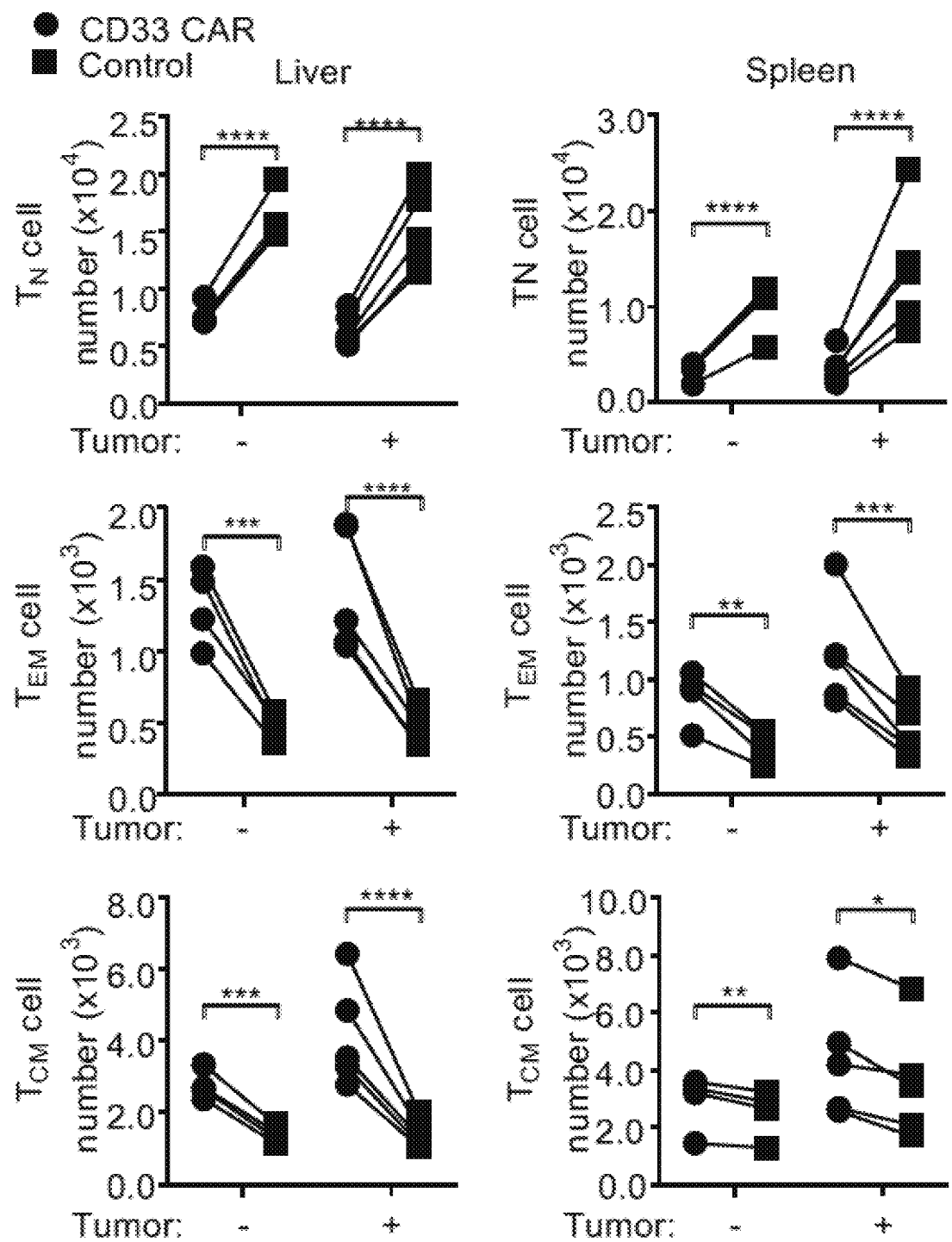
Figure 4C:
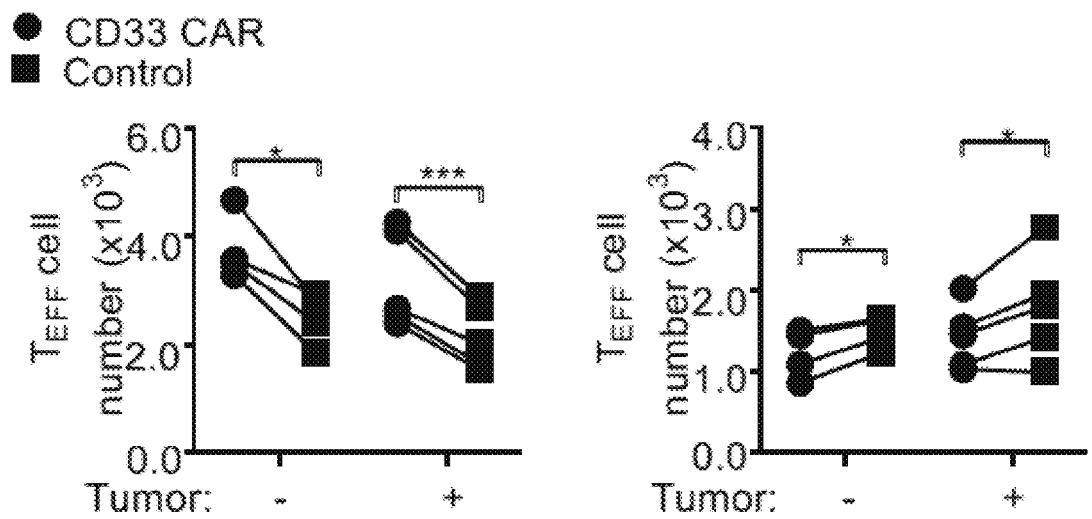
Figure 11A:
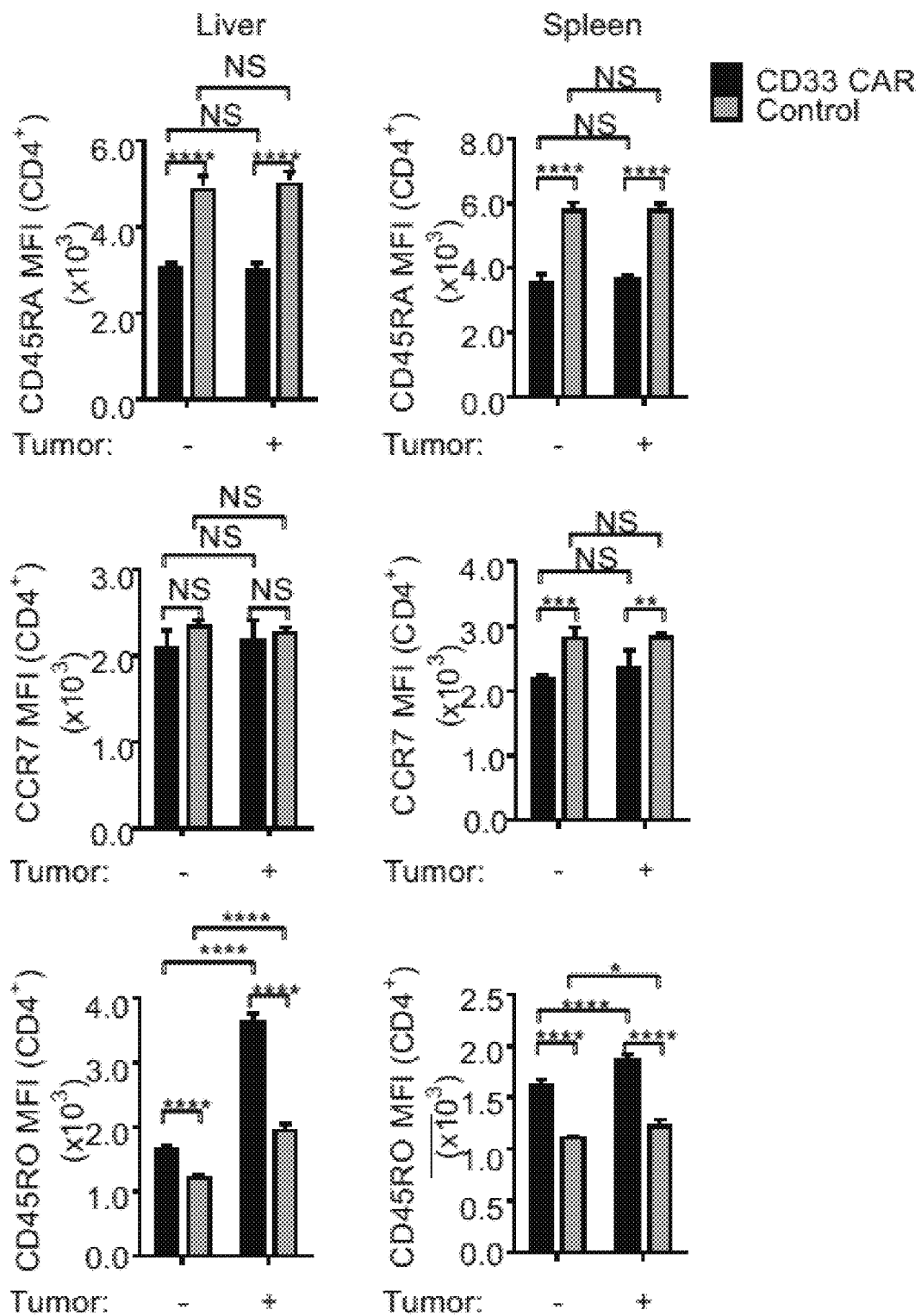
FIG. 11A-11C. CD33 CAR and control T cells were mixed 1:1 and transferred with or without MOLM-13-CD19 cells into NSG mice.
Figure 11B:
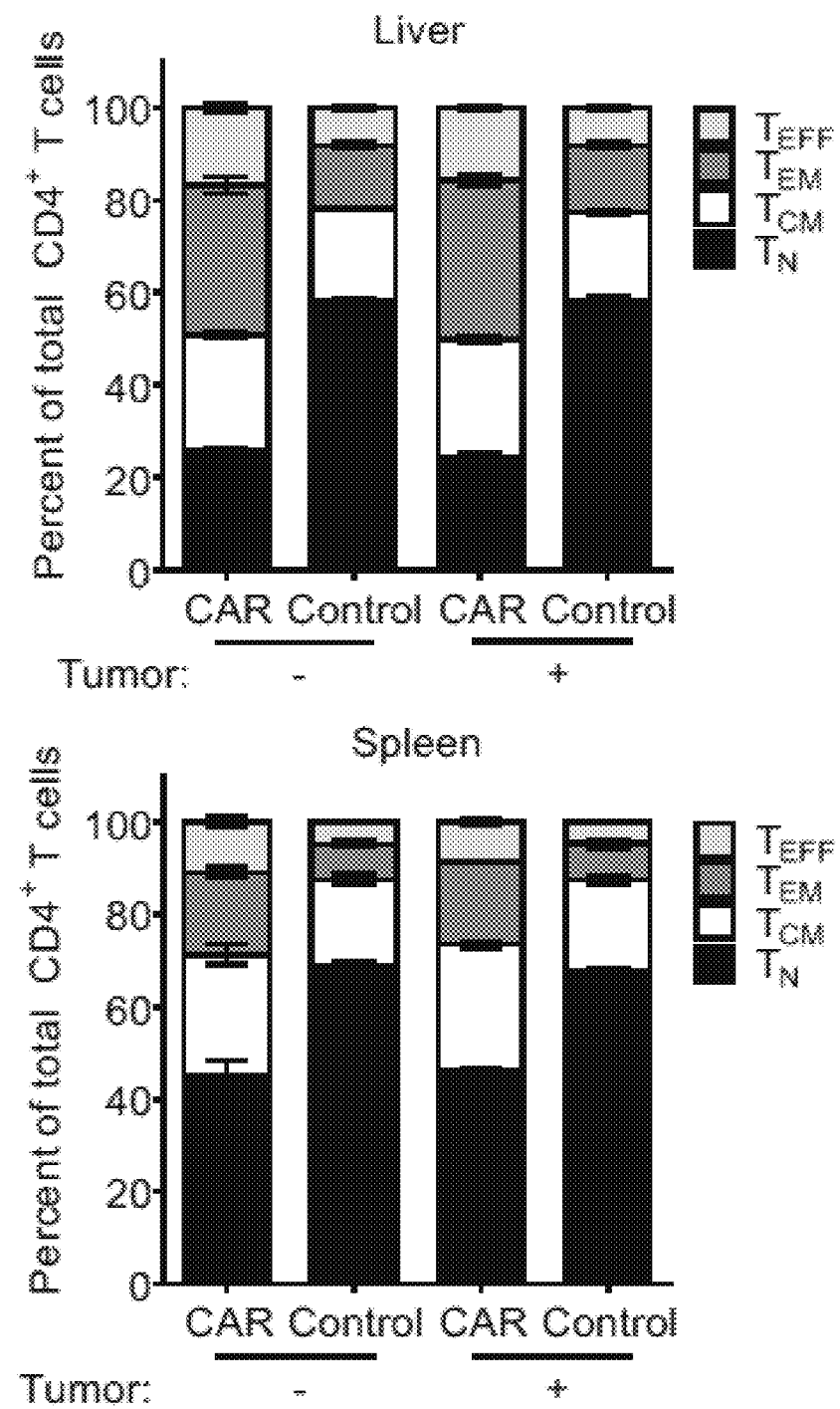
Figure 11C:
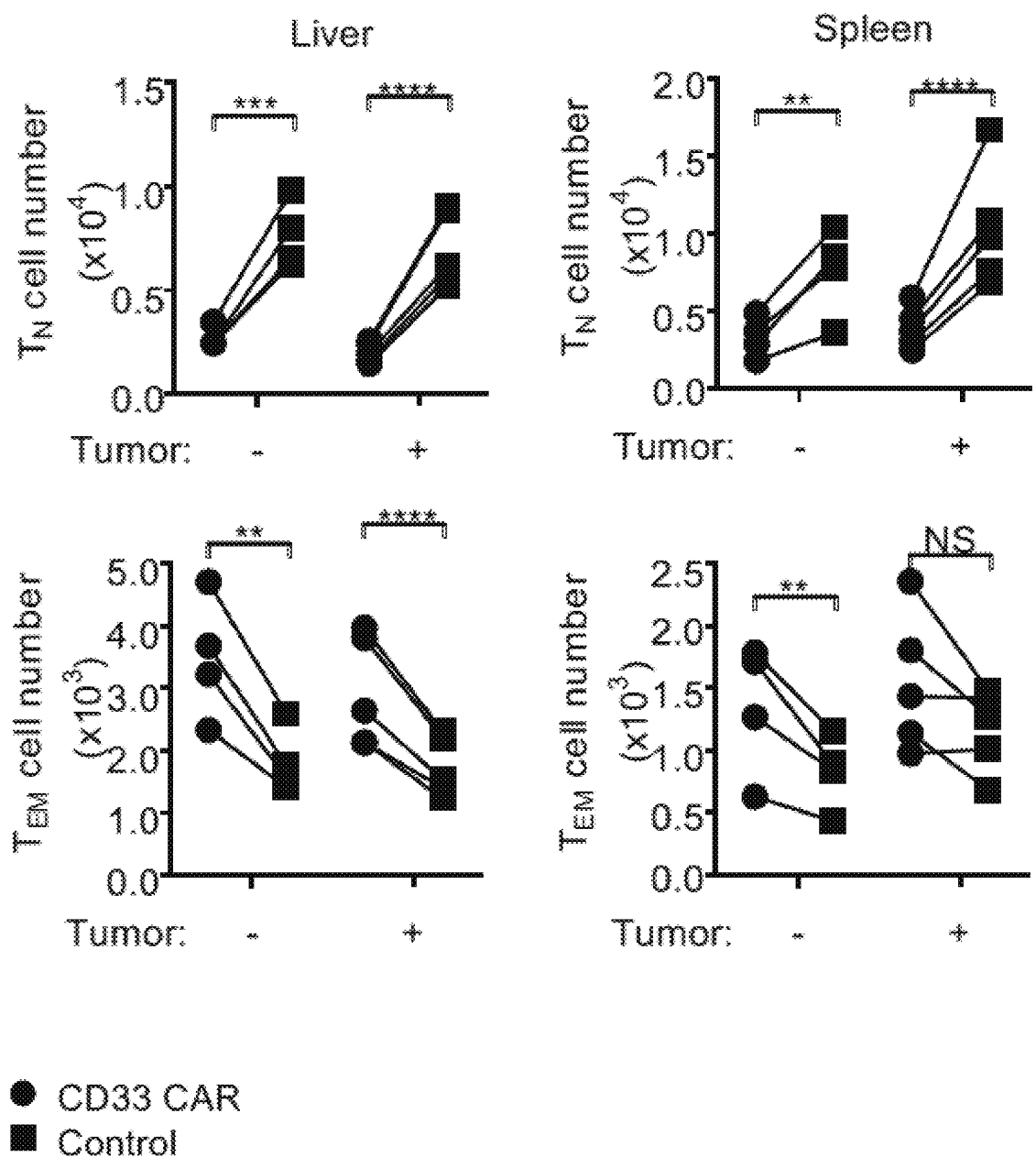
Figure 11C:
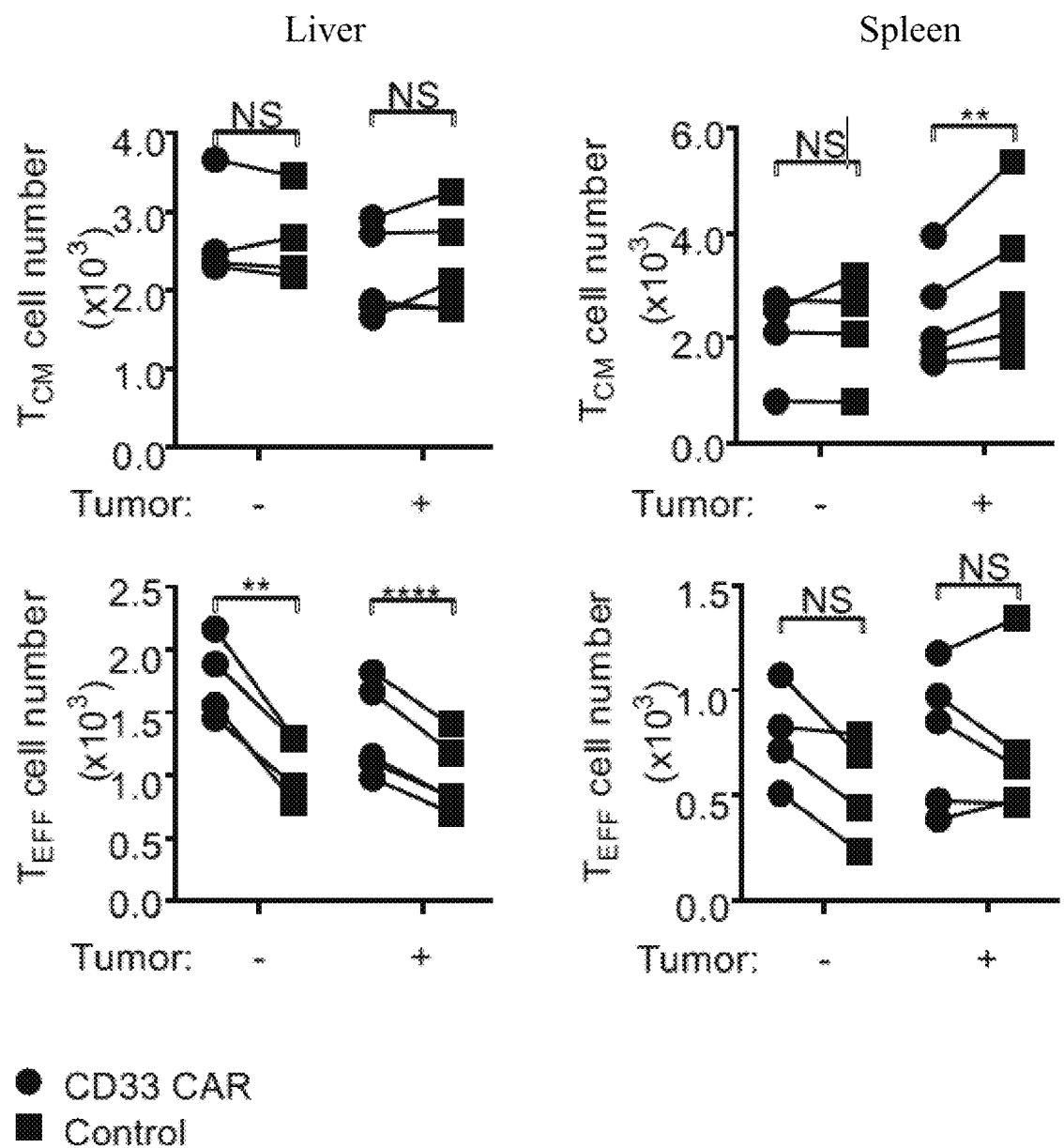

Pre-Transfer Differentiation Of CD33 CAR T Cells Prompts Diminished In Vivo Persistence The inventors next analyzed the differentiation status of the CD33 CAR T cells after co-transfer with control T cells. Studies were performed in the presence or absence of tumor. At day 5 post-transfer, CD8$^+$ CD33 CAR T cells showed significantly lower levels of CD45RA and CCR7, and increased CD45RO relative to control T cells (FIG. 4A). Correspondingly, CD8$^+$ CAR T cells showed elevated frequencies of effector subsets while control T cells maintained an increased percentage of CCR7$^+$CD45RA$^+$ $T_N$ cells (FIG. 4B and FIG. 4C). Similar differences were seen in CD4$^+$ T cells (FIG. 11A-FIG. 11C). Therefore, the perturbed subset proportions observed pre-transfer (ex vivo) are maintained after transfer (in vivo).

Inconsistent and minor differences in the expression of CD45RA and CCR7 on CAR T cell populations in the presence or absence of tumor were observed. In contrast to this variable modulation of CD45RA and CCR7, surface levels of CD45RO on CD8$^+$ and CD4$^+$ CD33 CAR T cells were substantially and consistently increased in the presence of tumor, suggesting specific tumor recognition (FIG. 4A and FIG. 11A) (26). A smaller increase in CD45RO expression on CD4$^+$ control cells in the presence of tumor was seen (FIG. 11A), which may be due in part to tumor recognition by heterogeneous T cells or antigen-non-specific effects of tumor on CD4$^+$ T cell survival or activation state. Increased CD45RO expression was associated with a modest decrease of the $T_N$ subset and more differentiated status of CD33 CAR T cells in the presence of tumor (FIG. 4B). Nevertheless, this impact of tumor was minimal when compared to the larger tumor-independent increase in effector phenotype in CD33 CAR relative to control T cells (FIG. 4B).

Figure 4D:
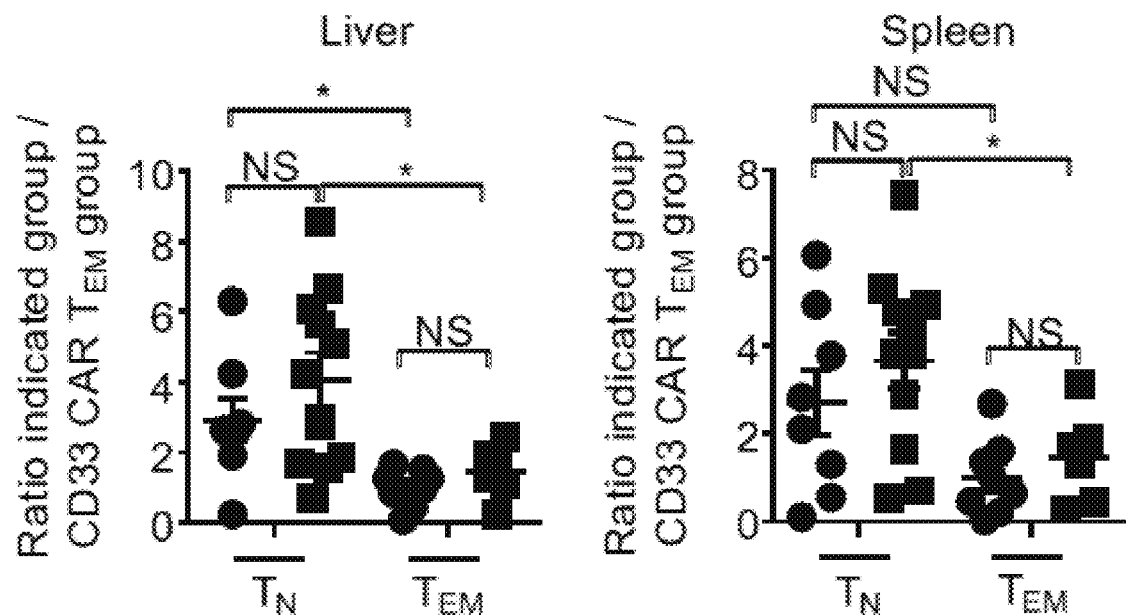

Several studies have associated high frequencies of effector subsets during adoptive T cell therapy with diminished therapeutic cell survival (30-32). The inventors hypothesized that the increased effector differentiation of CD33 CAR relative to control T cells contributes to their poor sustainability in vivo. To test this, the inventors sorted CD8$^+$ $T_N$ and ($T_{EM}$) subsets from ex vivo transduced CD33 CAR or control T cells and evaluated their persistence 5 days laterpost-transfer. Cell numbers were normalized to the mean total cell number in the CD33 CAR $T_{EM}$ group (FIG. 4D). There were no significant differences between the CAR and control groups for either $T_N$ or $T_{EM}$ cells, and transferred $T_N$ cells were better sustained than $T_{EM}$ cells in both groups. Therefore, the poorer in vivo persistence of CAR versus control T cells is largely associated with the decreased $T_N$ and increased $T_{EM}$ proportions in the pre-transfer populations, rather than an effect of the CAR itself on T cell survival after transfer.

CD33 CAR T Cells Exhibit A Distinct Transcriptional Profile

Figure 12A:
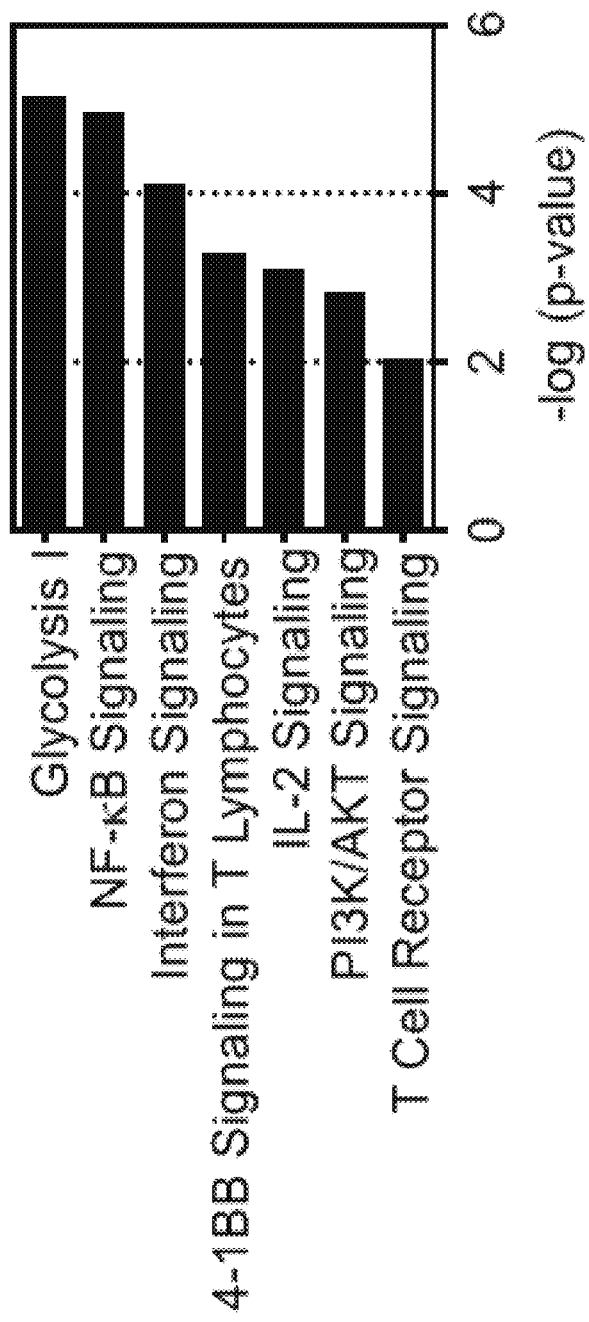
FIG. 12A-12C. Ingenuity Pathway Analysis (IPA) of genes differentially expressed (FDR<0.2) between CD8+ CD33 CAR and control T cells generated from three unique healthy donors, evaluated 12 days after initial activation.
Figure 12B:
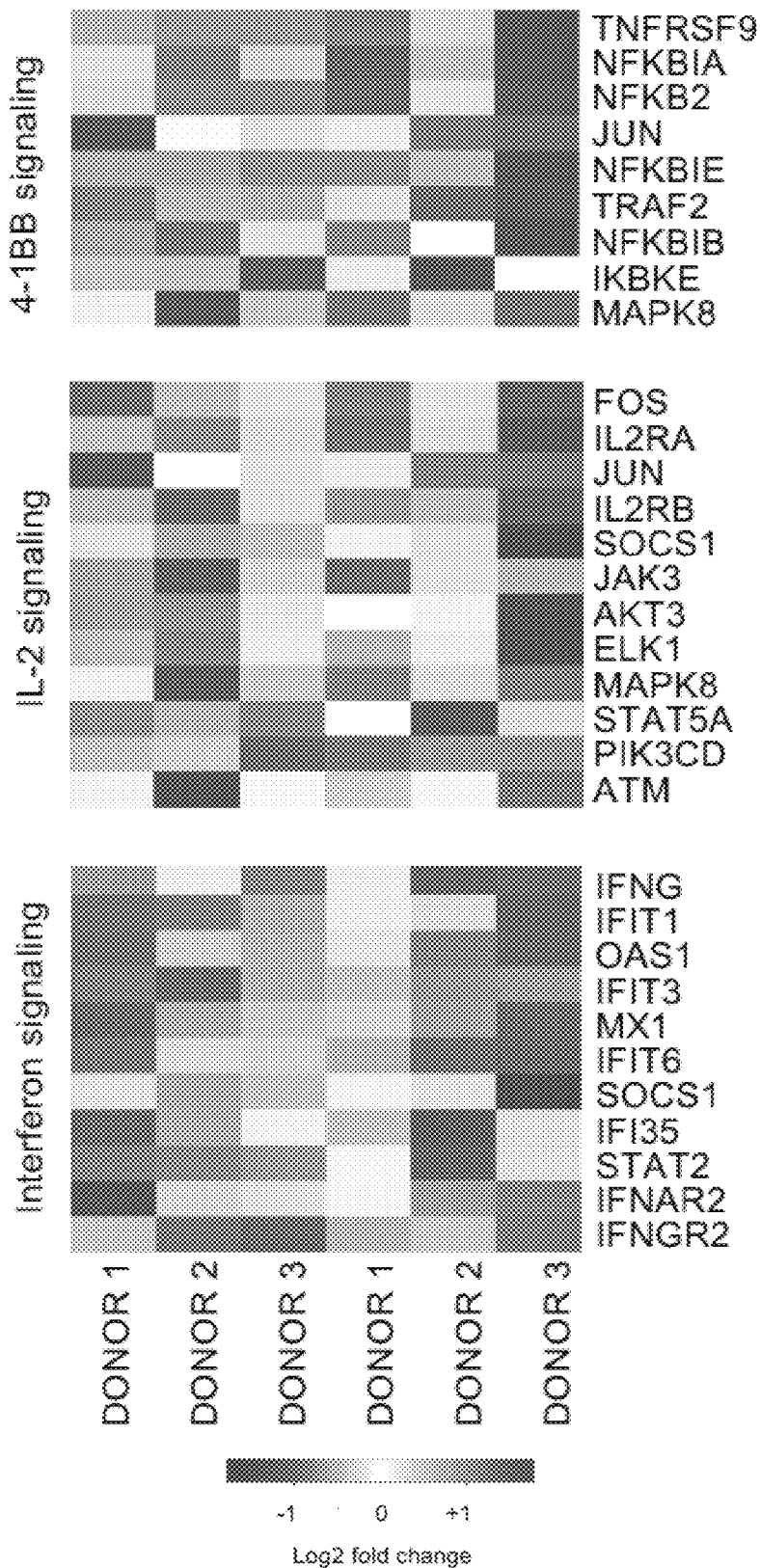
Figure 12B:
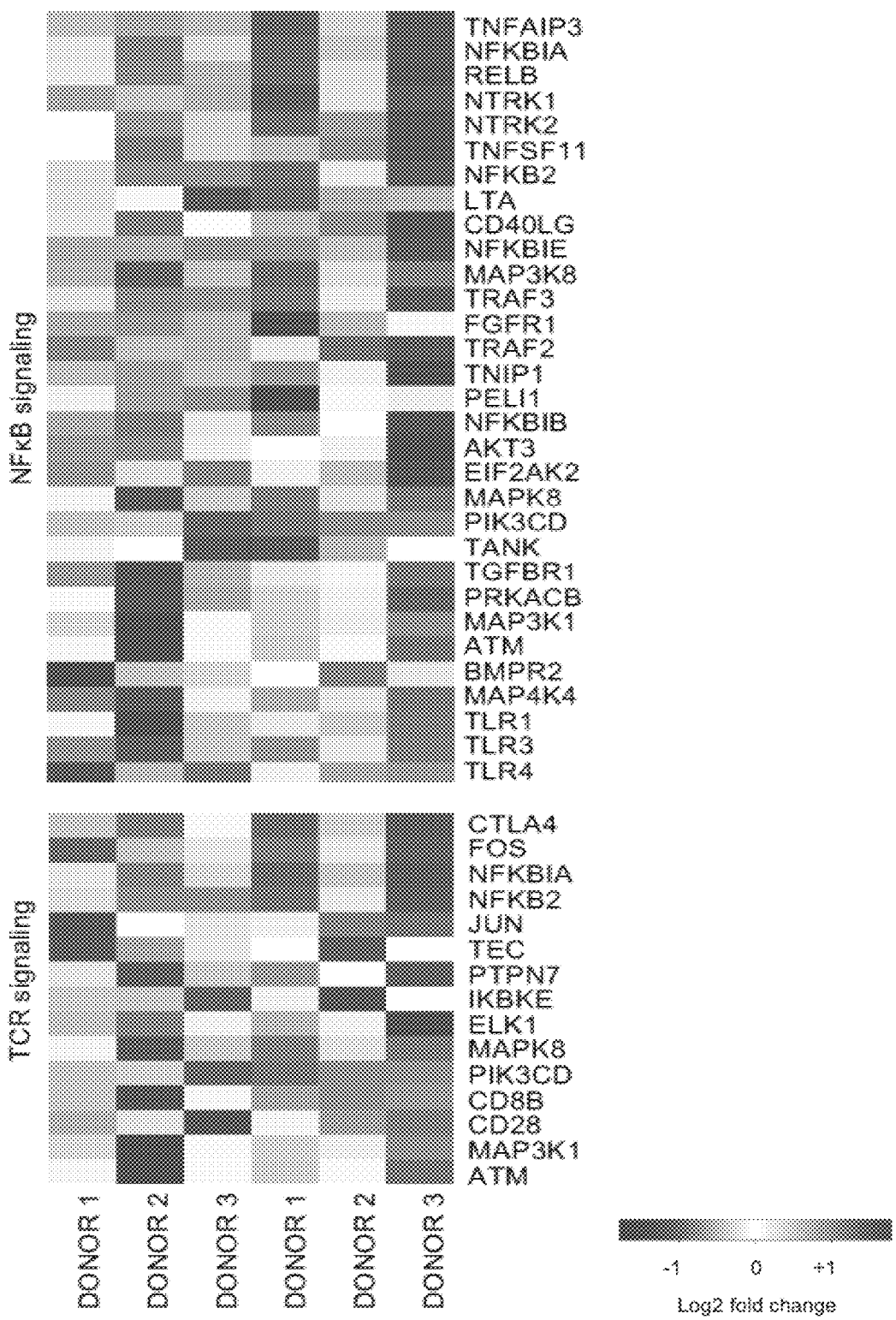

These findings indicated that tonic CAR signaling during ex vivo T cell expansion impacts the differentiation and in vivo persistence of CD33 CAR T cells. To further understand the influence of this tonic signaling, the inventors analyzed the transcriptomes of CD33 CAR and control T cells during ex vivo expansion. Approximately 500 genes were differentially expressed (FDR<0.05), and Ingenuity Pathway Analysis (IPA) of these genes (FDR<0.2) identified over 120 pathways that were significantly deregulated or dysregulated in CD33 CAR T cells (-log p value >2). Ingenuity upstream regulator analysis, which uses prior knowledge of anticipated effects of transcriptional regulators on target genes, identified TCR as the top upstream regulator of gene expression changes (P value: 2.71E-38, Activation z-score: 2.695), implying increased TCR signaling in CD33 CAR relative to control T cells [33]. Consistently, genes associated with TCR signaling were significantly up-regulated in CD33 CAR T cells (FIG. 12A and FIG. 12B).

Figure 5A:
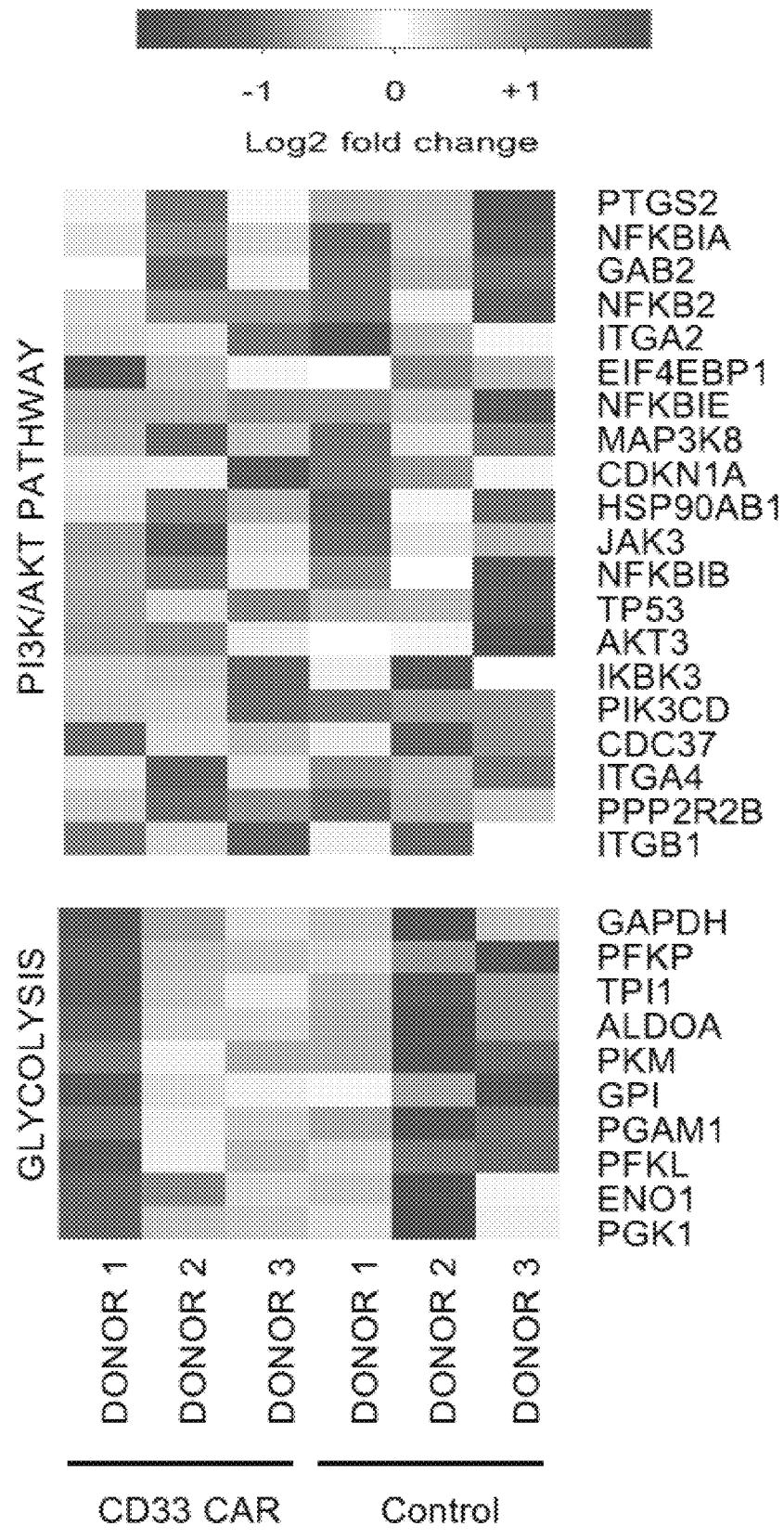
(FIG. 5A) Differentially expressed genes from select pathways identified by Ingenuity Pathway analysis (IPA) performed on transcriptional profiles from CD8+ CD33 CAR and control T cells generated from three unique healthy donors, evaluated 12 days after initial activation. Heat maps show genes in the glycolysis and P13K pathways that are uniquely dysregulated in CD8+ CD33 CART cells.
Figure 5B:
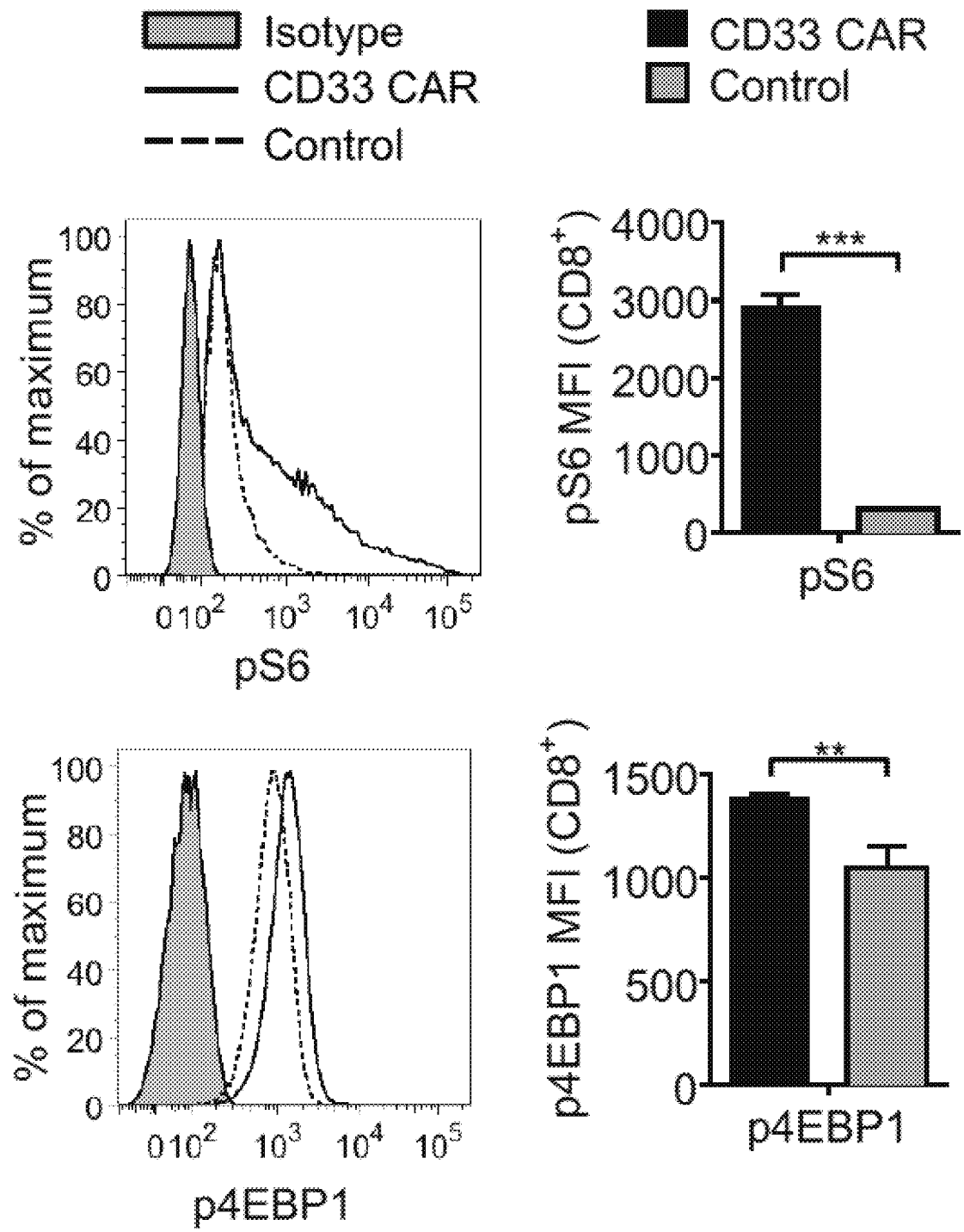
(FIG. 5B) Phospho-flow staining of pS6 and p4EBP-1 in control and CD33 CAR T cells at 12 days after initial stimulation. Histograms are representative of at least 3 independent experiments. Significance was determined by unpaired t-test.
Figure 12C:
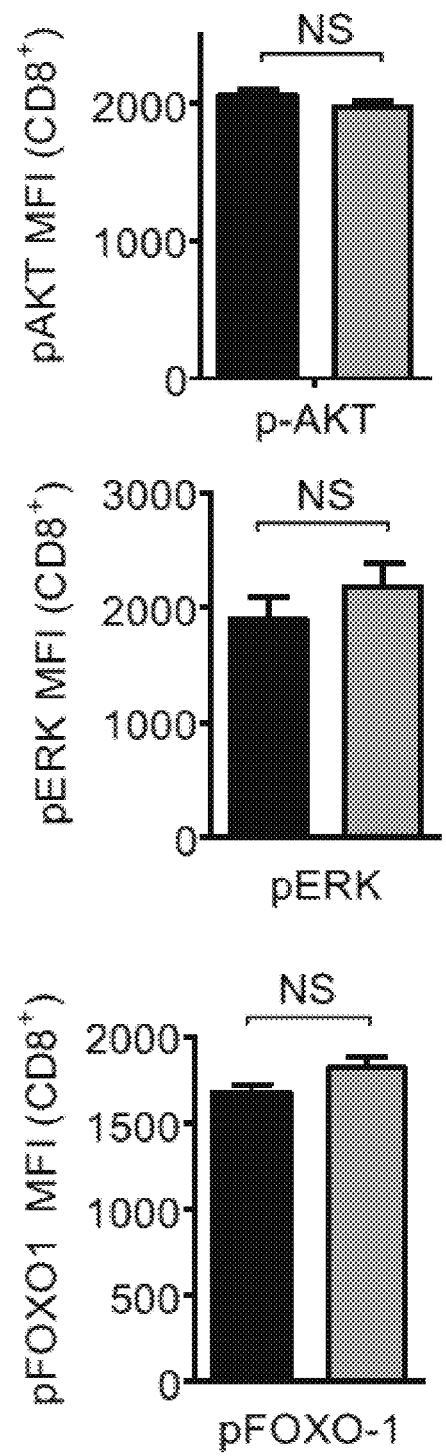

The inventors focused their analysis on downstream pathways of TCR signaling that could impact differentiation. Genes related to PI3K/AKT signaling (e.g., PTGS2, EIF4EBP1, AKT3) and glycolysis (e.g., GAPDH, PFKP, TPI1) were identified as significantly upregulated in CD33 CAR T cells (FIG. 5A). These were of particular interest as the PI3K/AKT pathway controls CD8$^+$ T cell differentiation, in part through mTOR-mediated effects on glycolysis (34). To further assess this pathway and other potential widespread signaling, the inventors analyzed the basal phosphorylation state of downstream targets of mTORC1, S6 and 4EBP-1, AKT and its downstream target FOXO1, and downstream TCR signaling molecule ERK, in CAR and control T cells 12 days after initial mitogen simulation. Levels of phospho-S6 and 4EBP-1 were significantly higher in CD33 CAR than control T cells (FIG. 5B). Levels of phospho-AKT, ERK, and FOXO1 were unchanged (FIG. 12C). These data imply that tonic signaling through the CD33 CAR constitutively promotes activation of some components of the PI3K/AKT pathway. Additional pathways were also significantly altered, including genes associated with 4-1BB, IL-2, and interferon signaling (FIG. 12A and FIG. 12B).

Figure 5C:
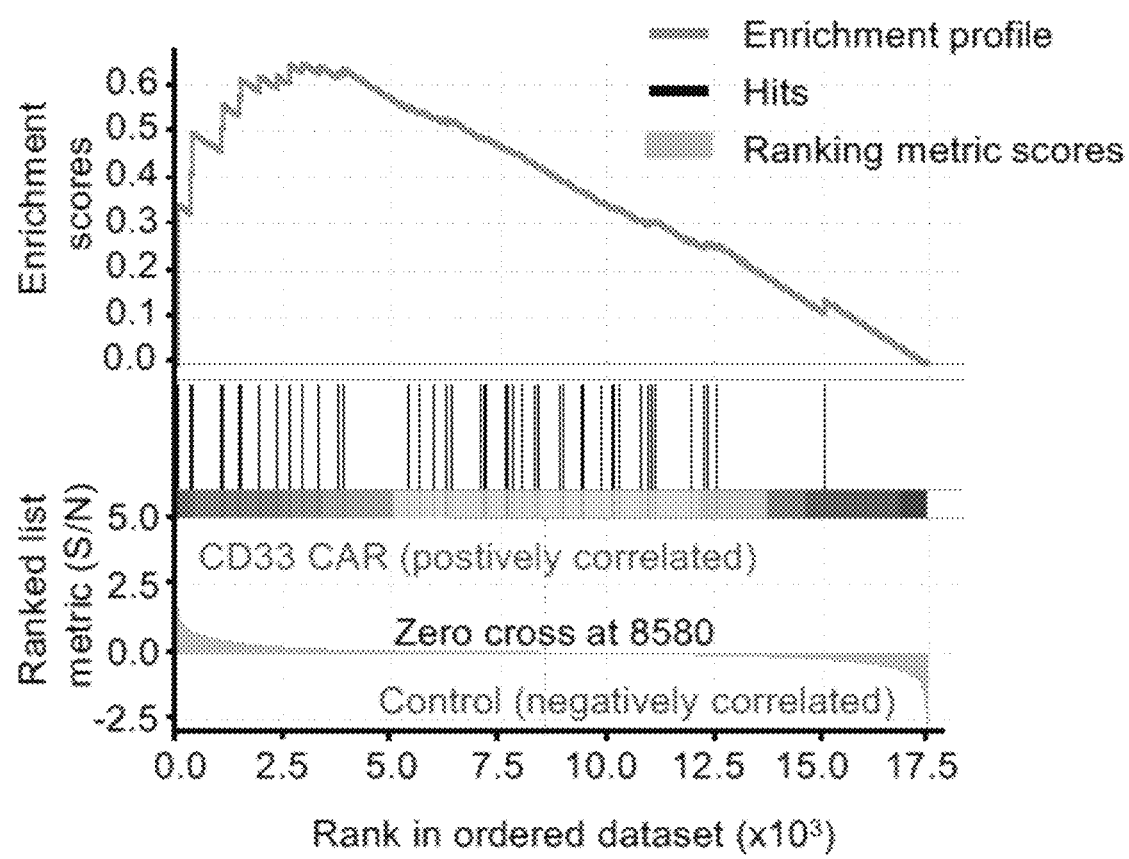
(FIG. 5C) Gene set enrichment analysis (GSEA) results from running CD8+ CD33 CAR versus control T cell rank list against the MSigDB C5 gene ontology sets. Heat map and enrichment plot for CD8+ TCR downstream signaling is shown.  p<0.01, *** p<0.001.
Figure 5C:
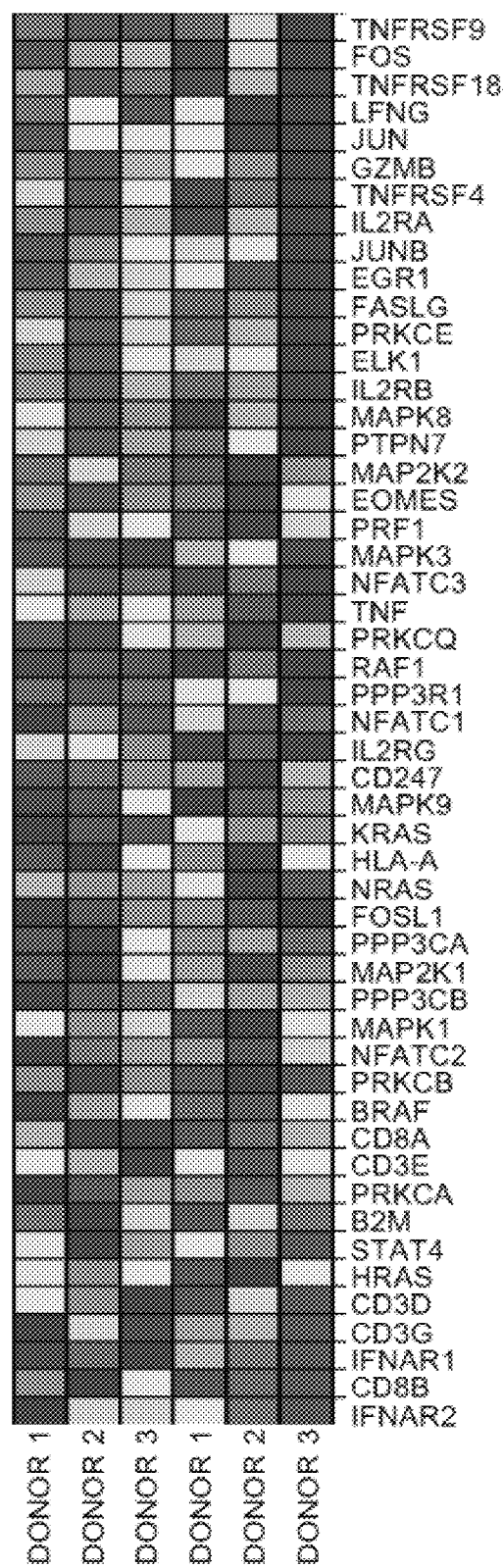

The inventors also conducted gene set enrichment analysis (GSEA) of CD8$^+$ CD33 CAR versus control T cells. Using the Molecular Signatures Database, 86 gene sets that are significantly enriched in CD33 CAR T cells were identified (FDR<0.05), including several that are associated with pathways downstream of TCR signaling (IL-2, STAT5A targets, 4-1BB signaling, and TCR calcium signaling). A gene set for CD8$^+$ TCR downstream signaling was also enriched in CD33 CAR T cells (FIG. 5C). Cumulatively, these findings are consistent with the ex vivo constitutive activation of the TCR and 4-1BB pathways through the CAR, despite the absence of ligand-mediated stimulation.

Figure 6A:
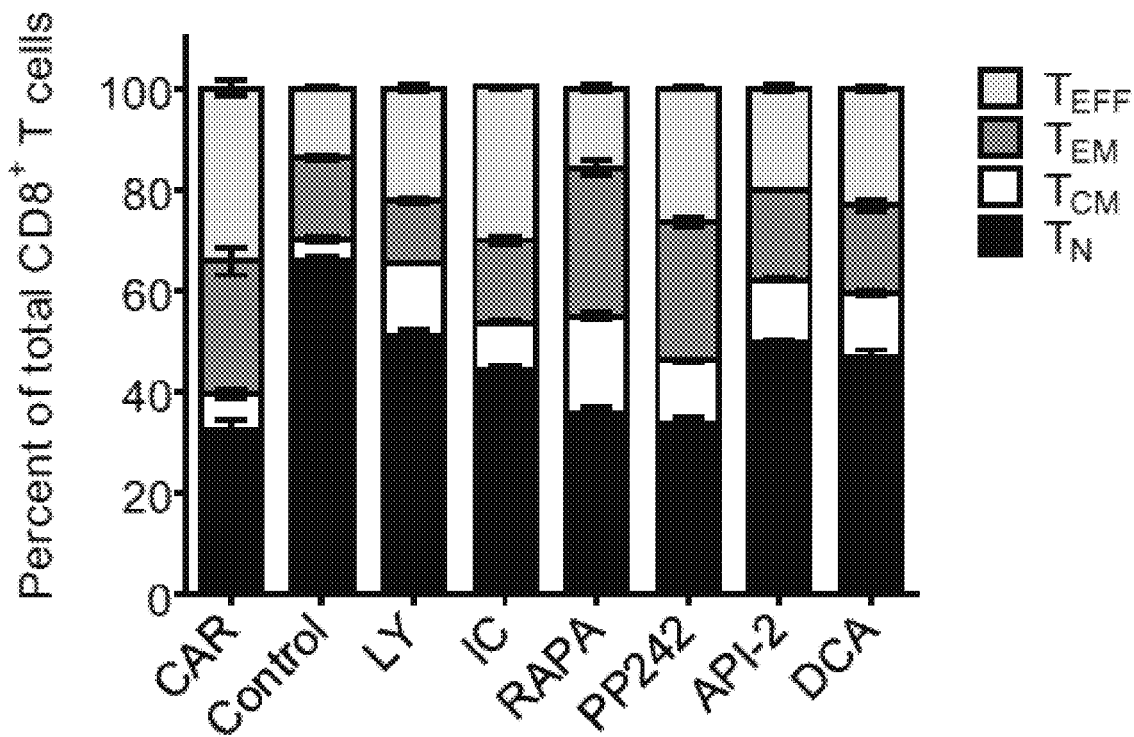
FIG. 6A-6D. PI3K/AKT inhibition restrained aberrant CD8 CAR T cell differentiation ex vivo. CD33 CAR or control T cells were labeled with CellTrace Violet 5 days after initial stimulation. Cells were treated with the indicated inhibitor (LY=LY294002; IC=IC87114; RAPA=Rapamycin) for 4 days and analyzed by flow cytometry.
Figure 6B:
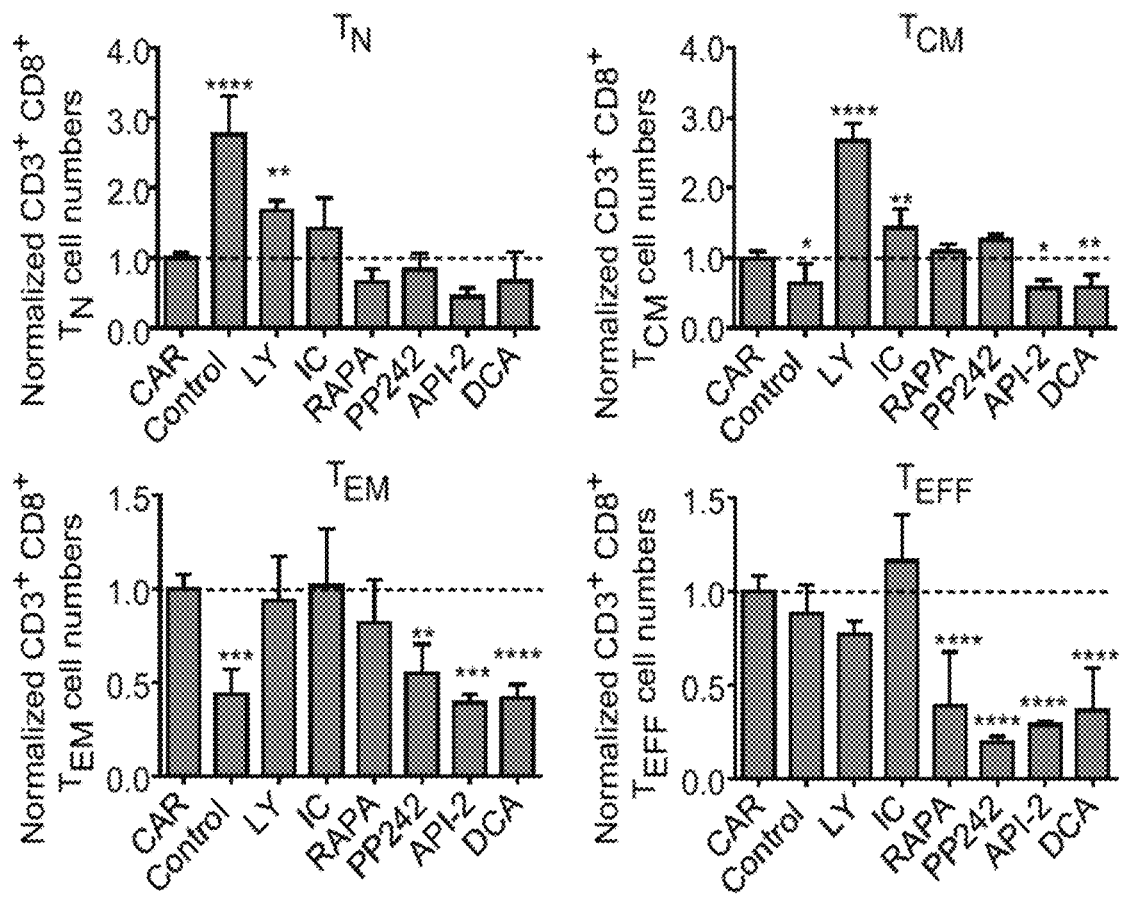
Figure 6C:
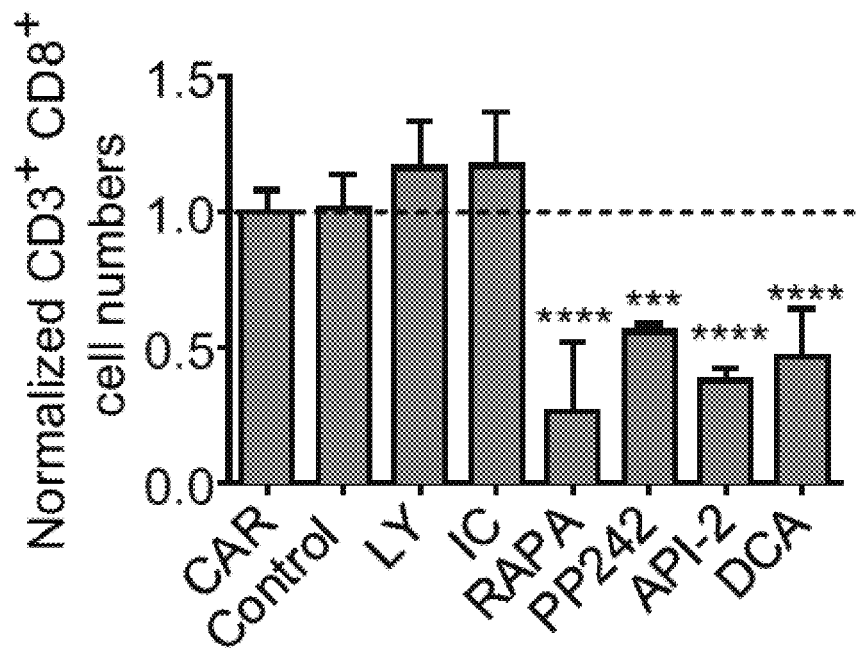

PI3K/AKT Signaling Pathway Drives CD8$^+$ CAR T Cell Effector Differentiation Ex Vivo Constitutive activation of AKT promotes terminal differentiation of CD8$^+$ T cells (35), while antagonism of PI3K/AKT/mTOR with rapamycin promotes memory cell development (35,36). To evaluate the role of PI3K/AKT/mTOR activation in altered differentiation of CD33 CAR T cells, the inventors added PI3K, AKT and mTOR inhibitors to CAR-transduced T cell cultures. LY294002 is a strong inhibitor of PI3K and IC87114 is a specific inhibitor of PI3K 110δ (37). After 4 days of treatment with PI3K inhibitors, the percent and number of CD8$^+$ $T_N$ and $T_{CM}$ cells increased significantly relative to untreated CD33 CAR T cells, but did not significantly alter CD8$^+$ $T_{EM}$ or $T_{EFF}$ cell numbers (FIGS. 6A and 6B). In contrast, the mTOR inhibitors rapamycin and PP242 showed no detectable effect on the $T_N$ and $T_{CM}$ populations, but decreased the number of CD8$^+$ $T_{EFF}$ cells (FIGS. 6A and 6B), consistent with the role of mTOR in promoting Tbet and effector cell differentiation (38). However, treatment with mTOR inhibitors also led to a substantial decrease in total CD8$^+$ CAR T cells (FIG. 6C). Treatment with the AKT inhibitor API-2 led to increased percentages of $T_N$ and $T_{CM}$ cells (FIG. 6A). However, the number of CD8$^+$ CAR T cells was greatly diminished with API-2 treatment (FIG. 6C), such that despite the increased $T_N$ and $T_{CM}$ percentages, the absolute numbers were decreased relative to the untreated CD33 CAR T cells (FIGS. 6B and 6C). As glycolysis related genes were also upregulated in CD33 CAR T cells (FIG. 5A), the inventors treated CD33 CAR T cells with the glycolysis inhibitor DCA. This increased the percentage of CD8$^+$ $T_N$ and $T_{CM}$ subsets (FIG. 6A), but also significantly inhibited T cell expansion (FIGS. 6B and 6C). Therefore, PI3K inhibition appears unique in the ability to suppress effector differentiation without diminishing therapeutic T cell accumulation during culture.

Figure 6D:
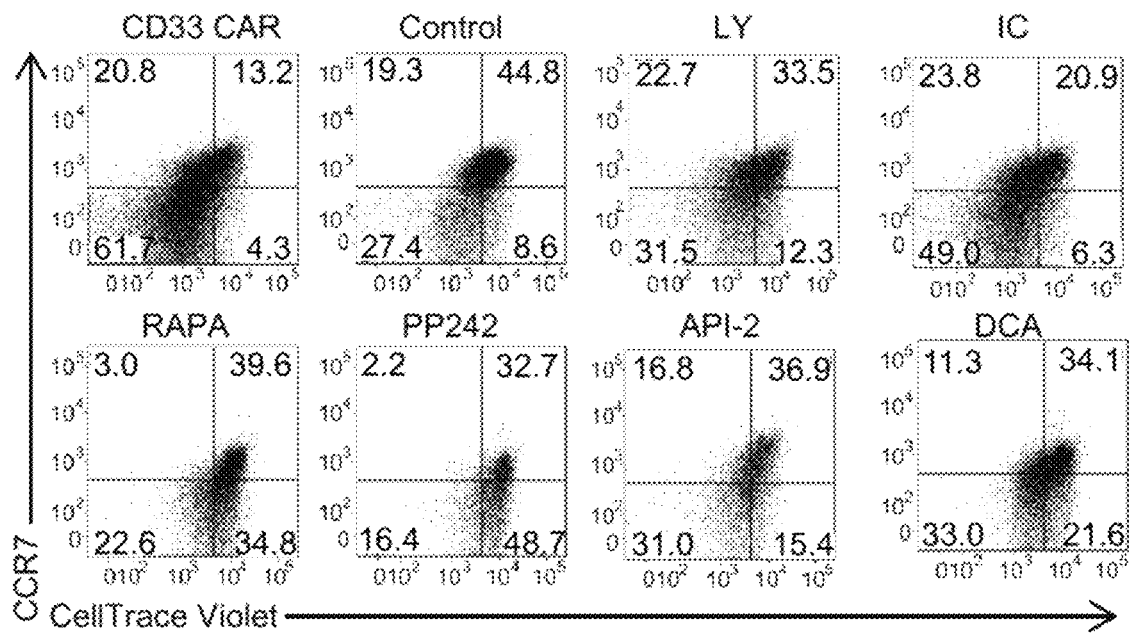
Figure 6D:
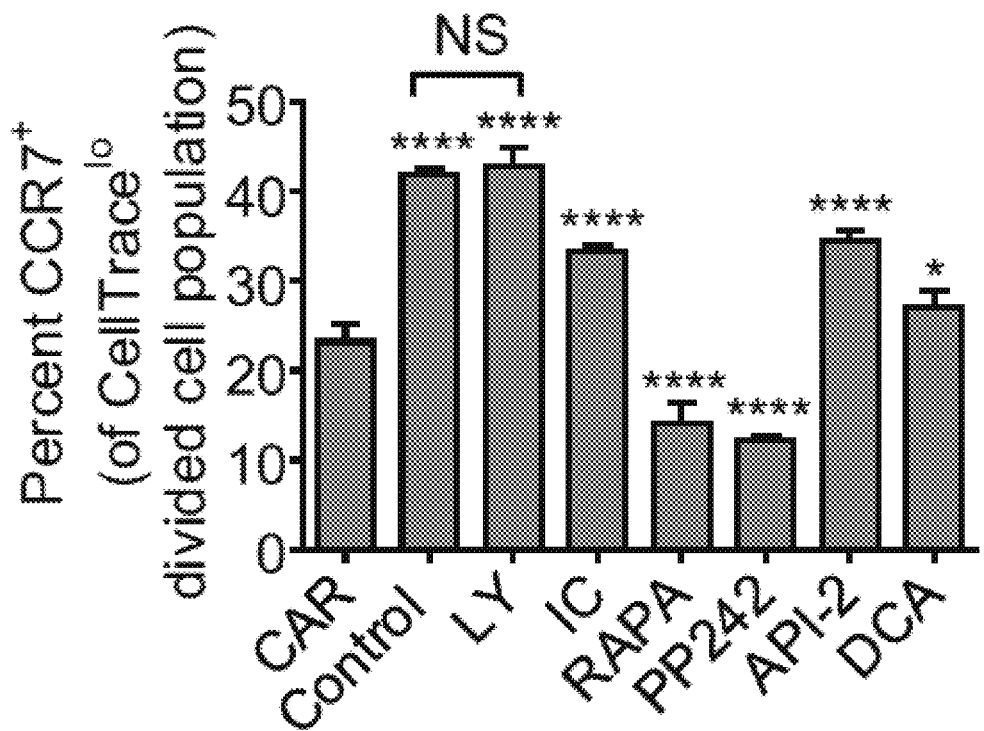
Figure 13:
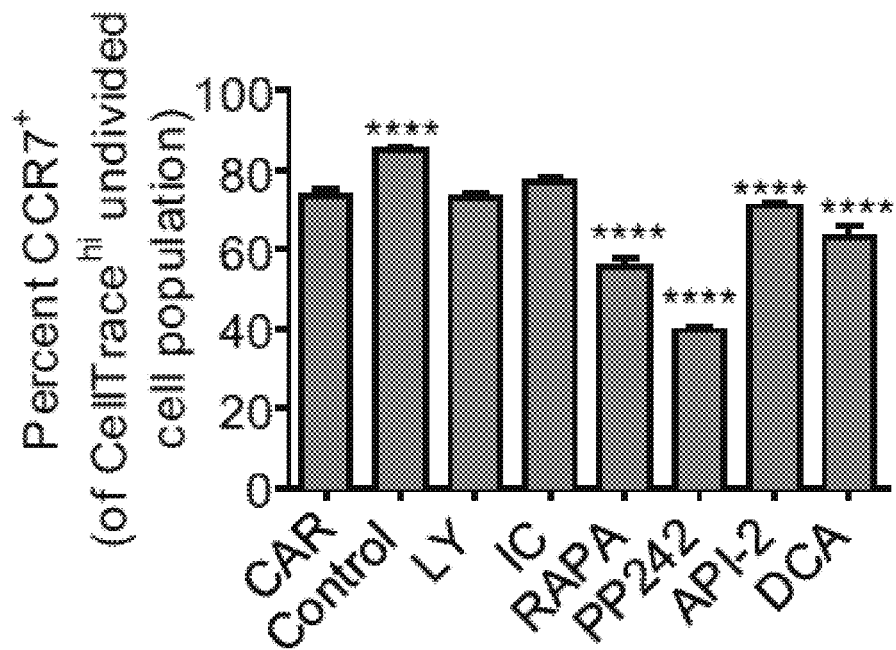
FIG. 13. CD33 CAR or control T cells were labeled with Celltrace Violet 5 days after initial activation. Cells were treated with the indicated inhibitors for 4 days and then analyzed by Flow cytometry.

Previous studies have shown that PI3K/AKT/mTOR signaling influences CD8$^+$ T cell proliferation and differentiation (39). To investigate the role of this pathway on proliferation and differentiation during CAR T cell expansion ex vivo, CD33 CAR T cells were labeled with a proliferation marker (e.g., CellTrace Violet) and treated with or without the various PI3K/AKT/mTOR inhibitors. Proliferation and CCR7 expression were measured 4 days later. As in FIG. 3F, CD33 CAR T cells proliferated more rapidly than control T cells. As untreated CD33 CAR T cells divided, about 25% of proliferating CD8$^+$ cells remained CCR7$^+$, compared to about 41% of control T cells (FIG. 6D). Control T cells also retained a large percentage of undivided cells that expressed high levels of CCR7 (FIG. 13A).

Treatment with PI3K inhibitors LY294002 and IC87114 increased the percentage of CD8$^+$ cells that maintained CCR7 expression after division to about 43% and 33% respectively. Notably there was no significant difference in the percent of cells expressing CCR7 after proliferation between the control T cells and CD33 CAR T cells treated with LY294002 (FIG. 6D). Treatment with PI3K inhibitors did not alter the percentage of CCR7$^+$ cells among undivided CD8$^+$ cells that had not undergone division (FIG. 13B). In contrast with the PI3K inhibitors, the mTOR inhibitors inhibited T cell proliferation rather than preserve CCR7 on divided T cells (FIGS. 6C and 6D). Treatment with the glycolysis inhibitor DCA and AKT inhibitor API-2 preserved CCR7 expression on proliferating cells, but to a lesser degree than the LY294002 (FIG. 6D). Taken together, these results indicate a role for increased PI3K signaling in CAR T cells in their enhanced effector differentiation ex vivo, and that inhibition of PI3K after transduction can limit effector differentiation without adversely impacting therapeutic T cell generation.

PI3K Inhibitor Treatment Ex Vivo Improves CD33 CAR T Cell Persistence In Vivo

Figure 7A:
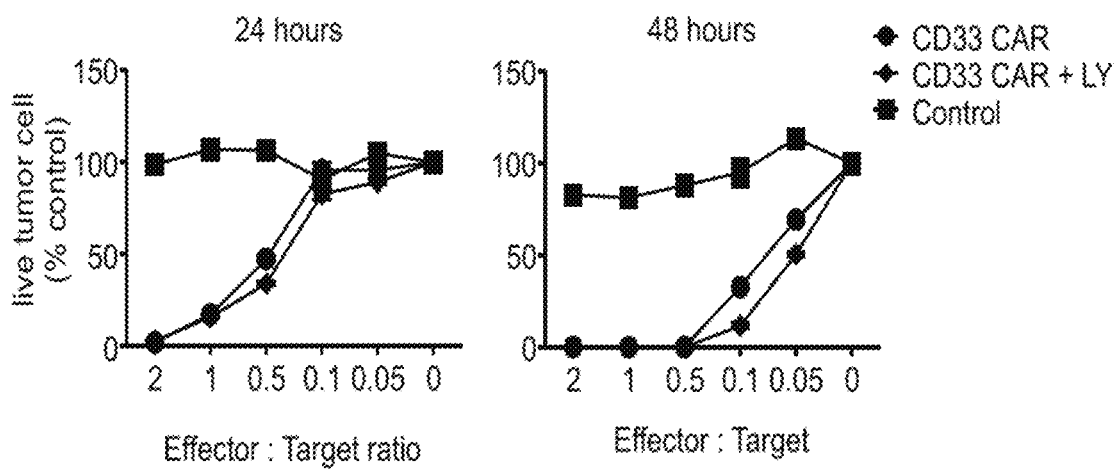
FIG. 7A-7E. PI3K/AKT inhibition during ex vivo expansion improved CAR T cell persistence and survival in vivo.
Figure 7B:
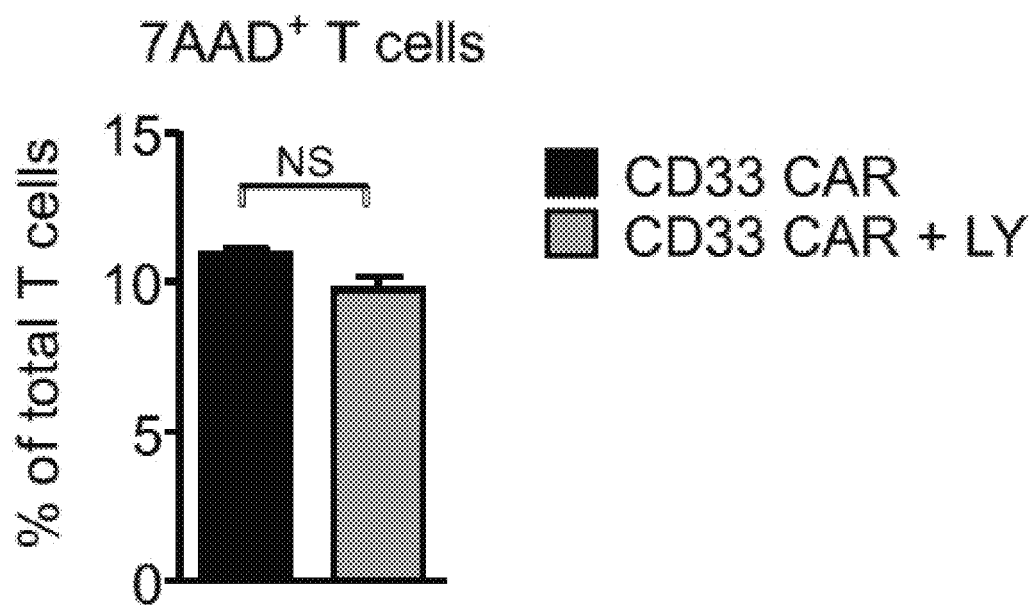
Figure 7C:
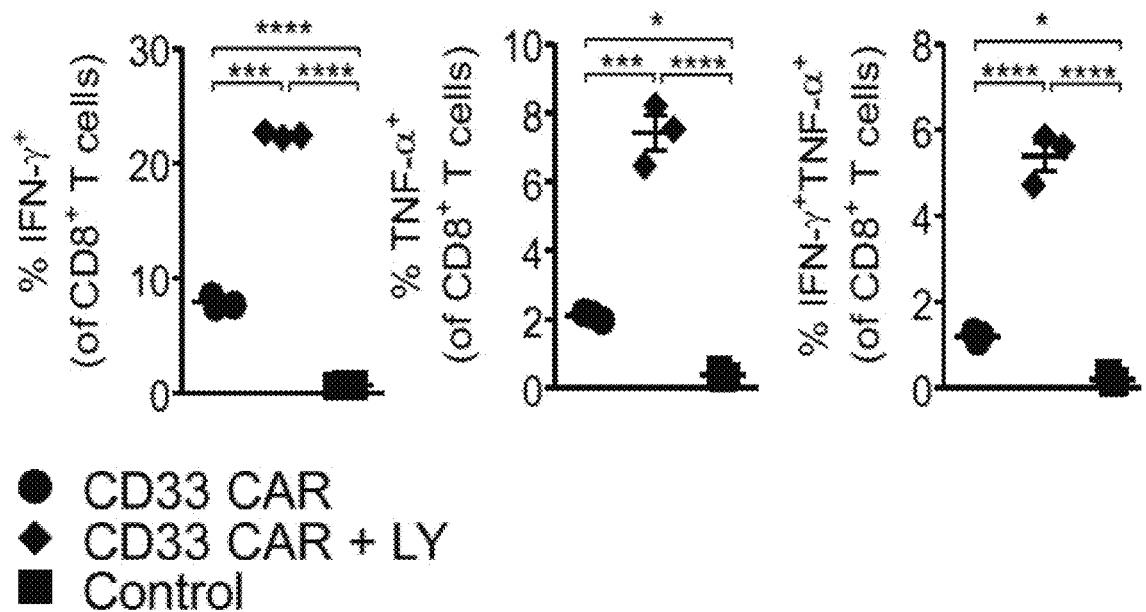
Figure 7C:
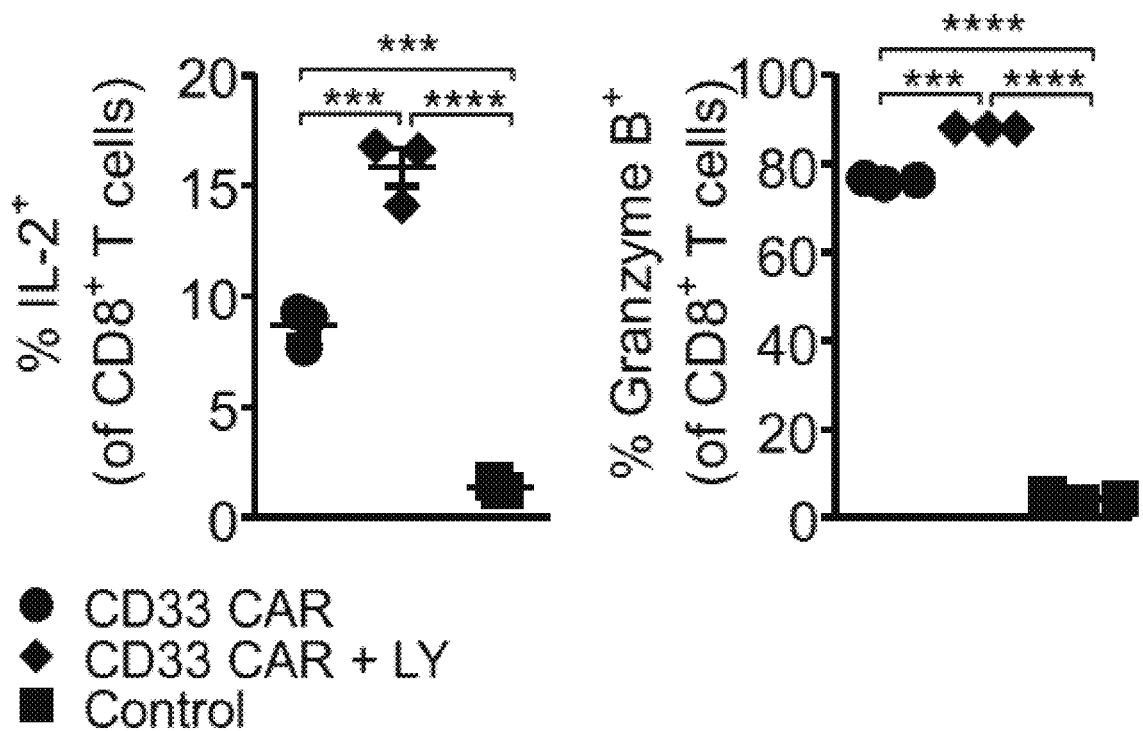
Figure 14A:
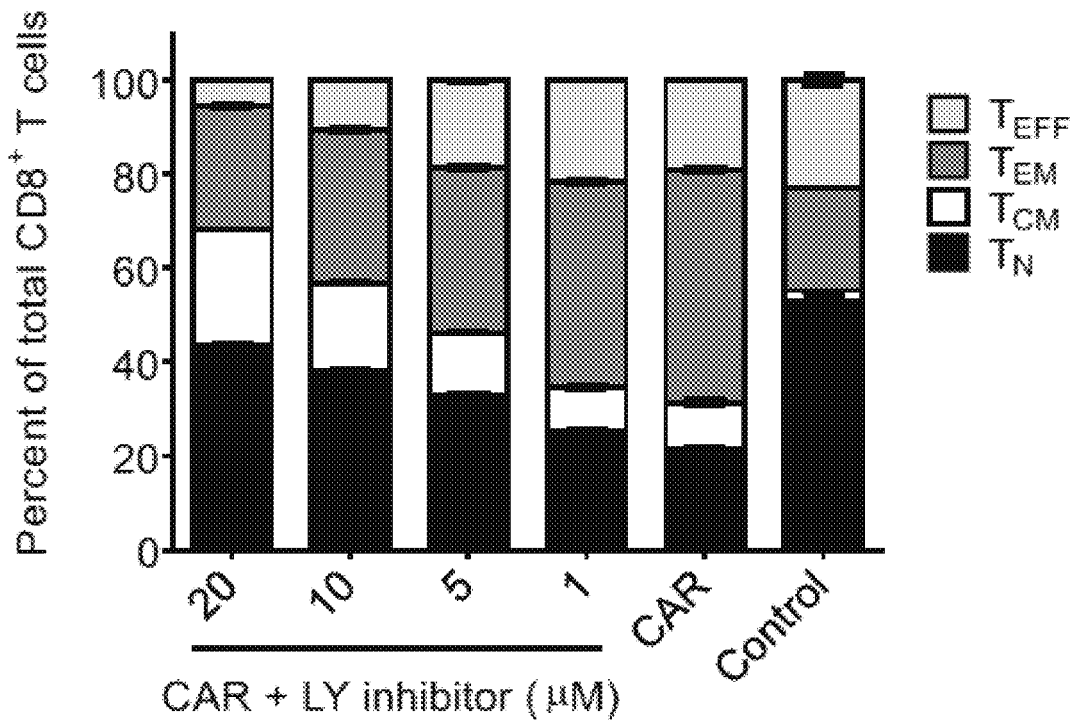
FIG. 14A-14C.
Figure 14B:
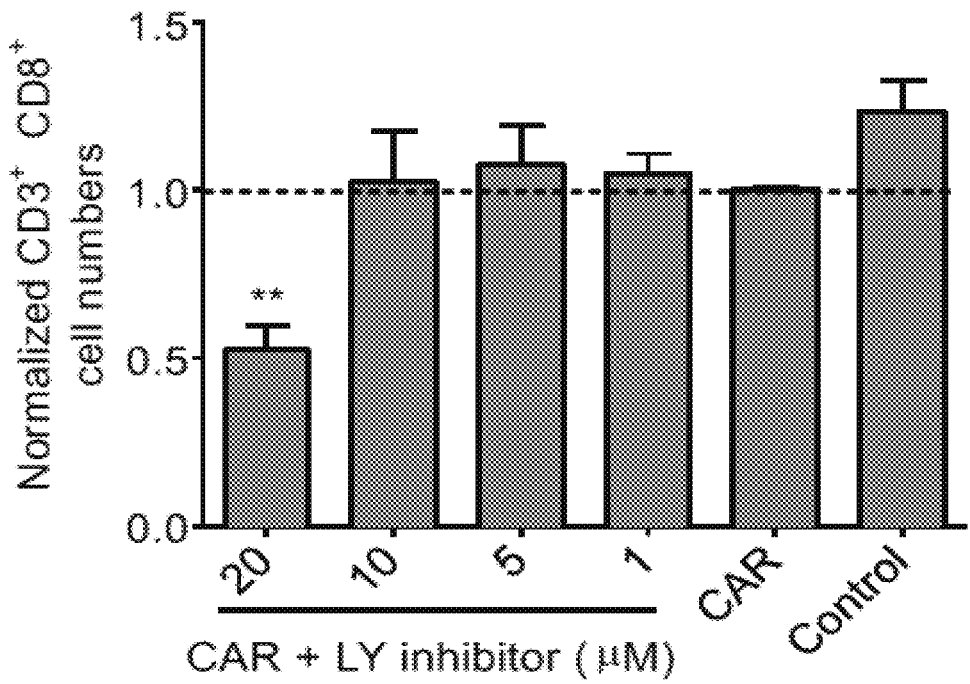

LY294002 generated a more robust response than IC87114 and was selected for further testing in vitro. Dose dependent effects of the inhibitor were determined and a concentration of 10 μM was selected for optimal effect on T cell differentiation with no reduction in total cell numbers (FIGS. 14A and 14B). PI3K inhibitor-treated CD33 CAR T cells were indistinguishable from untreated CD33 CAR T cells in in vitro killing assays at 24 and 48 hours (FIG. 7A). Inhibitor treatment during ex vivo culture had no effect on the percentage of 7AAD$^+$ cells after 5 days of expansion (FIG. 7B). Interestingly, inhibitor-treated CD33 CAR T cells also exhibited increased percentages of IFNγ$^+$, TNFα$^+$, IFNγ$^+$TNFα$^+$, IL-2$^+$, and granzyme B$^+$ cells relative to untreated CD33 CAR T cells after co-culture with MOLM-13-CD19 cells (FIG. 7C).

Figure 7D:
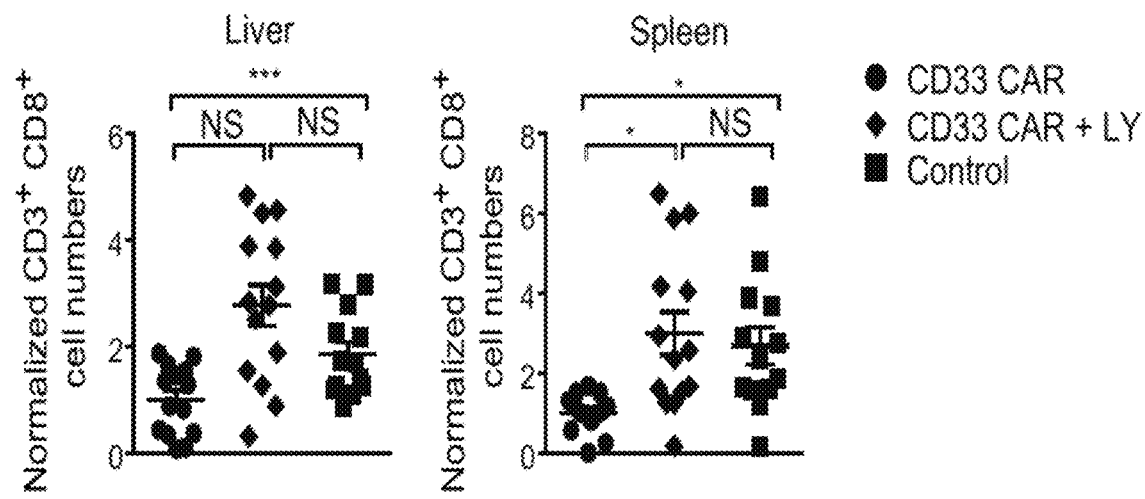
Figure 7E:
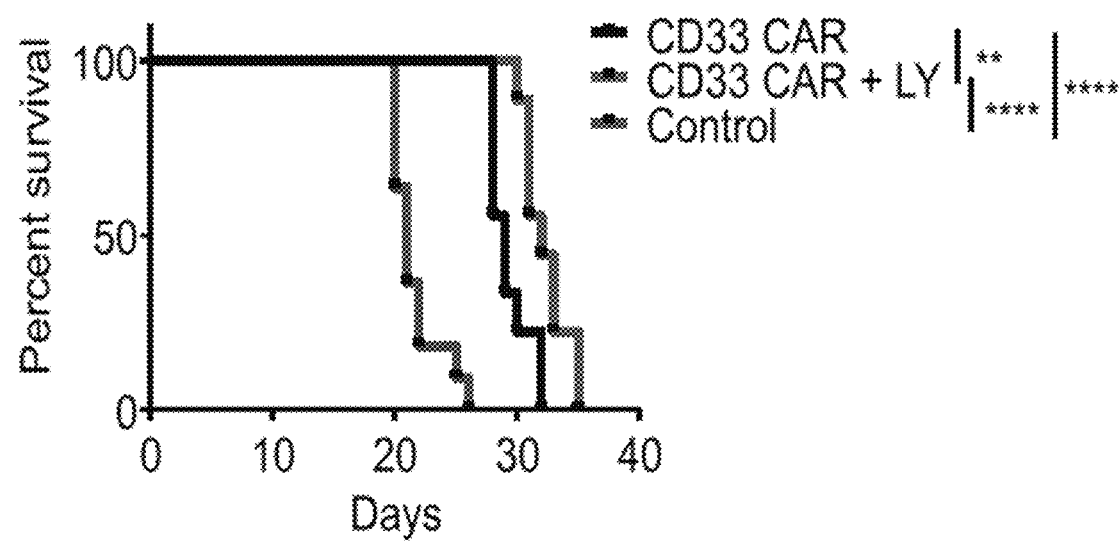
Figure 14C:
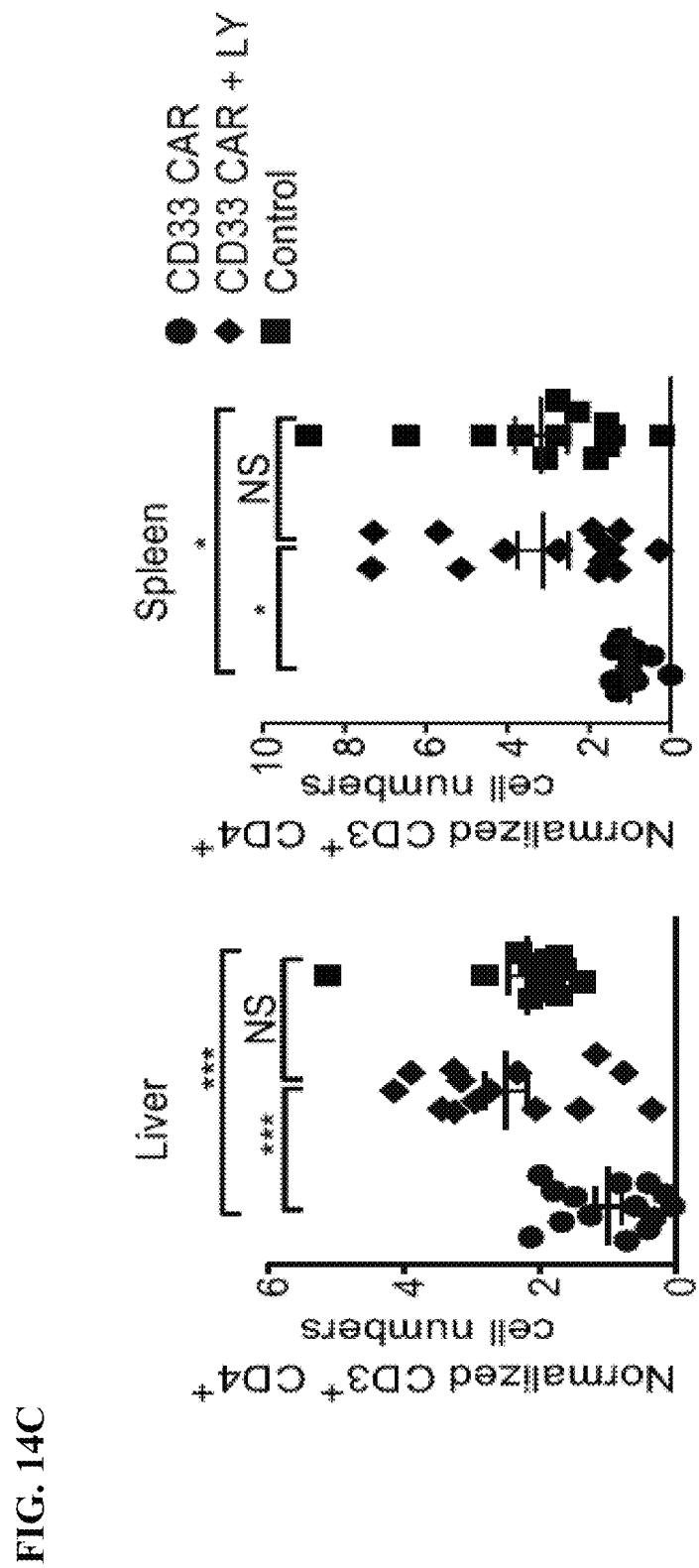

To determine if targeting PI3K signaling improved in vivo persistence of CAR T cells, PI3K inhibitor-treated CD33 CAR T cells, untreated CD33 CAR T cells, and control T cells were transferred into NSG mice without tumor. As above, about 2-3 fold more control T cells than untreated CD33 CAR T cells were identified in the mice 5 days post transfer (FIG. 7D). Inhibition of PI3K signaling during ex vivo expansion significantly improved the persistence of both CD8$^+$ and CD4$^+$ CD33 CAR T cells such that there was no significant difference in the numbers of PI3K inhibitor-treated CAR cells and untreated control T cells (FIG. 7D and FIG. 14C). To determine if PI3K inhibitor-treatment of CAR T cells enhanced survival in vivo, the above groups were transferred to NSG mice with MOLM-13-CD19 tumors and mice were monitored for survival. The inhibitor treated CD33 CAR T cells significantly extended median survival to 32 days from 29 days in the untreated CD33 CAR group (p=0.0049). These results indicate that PI3K signaling can be targeted to restrain aberrant activation of CAR T cells during ex vivo expansion without impacting therapeutic T cell expansion. Critically, inhibition of this pathway substantially enhances CAR T cell persistence post-transfer and significantly improves survival in an AML model.

Discussion

CAR T cells are an effective treatment of CD19$^+$leukemias and lymphomas (6), but how these cells can be optimized and best applied to other malignancies is uncertain. CAR T cell longevity and functional preservation after transfer are critical, yet the cellular parameters impacting these features are not fully resolved. The data shown here, using a CD33-specific CAR incorporating an established framework of 4-1BB-CD3ζ-signaling domains currently in clinical trials, demonstrates that in vivo T cell persistence is limited by tonic signaling through the CAR CD3ζ ITAMS. This diminished longevity of CAR T cells relative to control T cells was independent of antigen specificity, and was a trait acquired during pre-transfer (ex vivo) expansion. During this production phase, CAR-modified cells increasingly differentiated into shorter-lived effector forms. Signals through the PI3K pathway were identified as responsible for this altered differentiation and survival.

Naïve and central memory subsets have been associated with enhanced CAR persistence in vivo (18). One recent study suggested that ex vivo culture of CAR T cells with IL-7 and IL-15 improved survival and expansion by increasing the CD8$^+$ CCR7$^+$CD45RA$^+$ $T_N$ population (19). This included a sub-population of long-lived CCR7$^+$CD45RA$^+$ CD45RO⁻CD62L⁺CD95⁺ $T_{SCM}$ cells (40-42). Accordingly, the inventors found that transfer of a CCR7⁺CD45RA⁺$T_N$/$T_{SCM}$ population improved persistence in vivo relative to CCR7⁻CD45RA⁻$T_{EM}$ cells. This was true with CAR and control T cells, implying that CAR expression did not have a detectable impact post-transfer. Despite the emerging evidence indicating the importance of specific T cell subsets on CAR persistence and efficacy, the effects of CAR signaling on T cell differentiation remain poorly understood. The inventors show that tonic CAR signaling during ex vivo expansion led to reduced CCR7⁺CD45RA⁺$T_N$/$T_{SCM}$ cells and increased terminally differentiated effector subsets that correlate with poor persistence in vivo.

The structure of the CAR, including signaling and co-stimulatory domains, could predispose CAR T cells to chronic activation or exhaustion, leading to decreased efficacy. It is of note that the construct used here was designed to minimize CAR-intrinsic signaling, as the 4-1BB domain is associated with reduced exhaustion during ex vivo CAR T cell culture, and improved function in the G2D CAR (21). Furthermore, the GD2 CAR exhibited cell surface clustering that contributed to antigen-independent signaling. In contrast, the inventors did not observe clustering of CD19 or CD33 CARs (21). Thus, even with optimal signaling domains and in the absence of CAR clusters, tonic signaling persists and alters CAR T cell differentiation and in vivo persistence.

By mutating the CAR CD3ζ and 4-1BB domains, the inventors demonstrated that intrinsic signaling through the CD3ζ ITAMs increased terminal differentiation during ex vivo expansion. Replacement of critical ζ ITAM tyrosines with phenylalanines fully restored the $T_N$:$T_{EM}$ ratio of CD33 CAR T cells to that of control cells, although it abrogates CAR T cell function. Disruption of 4-1BB signaling did not alter CART cell differentiation; therefore, tonic 4-1BB signaling most likely does not produce a notable effect on differentiation status ex vivo, or, alternatively, any effect of 4-1BB was likely superseded by CD3ζ signals. These findings illustrate the relationship between CAR structure and in vivo outcomes of CAR mediated therapies and how the fate and therapeutic capacity of CAR T cells are influenced by ligand-independent alterations in programming during CAR T cell generation.

In addition to identifying the CAR structural features responsible for adversely impacting CAR T cell sustainability using genome-wide transcriptional profiling, the inventors identified CAR-specific signaling pathways that contributed to aberrant activation and differentiation of CD33 CAR T cells. The present results identified several pathways downstream of the TCR that were upregulated in CD33 CAR T cells, most notably the PI3K/AKT/mTOR and glycolytic pathways, which control T cell differentiation, metabolism, and fate (43, 44).

PI3K/AKT signaling may play different roles in CAR T cell function dependent on timing and environment. Increased PI3K/AKT signaling has been correlated to upregulation of Bcl-XL and increased cytokine responses in PSMA-specific CAR T cells, leading to improved efficacy (45). However, this was after T cell expansion and in the presence of antigen, where increased activity may improve CAR function. The role of constitutive, low level PI3K/AKT signaling during ex vivo culture prior to antigen exposure was not explored. Consistent with our results PI3K signaling during cell division influences T cell differentiation (39). Treatment with PI3K inhibitor during ex vivo CAR T cell expansion increased CCR7⁺CD45RA⁺$T_N$/$T_{SCM}$ and CCR7⁺CD45RA⁻ $T_{CM}$ populations, and decreased the CCR7⁻ CD45RA⁺ $T_{EFF}$ population. This translated to significant improvement in in vivo persistence, with inhibitor-treated CAR T cells maintaining total cell numbers comparable to that of control T cells. Further, PI3K inhibitor treatment was associated with unperturbed ex vivo proliferation and expansion of CAR T cells, and therefore can be incorporated into production regimens without impacting yield. This is particularly significant as inadequate CAR T cell yields limit production of adequate therapeutic product for many patients.

Inhibition of other pathways that related to PI3K-AKT pathway may similarly alter CAR T cell differentiation and improve function. BET bromodomain inhibitors target c-Myc, resulting in downregulation of Myc-dependent target genes (46). A recent report showed ex vivo culture with BET bromodomain inhibitors resulted in expansion of CD62L⁺ CCR7⁺ T cells with $T_N$ and $T_{CM}$ phenotypes, and adoptive transfer of inhibitor-treated CD19 CAR T cells extended survival in an ALL model (47). This is consistent with our result in that aberrant PI3K and mTOR signaling may also activate c-Myc resulting in altered metabolism and differentiation (48,49). Thus, inhibition of pathways upstream or downstream of PI3K signaling may also preserve a less differentiated phenotype.

Downstream of PI3K signaling, the role of mTOR signaling (35, 36, 50) and the metabolic regulation of glycolysis (43, 51) in CD8⁺ T cell fate determination are well characterized. Sustained AKT activation in vivo initiates transcriptional programs that lead to terminal differentiation of CD8⁺ T cells at the expense of T cell memory, via excessive activation of mTOR (36). Consistent with transcriptional evidence for enhanced constitutive activation of this pathway, the inventors observed increased phosphorylation of mTOR-regulated S6 and 4EBP-1 in CD33 CAR T cells during ex vivo culture. Despite this, and in contrast with PI3K inhibition, treatment with mTOR inhibitors did not correct the altered CAR T cell differentiation program. CD8⁺ effector T cells increase glycolytic activity to support high metabolic needs during rapid proliferation, and inhibition of glycolysis during activation abrogates effector cell formation (43, 51). Inhibition of glycolysis during ex vivo expansion of CD33 CART cells restored the $T_N$:$T_{EM}$ ratio to that of control cells. However, inhibition of these pathways severely reduced proliferative capacity, making these undesirable targets for inhibiting terminal differentiation of CD 33 CAR T cells.

These results have broader implications for CAR-mediated immunotherapy. Currently, CD3ζ is a key component of all CAR constructs undergoing clinical trials (52). Whereas structural modification or replacement of CD3ζ with similar ITAM domains, such as those of FcγR or CD3ε, may lessen the negative impact of tonic signaling through this domain, it is also possible that the impact of CD3ζ on T cell differentiation is intrinsically linked to signaling properties essential for CAR T cell activation. Selective inhibition of PI3K activity during ex vivo expansion enhances in vivo persistence without affecting CAR T cell generation. More importantly, these findings may form the basis for alternative approaches to improve cell-intrinsic features of therapeutic CAR T cells that enhance the clinical efficacy of cell-based immunotherapy for cancer.

Materials and Methods

Confocal imaging: CD33CAR and CD19CAR T cells were harvested 12 days after initial stimulation, stained with Alexa Fluor® 647 AffiniPure Goat Anti-Mouse IgG (Jackson Immunoresearch) on ice and fixed by 4% (vol/vol) neutral buffered paraformaldehyde solution. Images were acquired using a Zeiss LSM 780 microscope equipped with 63×/1.4 NA oil objective.

Proliferation and apoptosis assay: CD33 CAR or vector-transduced control T cells were labeled with CellTrace Violet (ThermoFisher) 5 days after their initial activation. 100U/ml IL-2 was added to cultures every 2 days. Proliferation was analyzed 4 days later by flow cytometric analysis of CellTrace Violet dilution. For apoptosis, CD33 CAR or vector-transduced control T cells were harvested 12 days after initial activation. Equal numbers were re-plated and cultured in fresh medium with IL-2 for 24 or 48 hours. Cells were labeled with Annexin V and 7AAD (BD Company) and analyzed by flow cytometry to determine percent of cells undergoing early and late apoptosis.

Inhibitor treatment during ex vivo culture: CD33 CAR or control transduced T cells were labeled with CellTrace Violet (ThermoFisher) 5 days after their initial activation. Small-molecule inhibitors of PI3K (LY294002, 10 µM; IC87114, 10 µM; Cell signaling), AKT (API-2, 1 µM), mTOR (rapamycin, 50 nM; PP242, 1 µM), and glycolysis (DCA, 10 mM) (Sigma) and 100 U/ml IL-2 were added to cultures every 2 days. Cells were analyzed 4 days later by flow cytometry.

Flow cytometry: Immunophenotypic analysis was performed using anti-human CD4 (clone OKT4), CD3 (UCHT1), CD33 (WM53), CD62L (DREG56), CD95 (DX2), CD69 (FN50), 4-1BB (4B4), TIM-3 (F38-2E2), LAG-3 (3DS223H), TNFα, (MAb11), and Grzb, (GB11) from eBioscience; CD8 (HIT8a), CD19 (HIB19), CD45 (HI30), CCR7 (G043H7), CD45RA (HI100), CD45RO (UCHL1), CD25 (BC96), PD-1 (EH12.2H7), IL2 (MQ1-17H12), and IFNγ, (4S.B3) from Biolegend; p-S6 Ribosomal Protein S235/236 (D57.2.2E), p-4E-BP1 Thr37/46 (236B4), p-AKT 5473 (clone:D9E, CST), p-FOXO1 Ser256, and p-ERK 1/2 (197G2) from Cell Signaling Technologies, with corresponding isotype control antibodies. Non-viable cells were excluded by 7AAD staining. For intracellular cytokine staining, T cells were stimulated with MOLM-13-CD19 cells at an E:T ratio of 1:1, and incubated for 24 and 48 hours. Then Brefeldin A (eBioscience) was added to the cultures and incubated for another 4 hours. An intracellular fixation and permeabilization buffer set (eBioscience) was used per manufacturer's instructions for intracellular cytokine staining. For phospho-flow, cells were fixed with a 1% paraformaldehyde solution and permeabilized with cold 90% methanol prior to staining. An LSR Fortessa (BD Biosciences) was used with FlowJo 9.6.6 software (Treestar) for the analysis. Flow sorting was performed with a Reflection (iCyt) cytometer (Sony Biotechnology).

Co-culture killing assay: CD33 CAR, CD19 CAR, or control T cells were incubated with MOLM-13-CD19 cells at the indicated effector to target ratios. Cells were collected and analyzed by quantitative flow cytometry at indicated time points. Cell numbers were normalized to added TrucountTM beads (BD Biosciences) as an internal control for quantitation.

Adoptive immunotherapy with CAR T cells: For adoptive immunotherapy experiments, $1 \times 10^6$ MOLM-13-CD19 cells were administered via tail vein into NSG mice and $6 \times 10^6$ CD33 CAR, CD19 CAR, or control T cells were administered retro-orbitally the same day. Mice were sacrificed at day 5 or day 18 post-transfer, when some control mice were noted to be developing constitutional illness in each experiment. Spleen, liver, and bone marrow were harvested and analyzed by flow cytometry. Mice were imaged using the Xenogen imaging system (Living Image software, Caliper Life Science) for visible tumor engraftment and re-imaged every 7 days to monitor tumor progression. For co-transfer experiments, $1.5 \times 10^6$ GFP$^+$CD33 CAR and $1.5 \times 10^6$ RFP$^+$ control T cells were administered together i.v. with or without tumor cells. To assess persistence of CAR T cell subsets, $1.5 \times 10^6$ CD8$^+$CCR7$^+$CD45RA$^+$ (naïve, $T_N$) and CD8$^+$CCR7$^-$CD45RA$^-$ (effector memory, $T_{EM}$) CAR T cells were sorted and transferred individually. Spleen and liver were harvested on day 5 post-transfer and analyzed by flow cytometry. To assess the persistence and survival of PI3K treated CAR T cells, $3 \times 10^6$ PI3K treated CD33 CAR, untreated CD33 CAR, or control T cells were administered intravenously (i.v.). Mice were sacrificed at day 5. Spleen and liver were harvested and analyzed by flow cytometry.

Bisulfite Sequencing Analysis of Human IFNγ Promoter

Naïve CD8+CD45RA+CD45RO−CCR7+CD95−T cells were sorted from donor samples and transduced with CD33 CAR or control vector. Genomic DNA was isolated from purified CD33 CAR or control T cells 9 days after activation and subjected to bisulfite treatment. Bisulfite modified DNA was PCR-amplified using IFNγ promoter specific primers, cloned, and sequences were analyzed using BISMA software, as previously described (Abdelsamed et. al., J. Exp. Med., in press).

RNA sequence: Total RNA was extracted from three samples of CD33 CAR or control T cells from three different donors, 12 days after initial stimulation by CD3/CD28, using TRIzol reagent (Life Technologies). RNA quality control parameters and RNA sequencing were performed at the St. Jude Children Research Hospital Genome Sequencing Facility following the standard Illumina protocol (Illumina). For RNA-seq analysis, paired-end sequencing was performed using the HighSeq platform with 100bp read length. Paired-end reads were aligned to the following 4 database files using BWA (0.5.10) aligner(44): (1) the human GRCh37-lite reference sequence; (2) RefSeq; (3) a sequence file representing all possible combinations of non-sequential pairs in RefSeq exons; (4) AceView database flat file downloaded from UCSC representing transcripts constructed from human ESTs. The mapping results from the (2) and (4) database files were aligned to human reference genome coordinates. In addition, reads were aligned using STAR 2.3.0(55) to the human GRCh 37-lite reference sequence without annotations. The final BAM file was constructed by selecting the best alignment among the five mappings. Read pair counts per gene for each sample were obtained using htseq-count version 0.6.1 (56) with Gencode vM5 (57) level 1 and 2 gene annotations. The read counts per gene were loaded into the R statistical environment. The counts were normalized using the lmFlt and eBayes functions with default parameters. P-value adjustments were done with false discovery rate (FDR) correction. Significance was defined as having a false discovery rate (FDR) <0.05. Voom normalized counts were analyzed through the use of QIAGEN's Ingenuity Pathway Analysis (IPA, QIAGEN Redwood City, qiagen.com/ingenuity). Counts were also analyzed by gene set enrichment analysis (GSEA) using the GSEA software (58) (broad.mit.edu/gsea/). All generated RNA-seq data are available at the Gene Expression Omnibus (GEO) with accession code GSE93386.

Statistical analysis: All figures are representative of at least three individual experiments unless otherwise noted.

All graphs report mean ±SEM. values of biological replicates. Statistical analysis was performed using GraphPad Prism 6. Specific tests used for each experiment are detailed in the figure legends.

Study approval: Animal experiments were performed in American Association for the Accreditation of Laboratory Animal Care-accredited, specific-pathogen-free facilities in the St. Jude Animal Resource Center following national, state and institutional guidelines. Animal protocols were approved by the St Jude Children's Research Hospital Animal Care and Use Committee. Human cells were acquired from anonymized, left over apheresis rings derived from leukoreduced platelet collections of healthy donors, use of which was approved by the St Jude Children's Research Hospital Institutional Review Board.

Example 3

CD33 CAR Mutants

Figure 15A:
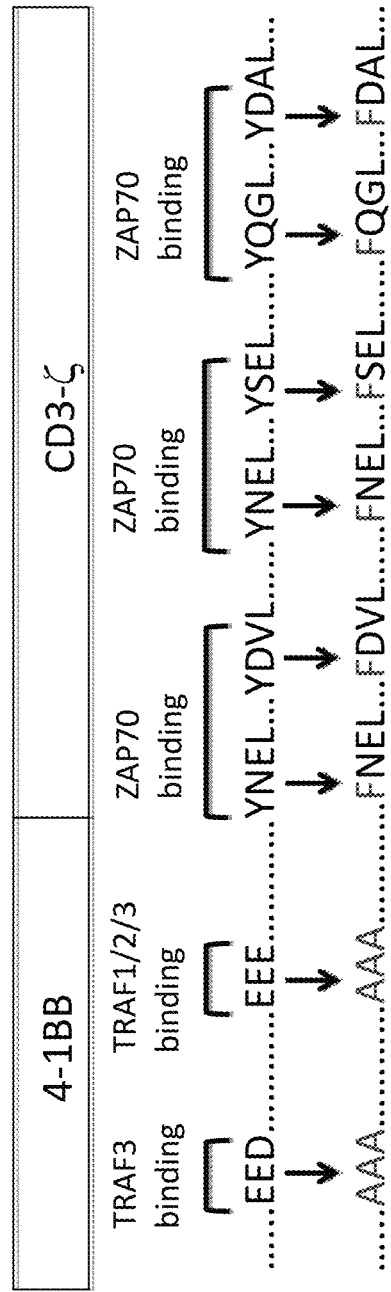
FIGS. 15A-15D.
Figure 15B:
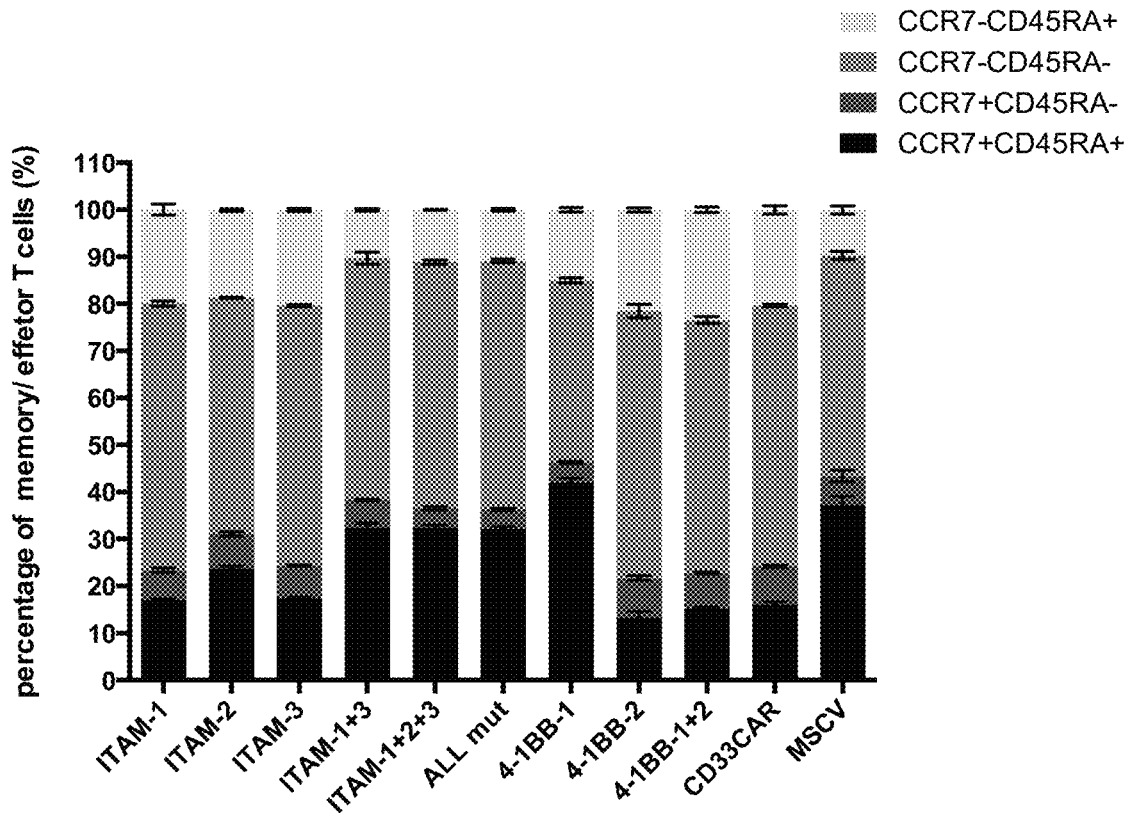
Figure 15C:
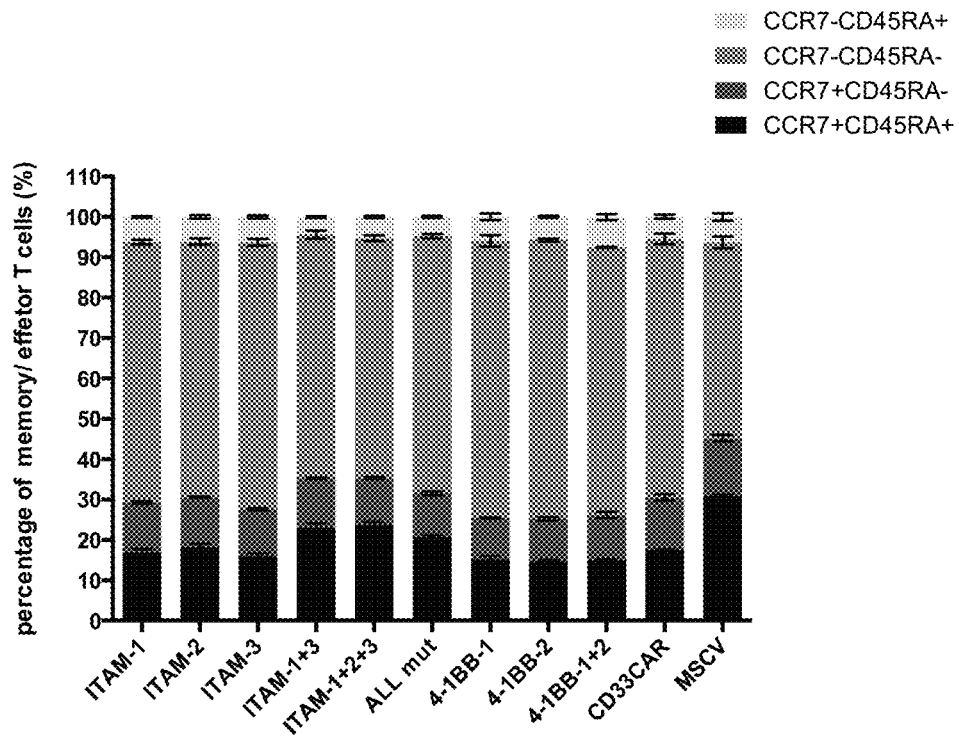
Figure 15D:
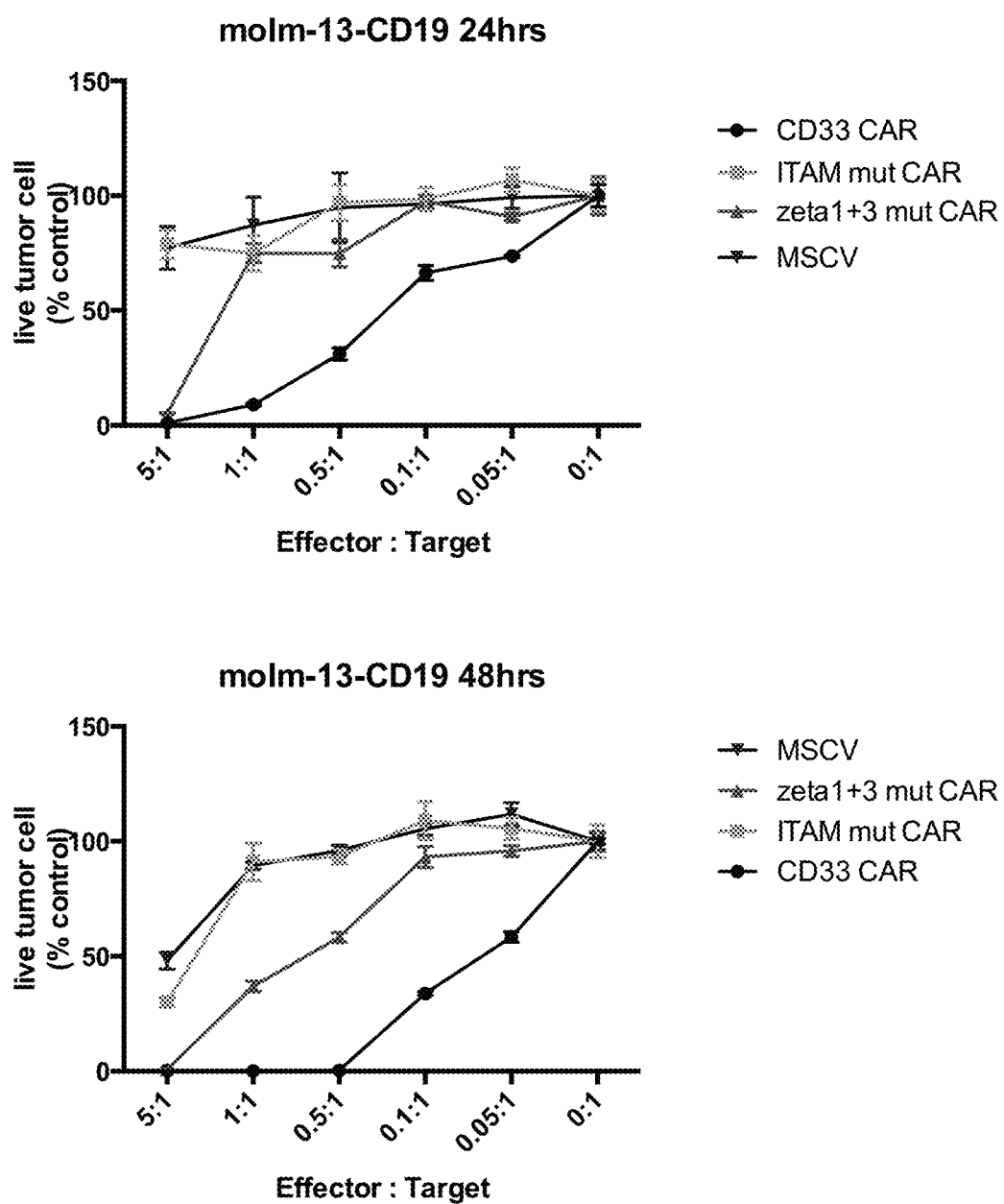

The CD33 ITAM1+3, CD33 ITAM1+2+3 and ALL mutants (FIG. 15A) had similar differentiation profiles as control T cells with culture. Each showed a significant increase in the proportion of TN cells and a decrease in the proportion of TEFF relative to CD33 CAR T cells. In contrast, mutation of the 4-1BB signaling domain alone (CD33 41BB 1+2) did not impact differentiation status. This indicates that cell intrinsic signaling through the CAR CD3ζ ITAM domains during ex vivo T cell expansion leads to a more activated and effector-differentiated phenotype. (FIG. 15B-15C) Although mutation of critical signaling components of the ζ domain lead to CAR T cells that are phenotypically similar to control T cells, it also resulted in abrogation of CAR T cell activity (partially in CD33 ITAM1+3 mutant and fully in CD33 ITAM1+2+3) (FIG. 15D).

Example 4

Four Day Treatment with PI3K Inhibitors

Figure 16A:
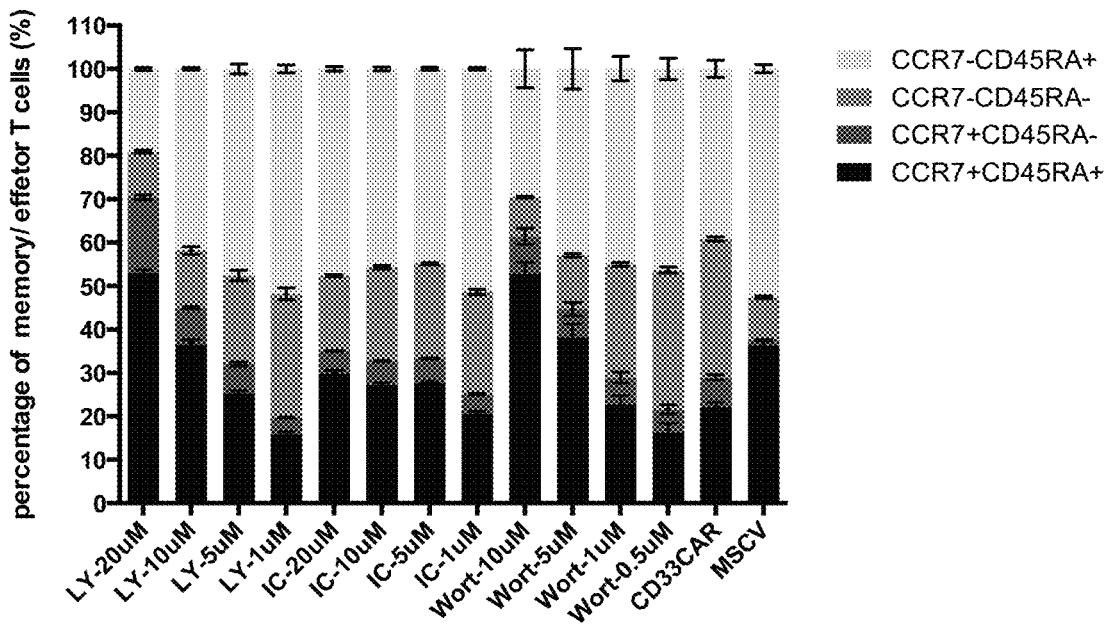
FIGS. 16A-16C.
Figure 16B:
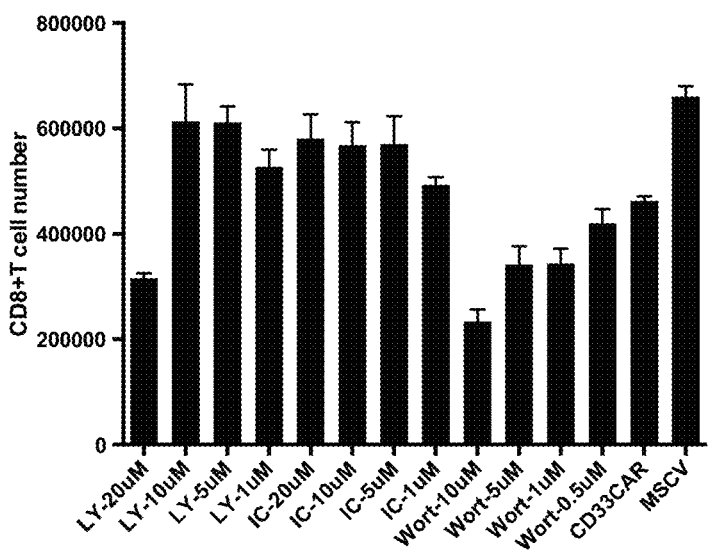
Figure 16C:
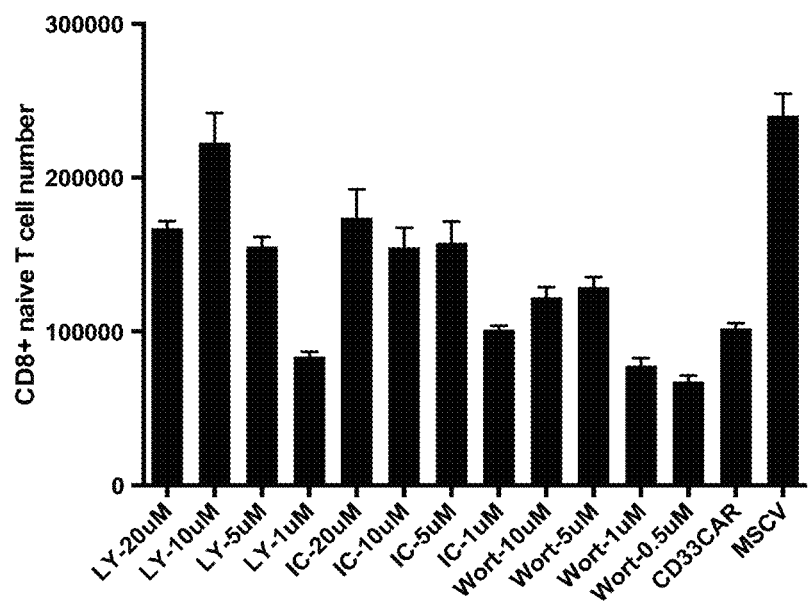
Figure 16C:
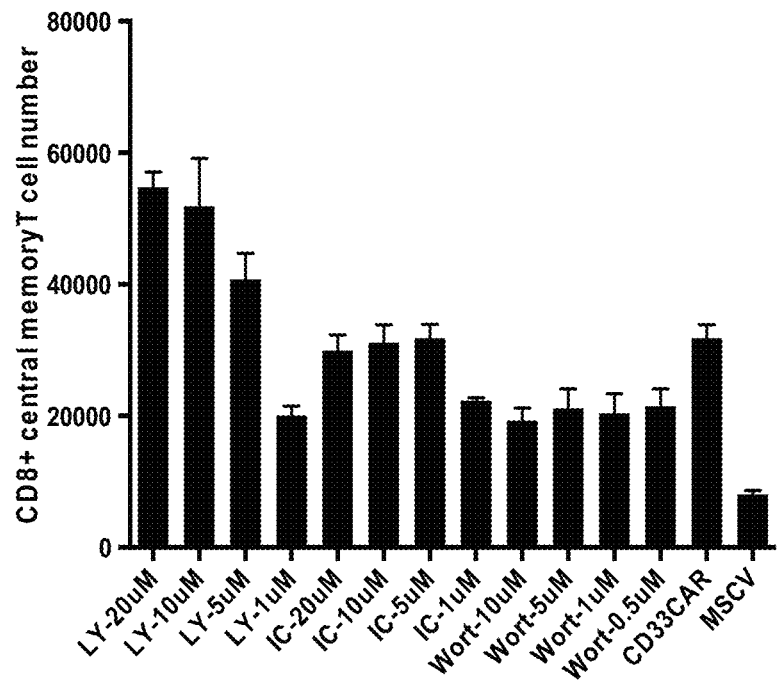
Figure 16C:
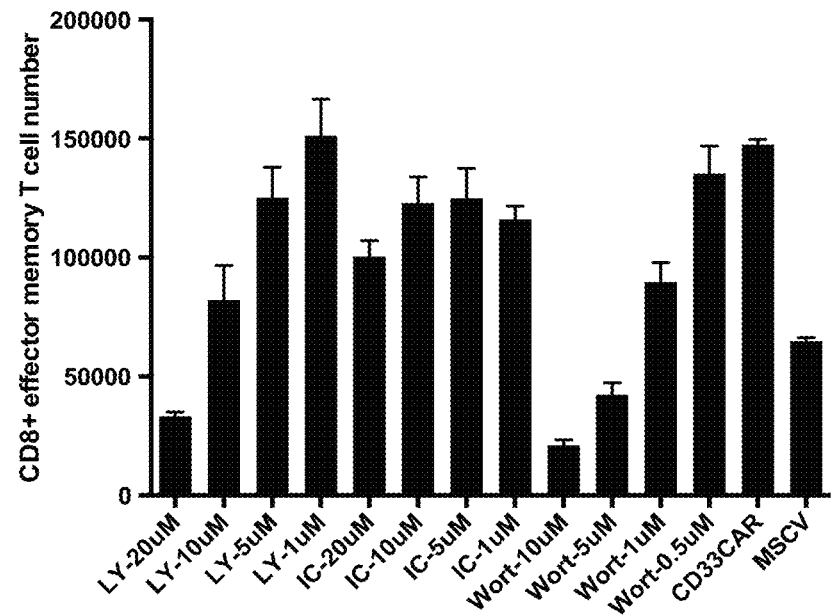
Figure 16C:
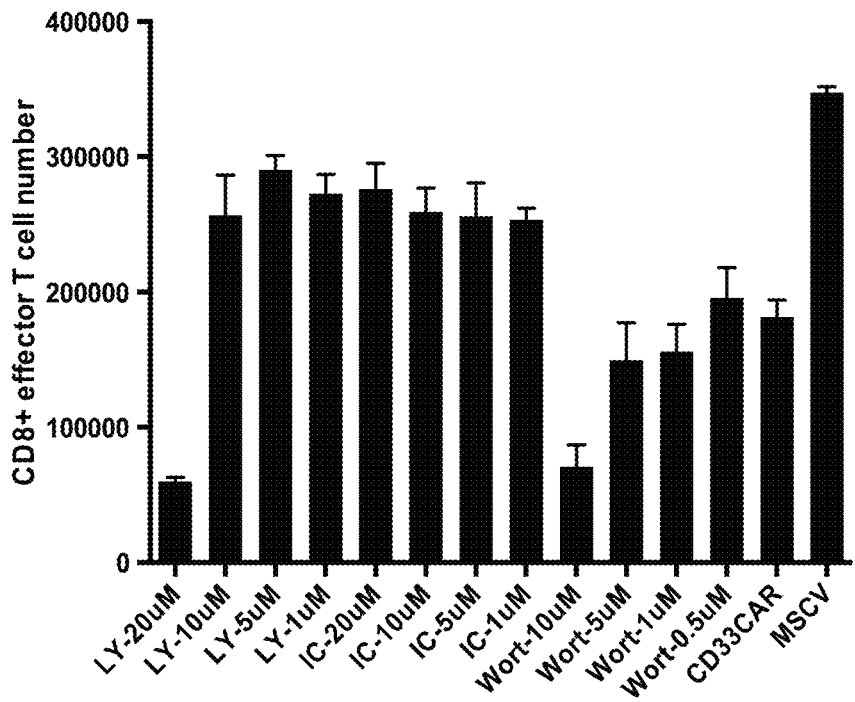

After 4 days of treatment with PI3K inhibitors (LY-294002, IC87114 or Wortmannin) at different concentrations (as indicated in FIGS. 16A-16C), the percent of CD8$^+$ TN and TCM cells increased significantly relative to untreated CD33 CAR T cells, while there was a significant decrease in CD8$^+$ TEM or TEFF cell percent. The number of CD8$^+$ TN and TCM cells increased significantly relative to untreated CD33 CAR T cells by treatment of LY-294002, while significantly decreased CD8$^+$ TEM or TEFF cell percent.

Methods

Day 1: Separated PBMCs from apheresis ring of donor. Enriched human T cells by Pan T cell negative selection kit. Activate human T cells by anti-human CD3 and anti-human CD28 (1 ug/ml) coated plates overnight.

Day2: Transduced human T cells with anti-CD33 CAR gamma-retrovirus or MSCV control by retronectin coated non-tissue culture plate.

Day3: Resuspend the cells and plate them in the IL-2 RPMI medium in the tissue culture plate.

Day5: Added LY-294002, IC87114, Wolimannin (PI3K inhibitor, different concentration) to the cultured T cells. 100U/ml IL-2 was added to cultures every 2 days. Cells were analyzed 4 days later by flow Cytometry.

Example 5

Single Dose of Inhibitor

Figure 17A:
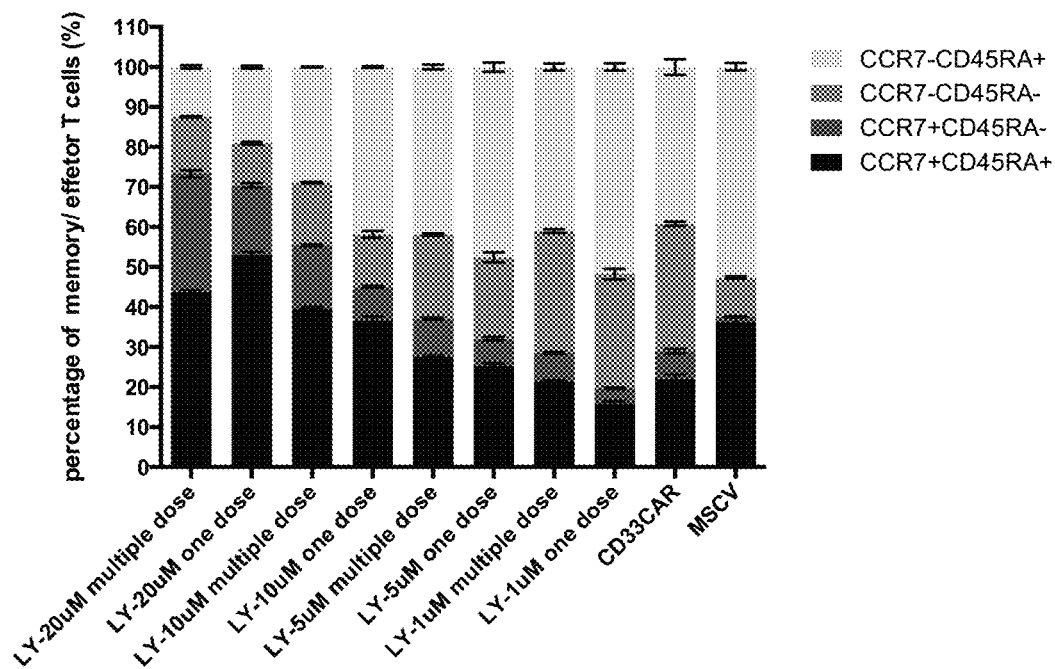
FIGS. 17A-17C.
Figure 17B:
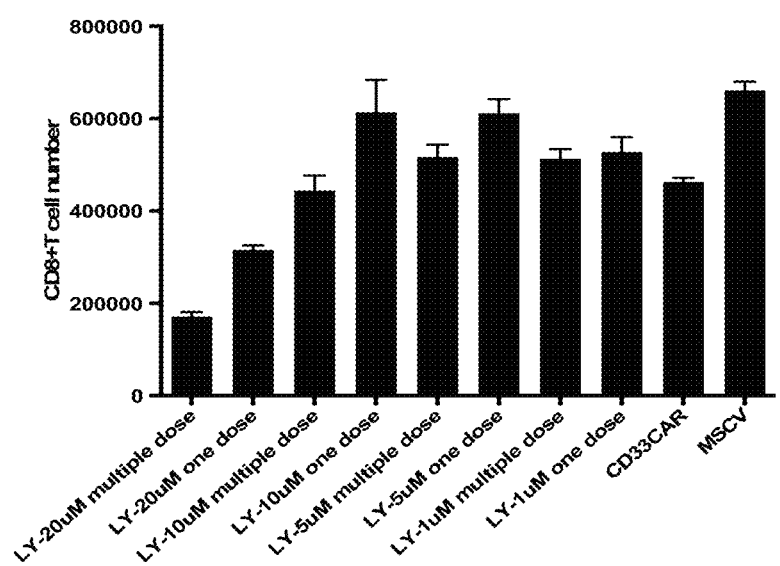
Figure 17C:
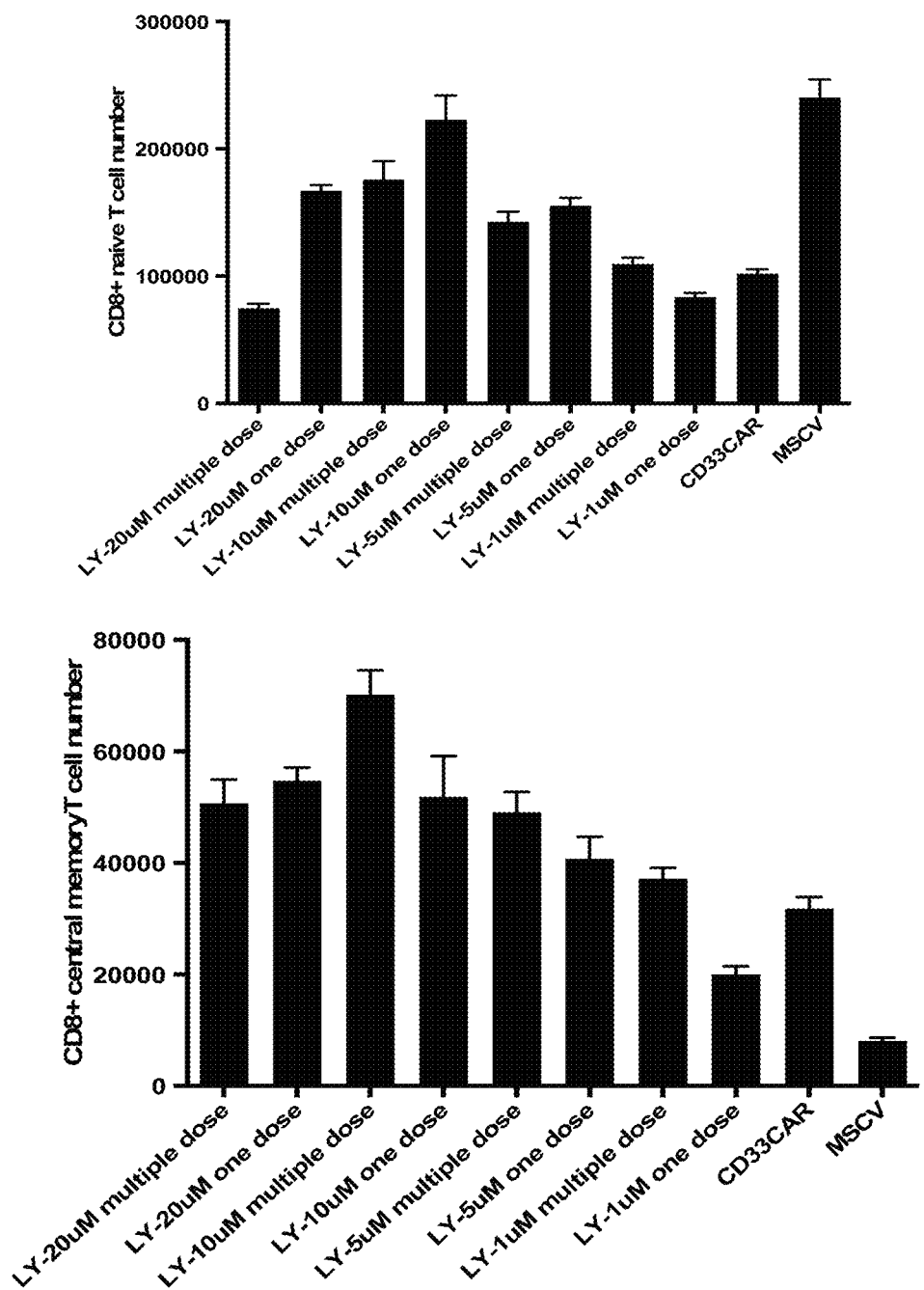
Figure 17C:
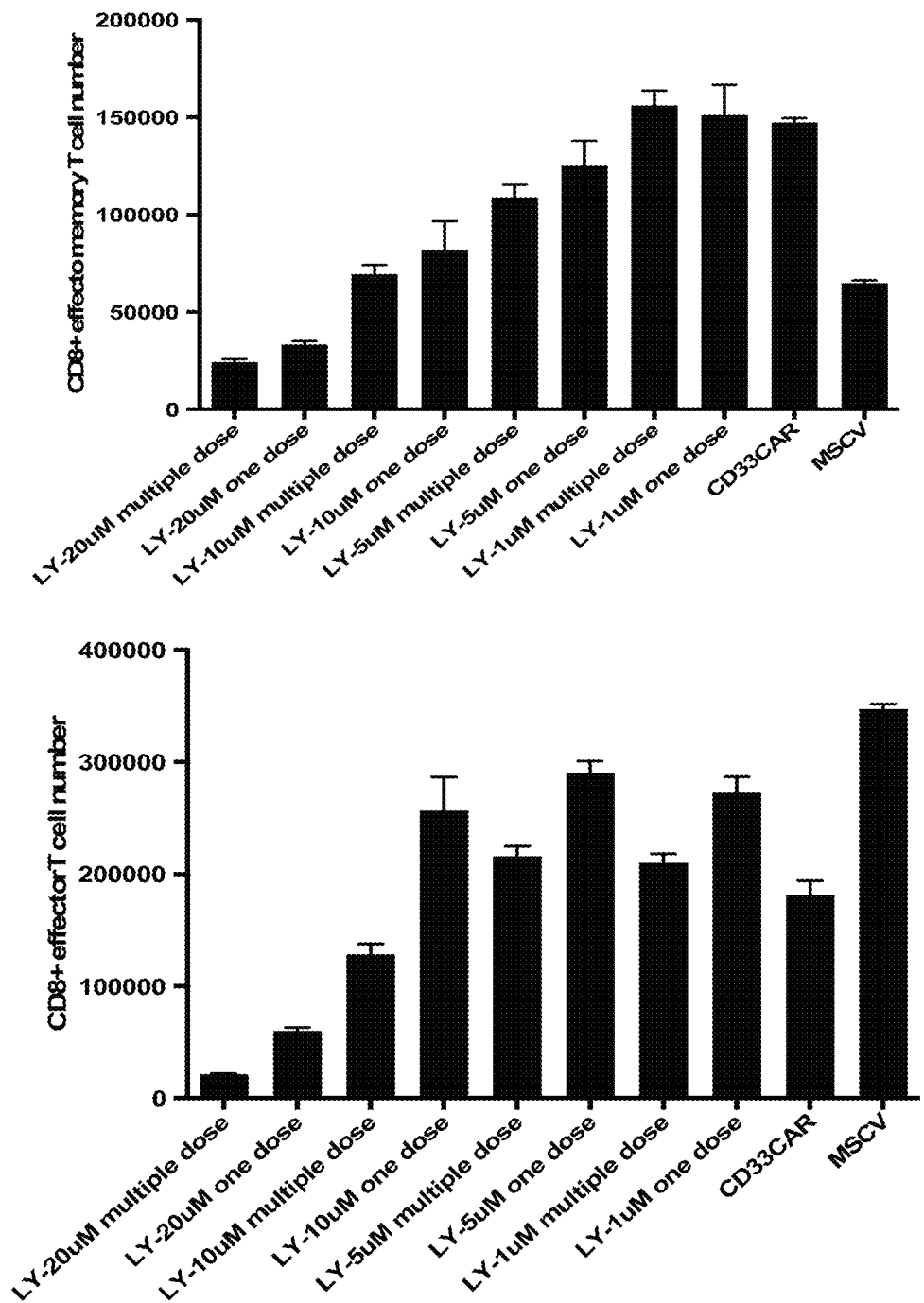

After 4 days of one dose or two doses treatment with PI3K inhibitor LY-294002 at different concentration, there was not very big difference on T cell differentiation between one dose treatment and two doses treatment. Other than this difference, the same protocol as Example 4 was followed. One dose of PI3K inhibitor at day 5 after initial stimulation by CD3/CD28 is enough to diminish the altered T cell differentiation (FIGS. 17A-17C).

Example 6

Treatment with c-Myc Inhibitor

Figure 18A:
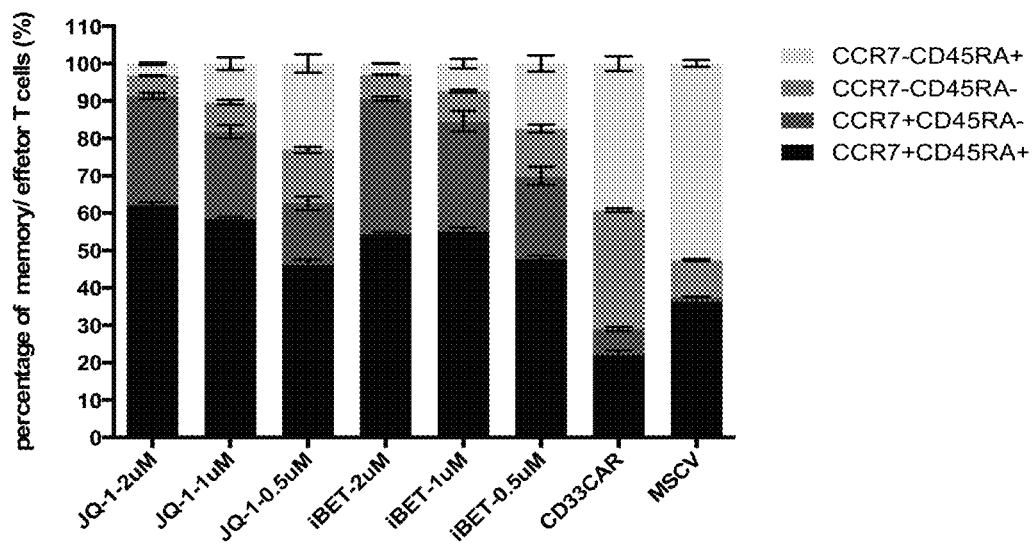
FIGS. 18A-18C.
Figure 18B:
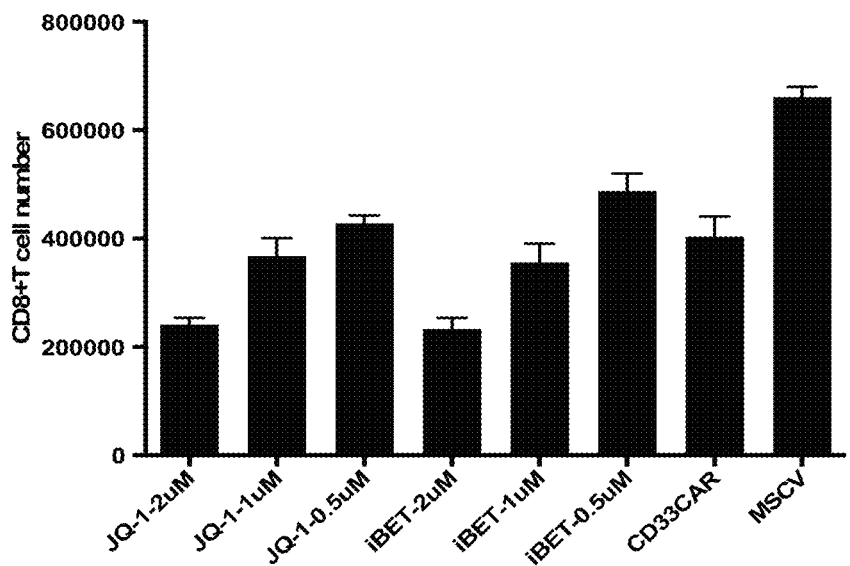
Figure 18C:
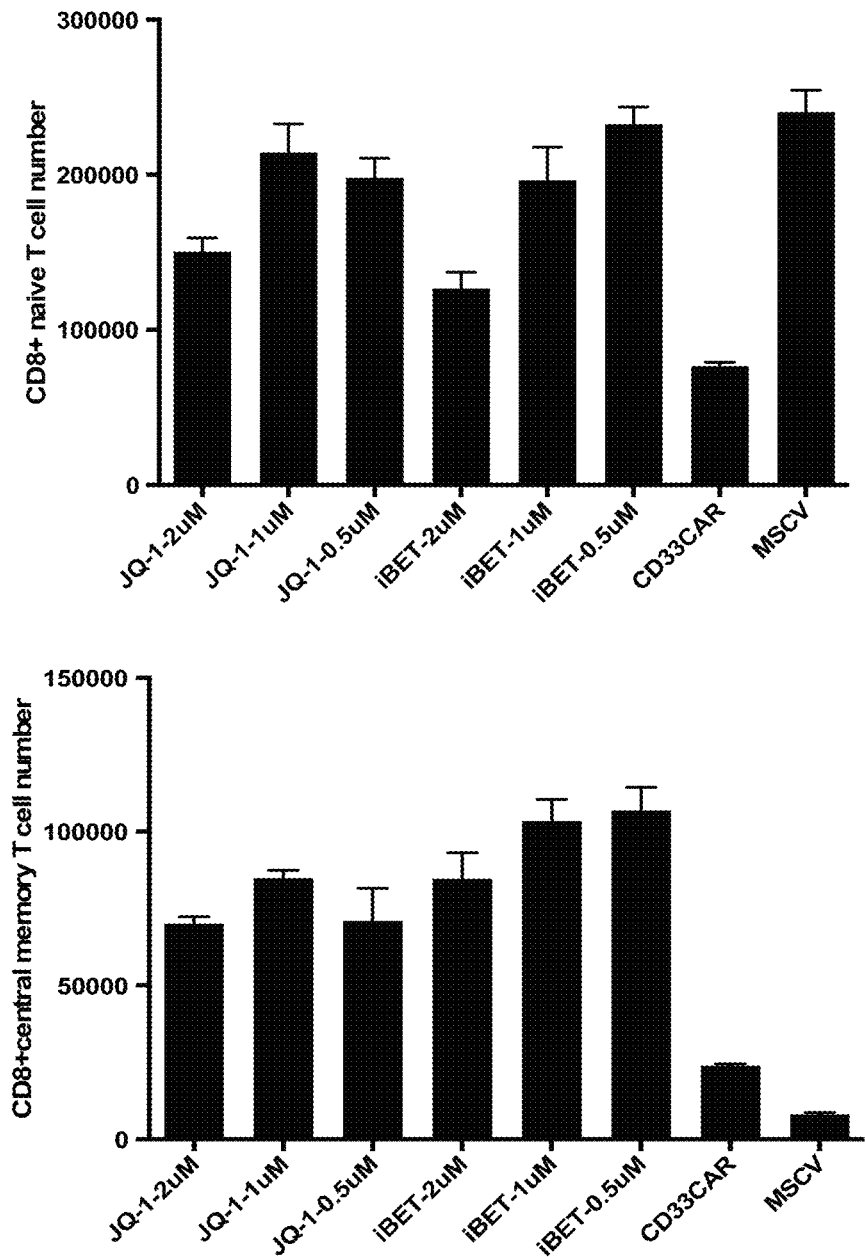
Figure 18C:
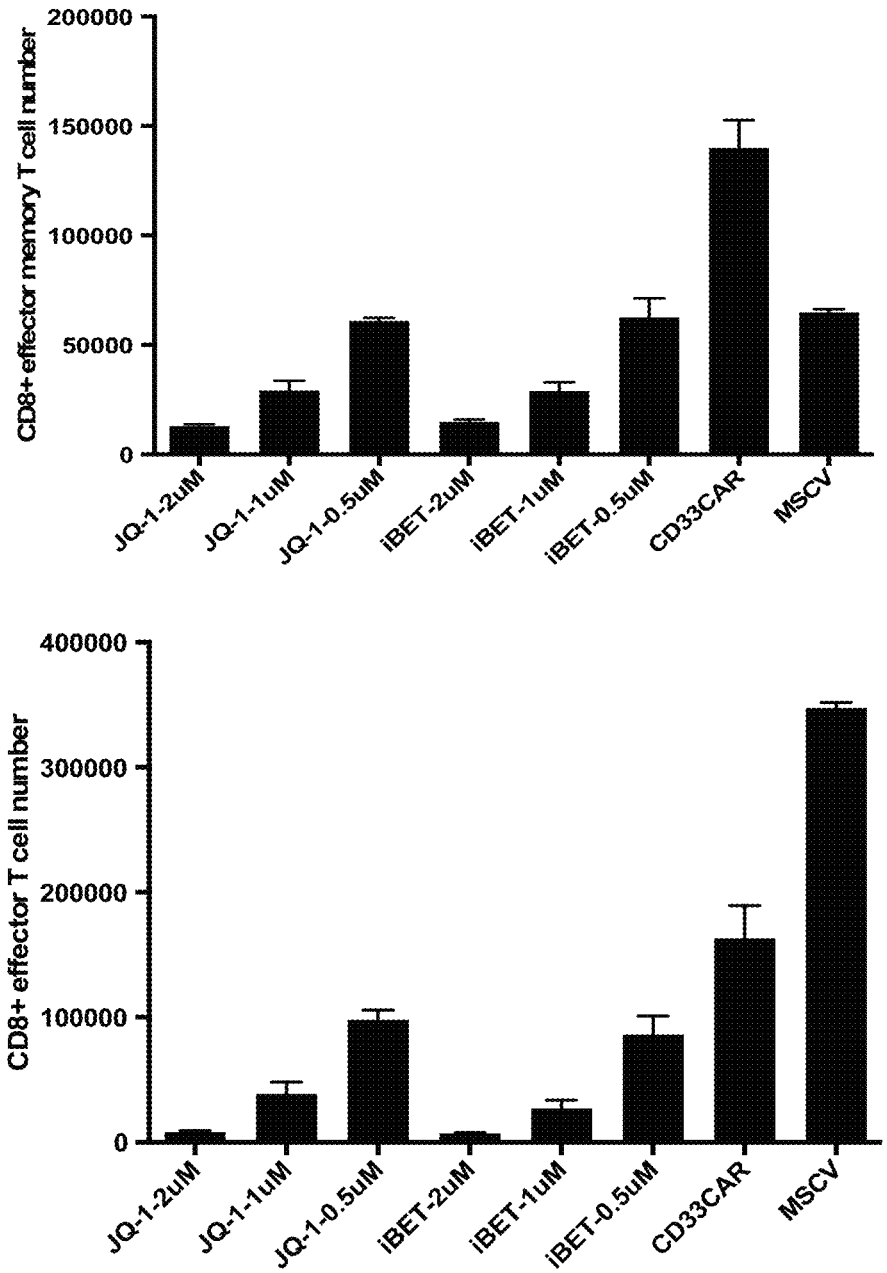

After 4 days of treatment with c-Myc inhibitors at different concentration, the percent and number of CD8$^+$ TN and TCM cells increased significantly relative to untreated CD33 CAR T cells, while significantly decreased CD8$^+$ TEM or TEFF cell percent and numbers (FIGS. 18A-18C). However, higher concentration of inhibitor treatment may diminish cell expansion. Dose dependent effects of the inhibitor were determined and a concentration of 0.5-1 µM was selected for optimal effect on T cell differentiation with no reduction in total cell numbers.

Methods

Day1-3: Separated PBMCs from apheresis ring of donor. Enriched human T cells by Pan T cell negative selection kit. Activate human T cells by anti-human CD3 and anti-human CD28 (1µg/ml) coated plates overnight.

Day2-4: Transduced human T cells with anti-CD33 CAR gamma-retrovirus or MSCV control by retronectin coated non-tissue culture plate.

Day3-5: Resuspend the cells and plate them in the IL-2 RPMI medium in the tissue culture plate.

Day5-7: Added JQ-1, iBET (c-Myc inhibitor, different concentration) to the cultured T cells. 100U/ml IL-2 was added to cultures every 2 days. Cells were analyzed 4 days later by flow Cytometry.

REFERENCES

1. Srivastava S, and Riddell S R. Engineering CAR-T cells: Design concepts. *Trends in immunology.* 2015; 36(8):494-502.
2. Kalos M, and June C H. Adoptive T cell transfer for cancer immunotherapy in the era of synthetic biology. *Immunity.* 2013;39(1):49-60.
3. Pule M A, Savoldo B, Myers G D, Rossig C, Russell H V, Dotti G, Huls MEI, Liu E, Gee A P, Mei Z, et al. Virus-specific T cells engineered to coexpress tumor-specific receptors: persistence and antitumor activity in individuals with neuroblastoma. *Nature medicine.* 2008;14(11):1264-70.
4. Savoldo B, Ramos C A, Liu E, Mims M P, Keating M J, Carrum G, Kamble R T, Bollard C M, Gee A P, Mei Z, et al. CD28 costimulation improves expansion and persistence of chimeric antigen receptor-modified T cells in lymphoma patients. *The Journal of clinical investigation.* 2011;121(5):1822-6.
5. Geiger T L, Nguyen P, Leitenberg D, and Flavell R A. Integrated src kinase and costimulatory activity enhances signal transduction through single-chain chimeric receptors in T lymphocytes. *Blood.* 2001;98(8): 2364-71.
6. Park J H, Geyer M B, and Brentjens R J. CD19-targeted CAR T-cell therapeutics for hematologic malignancies: interpreting clinical outcomes to date. *Blood.* 2016;127 (26):3312-20.
7. Casucci M, Nicolis di Robilant B, Falcone L, Camisa B, Norelli M, Genovese P, Gentner B, Gullotta F, Ponzoni M, Bernardi M, et al. CD44v6-targeted T cells mediate potent antitumor effects against acute myeloid leukemia and multiple myeloma. *Blood.* 2013;122(20): 3461-72.
8. Pizzitola I, Anjos-Afonso F, Rouault-Pierre K, Lassailly F, Tettamanti S, Spinelli O, Biondi A, Biagi E, and Bonnet D. Chimeric antigen receptors against CD33/CD123 antigens efficiently target primary acute myeloid leukemia cells in vivo. *Leukemia.* 2014;28(8): 1596-605.
9. Kenderian S S, Ruella M, Shestova O, Klichinsky M, Aikawa V, Morrissette J J, Scholler J, Song D, Porter D L, Carroll M, et al. CD33-specific chimeric antigen receptor T cells exhibit potent preclinical activity against human acute myeloid leukemia. *Leukemia.* 2015;29(8):1637-47.
10. O'Hear C, Heiber J F, Schubert I, Fey G, and Geiger T L. Anti-CD33 chimeric antigen receptor targeting of acute myeloid leukemia. *Haematologica.* 2015;100(3): 336-44.
11. Imai C, Mihara K, Andreansky M, Nicholson I C, Pui C H, Geiger T L, and Campana D. Chimeric receptors with 4-1BB signaling capacity provoke potent cytotoxicity against acute lymphoblastic leukemia. *Leukemia.* 2004;18(4):676-84.
12. Kalos M, Levine B L, Porter D L, Katz S, Grupp S A, Bagg A, and June C H. T cells with chimeric antigen receptors have potent antitumor effects and can establish memory in patients with advanced leukemia. *Science translational medicine.* 2011;3(95):95ra73.
13. Grupp S A, Kalos M, Barrett D, Aplenc R, Porter D L, Rheingold S R, Teachey D T, Chew A, Hauck B, Wright J F, et al. Chimeric antigen receptor-modified T cells for acute lymphoid leukemia. *The New England journal of medicine.* 2013;368(16):1509-18.
14. Maude S L, Frey N, Shaw P A, Aplenc R, Barrett D M, Bunin N J, Chew A, Gonzalez V E, Zheng Z, Lacey S F, et al. Chimeric antigen receptor T cells for sustained remissions in leukemia. *The New England journal of medicine.* 2014;371(16):1507-17.
15. Brentjens R J, Riviere I, Park R I, Davila M L, Wang X, Stefanski J, Taylor C, Yeh R, Bartido S, Borquez-Ojeda O, et al. Safety and persistence of adoptively transferred autologous CD19-targeted T cells in patients with relapsed or chemotherapy refractory B-cell leukemias. *Blood.* 2011;118(18):4817-28.
16. Davila M L, Riviere I, Wang X, Bartido S, Park J, Curran K, Chung S S, Stefanski J, Borquez-Ojeda O, Olszewska M, et al. Efficacy and toxicity management of 19-28z CAR T cell therapy in B cell acute lymphoblastic leukemia. *Science translational medicine.* 2014; 6(224): 224ra25.
17. Zhao Z, Condomines M, van der Stegen S J, Perna F, Kloss C C, Gunset G, Plotkin J, and Sadelain M. Structural Design of Engineered Costimulation Determines Tumor Rejection Kinetics and Persistence of CART Cells. *Cancer cell.* 2015;28(4):415-28.
18. Sommermeyer D, Hudecek M, Kosasih P L, Gogishvili T, Maloney D G, Turtle C J, and Riddell S R. Chimeric antigen receptor-modified T cells derived from defined $CD8^+$ and $CD4^+$ subsets confer superior antitumor reactivity in vivo. *Leukemia.* 2016;30(2): 492-500.
19. Xu Y, Zhang M, Ramos C A, Durett A, Liu E, Dakhova O, Liu H, Creighton C J, Gee A P, Heslop H E, et al. Closely related T-memory stem cells correlate with in vivo expansion of CAR.CD19-T cells and are preserved by IL-7 and IL-15. *Blood.* 2014;123(24): 3750-9.
20. Kawalekar O U, O'Connor R S, Fraietta J A, Guo L, McGettigan S E, Posey A D, Jr., Patel P R, Guedan S, Scholler J, Keith B, et al. Distinct Signaling of Coreceptors Regulates Specific Metabolism Pathways and Impacts Memory Development in CAR T Cells. *Immunity.* 2016;44(2):380-90.
21. Long A H, Haso W M, Shern J F, Wanhainen K M, Murgai M, Ingaramo M, Smith J P, Walker A J, Kohler M E, Venkateshwara V R, et al. 4-1BB costimulation ameliorates T cell exhaustion induced by tonic signaling of chimeric antigen receptors. *Nature medicine.* 2015;21(6):581-90.
22. Rabinovich, G. A., Gabrilovich, D. & Sotomayor, E. M. Immunosuppressive strategies that are mediated by tumor cells. *Annual review of immunology* 25, 267-296 (2007).
23. Leen, A. M., Rooney, C. M. & Foster, A. E. Improving T cell therapy for cancer. *Annual review of immunology* 25, 243-265 (2007).
24. Co M S, Avdalovic N M, Caron P C, Avdalovic M V, Scheinberg D A, and Queen C. Chimeric and humanized antibodies with specificity for the CD33 antigen. *Journal of immunology.* 1992;148(4):1149-54.
25. Dienz, O. & Rincon, M. The effects of IL-6 on CD4 T cell responses. *Clinical immunology* 130, 27-33 (2009).
26. Sallusto F, Geginat J, and Lanzavecchia A. Central memory and effector memory T cell subsets: function, generation, and maintenance. *Annual review of immunology.* 2004; 22(745-63).
27. Jang I K, Lee Z H, Kim Y J, Kim S H, and Kwon B S. Human 4-1BB (CD137) signals are mediated by TRAF2 and activate nuclear factor-kappa B. *Biochemical and biophysical research communications.* 1998; 242(3):613-20.
28. Arch R H, and Thompson C B. 4-1BB and Ox40 are members of a tumor necrosis factor (TNF)-nerve growth factor receptor subfamily that bind TNF receptor-associated factors and activate nuclear factor kappaB. *Molecular and cellular biology.* 1998;18(1):558-65.
29. Zhao Y, Wang Q J, Yang S, Kochenderfer J N, Zheng Z, Zhong X, Sadelain M, Eshhar Z, Rosenberg S A, and Morgan R A. A herceptin-based chimeric antigen receptor with modified signaling domains leads to enhanced survival of transduced T lymphocytes and antitumor activity. *Journal of immunology.* 2009;183 (9):5563-74.
30. Hinrichs C S, Borman Z A, Cassard L, Gattinoni L, Spolski R, Yu Z, Sanchez-Perez L, Muranski P, Kern S J, Logun C, et al. Adoptively transferred effector cells derived from naive rather than central memory $CD8^+$ T cells mediate superior antitumor immunity. *Proceedings of the National Academy of Sciences of the United States of America.* 2009;106(41):17469-74.
31. Wang X, Berger C, Wong C W, Forman S J, Riddell S R, and Jensen M C. Engraftment of human central memory-derived effector $CD8^+$ T cells in immunodeficient mice. *Blood.* 2011;117(6):1888-98.

32. Cieri N, Camisa B, Cocchiarella F, Forcato M, Oliveira G, Provasi E, Bondanza A, Bordignon C, Peccatori J, Ciceri F, et al. IL-7 and IL-15 instruct the generation of human memory stem T cells from naive precursors. *Blood.* 2013;121(4):573-84.
33. Kramer, A., Green, J., Pollard, J., Jr. & Tugendreich, S. Causal analysis approaches in Ingenuity Pathway Analysis. *Bioinformatics* 30, 523-530 (2014).
34. Kim E H, and Suresh M. Role of PI3K/Akt signaling in memory CD8 T cell differentiation. *Frontiers in immunology.* 2013;4(20).
35. Araki, K., et al. mTOR regulates memory CD8 T-cell differentiation. *Nature* 460, 108-112 (2009).
36. Kim E H, Sullivan J A, Plisch E H, Tejera M M, Jatzek A, Choi K Y, and Suresh M. Signal integration by Akt regulates CD8 T cell effector and memory differentiation. *Journal of immunology.* 2012;188(9):4305-14.
37. Kong D, and Yamori T. Advances in development of phosphatidylinositol 3-kinase inhibitors. *Current medicinal chemistry.* 2009;16(22):2839-54.
38. Kaech S M, and Cui W. Transcriptional control of effector and memory CD8+ T cell differentiation. *Nature reviews Immunology.* 2012;12(11):749-61.
39. Lin W H, Adams W C, Nish S A, Chen Y H, Yen B, Rothman N J, Kratchmarov R, Okada T, Klein U, and Reiner S L. Asymmetric PI3K Signaling Driving Developmental and Regenerative Cell Fate Bifurcation. *Cell reports.* 2015;13(10):2203-18.
40. Gattinoni L, Lugli E, Ji Y, Pos Z, Paulos C M, Quigley M F, Almeida J R, Gostick E, Yu Z, Carpenito C, et al. A human memory T cell subset with stem cell-like properties. *Nature medicine.* 2011;17(10):1290-7.
41. Flynn J K, and Gorry P R. Stem memory T cells (TSCM)-their role in cancer and HIV immunotherapies. *Clinical & translational immunology.* 2014;3(7):e20.
42. Sabatino M, Hu J, Sommariva M, Gautam S, Fellowes V, Hocker J D, Dougherty S, Qin H, Klebanoff C A, Fry T J, et al. Generation of clinical-grade CD19-specific CAR-modified CD8+ memory stem cells for the treatment of human B-cell malignancies. *Blood.* 2016;128(4):519-28.
43. Frauwirth K A, and Thompson C B. Regulation of T lymphocyte metabolism. *Journal of immunology.* 2004;172(8):4661-5.
44. Pollizzi K N, and Powell J D. Regulation of T cells by mTOR: the known knowns and the known unknowns. *Trends in immunology.* 2015;36(1):13-20.
45. Zhong, X. S., Matsushita, M., Plotkin, J., Riviere, I. & Sadelain, M. Chimeric antigen receptors combining 4-1BB and CD28 signaling domains augment PI3kinase/AKT/Bcl-XL activation and CD8+ T cell-mediated tumor eradication. *Mol Ther* 18, 413-420 (2010).
46. Delmore, J. E., et al. BET bromodomain inhibition as a therapeutic strategy to target c-Myc. *Cell* 146, 904-917 (2011).
47. Kagoya, Y., et al. BET bromodomain inhibition enhances T cell persistence and function in adoptive immunotherapy models. *The Journal of clinical investigation* 126, 3479-3494 (2016).
48. Chapman, N. M. & Chi, H. mTOR Links Environmental Signals to T Cell Fate Decisions. *Frontiers in immunology* 5, 686 (2014).
49. Wang, R., et al. The transcription factor Myc controls metabolic reprogramming upon T lymphocyte activation. *Immunity* 35, 871-882 (2011).
50. Pollizzi K N, Patel C H, Sun I H, Oh M H, Waickman A T, Wen J, Delgoffe G M, and Powell J D. mTORC1 and mTORC2 selectively regulate CD8(+) T cell differentiation. *The Journal of clinical investigation.* 2015;125(5):2090-108.
51. Sukumar M, Liu J, Ji Y, Subramanian M, Crompton J G, Yu Z, Roychoudhuri R, Palmer D C, Muranski P, Karoly E D, et al. Inhibiting glycolytic metabolism enhances CD8+ T cell memory and antitumor function. *The Journal of clinical investigation.* 2013;123(10):4479-88.
52. Dotti, G., Gottschalk, S., Savoldo, B. & Brenner, M. K. Design and development of therapies using chimeric antigen receptor-expressing T cells. Immunological reviews 257, 107-126 (2014).
53. Nicholson I C, Lenton K A, Little D J, Decorso T, Lee F T, Scott A M, Zola H, and Hohmann AW. Construction and characterisation of a functional CD19 specific single chain FAT fragment for immunotherapy of B lineage leukaemia and lymphoma. *Molecular immunology.* 1997;34(16-17):1157-65.
54. Li H, and Durbin R. Fast and accurate short read alignment with Burrows-Wheeler transform. *Bioinformatics.* 2009;25(14):1754-60.
55. Dobin A, Davis C A, Schlesinger F, Drenkow J, Zaleski C, Jha S, Batut P, Chaisson M, and Gingeras T R. STAR: ultrafast universal RNA-seq aligner. *Bioinformatics.* 2013;29(1):15-21.
56. Anders S, Pyl P T, and Huber W. HTSeq-a Python framework to work with high-throughput sequencing data. *Bioinformatics.* 2015;31(2):166-9.
57. Harrow J, Frankish A, Gonzalez J M, Tapanari E, Diekhans M, Kokocinski F, Aken B L, Barrell D, Zadissa A, Searle S, et al. GENCODE: the reference human genome annotation for The ENCODE Project. *Genome research.* 2012;22(9):1760-74.
58. Subramanian A, Tamayo P, Mootha V K, Mukherjee S, Ebert B L, Gillette M A, Paulovich A, Pomeroy S L, Golub T R, Lander E S, et al. Gene set enrichment analysis: a knowledge-based approach for interpreting genome-wide expression profiles. *Proceedings of the National Academy of Sciences of the United States of America.* 2005;102(43):15545-50.
59. Dienz, O. & Rincon, M. The effects of IL-6 on CD4 T cell responses. *Clinical immunology* 130, 27-33 (2009).

LIST OF SEQUENCES:
[hCD8-CD33scFv-41BB-CD3 (hinge and transmembrane domain of CD8α; 4-1BB; CD3ζ signaling domain)]

SEQ ID NO:1

GAATTCGCCCTTCCACCATGGCCTTACCAGTGACCGCCTTGCTCCTGCCGCTGGCCT

TGCTGCTCCACGCCGCCAGGCCGGACATTCAGATGACCCAGTCACCATCCAGCCTC

AGTGCTTCTGTTGGGGACCGAGTTACCATCACTTGTCGCGCAAGCGAATCTGTCGAC

AACTATGGCATAAGTTTTATGAATTGGTTTCAGCAGAAGCCAGGAAAGGCACCGAA

```
GCTGCTTATCTACGCTGCAAGTAATCAAGGATCCGGCGTGCCTAGCCGGTTCTCCGG

ATCAGGATCCGGGACAGACTTTACATTGACAATTTCTAGCCTGCAGCCAGATGATTT

TGCAACCTACTACTGTCAACAGTCTAAGGAAGTTCCCTGGACGTTTGGGCAGGGCA

CCAAGGTTGAGATCAAGGGCGGCGGCGGGTCCGGAGGTGGCGGGTCCGGCGGCGG

TGGCTCCGGGGGGGGGTAGCCAGGTCCAGCTCGTACAAAGTGGTGCCGAGGTGA

AGAAACCCGGGAGCAGCGTGAAAGTGTCCTGTAAGGCCAGTGGCTACACCTTTACA

GACTACAATATGCACTGGGTGCGCCAGGCGCCCGGCCAGGGCCTTGAGTGGATAGG

CTACATTTATCCCTACAATGGCGGAACCGGATACAATCAGAAGTTTAAGAGCAAGG

CAACAATTACCGCTGATGAGTCCACTAACACCGCTTACATGGAATTGAGCAGTCTTC

GATCCGAAGACACTGCCGTGTATTACTGTGCCCGAGGAAGACCTGCCATGGACTAC

TGGGGTCAGGGAACTCTGGTAACCGTCTCTAGCGCGGCCGCAACCACGACGCCAGC

GCCGCGACCACCAACACCGGCGCCCACCATCGCGTCGCAGCCCCTGTCCCTGCGCC

CAGAGGCGTGCCGGCCAGCGGCGGGGGCGCAGTGCACACGAGGGGGCTGGACTT

CGCCTGTGATATCTACATCTGGGCGCCCTTGGCCGGGACTTGTGGGGTCCTTCTCCT

GTCACTGGTTATCACCCTTTACTGCAAACGGGGCAGAAAGAAACTCCTGTATATATT

CAAACAACCATTTATGAGACCAGTACAAACTACTCAAGAGGAAGATGGCTGTAGCT

GCCGATTTCCAGAAGAAGAAGAAGGAGGATGTGAACTGAGAGTGAAGTTCAGCAG

GAGCGCAGACGCCCCCGCGTACCAGCAGGGCCAGAACCAGCTCTATAACGAGCTCA

ATCTAGGACGAAGAGAGGAGTACGATGTTTTGGACAAGAGACGTGGCCGGGACCCT

GAGATGGGGGGAAAGCCGAGAAGGAAGAACCCTCAGGAAGGCCTGTACAATGAAC

TGCAGAAAGATAAGATGGCGGAGGCCTACAGTGAGATTGGGATGAAAGGCGAGCG

CCGGAGGGGCAAGGGGCACGATGGCCTTTACCAGGGTCTCAGTACAGCCACCAAGG

ACACCTACGACGCCCTTCACATGCAGGCCCTGCCCCCTCGCTAACTCGAG
```

[hCD8-CD33scFv-41BB-CD3]  
SEQ ID NO:2

IRPSTMALPVTALLLPLALLLHAARPDIQMTQSPSSLSASVGDRVTITCRASESVDNYGIS
FMNWFQQKPGKAPKLLIYAASNQGSGVPSRFSGSGSGTDFTLTISSLQPDDFATYYCQQ
SKEVPWTFGQGTKVEIKGGGGSGGGGSGGGGSGGGGSQVQLVQSGAEVKKPGSSVKV
SCKASGYTFTDYNMHWVRQAPGQGLEWIGYIYPYNGGTYNQKFKSKATITADESTNT
AYMELSSLRSEDTAVYYCARGRPAMDYWGQGTLVTVSSAAATTTPAPRPPTPAPTIAS
QPLSLRPEACRPAAGGAVHTRGLDFACDIYIWAPLAGTCGVLLLSLVITLYCKRGRKKL
LYIFKQPFMRPVQTTQEEDGCSCRFPEEEEGGCELRVKFSRSADAPAYQQGQNQLYNEL
NLGRREEYDVLDKRRGRDPEMGGKPRRKNPQEGLYNELQKDKMAEAYSEIGMKGERR
RGKGHDGLYQGLSTATKDTYDALHMQALPPR*LE

[anti-CD 33 scFv]  
SEQ ID NO:3

DIQMTQSPSSLSASVGDRVTITCRASESVDNYGISFMNWFQQKPGKAPKLLIYAASNQG
SGVPSRFSGSGSGTDFTLTISSLQPDDFATYYCQQSKEVPWTFGQGTKVEIKGGGGSGG
GGSGGGGSGGGGSQVQLVQSGAEVKKPGSSVKVSCKASGYTFTDYNMHWVRQAPGQ
GLEWIGYIYPYNGGTYNQKFKSKATITADESTNTAYMELSSLRSEDTAVYYCARGRP
AMDYWGQGTLVTVSS

-continued

[human 4-1BB]
SEQ ID NO:4
MGNSCYNIVATLLLVLNFERTRSLQDPCSNCPAGTFCDNNRNQICSPCPPNSFSSAGGQR

TCDICRQCKGVFRTRKECSSTSNAECDCTPGFHCLGAGCSMCEQDCKQGQELTKKGCK

DCCFGTFNDQKRGICRPWTNCSLDGKSVLVNGTKERDVVCGPSPADLSPGASSVTPPAP

AREPGHSPQIISFFLALTSTALLFLLFFLTLRFSVVKRGRKKLLYIFKQPFMRPVQTTQEE

DGCSCRFPEEEEGGCEL

[CD3ζ signaling domain]
SEQ ID NO:5
FSRSADAPAYQQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALPPR

[hinge and transmembrane domain of CD8α]
SEQ ID NO:6
TTTPAPRPPTPAPTIASQPLSLRPEACRPAAGGAVHTRGLDFACDIYIWAPLAGTCGVLL

LSLVITLYC

[signal peptide of CD8α]
SEQ ID NO:7
MALPVTALLLPLALLLHAARP

[anti-CD33 single chain variable fragment]
SEQ ID NO:8
GACATTCAGATGACCCAGTCACCATCCAGCCTCAGTGCTTCTGTTGGGGACCGAGTT

ACCATCACTTGTCGCGCAAGCGAATCTGTCGACAACTATGGCATAAGTTTTATGAAT

TGGTTTCAGCAGAAGCCAGGAAAGGCACCGAAGCTGCTTATCTACGCTGCAAGTAA

TCAAGGATCCGGCGTGCCTAGCCGGTTCTCCGGATCAGGATCCGGGACAGACTTTA

CATTGACAATTTCTAGCCTGCAGCCAGATGATTTTGCAACCTACTACTGTCAACAGT

CTAAGGAAGTTCCCTGGACGTTTGGGCAGGGCACCAAGGTTGAGATCAAGGGCGGC

GGCGGGTCCGGAGGTGGCGGGTCCGGCGGCGGTGGCTCCGGGGGGGGGGTAGCC

AGGTCCAGCTCGTACAAAGTGGTGCCGAGGTGAAGAAACCCGGGAGCAGCGTGAA

AGTGTCCTGTAAGGCCAGTGGCTACACCTTTACAGACTACAATATGCACTGGGTGC

GCCAGGCGCCCGGCCAGGGCCTTGAGTGGATAGGCTACATTTATCCCTACAATGGC

GGAACCGGATACAATCAGAAGTTTAAGAGCAAGGCAACAATTACCGCTGATGAGTC

CACTAACACCGCTTACATGGAATTGAGCAGTCTTCGATCCGAAGACACTGCCGTGT

ATTACTGTGCCCGAGGAAGACCTGCCATGGACTACTGGGGTCAGGGAACTCTGGTA

ACCGTCTCTAGC

[human 4-1BB]
SEQ ID NO:9
<u>AAACGGGGCAGAAAGAAACTCCTGTATATATTCAAACAACCATTTATGAGACCAGT</u>

<u>ACAAACTACTCAAGAGGAAGATGGCTGTAGCTGCCGATTTCCAGAAGAAGAAGAA</u>

<u>GGAGGATGTGAACTGAGA</u>

[CD3ζ signaling domain]
SEQ ID NO:10
<u>AGTTCAGCAGGAGCGCAGACGCCCCCGCGTACCAGCAGGGCCAGAACCAGCTCTAT</u>

<u>AACGAGCTCAATCTAGGACGAAGAGAGGAGTACGATGTTTTGGACAAGAGACGTG</u>

<u>GCCGGGACCCTGAGATGGGGGGAAAGCCGAGAAGGAAGAACCCTCAGGAAGGCCT</u>

-continued

GTACAATGAACTGCAGAAAGATAAGATGGCGGAGGCCTACAGTGAGATTGGGATG

AAAGGCGAGCGCCGGAGGGGCAAGGGGCACGATGGCCTTTACCAGGGTCTCAGTA

CAGCCACCAAGGACACCTACGACGCCCTTCACATGCAGGCCCTGCCCCCTCGCTAA

C

[hinge and transmembrane domain of CD8α]
SEQ ID NO:11
ACCACGACGCCAGCGCCGCGACCACCAACACCGGCGCCCACCATCGCGTCGCAGCC

CCTGTCCCTGCGCCCAGAGGCGTGCCGGCCAGCGGCGGGGGGCGCAGTGCACACGA

GGGGGCTGGACTTCGCCTGTGATATCTACATCTGGGCGCCCTTGGCCGGGACTTGTG

GGGTCCTTCTCCTGTCACTGGTTATCACCCTTTACTGCAA

[signal peptide of CD8α]
SEQ ID NO:12
ATGGCCTTACCAGTGACCGCCTTGCTCCTGCCGCTGGCCTTGCTGCTCCACGCCGCC

AGGCCG

[hinge domain of CD8α]
SEQ ID NO:13
TTTPAPRPPTPAPTIASQPLSLRPEACRPAAGGAVHTRGLDFACD

[transmembrane domain of CD8α]
SEQ ID NO:14
IYIWAPLAGTCGVLLLSLVIT

[hinge domain of CD8α]
SEQ ID NO:15
ACCACGACGCCAGCGCCGCGACCACCAACACCGGCGCCCACCATCGCGTCGCAGCC

CCTGTCCCTGCGCCCAGAGGCGTGCCGGCCAGCGGCGGGGGGCGCAGTGCACACGA

GGGGGCTGGACTTCGCCTGTGAT

[transmembrane domain of CD8α]
SEQ ID NO:16
ATCTACATCTGGGCGCCCTTGGCCGGGACTTGTGGGGTCCTTCTCCTGTCACTGGTT

ATCACCCTTTACTGCAA

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

SEQUENCE LISTING

```
<160> NUMBER OF SEQ ID NOS: 16

<210> SEQ ID NO 1
<211> LENGTH: 1508
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gaattcgccc ttccaccatg gccttaccag tgaccgcctt gctcctgccg ctggccttgc      60
tgctccacgc cgccaggccg gacattcaga tgacccagtc accatccagc ctcagtgctt     120
```

```
ctgttgggga ccgagttacc atcacttgtc gcgcaagcga atctgtcgac aactatggca    180
taagttttat gaattggttt cagcagaagc caggaaaggc accgaagctg cttatctacg    240
ctgcaagtaa tcaaggatcc ggcgtgccta gccggttctc cggatcagga tccgggacag    300
actttacatt gacaatttct agcctgcagc cagatgattt tgcaacctac tactgtcaac    360
agtctaagga agttccctgg acgtttggc  agggcaccaa ggttgagatc aagggcggcg    420
gcgggtccgg aggtggcggg tccgcggcg  gtggctccgg gggggggggt agccaggtcc    480
agctcgtaca aagtggtgcc gaggtgaaga acccgggag  cagcgtgaaa gtgtcctgta    540
aggccagtgg ctacaccttt acagactaca atatgcactg ggtgcgccag gcgcccggcc    600
agggccttga gtggataggc tacatttatc cctacaatgg cggaaccgga tacaatcaga    660
agtttaagag caaggcaaca attaccgctg atgagtccac taacaccgct acatggaat     720 tgagcagtct tcgatccgaa gacactgccg tgtattactg tgcccgagga agacctgcca    780
tggactactg gggtcaggga actctggtaa ccgtctctag cgcggccgca accacgacgc    840
cagcgccgcg accaccaaca ccggcgccca ccatcgcgtc gcagccctg  tccctgcgcc    900 cagaggcgtg ccggccagcg gcgggggggcg cagtgcacac gagggggctg gacttcgcct    960
gtgatatcta catctgggcg cccttggccg ggacttgtgg ggtccttctc ctgtcactgg   1020
ttatcaccct ttactgcaaa cggggcagaa agaaactcct gtatatattc aaacaaccat   1080
ttatgagacc agtacaaact actcaagagg aagatggctg tagctgccga tttccagaag   1140
aagaagaagg aggatgtgaa ctgagagtga agttcagcag gagcgcagac gcccccgcgt   1200
accagcaggg ccagaaccag ctctataacg agctcaatct aggacgaaga gaggagtacg   1260
atgttttgga caagagacgt ggccgggacc ctgagatggg gggaaagccg agaaggaaga   1320
accctcagga aggcctgtac aatgaactgc agaaagataa gatggcggag cctacagtg    1380 agattgggat gaaaggcgag cgccggaggg gcaaggggca cgatggcctt taccagggtc   1440
tcagtacagc caccaaggac acctacgacg cccttcacat gcaggccctg cccctcgct   1500 aactcgag                                                            1508
```

<210> SEQ ID NO 2
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ile Arg Pro Ser Thr Met Ala Leu Pro Val Thr Ala Leu Leu Leu Pro
1               5                   10                  15

Leu Ala Leu Leu Leu His Ala Ala Arg Pro Asp Ile Gln Met Thr Gln
            20                  25                  30

Ser Pro Ser Ser Leu Ser Ala Ser Val Gly Asp Arg Val Thr Ile Thr
        35                  40                  45

Cys Arg Ala Ser Glu Ser Val Asp Asn Tyr Gly Ile Ser Phe Met Asn
    50                  55                  60

Trp Phe Gln Gln Lys Pro Gly Lys Ala Pro Lys Leu Leu Ile Tyr Ala
65                  70                  75                  80

Ala Ser Asn Gln Gly Ser Gly Val Pro Ser Arg Phe Ser Gly Ser Gly
                85                  90                  95

Ser Gly Thr Asp Phe Thr Leu Thr Ile Ser Ser Leu Gln Pro Asp Asp
            100                 105                 110

Phe Ala Thr Tyr Tyr Cys Gln Gln Ser Lys Glu Val Pro Trp Thr Phe
            115                 120                 125

Gly Gln Gly Thr Lys Val Glu Ile Lys Gly Gly Gly Ser Gly Gly
        130                 135                 140

Gly Gly Ser Gly Gly Gly Ser Gly Gly Gly Ser Gln Val Gln
145                 150                 155                 160

Leu Val Gln Ser Gly Ala Glu Val Lys Lys Pro Gly Ser Ser Val Lys
                165                 170                 175

Val Ser Cys Lys Ala Ser Gly Tyr Thr Phe Thr Asp Tyr Asn Met His
                180                 185                 190

Trp Val Arg Gln Ala Pro Gly Gln Gly Leu Glu Trp Ile Gly Tyr Ile
            195                 200                 205

Tyr Pro Tyr Asn Gly Gly Thr Gly Tyr Asn Gln Lys Phe Lys Ser Lys
        210                 215                 220

Ala Thr Ile Thr Ala Asp Glu Ser Thr Asn Thr Ala Tyr Met Glu Leu
225                 230                 235                 240

Ser Ser Leu Arg Ser Glu Asp Thr Ala Val Tyr Tyr Cys Ala Arg Gly
                245                 250                 255

Arg Pro Ala Met Asp Tyr Trp Gly Gln Gly Thr Leu Val Thr Val Ser
            260                 265                 270

Ser Ala Ala Ala Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
        290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Lys Arg Gly Arg Lys Lys Leu
                340                 345                 350

Leu Tyr Ile Phe Lys Gln Pro Phe Met Arg Pro Val Gln Thr Thr Gln
            355                 360                 365

Glu Glu Asp Gly Cys Ser Cys Arg Phe Pro Glu Glu Glu Glu Gly Gly
        370                 375                 380

Cys Glu Leu Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg

<210> SEQ ID NO 3
<211> LENGTH: 247
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 3

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Asp Asp Phe Ala Thr Tyr Tyr Cys Gln Gln Ser Lys
                85                  90                  95

Glu Val Pro Trp Thr Phe Gly Gln Gly Thr Lys Val Glu Ile Lys Gly
            100                 105                 110

Gly Gly Gly Ser Gly Gly Gly Ser Gly Gly Gly Ser Gly Gly Gly Gly
        115                 120                 125

Gly Gly Ser Gln Val Gln Leu Val Gln Ser Gly Ala Glu Val Lys Lys
    130                 135                 140

Pro Gly Ser Ser Val Lys Val Ser Cys Lys Ala Ser Gly Tyr Thr Phe
145                 150                 155                 160

Thr Asp Tyr Asn Met His Trp Val Arg Gln Ala Pro Gly Gln Gly Leu
                165                 170                 175

Glu Trp Ile Gly Tyr Ile Tyr Pro Tyr Asn Gly Gly Thr Gly Tyr Asn
            180                 185                 190

Gln Lys Phe Lys Ser Lys Ala Thr Ile Thr Ala Asp Glu Ser Thr Asn
        195                 200                 205

Thr Ala Tyr Met Glu Leu Ser Ser Leu Arg Ser Glu Asp Thr Ala Val
    210                 215                 220

Tyr Tyr Cys Ala Arg Gly Arg Pro Ala Met Asp Tyr Trp Gly Gln Gly
225                 230                 235                 240

Thr Leu Val Thr Val Ser Ser
                245
```

<210> SEQ ID NO 4
<211> LENGTH: 255
<212> TYPE: PRT
<213> ORGANISM: Homo sapiens

<400> SEQUENCE: 4

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
```

-continued

Ala Gly Cys Ser Met Cys Glu Gln Asp Cys Lys Gln Gly Gln Glu Leu
                85                  90                  95
                                100                 105                 110

Thr Lys Lys Gly Cys Lys Asp Cys Cys Phe Gly Thr Phe Asn Asp Gln
                115                 120                 125

Lys Arg Gly Ile Cys Arg Pro Trp Thr Asn Cys Ser Leu Asp Gly Lys
                130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
                180                 185                 190

Ala Leu Thr Ser Thr Ala Leu Leu Phe Leu Leu Phe Phe Leu Thr Leu
                195                 200                 205

Arg Phe Ser Val Val Lys Arg Gly Arg Lys Lys Leu Leu Tyr Ile Phe
                210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 5
<211> LENGTH: 109
<212> TYPE: PRT
<213> ORGANISM: Homo sapiens

<400> SEQUENCE: 5

Phe Ser Arg Ser Ala Asp Ala Pro Ala Tyr Gln Gln Gly Gln Asn Gln
1               5                   10                  15

Leu Tyr Asn Glu Leu Asn Leu Gly Arg Arg Glu Glu Tyr Asp Val Leu
                20                  25                  30

Asp Lys Arg Arg Gly Arg Asp Pro Glu Met Gly Gly Lys Pro Arg Arg
                35                  40                  45

Lys Asn Pro Gln Glu Gly Leu Tyr Asn Glu Leu Gln Lys Asp Lys Met
                50                  55                  60

Ala Glu Ala Tyr Ser Glu Ile Gly Met Lys Gly Glu Arg Arg Arg Gly
65                  70                  75                  80

Lys Gly His Asp Gly Leu Tyr Gln Gly Leu Ser Thr Ala Thr Lys Asp
                85                  90                  95

Thr Tyr Asp Ala Leu His Met Gln Ala Leu Pro Pro Arg
                100                 105

<210> SEQ ID NO 6
<211> LENGTH: 69
<212> TYPE: PRT
<213> ORGANISM: Homo sapiens

<400> SEQUENCE: 6

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
                35                  40                  45

Trp Ala Pro Leu Ala Gly Thr Cys Gly Val Leu Leu Leu Ser Leu Val

Ile Thr Leu Tyr Cys
65

<210> SEQ ID NO 7
<211> LENGTH: 21
<212> TYPE: PRT
<213> ORGANISM: Homo sapiens

<400> SEQUENCE: 7

Met Ala Leu Pro Val Thr Ala Leu Leu Leu Pro Leu Ala Leu Leu Leu
1               5                   10                  15

His Ala Ala Arg Pro
            20

<210> SEQ ID NO 8
<211> LENGTH: 741
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gacattcaga tgacccagtc accatccagc ctcagtgctt ctgttgggga ccgagttacc      60
atcacttgtc gcgcaagcga atctgtcgac aactatggca taagtttat gaattggttt     120 cagcagaagc caggaaaggc accgaagctg cttatctacg ctgcaagtaa tcaaggatcc     180
ggcgtgccta gccggttctc cggatcagga tccgggacag actttacatt gacaatttct     240
agcctgcagc cagatgattt tgcaacctac tactgtcaac agtctaagga agttccctgg     300
acgtttgggc agggcaccaa ggttgagatc aagggcggcg gcgggtccgg aggtggcggg     360
tccggcggcg gtggctccgg ggggggggt agccaggtcc agctcgtaca aagtggtgcc     420
gaggtgaaga aacccgggag cagcgtgaaa gtgtcctgta aggccagtgg ctacaccttt     480
acagactaca atatgcactg ggtgcgccag gcgcccggcc agggccttga gtggataggc     540
tacatttatc cctacaatgg cggaaccgga tacaatcaga agtttaagag caaggcaaca     600
attaccgctg atgagtccac taacaccgct tacatggaat tgagcagtct tcgatccgaa     660
gacactgccg tgtattactg tgcccgagga agacctgcca tggactactg gggtcaggga     720
actctggtaa ccgtctctag c                                               741

<210> SEQ ID NO 9
<211> LENGTH: 129
<212> TYPE: DNA
<213> ORGANISM: Homo sapiens

<400> SEQUENCE: 9
aaacggggca gaaagaaact cctgtatata ttcaaacaac catttatgag accagtacaa      60
actactcaag aggaagatgg ctgtagctgc cgatttccag aagaagaaga aggaggatgt     120
gaactgaga                                                             129

<210> SEQ ID NO 10
<211> LENGTH: 333
<212> TYPE: DNA
<213> ORGANISM: Homo sapiens

<400> SEQUENCE: 10
agttcagcag gagcgcagac gcccccgcgt accagcaggg ccagaaccag ctctataacg      60
agctcaatct aggacgaaga gaggagtacg atgtttga caagagacgt ggccgggacc    120
ctgagatggg gggaaagccg agaaggaaga accctcagga aggcctgtac aatgaactgc    180
agaaagataa gatggcggag gcctacagtg agattggat gaaggcgag cgccggaggg    240 gcaaggggca cgatggcctt taccagggtc tcagtacagc caccaaggac acctacgacg    300
cccttcacat gcaggccctg cccctcgct aac    333

<210> SEQ ID NO 11
<211> LENGTH: 209
<212> TYPE: DNA
<213> ORGANISM: Homo sapiens

<400> SEQUENCE: 11
accacgacgc cagcgccgcg accaccaaca ccggcgccca ccatcgcgtc gcagcccctg    60
tccctgcgcc cagaggcgtg ccggccagcg gcgggggggcg cagtgcacac gaggggggctg    120 gacttcgcct gtgatatcta catctgggcg cccttggccg ggacttgtgg ggtccttctc    180
ctgtcactgg ttatcaccct ttactgcaa    209

<210> SEQ ID NO 12
<211> LENGTH: 63
<212> TYPE: DNA
<213> ORGANISM: Homo sapiens

<400> SEQUENCE: 12
atggccttac cagtgaccgc cttgctcctg ccgctggcct tgctgctcca cgccgccagg    60
ccg    63

<210> SEQ ID NO 13
<211> LENGTH: 45
<212> TYPE: PRT
<213> ORGANISM: Homo sapiens

<400> SEQUENCE: 13

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45

<210> SEQ ID NO 14
<211> LENGTH: 21
<212> TYPE: PRT
<213> ORGANISM: Homo sapiens

<400> SEQUENCE: 14

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 15
<211> LENGTH: 135
<212> TYPE: DNA
<213> ORGANISM: Homo sapiens

<400> SEQUENCE: 15
accacgacgc cagcgccgcg accaccaaca ccggcgccca ccatcgcgtc gcagcccctg    60

```
tccctgcgcc cagaggcgtg ccggccagcg gcggggggcg cagtgcacac gaggggggctg    120 gacttcgcct gtgat                                                     135

<210> SEQ ID NO 16
<211> LENGTH: 74
<212> TYPE: DNA
<213> ORGANISM: Homo sapiens

<400> SEQUENCE: 16
atctacatct gggcgcoctt ggccgggact tgtggggtcc ttctcctgtc actggttatc    60 acccttact gcaa                                                       74
```

What is claimed is:

1. A polynucleotide encoding a chimeric receptor comprising (a) an extracellular ligand-binding domain comprising an anti-CD33 single chain variable fragment (scFv) comprising the amino acid sequence SEQ ID NO:3, (b) a CD8α hinge comprising the amino acid sequence SEQ ID NO:13, (c) a transmembrane domain, and (d) a cytoplasmic domain comprising a 4-1BB signaling domain and a CD3ζ signaling domain.

2. The polynucleotide of claim 1, wherein the nucleotide sequence encoding the anti-CD33 scFv comprises SEQ ID NO:8.

3. The polynucleotide of claim 1, wherein the 4-1BB signaling domain comprises amino acids 214-255 of SEQ ID NO:4.

4. The polynucleotide of claim 3, wherein the nucleotide sequence encoding the 4-1BB signaling domain comprises SEQ ID NO:9.

5. The polynucleotide of claim 1, wherein the CD3ζ signaling domain comprises the amino acid sequence SEQ ID NO:5.

6. The polynucleotide of claim 5, wherein the nucleotide sequence encoding the CD3ζ signaling domain comprises SEQ ID NO:10.

7. The polynucleotide of claim 1, wherein the hinge and transmembrane domain is the hinge and transmembrane domain of CD8α.

8. The polynucleotide of claim 7, wherein the hinge and transmembrane domain of CD8α comprises the amino acid sequence SEQ ID NO:6.

9. The polynucleotide of claim 8, wherein the nucleotide sequence encoding the hinge and transmembrane domain of CD8α comprises SEQ ID NO:11.

10. The polynucleotide of claim 1, wherein the nucleotide sequence encoding the CD8a hinge comprises SEQ ID NO: 15.

11. The polynucleotide of claim 1, wherein the transmembrane domain is a CD8α transmembrane domain comprising the amino acid sequence SEQ ID NO: 14.

12. The polynucleotide of claim 11, wherein the nucleotide sequence encoding the CD8α transmembrane domain comprises SEQ ID NO:16.

13. The polynucleotide of claim 1, wherein the extracellular ligand-binding domain comprises a signal peptide of CD8α.

14. The polynucleotide of claim 13, wherein the signal peptide of CD8α comprises the amino acid sequence SEQ ID NO:7.

15. The polynucleotide of claim 14, wherein the nucleotide sequence encoding the signal peptide of CD8α comprises SEQ ID NO:12.

16. The polynucleotide of claim 1, wherein the chimeric receptor comprises the amino acid sequence SEQ ID NO:2.

17. The polynucleotide of claim 16, wherein the nucleotide sequence encoding the chimeric receptor comprises SEQ ID NO:1.

18. A vector comprising the polynucleotide of claim 1, wherein the polynucleotide is operatively linked to at least one regulatory element for expression of the chimeric receptor.

19. A chimeric receptor comprising (a) an extracellular ligand-binding domain comprising an anti-CD33 single chain variable fragment (scFv) comprising the amino acid sequence SEQ ID NO:3, (b) a CD8α hinge comprising the amino acid sequence SEQ ID NO:13, (c) a transmembrane domain, and (d) a cytoplasmic domain comprising a 4-1BB signaling domain and a CD3ζ signaling domain.

20. An isolated host cell comprising the chimeric receptor of claim 19.

21. An isolated host cell comprising the polynucleotide of claim 1.

22. An isolated host cell comprising the vector of claim 18.

23. A method for preparing T lymphocytes comprising:
  a. activating a T lymphocyte;
  b. transducing the T lymphocyte with the polynucleotide of claim 1;
  c. expanding the transduced T lymphocyte; and
  d. treating the transduced T lymphocyte with an inhibitor, wherein the inhibitor is a phosphoinositide 3-kinase (PI3K) / Akt pathway inhibitor, an oncogene inhibitor, an oncoprotein inhibitor, and/or a glycolysis inhibitor.

* * * * *